US008309697B2

(12) United States Patent
Sodroski et al.

(10) Patent No.: US 8,309,697 B2
(45) Date of Patent: Nov. 13, 2012

(54) METHODS AND COMPOSITIONS FOR THE TREATMENT AND PREVENTION OF HIV INFECTION USING TRIM5α

(75) Inventors: Joseph Sodroski, Medford, MA (US); Matthew Stremlau, Brookline, MA (US); Christopher M. Owens, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 264 days.

(21) Appl. No.: 12/689,800

(22) Filed: Jan. 19, 2010

(65) Prior Publication Data

US 2010/0129438 A1 May 27, 2010

Related U.S. Application Data

(60) Division of application No. 11/510,500, filed on Aug. 25, 2006, now Pat. No. 7,659,382, which is a continuation of application No. PCT/US2005/005458, filed on Feb. 17, 2005.

(60) Provisional application No. 60/548,139, filed on Feb. 25, 2004.

(51) Int. Cl.
*C07H 21/02* (2006.01)
*C12N 1/12* (2006.01)
*C12N 15/00* (2006.01)
*A61K 38/00* (2006.01)

(52) U.S. Cl. .................. 536/23.1; 435/320.1; 435/252.3; 530/350

(58) Field of Classification Search .......................... None
See application file for complete search history.

(56) References Cited

OTHER PUBLICATIONS

Ozato K. et al. "TRIM family proteins and their emerging roles in innate immunity" Nature Reviews Immunology 8:849-860; 2008.*
Arts, E. J., and M. A. Wainberg, "Human immunodeficiency virus type 1 reverse transcriptase and early events in reverse transcription," Adv. Virus Res. 46:97-163 (1996).
Barre-Sinoussi, F., et al., "Isolation of a T-lymphotropic retrovirus from a patient at risk for acquired immune deficiency syndrome (AIDS)," Science 220:868-871 (1983).
Berti et al., "TRIM9 is specifically expressed in the embryonic and adult nervous system," Mech. Dev., 113(2):159-162 (2002).
Besnier, C, et al., "Restriction of lentivirus in monkeys," Proc. Natl. Acad. Sci. USA 99:11920-11925 (2002).
Bieniasz P. D., "Restriction factors: a defense against retroviral infection," Trends Microbiol. 11:286-291 (2003).
Bonilla, W.V. et al., "Effects of Promyelocytic Leukemia Protein on Virus-Host Balance," J. Virol. 76(8):3810-3818 (2002).
Borden, K.L., "RING fingers and B-boxes: zinc-binding protein-protein interaction domains," Biochem. Cell Biol., 76:351-358 (1998).

Butler, S., et al., "A quantitative assay for HIV DNA integration in vivo," Nat. Med. 7, 631-634 (2001).
Chee, A.V. et al., "Promyelocytic Leukemia Protein Mediates Interferon-Based Anti-Herpes Simplex Virus 1 Effects," J. Virol. 77(12):7101-7105 (2003).
Clavel, F., "Editorial Review HIV-2, the West African AIDS Virus," AIDS 1:135-140 (1987).
Cowan, S., et al., "Cellular inhibitors with Fv1-like activity restrict human and simian immunodeficiency virus tropism," Proc. Natl. Acad. Sci. USA 99:11914-11919 (2002).
Daniel, M. D., et al., "Isolation of T-cell tropic HTLV-III-like retrovirus from macaques," Science 228:1201-1204 (1985).
Desrosiers, R. C., "The simian immunodeficiency viruses," Ann. Rev. Immunol. 8: 557-578 (1990).
Dorfman, T. & Göttlinger, H.G., "The Human Immunodeficiency Virus Type I Capsid p2 Domain Confers Sensitivity to the Cyclophilin-Binding Drug SDZ NIM 811," J. Virol. 70, 5751-5757 (1996).
Fassati, A. and Goff, S.P., "Characterization of Intracellular Reverse Transcription Complexes of Human Immunodeficiency Virus Type 1," J. Virol. 75, 3626-3635 (2001).
Fauci, A., et al., "NIH conference. Acquired immunodeficiency syndrome: epidemiologic, clinical, immunologic, and therapeutic considerations,"Ann. Int.Med. 100:91-106 (1984).
Feng, Y., et al., "HIV-1 entry cofactor: functional cDNA clonong of a seven-transmembrane, G protein-coupled receptor," Science 272, 872-877 (1996).
Forshey et al., "Formation of a Human Immunodeficiency Virus Type 1 Core of Optimal Stability is Crucial for Viral Replication," J. Virol. 76(11):5667-5677 (2002).
Freed, E. O., "HIV-1 gag proteins: diverse functions in the virus life cycle," Virology 251:1-15 (1998).
Gallo, R. C., et al., "Frequent detection and isolation of cytopathic retroviruses (HTLV-III) from patients with AIDS and at risk for AIDS," Science 224:500-503 (1984).
Hatziioannou, T., et al., "Restriction of multiple divergent retroviruses by Lv1 and Ref1," EMBO J. 22:385-394 (2003).
Hatziioannou, T., et al., "Retrovirus resistance factors Ref1 and Lv1 are species-specific variants of TRIM5α," Proc. Natl. Acad. Sci. USA 101:10774-10779 (2004).

(Continued)

*Primary Examiner* — Bo Peng
(74) *Attorney, Agent, or Firm* — Foley Hoag LLP

(57) ABSTRACT

The invention provides novel TRIM polypeptides, proteins, and nucleic acid molecules. In addition to isolated, full-length TRIM proteins, the invention further provides isolated TRIM fusion proteins, antigenic peptides and anti-TRIM antibodies. The invention also provides TRIM nucleic acid molecules, recombinant expression vectors containing a nucleic acid molecule of the invention, host cells into which the expression vectors have been introduced and non-human transgenic animals in which an TRIM gene has been introduced or disrupted. The present invention also provides methods and compositions for the diagnosis and treatment of viral infection and/or replication, e.g., HIV infection. The invention further provides methods for identifying a compound capable of treating or preventing viral infection and/or replication, e.g., HIV infection and AIDS. In addition, the invention provides a method for treating a subject having a viral infection and/or replication, e.g., HIV infection using the modulators of the invention.

17 Claims, 29 Drawing Sheets

OTHER PUBLICATIONS

Hatziioannou, T., et al., "Species-Specific Tropism Determinants in the Human Immunodeficiency Virus Type I Capsid," J. Virol. 78:6005-6012 (2004).

Henry, J., et al., "B30.2-like Domain Proteins: Update and New Insights into a Rapidly Expanding Family of Proteins," "Restriction of HIV-1 (subtype B) replication at the entry step in rhesus macaque cells," Mol. Biol. Evol. 15:1696-1705 (1998).

Himathongkham, S., and P. A. Luciw, "Restriction of HIV-1 (subtype B) replication at the entry step in rhesus macaque cells," Virology 219:485-488 (1996).

Hofmann, W., et al., "Species-Specific, Postentry Barriers to Primate Immunodeficiency Virus Infection," J. Virol. 73, 10020-10028 (1999).

Ishii, T., et al., "Carboxy-terminal cytoplasmic domain of mouse butyrophilin specifically associates with a 150-kDa protein of mammary epithelial cells and milk fat globule membrane," Biochim. Biophys. Acta 1245:285-292 (1995).

Jarvis et al., "Immediate-early baculovirus vectors for foreign gene expression in transformed or infected insect cells," Protein Expr. Purif., 8(2):191-203 (1996).

Kanki, P.J. et al., "Isolation of T-Lymphotropic Retrovirus Related to HTLV-III/LAV from Wild-Caught African Green Monkeys," Science 230:951-954 (1985).

Keckesova, Z., et al., "The human and African green monkey TRIM5α genes encode Ref1 and Lv1 retroviral restriction factor activities," Proc. Natl. Acad. Sci. USA 101:10780-10785 (2004).

Klotzbucher et al., "A Method for Analyzing the Ubiquitination and Degradation of Aurora-A," Biol. Proced. Online 4(1):62-69 (2002).

Kootstra, N. A., et al., "Abrogation of postentry restriction of HIV-1-based lentiviral vector transduction in simian cells," Proc. Natl. Acad. Sci. USA 200:1298-1303 (2003).

LaBonte, J.A. et al., "Blockade of HIV-1 Infection of New World Monkey Cells Occurs Primarily at the Stage of Virus Entry," J. Exp. Med. 196:431-445 (2002).

Letvin, N. L., et al., "Introduction of AIDS-like disease in macaque monkeys with T-cell tropic retrovirus STLV-III," Science 230:71-739,19 (1985).

Li, J., et al., "Infection of Cynomolgus Monkeys with a Chimeric HIV-1/SIV$_{mac}$ Virus That Expresses the HIV-1 Envelope Glycoproteins," J. AIDS 5, 639-646 (1992).

Marcello, A. et al., "Recruitment of human cyclin T1 to nuclear bodies through direct interaction with the PML protein," EMBO J. 22(9):2156-2166 (2003).

Mariani, R. et al., "Species-Specific Exclusion of APOBEC3G from HIV-1 Virions by Vif," Cell 114:21-31 (2003).

Munk, C, et al., "A dominant block to HIV-1 replication at reverse transcription in simian cells," Proc. Natl. Acad. Sci. USA 99:13843-13848 (2002).

NCBI RefSeq NM_033034 (gi:14719417) Aug. 16, 2009.

NCBI RefSeq NM_033092 (gi:15011943) Aug. 16, 2009.

Nakayama et al., "A Specific Region of 37 Amino Acid Residues in the SPRY (B30.2) Domain of African Green Monkey Trims Determines Species-Specific Restriction of Simian Immunodeficiency Virus SIVmac Infection," Virology, 79(14):8870-7 (2005).

Niikura, T., et al., "A tripartite motif protein TRIM11 binds and destabilizes Humanin, a neuroprotective peptide against Alzheimer's disease-relevant insults," Eur. J. Neurosci. 17:1150-1158 (2003).

Nisole, S., et al., "A Trim5-cyclophilin A fusion protein found in owl monkey kidney cells can restrict HIV-1," Proc. Natl. Acad. Sci. USA, in press (2004).

Owens, C. M., et al., "Binding and Susceptibility to Postentry Restriction Factors in Monkey Cells are Specified by Distinct Regions of the Human Immunodeficiency Virus Type 1 Capsid," J. Virol. 78:5423-5437 (2004).

Owens, C. M., et al., "Human and Simian Immunodeficiency Virus Capsid Proteins are Major Viral Determinants of Early, Postentry Replication Blocks in Simian Cells," J. Virol. 77:726-731 (2003).

Pieribone, D., "The HIV Life Cycle," AEGiS-ACRIA: ACRIA News—The HIV Life Cycle—Winter 2002/2003 ww.aegis.com/pubs/cria/2003/CR030111.html (2003).

Reddy, B.A., et al., "A novel zinc finger coiled-coil domain in a family of nuclear proteins," Trends Biochem. Sci., 17:344-345 (1992).

Reymond, A., et al., "The tripartite motif family identifies cell compartments," EMBO J. 20:2140-2151 (2001).

Rho, H. M., et al., "Characterization of the Reverse Transcriptase from a New Retrovirus (HTLV) Produced by a Human Cutaneous T-Cell Lymphoma Cell Line," Virology 112:355-360 (1981).

Rhodes, D.A. et al., "The 52 000 MW Ro/SS-A autoantigen in Sjögren's syndrome/systemic lupus erythematosus (Ro52) is an interferon-γ inducible tripartite motif protein associated with membrane proximal structures," Immunol. 106:246-256 (2002).

Sawyer et al., "Positive selection of primate TRIM5α identifies a critical species-specific retroviral restriction domain," PNAS, 102(8):2832-2837 (2005).

Sayah, D. M., et al., "Cyclophilin A retrotransposition into TRIM5 explains owl monkey resistance to HIV-1," Nature, in press (2004).

Schwartz, O. et al., "Antiviral Activity of the Proteasome on Incoming Human Immunodeficiency Virus Type 1," J. Virol. 72(5):3845-3850 (1998).

Seto, M. H., et al., "Protein Fold Analysis of the B30.2-Like Domain," Proteins: Structure, Function, and Genetics 35:235-249 (1999).

Shibata, R., et al., "Early replication block of human immunodeficiency virus type 1 in monkey cells," J. Gen. Virol. 76:2723-2730 (1995).

Stremlau et al., "Species-specific variation in the B30.2(SPRY) domain of TRIM5α determines the potency of human immunodeficiency virus restriction," J. Virol., 79(5):3139-45 (2005).

Stremlau, M., et al., "The cytoplasmic body component TRIM5alpha restricts HIV-1 infection in Old World monkeys," Nature 427:848-853 (2004).

Toniato, E. et al., "TRIM8/GERP Ring Finger Protein Interacts with SOCS-1," J. Biol. Chem. 277(40):37315-37322 (2002).

Towers, G., et al., "A conserved mechanism of retrovirus restriction in mammals," Proc. Natl. Acad. Sci. USA 97:12295-12299 (2000).

Towers, G., et al., "Abrogation of Ref1 Retrovirus Restriction in Human Cells," J. Virol. 76:2548-2550 (2002).

Towers, G., et al., "Cyclophilin A modulates the sensitivity of HIV-1 to host restriction factors," Nat. Med. 9:1138-1143 (2003).

Turelli, P. et al., "Cytoplasmic Recruitment of INI1 and PML on Incoming HIV Preintegration Complexes: Interference with Early Steps of Viral Replication," Mol. Cell 7:1245-1254 (2001).

Waterman, H., et al.,"The Ring Finger of c-Cbl Mediates Desensitization of the Epidermal Growth Factor Receptor," J. Biol. Chem. 274, 22151-22154 (1999).

Whitcomb, J. M., and S. H. Hughes, "Retroviral reverse transcription and integration: progress and problems," Annu. Rev. Cell. Biol. 8:275-306 (1992).

Xu, L., et al., "BTBD1 and BTBD2 colocalize to cytoplasmic bodies with the RBCC/tripartite motif protein," Exp. Cell Res. 288, 84-93 (2003).

Yap, M. W., et al., "Trim5α protein restricts both HIV-1 and murine leukemia virus," Proc. Natl. Acad. Sci. USA 101:10786-10791 (2004).

International Search Report dated Jun. 4, 2008 from PCT/US05/05458.

Supplementary European Search Report dated Jan. 11, 2011 from EP 05723412.2.

Sodrosky, J.G., "Innate intracellular immunity to retroviruses," Harvey Lectures, 100:143-153 (2004-2005).

* cited by examiner

```
                          ┌─────────────────────────RING──────────────────────────┐
TRIM5α Rh    MASGILLNVKEEVTCPICLELLTEPLSLHCGHSFCQACITANHKKSMLYKEGERSCPVCR      60
TRIM5α Hu    .........V.............Q......D..............L.......D-...S.      59
                                                          ┌────B-Box 2────
TRIM5α Rh    ISYQPENIQPNRHVANIVEKLREVKLSPEEGQKVDHCARHGEKLLFCQEDSKVICWLCE     120
TRIM5α Hu    .............R...........................................G.    118
             ──┐  ┌─────────────── Coiled-coil domain
TRIM5α Rh    RSQEHRGHHTFLMEEVAQEYHVKLQTALEMLRQKQQEAAEKLEADIREEKASWKIQIDYDK    180
TRIM5α Hu    ..........T....R..Q......A..........E...............T..Q...    178

TRIM5α Rh    TNVSADFEQLREILDWEESNELQNLEKEEDILKSLTKSETEMVQQTQYMRELISELEHR      240
TRIM5α Hu    ..L...........D.................N...........SL....D......      238

TRIM5α Rh    LQGSMMDLLQGVDGIIKRIENMTLKKPKTFHKNQRRVFRAPDLKGMLDMFRELTDARRYW    300
TRIM5α Hu    ...V.E........V...T.V.....E..P...........EV......V.......      298
                                                        ┌──B30.2(SPRY) domain
TRIM5α Rh    VDVTLATNNISHAVIAEDKRQVSSRNPQIMYQAPGTLFTFPSLTNFNYCTGVLGSQSITS    360
TRIM5α Hu    ...V.P....C...S........PK..I.G.R..RYQT--FV.......I.......      356

TRIM5α Rh    GKHYWEVDVSKKSAWILGVCAGFQSDAMYNIEQNENYQPKYGYWVIGLQEGVKYSVFQDG    420
TRIM5α Hu    ................T...............P..C...K.............E....C.A...S    416

TRIM5α Rh    SSHTPFAPFIVPLSVIICPDRVGVFVDYEACTVSFFNITNHGFLIYKFSQCSFSKPVFPY    480
TRIM5α Hu    .F...SV....................L.............................H...Q....    476

TRIM5α Rh    LNPRKCTVPMTLCSPSS   497
TRIM5α Hu    .......G.........   493
```

Figure 1A

EXON 1   196 bp
gaaaagggagattgagtgggaatgcctctagttcccacggctcctcctgtgaacagcaca
gctacacggcccggctgattcattcagagggcgggactcaccaggccctacgtggagaaa
tgccattggcccata<u>gtttatctttcac</u>tttcctgccctgagtgtgagcaagaatttcct
GCGGTTCCTCTAGGAAAATTCCTTTGTGCAGATCAGGCCCGTGGATTGGTGAGTGAATCC
TAACCACGTCTTCCCTGGCCTGTCTTCACTCTTCTCCCCAGAATCACCCACTTCTGCACTG
GTGTCTGAAGGTGTATTGAGTGATTTTGTGGAGGGCAGAAGTAGGAAGTCTTTGGGACAA
AACTGTATTTACCTTG
gtgagtttaacttatctgaaaagctgtgcggggtggggaaaagacacagttcacagact
tcttgctgccagagctgactgaggggaacagagccgcctggcgggcaggcagatttgaaa
gaagggagagctttaaagtgaagggctttgtttcccgaaggctggttattttccatgct
EXON 2   478 bp
gtatttaaggtgattatgaaaagcccttattaccaggtaaccaaacaccttttcttattt
ctccccttttttgtccttaattattttcatcttgcccattttctaattgtgcacaatca
atatcctttctatttctacctttcttacttggtcccattttaaccttcccaatcatgcag
GGATCTGTGAACAAGAGGAACCTCAGCAGCCAGGACAGGCAGGAGCAGTGGAATAGCTAC
TA<i>TG</i>GCTTCTGGAATCCTGGTTAATGTAAAGGAGGAGGTGACCTGCCCCATCTGCCTGGA
ACTCCTGACACAACCCCTGAGCCTGGACTGCGGCCACAGCTTCTGCCAAGCATGCCTCAC
TGCAAACCACAAGAAGTCCATGCTAGACAAAGGAGAGAGTAGCTGCCCTGTGTGCCGGAT
CAGTTACCAGCCTGAGAACATACGGCCTAATCGGCATGTAGCCAACATAGTGGAGAAGCT
CAGGGAGGTCAAGTTGAGCCCAGAGGGGCAGAAAGTTGATCATTGTGCACGCCATGGAGA
GAAACTTCTACTCTTCTGTCAGGAGGACGGGAAGGTCATTTGCTGGCTTTGTGAGCGGTC
TCAGGAGCACCGTGGTCACCACACGTTCCTCACAGAGGAGGTTGCCCGGGAGTACCAA
gtaagagactgggatggaaggaagagagggcagaaaatgggaccagatggaaaattttca
ctttgcctttgacattaactgccttgtcatgatagacctgagacccgggattatttttt
catgctatgcttaacttctgaggctttaaggatggttttttgcatttcacccaattacag
EXON 3   96 bp
gatgtagggagcacattcaccaatgtaagttttcttccaagtcatggattctcattgcca
ttctcacagtttctgcaaatttgtttcttctgagatcaacctgatttatttcatgtttat
actctatctaggtgctggaaaacctcatagcttgactatggtgtgattcctttctcacag
GTGAAGCTCCAGGCAGCTCTGGAGATGCTGAGGCAGAAGCAGCAGGAAGCTGAAGAGTTA
GAAGCTGACATCAGAAGAGAAAGCTTCCTGGAAG
gcaagaggatgtggttcccgaaggagttagctagaaatctgggcaggaccaggggaagga
gctttcttcctctttattccctgacatttgataagtccagaagtcatttgattagtcctc
ttcatcctttccctgatggggtgtggtggctgaggagtgaatatgtcacagtgaacacag
EXON 4   231 bp
gtcattgttttaaaatgtcatgaaggaaaagaaataggaaaaggcagcttcctaagacc
tactctcctgctactatgtccctccttgtgagaactccccaaaagaaacagctccttt
ctggctaacagcctctgcctggtagactgagtgccccttctcttctcttatctctgaag
ACTCAAATACAGTATGACAAAACCAACGTCTTGGCAGATTTTGAGCAACTGAGAGACATC
CTGGACTGGGAGGAGAGCAATGAGCTGCAAAACCTGGAGAAGGAGGAGGAAGACATTCTG
AAAAGCCTTACGAACTCTGAAACTGAGATGGTGCAGCAGACCCAGTCCCTGAGAGAGCTC
ATCTCAGATCTGGAGCATCGGCTGCAGGGGTCAGTGATGGAGCTGCTTCAG
gtaaaaagtggaagaagcctgagcactgagattaaagaaaagtgaaggctatttccttc
tctgcgttgctgtgcttttttctaatattaacaatgttctctgcaggaccgcttttctgaa
tcaattgctgaagttataagaataattgaatgtagaagtagcaagagataatcccattt
EXON 5   23 bp
tggaaatctcacatgagtcttctgggatgattgccttgagtcttatctttgcttttttgt
ctttcacactgtcaccatctccattctcagcacattaggaaccggggggaaatgtgatgaa
gctttataagtgaggagagactctttctttcttaattgatgttttctctcttcttcctag
GGTGTGGATGGCGTCATAAAAAG
gtatgtgtgggaggacagagatggtcctttgtgcagtgaggagagatttatagccatta
gaattgtcctgggtttaattagaataaaacatctcccagggcagaaaaatttcgatattg
ttttatcataaatttctggtcataaatcagcattcgaatgttctataactattaagaata
EXON 6   101 bp
aaggcaaacatgagaacattttgtttgcctccagggtcaagagtttgcactctcccttct
caggatccccaagaagagagttcaagtgcctcaatggttgaaatgataggaagtcaggg
gtgttccacggacacaaggtcaaaggtttggaagttttttttttttttttaattcttag

Figure 8

GACGGAGAACGTGACCTTGAAGAAGCCAGAAACTTTTCCAAAAAATCAAAGGAGAGTGTT
TCGAGCTCCTGATCTGAAAGGAATGCTAGAAGTGTTTAGAG
gtgaggagagctagatcaacaacagggttatggaattcaagtggtgttagggtgctaaat
agggaagagggtgcagtttccaaatatggatagaggggatagggaggatagatattgtc
tgctgctgatgggattatatttaatgggaaatggctaggtggctgtttcatctcatcatt
EXON 7   27 bp
tctgctgctgatgggattatatttaatgggaaatggctaggtggctgtttcatctcatca
ttcagcaatttactgccctaccatagggcatacctactctttccctaatctggagagaaa
atgaatttcagtgctgactcctttgtttgtattcaatattgtgcatttttatcatttcag
AGCTGACAGATGTCCGACGCTACTGGG
gtaaggagaagtcacattatcataagccaccctgcggcttatcattattattatctttat
cttttagaattttatgttctctattaggctcatgttttaagatttatgattctccttcca
agacacacataacttaccectccttataacttctaaacaaggttcctcccagttttctct
EXON 8   1838 bp
ctattaggctcatgttttaagatttatgattctccttccaagacacacataacttacccc
tccttataacttctaaacaaggttcctcccagtttctctcaagtctttatcaagatttc
tctcatatcacaaataaagttacattatcccttagctgacctgttaattttttctacag
TTGATGTGACAGTGGCTCCAAACAACATTTCATGTGCTGTCATTTCTGAAGATAAGAGAC
AAGTGAGCTCTCCGAAACCACAGATAATATATGGGGCACGAGGGACAAGATACCAGACAT
TTGTGAATTTCAATTATTGTACTGGCATCCTGGGCTCTCAAAGTATCACATCAGGGAAAC
ATTACTGGGAGGTAGACGTGTCCAAGAAAACTGCTTGGATCCTGGGGGTATGTGCTGGCT
TCCAACCTGATGCAATGTGTAATATTGAAAAAAATGAAAATTATCAACCTAAATACGGCT
ACTGGGTTATAGGGTTAGAGGAAGGAGTTAAATGTAGTGCTTTCCAGGATAGTTCCTTCC
ATACTCCTTCTGTTCCTTTCATTGTGCCCCTCTCTGTGATTATTTGTCCTGATCGTGTTG
GAGTTTTCCTAGACTATGAGGCTTGCACTGTCTCATTCTTCAATATCACAAACCATGGAT
TTCTCATCTATAAGTTTTCTCACTGTTCTTTTTCTCAGCCTGTATTTCCATATTTAAATC
CTAGAAAATGTGGAGTCCCCATGACTCTGTGCTCACCAAGCTCT*TGA*ACCTTCTTACACA
CTCAGCCCCTTCTGTACAGCACCTCTTGTCCAGGTGCATCTCATACACCTGAACTCATTT
GCATCATTTTAACCATCTTTTCCTTGCTGTCTCCCTTCTTTCTATTTGAACGTCCTTCAC
TCATCAGTAAAATGTAATAATTGCCTTGTGCCATATTGTCCCCAATATTTTATTGACATT
TGATAGCAATTTTTTTCATCATTTTCCGTACTCCTAAGGAAAACTGACCTATACCTCATA
AAATGAGACCGCTATTTAGGTATTACTTCTGCCAGATATTTATCACCCAATTGCCTCTGA
CACTGACTAAGAAGATGAAGAAAAGCTTTTCAACAGCCTTTCTATATCATCGTGTGATAA
TTGTTCACCAATGAATGAGTCCTTAGCCCTGTGTCAGTTTACCCTCGATGCCCTTATTTG
TGAGTTAAAGAGAAAATATCATAAATGGTATACTCTTAAGTATAGAGGTTTTGTATCTAG
AGGATCTCAGTTCAACTCCTGTCTCTCCATATACCAGCAGTGTAACTGTGAATAACATAC
TTAAATGGCTGTGCTTATTTCCTTTTCTTTTCTTTTTTCTTTTTTTTTTTTTTGAGATG
AAGTTTTGCTCTTGTTCCCCAGGCTGGAGTGCAATGGCACGATCTCGGTTCACTGCAACC
TCCACCTCTCAGATTCAAGCAATTCTCCTGCCTCAGCCTCCCAAGTAGCTGGGATTACAG
GTGCCCACCACCACCCCTGGCTAAATTTGTATTTTCAGTAGAGACGGGGTTTCCCCATGT
TGGTTAGGCTCGTCTAGAACCTCTGACCTCAGGTGATCCACCCGCCTCGGCCTCCCAAAG
TGCTGGGATTACAGGCGTGAGCCACGGCGCCCAGCCTGTGCTTATTTTCTTAAAATAATT
TTTGTATTAAAAACTTCACATTAAATAAGTGCTAATGTTTTATTGCATAGTAGGGTGACT
AGAGTTAACAATAACCTATTGCATATATTTTGAAATAGCTAGAAGAGAGGATTTTGAAAG
TTCTCAACACAAAGAAATGACACATATTTGAGGTGATGGATATGCTAATTACCCTGGTTC
GGTTATTACGCAATGTATACATGTATCAAAACATCACACTGTACCACATAAATATGTATA
TTTATTATTTGTCAATTAAAAGCAAAATAAAACAAAAAACCTTCATCTAATACTTTGGAT
CATTGTGAAAAAATAAATTCCTGAAGTATAAAGCATCT
atctaagtgtcttgatctaataagtacttgttctacaaattattgaaaaacataaactct
gttaatgtctcatggaacaggttgtgccttcagggaaactaggattggatttactaaatt
ctcattttttagatctcagatactactgtcaaaatgacttcaattctgccttctatatat

Figure 8
(continued)

SEQUENCE LISTING

```
<160> NUMBER OF SEQ ID NOS: 76

<210> SEQ ID NO 1
<211> LENGTH: 3118
<212> TYPE: DNA
<213> ORGANISM: Rhesus macaque

<400> SEQUENCE: 1
gatgttggcc attacggccg gggtaggaaa attcctttgc gcagatcagg cccctggatt     60
ggtgactgaa tcctaaccgt gtctttcctg gcctgccttc actcttctcc ccagactcac    120
tacttctgca ctggtgtctg aaggtgtatt gagtgacttt gtggagggca gaagtaggaa    180
gtctttggga caaaactgaa tttaccttgg gatctgtgaa caagacgaac ctcagcagcc    240
aggacaggca ggagcagtgg agaagctgct atggcttctg gaatcctgct taatgtaaag    300
gaggaggtga cctgtcccat ctgcctggaa ctcctgacag aacccctgag tctgcactgc    360
ggccacagct tctgccaagc gtgcatcact gcgaaccaca agaagtccat gctatacaaa    420
gaaggagaga gaagctgccc tgtgtgccgg atcagttacc agcctgagaa catacagcct    480
aatcggcatg tagccaacat agtggagaag ctcagggagg tcaagttgag cccagaagag    540
ggacagaagg ttgatcactg tgcacgccat ggagagaaac tcctactctt ctgtcaggag    600
gacagcaagg tcatttgctg gctttgtgag cggtctcagg agcaccgtgg tcaccacact    660
ttcctcatgg aggaggttgc ccaggagtac catgtgaagc tccagacagc tctggagatg    720
ctgaggcaga agcagcagga agctgaaaag ttggaagctg acatcagaga agagaaagct    780
tcctggaaga ttcaaataga ctacgacaaa accaacgtct cggcagattt tgagcaactg    840
agagagatcc tggactggga ggagagcaat gagctgcaga acctggagaa ggaggaagaa    900
gacattctga aaagccttac gaagtctgaa acggagatgg tgcagcagac ccagtacatg    960
```

| | | | | |
|---|---|---|---|---|
| agagagctca | tctcagaact | ggagcatcgg | ttgcaggggt | caatgatgga | tctactgcag | 1020 |
| ggtgtggatg | gcatcattaa | aaggattgag | aacatgacct | tgaagaagcc | aaaaactttt | 1080 |
| cacaaaaatc | aaaggagagt | gtttcgagct | cctgatctga | aggaatgct | agacatgttt | 1140 |
| agagagctaa | cagatgcccg | acgctactgg | gttgatgtga | cactggctac | aaacaacatt | 1200 |
| tcgcatgctg | tcattgctga | agataagaga | caagtgagct | ctcggaaccc | acagataatg | 1260 |
| tatcaggcac | cagggacatt | atttacgttt | ccgtcactca | cgaatttcaa | ttattgtact | 1320 |
| ggcgtcctgg | gctcccaaag | tatcacatca | gggaagcatt | actgggaggt | agatgtgtcc | 1380 |
| aagaaaagtg | cttggatcct | gggggtatgt | gctggcttcc | aatccgatgc | aatgtataat | 1440 |
| attgaacaaa | atgaaaatta | tcaacctaaa | tatggctact | gggttatagg | gttacaggaa | 1500 |
| ggagttaaat | atagtgtttt | ccaggatggt | tcctcacata | ctccttttgc | tccttttcatt | 1560 |
| gtgcccctct | ctgtgattat | ttgtcctgat | cgtgttggag | ttttcgtaga | ctatgaggct | 1620 |
| tgcactgtct | cattcttcaa | tatcacaaac | catggatttc | tcatctataa | gttttctcag | 1680 |
| tgttcttttt | ctaagcctgt | atttccatat | ttaaatccca | gaaaatgtac | agtccccatg | 1740 |
| actctgtgct | caccaagctc | ttgaaccttc | ttacacactc | agcccttgt | gtacagcacc | 1800 |
| tcttgtccat | gtgcatctca | tacacctgaa | ctcagttgca | tcattttaac | catcttttcc | 1860 |
| ttgctgtctc | tattctttct | atttgaacgt | cctgcactca | tcagtgaaat | gtgataatta | 1920 |
| tcttgtgcca | tattctcccc | aatatttat | tgacatttga | tagcaattgt | tttcatcatt | 1980 |
| ttccatactc | ccaaggaaaa | ctgacctata | cctcataaaa | ggagaccact | atttaggtat | 2040 |
| tacttctgcc | aaatatttat | catccagttg | cctctgacac | tgactaagaa | gatgaaaaaa | 2100 |
| agcttttcaa | cagcctttct | atatcatcgt | gtgatagttg | ttcaccaatg | aatgagtcct | 2160 |
| tagtcctgtg | tcagtttacc | cttgatgccc | ttatttgtga | aagagttaaa | gagaaaatat | 2220 |
| cataaatggt | atactctaag | tgtagaggtt | ttgtatctag | aggatctgag | ttcaactcct | 2280 |
| gtctctccat | gtactagcag | tataactgtg | aatagcatac | ttaaatggct | gtacttcttt | 2340 |
| tcttttcttt | cttttttttt | ttttgagatg | gagttttgct | ctcattcctc | aggctggagt | 2400 |
| gaaatggtgc | gatctcggct | cactgcaacc | tccgcttccc | agattcaagc | aattctccta | 2460 |
| cctcagcctc | ccaagttgct | gggattagag | gggcccacca | ccaccccgg | ctaaatttgt | 2520 |
| atttttacta | gagacggggt | ttccccatgt | tgtgttggtt | aggctcgtct | aaaactcctg | 2580 |
| acctcaggtg | atccacccgc | ctcggcctgc | caaagtgctg | ggattacagg | catgagctac | 2640 |
| cgcgcccagc | ctgtgcttat | tttcttaaaa | taattttgt | attaaaaact | tcccattaaa | 2700 |
| taagtcctaa | atgtttatc | gcatagtagg | gtgactagag | ttaacaataa | catttttgcat | 2760 |
| atattttgaa | gtagctagaa | gagaggattt | tgaaagttct | caacacgaag | aaatgacaca | 2820 |
| tatttgaggt | gatggatatg | ctaattaccc | tggtttgatt | attacacaat | atatacatat | 2880 |
| gtcaaaacat | catactatac | cacataaata | tgtacattta | ttatttgtca | attaaaagca | 2940 |
| aaataaaaca | aaaaaccttc | atctaatact | ttggatcatt | gtgaaaaaat | aaattcctga | 3000 |
| agtataaagc | attaaaaaaa | aaaaaaaaaa | aaaaaaaaaa | aaaacatgtc | ggccgcctcg | 3060 |
| gccaaacatc | gataaaataa | aagattttat | ttagtctcca | gaaaaggggg | aagaagc | 3118 |

<210> SEQ ID NO 2
<211> LENGTH: 497
<212> TYPE: PRT
<213> ORGANISM: Rhesus macaque -continued

<400> SEQUENCE: 2

```
Met Ala Ser Gly Ile Leu Leu Asn Val Lys Glu Glu Val Thr Cys Pro
 1               5                  10                  15

Ile Cys Leu Glu Leu Leu Thr Glu Pro Leu Ser Leu His Cys Gly His
             20                  25                  30

Ser Phe Cys Gln Ala Cys Ile Thr Ala Asn His Lys Lys Ser Met Leu
         35                  40                  45

Tyr Lys Glu Gly Glu Arg Ser Cys Pro Val Cys Arg Ile Ser Tyr Gln
     50                  55                  60

Pro Glu Asn Ile Gln Pro Asn Arg His Val Ala Asn Ile Val Glu Lys
 65                  70                  75                  80

Leu Arg Glu Val Lys Leu Ser Pro Glu Glu Gly Gln Lys Val Asp His
                 85                  90                  95

Cys Ala Arg His Gly Glu Lys Leu Leu Leu Phe Cys Gln Glu Asp Ser
            100                 105                 110

Lys Val Ile Cys Trp Leu Cys Glu Arg Ser Gln Glu His Arg Gly His
        115                 120                 125

His Thr Phe Leu Met Glu Glu Val Ala Gln Glu Tyr His Val Lys Leu
    130                 135                 140

Gln Thr Ala Leu Glu Met Leu Arg Gln Lys Gln Gln Glu Ala Glu Lys
145                 150                 155                 160

Leu Glu Ala Asp Ile Arg Glu Glu Lys Ala Ser Trp Lys Ile Gln Ile
                165                 170                 175

Asp Tyr Asp Lys Thr Asn Val Ser Ala Asp Phe Glu Gln Leu Arg Glu
            180                 185                 190

Ile Leu Asp Trp Glu Glu Ser Asn Glu Leu Gln Asn Leu Glu Lys Glu
        195                 200                 205

Glu Glu Asp Ile Leu Lys Ser Leu Thr Lys Ser Glu Thr Glu Met Val
    210                 215                 220

Gln Gln Thr Gln Tyr Met Arg Glu Leu Ile Ser Glu Leu Glu His Arg
225                 230                 235                 240

Leu Gln Gly Ser Met Met Asp Leu Leu Gln Gly Val Asp Gly Ile Ile
                245                 250                 255

Lys Arg Ile Glu Asn Met Thr Leu Lys Lys Pro Lys Thr Phe His Lys
            260                 265                 270

Asn Gln Arg Arg Val Phe Arg Ala Pro Asp Leu Lys Gly Met Leu Asp
        275                 280                 285

Met Phe Arg Glu Leu Thr Asp Ala Arg Arg Tyr Trp Val Asp Val Thr
    290                 295                 300

Leu Ala Thr Asn Asn Ile Ser His Ala Val Ile Ala Glu Asp Lys Arg
305                 310                 315                 320

Gln Val Ser Ser Arg Asn Pro Gln Ile Met Tyr Gln Ala Pro Gly Thr
                325                 330                 335

Leu Phe Thr Phe Pro Ser Leu Thr Asn Phe Asn Tyr Cys Thr Gly Val
            340                 345                 350

Leu Gly Ser Gln Ser Ile Thr Ser Gly Lys His Tyr Trp Glu Val Asp
        355                 360                 365

Val Ser Lys Lys Ser Ala Trp Ile Leu Gly Val Cys Ala Gly Phe Gln
    370                 375                 380

Ser Asp Ala Met Tyr Asn Ile Glu Gln Asn Glu Asn Tyr Gln Pro Lys
385                 390                 395                 400

Tyr Gly Tyr Trp Val Ile Gly Leu Gln Glu Gly Val Lys Tyr Ser Val
                405                 410                 415
```

```
Phe Gln Asp Gly Ser Ser His Thr Pro Phe Ala Pro Phe Ile Val Pro
                420                 425                 430

Leu Ser Val Ile Ile Cys Pro Asp Arg Val Gly Val Phe Val Asp Tyr
            435                 440                 445

Glu Ala Cys Thr Val Ser Phe Phe Asn Ile Thr Asn His Gly Phe Leu
    450                 455                 460

Ile Tyr Lys Phe Ser Gln Cys Ser Phe Ser Lys Pro Val Phe Pro Tyr
465                 470                 475                 480

Leu Asn Pro Arg Lys Cys Thr Val Pro Met Thr Leu Cys Ser Pro Ser
                485                 490                 495

Ser

<210> SEQ ID NO 3
<211> LENGTH: 9
<212> TYPE: PRT
<213> ORGANISM: HIV-1

<400> SEQUENCE: 3

Arg Lys Lys Arg Arg Gln Arg Arg
1               5

<210> SEQ ID NO 4
<211> LENGTH: 13
<212> TYPE: PRT
<213> ORGANISM: HIV-1

<400> SEQUENCE: 4

Gly Arg Lys Lys Arg Arg Gln Arg Arg Thr Pro Gln
1               5                   10

<210> SEQ ID NO 5
<211> LENGTH: 11
<212> TYPE: PRT
<213> ORGANISM: HIV-1

<400> SEQUENCE: 5

Tyr Gly Arg Lys Lys Arg Arg Gln Arg Arg
1               5                   10

<210> SEQ ID NO 6
<211> LENGTH: 26
<212> TYPE: PRT
<213> ORGANISM: Homo sapiens

<400> SEQUENCE: 6

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 7
<211> LENGTH: 17
<212> TYPE: PRT
<213> ORGANISM: Caiman crocodylus

<400> SEQUENCE: 7

Met Gly Leu Gly Leu His Leu Leu Val Leu Ala Ala Ala Leu Gln Gly
1               5                   10                  15

Ala

<210> SEQ ID NO 8
<211> LENGTH: 23
```

```
<212> TYPE: PRT
<213> ORGANISM: HIV-1

<400> SEQUENCE: 8

Gly Ala Leu Phe Leu Gly Phe Leu Gly Ala Ala Gly Ser Thr Met Gly
 1               5                  10                  15

Ala Pro Lys Ser Lys Arg Lys
            20

<210> SEQ ID NO 9
<211> LENGTH: 16
<212> TYPE: PRT
<213> ORGANISM: Drosophila

<400> SEQUENCE: 9

Arg Gln Ile Lys Ile Trp Phe Gln Asn Arg Arg Met Lys Trp Lys Lys
 1               5                  10                  15

<210> SEQ ID NO 10
<211> LENGTH: 5
<212> TYPE: PRT
<213> ORGANISM: HIV-1
<220> FEATURE:
<221> NAME/KEY: VARIANT
<222> LOCATION: 1,5
<223> OTHER INFORMATION: Xaa may be any amino acid

<400> SEQUENCE: 10

Xaa Arg Gly Asp Xaa
 1               5

<210> SEQ ID NO 11
<211> LENGTH: 24
<212> TYPE: PRT
<213> ORGANISM: Influenza

<400> SEQUENCE: 11

Gly Leu Phe Glu Ala Ile Ala Gly Phe Ile Glu Asn Gly Trp Glu Gly
 1               5                  10                  15

Met Ile Asp Gly Gly Gly Tyr Cys
            20

<210> SEQ ID NO 12
<211> LENGTH: 27
<212> TYPE: PRT
<213> ORGANISM: Artificial Sequence
<220> FEATURE:
<223> OTHER INFORMATION: synthetic peptide

<400> SEQUENCE: 12

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 13
<211> LENGTH: 8
<212> TYPE: PRT
<213> ORGANISM: Artificial Sequence
<220> FEATURE:
<223> OTHER INFORMATION: synthetic peptide

<400> SEQUENCE: 13

Asp His Gln Leu Asn Pro Ala Phe
 1               5
```

<210> SEQ ID NO 14
<211> LENGTH: 8
<212> TYPE: PRT
<213> ORGANISM: Homo sapiens

<400> SEQUENCE: 14

Phe Cys Tyr Trp Lys Thr Cys Thr
 1               5

<210> SEQ ID NO 15
<211> LENGTH: 3401
<212> TYPE: DNA
<213> ORGANISM: Homo sapiens

<400> SEQUENCE: 15

```
tgcgttgtac cctttacgt gaggcggtga cggcggttcg gaagtcgtct ggcctcccg      60 cggccgctcg cagcttgctg gcctctcccg cgcctcacgt cggactccgt ctccgcggca    120
gggaagcagc atggaagctg aggacatcca ggaggagttg acctgcccca tctgcctgga    180
ctatttccag gacccggtgt ccatcgagtg cggccacaac ttctgccgcg gctgcctgca    240
ccgcaactgg gcgccgggcg gcggcccgtt ccctgcccc gaatgtcggc acccatcggc     300
gcccgccgcg ctgcgaccca actgggccct ggccaggctg actgagaaga cgcagcgccg    360
gcgcctgggc cccgtgcccc gggcctgtg cggccgccac tgggagccgc tgcggctctt     420
ctgcgaggac gaccagcggc cagtgtgcct ggtgtgcagg gagtcccagg agcaccagac    480
tcacgccatg gcacccatcg acgaggcctt cgagagctac cggacaggta actttgacat    540
ccacgtggat gaatggaaga aagactaat taggctgctc ttgtaccatt ctaagcagga    600
ggagaaactt cttaagtctc agcgtaatct cgtggccaag atgaagaaag tcatgcattt    660
acaggatgta gaagtgaaga acgccacaca gtggaaggat aagataaga gtcagcgaat    720 gagaatcagc acggagttt caaagctgca aacttcctg gttgaagaag aggacctgtt     780
tcttcagaga ttgaacaaag aagaagaaga gacgaagaag aagctgaatg agaacacgtt    840
aaaactcaat caaactatcg cttcattgaa gaagctcatc ttagaggtgg gggagaagag    900
ccaggctccc accctggagc tgcttcagaa tccaaaagaa gtgttgacca ggagtgagat    960
ccaggatgtg aactattccc ttgaagctgt gaaggtgaag acagtgtgcc agataccatt   1020
gatgaaggaa atgctaaagc gattccaagt ggctgtaaac ctagctgaag acacagctca   1080
tcccaaactc gtcttctccc aggaagggag atacgtgaaa aatacagcat cagccagttc   1140
ttggccagtg ttttcttcag catggaacta ctttgctgga tggaggaatc ctcagaagac   1200
tgcttttgta gagagatttc agcacttacc ctgtgttctg ggaaaaaacg ttttcacctc   1260
agggaaacat tactgggaag ttgagagtag agatagtctg gaggttgctg ttggggtgtg   1320
tcgggaggac gtcatgggaa ttactgatcg ttcaaaaatg tccccagatg tgggcatctg   1380
ggcgatttat tggagtgctg ctggctattg gccttgata ggcttccctg gaactcccac   1440
ccagcaagag ccagctctcc accgagtggg ggtttacctg gatcgtggga ctgggaatgt   1500
ctccttctac agcgctgtgg acggagtgca cctgcacacc ttttcttgtt cttctgtctc   1560
acgcctccgg ccatttttt ggttgagtcc attagcatct ttagtcattc caccagtgac    1620
tgataggaaa tgaggctttt cttcccctga ccaaaactcc ttcctgtag tccagctgag    1680 ggacacacat ccctgggccc tcttctgccc ttcatgtctc tatcctggat ggtccatctt   1740
ctgggtctcc ctaacggtac cgtttggtat ctgcccttg tgtgcttcac aagaggcagt    1800
cccatgggag gtgggtctgg ccaatggaga tgggacagga aattttccaa gacgcttttg   1860
```

```
ggaaatcttt tgtagcttt taaagagatg tgcggggaag acatatggat gttagcagcc    1920
atattggaac tgagaacaca ggaatggtgg aaaggtagaa gaaacagagt ttttgttgcc    1980
gttgtgaaat tgttgaaatt tccttcatgc caagcttctt gttatatgag ataattacgc    2040
ccttattgta taagacaatt ttagttgtat ttggttactt gcagcctgaa gtaccgtaac    2100
tgcactaaag ggacgtagtg tgaacatccc gcagtatagg cttaagtcac ttttgtgaaa    2160
tttgacaaag gcatagaatc ttttctatc cagtcaggca ttgcctattc tttccagtaa     2220
ctactgattc ccccactttt ctgtcttaga aaattgtggg aatccccct cactctgcct     2280 atgttgcact ctctctcttc ccaaccataa ctctgccctc agctattaac tgtgctgtgt    2340
atttatcaag ttggtatgtt gtatgtacag tgttattcat gtcatcatga aatgttgaa     2400 cgcttgttaa atacctttg ctagcctctt catatgctgt tgcatatgac tctcatcaca     2460
actcagtgag atggaaagac aaatcctatt tgtacaaatg agaaaactga actctttaga    2520
gtaactagct cagtattggc cagctggtaa atggcagtgt tgggattaaa atccagttct    2580
tatctactct ccctttattc agaagcattt attggatgtt gatctttgtt tcaggttttg    2640
attttgttac tttttatac tgtgtatatt ttcctcagtc tacccttctg ctctagattg     2700
tctggactca ggagattgtg gcagttactg gatagttatt tttaagataa tgattgcttt    2760
tctctgttta tataagtcat gtgtacttat tgtagaaagt ttgtaagatg caaaaagtat    2820
aaaaattaaa gttatgcact actaacattt caatatattt tctcccagat tttcaataaa    2880
gactttcagg cagtgattta acgaggattt tattttaact tatattttag tttaagggga    2940
acacgtgcag gtttgttcta tagatcaatt acatgtcaca ggggtttggt gtacatatta    3000
tttcattacc caggtaataa gcatagtacc caatagatac ttttttgata ccccacccctc    3060 ctccaccctc taccctcaag tagtccctgg tgtctgttgt tccctttttt gtgtccatgg    3120
gtactcaatg tttagctctc ccttatacgt gagaacatgt gatgtttggt tttctgttca    3180
tgtgttggtt tgcttagggt aatggcctcc agctccatcc atgttgctgc aaagacatga    3240
tctcattctt tttttatggc tgcatagtat tccatggtgt atatgtacta tgttttcttt    3300
atccagtcta ctgttgatgg gcatttaggt tgattccatg tctttgctat tgtgaatagt    3360
gctgcaatga atatatacat gcaaaaaaaa aaaaaaaaa a                          3401
```

<210> SEQ ID NO 16
<211> LENGTH: 500
<212> TYPE: PRT
<213> ORGANISM: Homo sapiens

<400> SEQUENCE: 16

Met Glu Ala Glu Asp Ile Gln Glu Glu Leu Thr Cys Pro Ile Cys Leu
1               5                   10                  15

Asp Tyr Phe Gln Asp Pro Val Ser Ile Glu Cys Gly His Asn Phe Cys
            20                  25                  30

Arg Gly Cys Leu His Arg Asn Trp Ala Pro Gly Gly Gly Pro Phe Pro
        35                  40                  45

Cys Pro Glu Cys Arg His Pro Ser Ala Pro Ala Ala Leu Arg Pro Asn
    50                  55                  60

Trp Ala Leu Ala Arg Leu Thr Glu Lys Thr Gln Arg Arg Arg Leu Gly
65                  70                  75                  80

Pro Val Pro Pro Gly Leu Cys Gly Arg His Trp Glu Pro Leu Arg Leu
                85                  90                  95

Phe Cys Glu Asp Asp Gln Arg Pro Val Cys Leu Val Cys Arg Glu Ser

-continued

```
                    100                 105                 110
Gln Glu His Gln Thr His Ala Met Ala Pro Ile Asp Glu Ala Phe Glu
            115                 120                 125
Ser Tyr Arg Thr Gly Asn Phe Asp Ile His Val Asp Glu Trp Lys Arg
        130                 135                 140
Arg Leu Ile Arg Leu Leu Tyr His Ser Lys Gln Glu Glu Lys Leu
145                 150                 155                 160
Leu Lys Ser Gln Arg Asn Leu Val Ala Lys Met Lys Lys Val Met His
                165                 170                 175
Leu Gln Asp Val Glu Val Lys Asn Ala Thr Gln Trp Lys Asp Lys Ile
            180                 185                 190
Lys Ser Gln Arg Met Arg Ile Ser Thr Glu Phe Ser Lys Leu His Asn
        195                 200                 205
Phe Leu Val Glu Glu Asp Leu Phe Leu Gln Arg Leu Asn Lys Glu
210                 215                 220
Glu Glu Glu Thr Lys Lys Lys Leu Asn Glu Asn Thr Leu Lys Leu Asn
225                 230                 235                 240
Gln Thr Ile Ala Ser Leu Lys Lys Leu Ile Leu Glu Val Gly Glu Lys
                245                 250                 255
Ser Gln Ala Pro Thr Leu Glu Leu Leu Gln Asn Pro Lys Glu Val Leu
            260                 265                 270
Thr Arg Ser Glu Ile Gln Asp Val Asn Tyr Ser Leu Glu Ala Val Lys
        275                 280                 285
Val Lys Thr Val Cys Gln Ile Pro Leu Met Lys Glu Met Leu Lys Arg
        290                 295                 300
Phe Gln Val Ala Val Asn Leu Ala Glu Asp Thr Ala His Pro Lys Leu
305                 310                 315                 320
Val Phe Ser Gln Glu Gly Arg Tyr Val Lys Asn Thr Ala Ser Ala Ser
                325                 330                 335
Ser Trp Pro Val Phe Ser Ser Ala Trp Asn Tyr Phe Ala Gly Trp Arg
            340                 345                 350
Asn Pro Gln Lys Thr Ala Phe Val Glu Arg Phe Gln His Leu Pro Cys
        355                 360                 365
Val Leu Gly Lys Asn Val Phe Thr Ser Gly Lys His Tyr Trp Glu Val
370                 375                 380
Glu Ser Arg Asp Ser Leu Glu Val Ala Val Gly Val Cys Arg Glu Asp
385                 390                 395                 400
Val Met Gly Ile Thr Asp Arg Ser Lys Met Ser Pro Asp Val Gly Ile
                405                 410                 415
Trp Ala Ile Tyr Trp Ser Ala Ala Gly Tyr Trp Pro Leu Ile Gly Phe
            420                 425                 430
Pro Gly Thr Pro Thr Gln Gln Glu Pro Ala Leu His Arg Val Gly Val
        435                 440                 445
Tyr Leu Asp Arg Gly Thr Gly Asn Val Ser Phe Tyr Ser Ala Val Asp
        450                 455                 460
Gly Val His Leu His Thr Phe Ser Cys Ser Ser Val Ser Arg Leu Arg
465                 470                 475                 480
Pro Phe Phe Trp Leu Ser Pro Leu Ala Ser Leu Val Ile Pro Pro Val
                485                 490                 495
Thr Asp Arg Lys
            500

<210> SEQ ID NO 17
<211> LENGTH: 3323
```

```
<212> TYPE: DNA
<213> ORGANISM: Homo sapiens

<400> SEQUENCE: 17
tgcgttgtac cctttttacgt gaggcggtga cggcggttcg gaagtcgtct ggcctccccg    60
cggccgctcg cagcttgctg gcctctcccg cgcctcacgt cggactccgt ctccgcggca   120
gggaagcagc atggaagctg aggacatcca ggaggagttg acctgcccca tctgcctgga   180
ctatttccag gacccggtgt ccatcgagtg cggccacaac ttctgccgcg gctgcctgca   240
ccgcaactgg gcgccgggcg gcggcccgtt cccctgcccc gaatgtcggc acccatcggc   300
gcccgccgcg ctgcgaccca ctgggccct ggccaggctg actgagaaga cgcagcgccg   360
gcgcctgggc ccgtgccccc gggcctgtg cggccgccac tgggagccgc tgcggctctt   420
ctgcgaggac gaccagcggc cagtgtgcct ggtgtgcagg gagtcccagg agcaccagac   480
tcacgccatg gcacccatcg acgaggcctt cgagagctac cgggagaaac ttcttaagtc   540
tcagcgtaat ctcgtggcca agatgaagaa agtcatgcat ttacaggatg tagaagtgaa   600
gaacgccaca cagtggaagg ataagataaa gagtcagcga atgagaatca gcacggagtt   660
ttcaaagctg cacaacttcc tggttgaaga agaggacctg tttcttcaga gattgaacaa   720
agaagaagaa gagacgaaga agaagctgaa tgagaacacg ttaaaactca atcaaactat   780
cgcttcattg aagaagctca tcttagaggt ggggagaag agccaggctc ccaccctgga   840
gctgcttcag aatccaaaag aagtgttgac caggagtgag atccaggatg tgaactattc   900
ccttgaagct gtgaaggtga agacagtgtg ccagatacca ttgatgaagg aaatgctaaa   960
gcgattccaa gtggctgtaa acctagctga agacacagct catcccaaac tcgtcttctc  1020
ccaggaaggg agatacgtga aaaatacagc atcagccagt tcttggccag tgttttcttc  1080
agcatggaac tactttgctg gatggaggaa tcctcagaag actgcttttg tagagagatt  1140
tcagcactta ccctgtgttc tgggaaaaaa cgtttttcacc tcagggaaac attactggga  1200
agttgagagt agagatagtc tggaggttgc tgttggggtg tgtcgggagg acgtcatggg  1260
aattactgat cgttcaaaaa tgtccccaga tgtgggcatc tggcgatttt attggagtgc  1320
tgctggctat tggcccttga taggcttccc tggaactccc acccagcaag agccagctct  1380
ccaccgagtg ggggtttacc tggatcgtgg gactgggaat gtctccttct acagcgctgt  1440
ggacggagtg cacctgcaca cctttttctg ttcttctgtc tcacgcctcc ggccattttt  1500
ttggttgagt ccattagcat ctttagtcat tccaccagtg actgatagga aatgaggctt  1560
ttcttcccct gaccaaaact ccttccctgt agtccagctg agggacacac atccctgggc  1620
cctcttctgc ccttcatgtc tctatccgg atggtccatc ttctgggtct ccctaacggt  1680
accgtttggt atctgccctt tgtgtgcttc acaagaggca gtcccatggg aggtgggtct  1740
ggccaatgga gatgggacag gaaatttttcc aagacgcttt tgggaaatct tttttgtagct  1800 tttaaagaga tgtgcgggga agacatatgg atgttagcag ccatattgga actgagaaca  1860
caggaatggt ggaaaggtag aagaaacaga gttttttgttg ccgttgtgaa attgttgaaa  1920
tttccttcat gccaagcttc ttgttatatg agataaattac gcccttattg tataagacaa  1980
ttttagttgt atttggttac ttgcagcctg aagtaccgta actgcactaa agggacgtag  2040
tgtgaacatc ccgcagtata ggcttaagtc acttttgtga aatttgacaa aggcatgaaa  2100 tcttttttcta tccagtcagg cattgcctat tctttccagt aactactgat tcccccactt  2160
ttctgtctta gaaaattgtg ggaatccccc ctcactctgc ctatgttgca ctctctctct  2220
tcccaaccat aactctgccc tcagctatta actgtgctgt gtatttatca agttggtatg  2280
```

```
ttgtatgtac agtgttattc atgtcatcat gagaatgttg aacgcttgtt aaataccttt    2340
tgctagcctc ttcatatgct gttgcatatg actctcatca caactcagtg agatggaaag    2400
acaaatccta tttgtacaaa tgagaaaact gaactcttta gagtaactag ctcagtattg    2460
gccagctggt aaatggcagt gttgggatta aaatccagtt cttatctact ctcccttat    2520 tcagaagcat ttattggatg ttgatctttg tttcaggttt tgattttgtt acttttttat    2580
actgtgtata ttttcctcag tctacccttc tgctctagat tgtctggact caggagattg    2640
tggcagttac tggatagtta tttttaagat aatgattgct tttctctgtt tatataagtc    2700
atgtgtactt attgtagaaa gtttgtaaga tgcaaaaagt ataaaaatta aagttatgca    2760
ctactaacat ttcaatatat tttctcccag attttcaata aagactttca ggcagtgatt    2820
taacgaggat tttatttaa cttatatttt agtttaaggg gaacacgtgc aggtttgttc    2880
tatagatcaa ttcatgtca caggggtttg gtgtacatat tatttcatta cccaggtaat    2940
aagcatagta cccaatagat acttttttga taccccaccc tcctccaccc tctaccctca    3000
agtagtccct ggtgtctgtt gttcccttt ttgtgtccat gggtactcaa tgtttagctc    3060
tcccttatac gtgagaacat gtgatgtttg gttttctgtt catgtgttgg tttgcttagg    3120
gtaatggcct ccagctccat ccatgttgct gcaaagacat gatctcattc ttttttatg    3180 gctgcatagt attccatggt gtatatgtac tatgttttct ttatccagtc tactgttgat    3240
gggcatttag gttgattcca tgtctttgct attgtgaata gtgctgcaat gaatatatac    3300
atgcaaaaaa aaaaaaaaaa aaa                                             3323
```

<210> SEQ ID NO 18
<211> LENGTH: 474
<212> TYPE: PRT
<213> ORGANISM: Homo sapiens

<400> SEQUENCE: 18

```
Met Glu Ala Glu Asp Ile Gln Glu Glu Leu Thr Cys Pro Ile Cys Leu
 1               5                  10                  15

Asp Tyr Phe Gln Asp Pro Val Ser Ile Glu Cys Gly His Asn Phe Cys
            20                  25                  30

Arg Gly Cys Leu His Arg Asn Trp Ala Pro Gly Gly Pro Phe Pro
        35                  40                  45

Cys Pro Glu Cys Arg His Pro Ser Ala Pro Ala Ala Leu Arg Pro Asn
    50                  55                  60

Trp Ala Leu Ala Arg Leu Thr Glu Lys Thr Gln Arg Arg Arg Leu Gly
65                  70                  75                  80

Pro Val Pro Pro Gly Leu Cys Gly Arg His Trp Glu Pro Leu Arg Leu
                85                  90                  95

Phe Cys Glu Asp Asp Gln Arg Pro Val Cys Leu Val Cys Arg Glu Ser
            100                 105                 110

Gln Glu His Gln Thr His Ala Met Ala Pro Ile Asp Glu Ala Phe Glu
        115                 120                 125

Ser Tyr Arg Glu Lys Leu Leu Lys Ser Gln Arg Asn Leu Val Ala Lys
    130                 135                 140

Met Lys Lys Val Met His Leu Gln Asp Val Glu Val Lys Asn Ala Thr
145                 150                 155                 160

Gln Trp Lys Asp Lys Ile Lys Ser Gln Arg Met Arg Ile Ser Thr Glu
                165                 170                 175

Phe Ser Lys Leu His Asn Phe Leu Val Glu Glu Glu Asp Leu Phe Leu
            180                 185                 190
```

Gln Arg Leu Asn Lys Glu Glu Glu Thr Lys Lys Leu Asn Glu
        195                 200                 205

Asn Thr Leu Lys Leu Asn Gln Thr Ile Ala Ser Leu Lys Lys Leu Ile
210                 215                 220

Leu Glu Val Gly Glu Lys Ser Gln Ala Pro Thr Leu Glu Leu Leu Gln
225                 230                 235                 240

Asn Pro Lys Glu Val Leu Thr Arg Ser Glu Ile Gln Asp Val Asn Tyr
                245                 250                 255

Ser Leu Glu Ala Val Lys Val Lys Thr Val Cys Gln Ile Pro Leu Met
                260                 265                 270

Lys Glu Met Leu Lys Arg Phe Gln Val Ala Val Asn Leu Ala Glu Asp
            275                 280                 285

Thr Ala His Pro Lys Leu Val Phe Ser Gln Gly Arg Tyr Val Lys
        290                 295                 300

Asn Thr Ala Ser Ala Ser Ser Trp Pro Val Phe Ser Ser Ala Trp Asn
305                 310                 315                 320

Tyr Phe Ala Gly Trp Arg Asn Pro Gln Lys Thr Ala Phe Val Glu Arg
                325                 330                 335

Phe Gln His Leu Pro Cys Val Leu Gly Lys Asn Val Phe Thr Ser Gly
            340                 345                 350

Lys His Tyr Trp Glu Val Glu Ser Arg Asp Ser Leu Glu Val Ala Val
        355                 360                 365

Gly Val Cys Arg Glu Asp Val Met Gly Ile Thr Asp Arg Ser Lys Met
370                 375                 380

Ser Pro Asp Val Gly Ile Trp Ala Ile Tyr Trp Ser Ala Ala Gly Tyr
385                 390                 395                 400

Trp Pro Leu Ile Gly Phe Pro Gly Thr Pro Thr Gln Gln Glu Pro Ala
                405                 410                 415

Leu His Arg Val Gly Val Tyr Leu Asp Arg Gly Thr Gly Asn Val Ser
            420                 425                 430

Phe Tyr Ser Ala Val Asp Gly Val His Leu His Thr Phe Ser Cys Ser
        435                 440                 445

Ser Val Ser Arg Leu Arg Pro Phe Phe Trp Leu Ser Pro Leu Ala Ser
    450                 455                 460

Leu Val Ile Pro Pro Val Thr Asp Arg Lys
465                 470

<210> SEQ ID NO 19
<211> LENGTH: 3230
<212> TYPE: DNA
<213> ORGANISM: Homo sapiens

<400> SEQUENCE: 19
ggtggaggac gcggctgctt caagtccttg gctctgatcc aggccacaga ttccaggatt      60
ctacaggcag gaaacatctt agaaatcagg gttgggcagg caggagccag gagagtagct     120
acaatgactt caccagtact ggtggacata cgagaagagg tgacctgccc tatctgcctg     180
gagctcctaa cagaacccct gagcatagac tgtggccaca gcttctgcca agcctgcatc     240
acaccaaatg gcagggaatc agtgattggt caagaagggg aaagaagctg ccctgtgtgc     300
cagaccagct accagccagg gaacctgcgg cctaatcggc atctggccaa catagtgagg     360
cggctcagag aggtagtgtt gggccctggg aagcagctga aagcagttct ttgtgcagac     420
catggagaaa aactgcagct cttctgtcag gaggatggga aggtcatttg ctggctttgt     480
gagcggtctc aggagcaccg tggtcaccac acgttcctcg tggaggaggt tgcccaggag     540

```
taccaggaga agtttcagga gtctctaaag aagctgaaga acgaggagca ggaagctgag    600
aagctaacag cttttatcag agagaagaag acatcctgga agaatcagat ggagcctgag    660
agatgcagga tccagacaga gtttaatcag ctgcgaaata tcctagacag agtggagcaa    720
cgggagctga aaaagctgga acaggaagag aagaaggggc tacgaattat agaagaggct    780
gagaatgatc tggtccacca gacccagtcg ctgcgagagc tcatctcgga tctggagcgt    840
cgatgtcagg ggtcaacaat ggagctgctg caggatgtga gtgatgtcac agaaaggagt    900
gagttctgga ccctgaggaa gccagaagct ctccctacaa agctgagaag tatgttccga    960
gccccagatc tgaaaaggat gctgcgagtg tgtagagagc tgacagatgt ccaaagctac   1020
tgggttgacg tgaccctgaa tccacacaca gctaatttaa atcttgtcct ggctaaaaac   1080
cggagacaag tgaggtttgt gggagctaaa gtatctggac cttcctgtct ggaaaagcat   1140
tatgactgta gtgtcctggg ctcccagcac ttctcctctg gtaagcatta ctgggaggta   1200
gatgtggcca agaagactgc ctggatccta ggggtatgca gcaattcact gggacctaca   1260
ttctctttca accatttgc tcaaaatcac agtgcttact ccaggtatca gcctcagagt   1320
ggatactggg tgattgggtt acagcataac catgaatata gggcctatga ggattcttcc   1380
ccttccctgc ttctctccat gacagtgccc cctcgccgtg ttggggtttt cttagattat   1440
gaggctggta ctgtctcctt ttataatgtc acaaaccatg gcttccccat ctacactttc   1500
tctaaatatt actttcccac tactctttgt ccatatttta atccttgcaa ctgtgtaatt   1560
cctatgaccc tgcgtcgtcc aagctcttga atattcttct gttcccaccc acttctgata   1620
agtaccctga ggcttatcag catgtgattc tcccttctga tcttctgttt ttctgtgttc   1680
tcaattcttt tgttgttttt tggttttga atcttttttg agatggaatc tcgctctgtc   1740
gcccaggctg gagtgcactg gcgcaatctc ggctcactgc aacctctgcc tcctgggttc   1800
aagcgaacct cctgcctcag catcccaagt agctgggatt acaggcaccc accaccatgc   1860
ccaactaatt tttgtatttt tatagagata gggtttcacc gtgttggcca ggctgatctc   1920
gaactcctga ccgcaagtga tccacccgcc tcggtctccc aaagtgctgg gattacagat   1980
gtgagccgcc gcgcccagac agttctttcg ttttaaacag ttactcagta ctaggatgca   2040
cccagtggtg agagtaagca tctttgactg atgacaggtc ttgaggtgga tagggggcgc   2100
tttcagtatt ttgccattaa gcatagtatt tgatgcaggt ttttttttgat tgatgcaggg   2160 gatcaaattt aggaagttct gatctgttaa tttactacaa gttttgtat aaaatgaaaa   2220 ctcgtattct acctatgtct tttctgtaaa ttattgagac aattgtgtat cattttgtt    2280 ctgttaatgt ggcttagtac attgatttac ttcaatttgt taccacaact tgctgaaata   2340
caccattatt atttgttgta tgcaatactg gatttatttt gataacgtat tgtttagatt   2400
ttgttctcat ctatgttaat gaaagaaatt ggcctgtatt tttacattct tgtaatatct   2460
ttgccaggtt ctataaaatg caataataag caaataaatt actttgtttt tgtataagta   2520
tgtataggat tgagctctaa aaccaaacca ttataatgat aatttgggta gcttcaaact   2580
caaattgaag agagtcttca ctacaatctt cactacaacc tttggccttc ctctctacat   2640
ttaagagtag caatagaaca ataaaaaaaa atacgtcttt caaattaatt gcagtaaaaa   2700
caaaagagta gtggggagag aaaaacaatc caatacatat ttttctctca gaatagaaag   2760
aaaacacaaa gagaaaatat gaacaatata aagcacttaa aggaagagga tgatttcttc   2820
cagcttttcc acactctctt tatgcgcagg aacaaacagc tgttgagtga gctgctatga   2880
ctttggtaga gaggtgcaat atgttttttg aaccagctat aaaagaaatt aagaggtaca   2940
```

```
tgtgagggta gaaacaaata tcaaggatga aatggcact ggctgtccca tatggtatcc      3000
aggagccacc aatgtctgtt gagtacttca tacatgccta gtctgaattg agatgtgctc      3060
aatgtataaa atatatacca gatttcaaat acctacttca aaaataatg taaaatatct      3120 cactaataac ttttcctttg tgtattgcaa tgataatatg ttggctctat tggattaaat      3180
aaagtatgtt attcatttta aaaaaaaaaa aaaaaaaaaa aaaaaaaaaa                  3230

<210> SEQ ID NO 20
<211> LENGTH: 488
<212> TYPE: PRT
<213> ORGANISM: Homo sapiens

<400> SEQUENCE: 20

Met Thr Ser Pro Val Leu Val Asp Ile Arg Glu Glu Val Thr Cys Pro
  1               5                  10                  15

Ile Cys Leu Glu Leu Leu Thr Glu Pro Leu Ser Ile Asp Cys Gly His
             20                  25                  30

Ser Phe Cys Gln Ala Cys Ile Thr Pro Asn Gly Arg Glu Ser Val Ile
         35                  40                  45

Gly Gln Glu Gly Glu Arg Ser Cys Pro Val Cys Gln Thr Ser Tyr Gln
     50                  55                  60

Pro Gly Asn Leu Arg Pro Asn Arg His Leu Ala Asn Ile Val Arg Arg
 65                  70                  75                  80

Leu Arg Glu Val Val Leu Gly Pro Gly Lys Gln Leu Lys Ala Val Leu
                 85                  90                  95

Cys Ala Asp His Gly Glu Lys Leu Gln Leu Phe Cys Gln Glu Asp Gly
            100                 105                 110

Lys Val Ile Cys Trp Leu Cys Glu Arg Ser Gln Glu His Arg Gly His
        115                 120                 125

His Thr Phe Leu Val Glu Glu Val Ala Gln Glu Tyr Gln Glu Lys Phe
    130                 135                 140

Gln Glu Ser Leu Lys Lys Leu Lys Asn Glu Glu Gln Glu Ala Glu Lys
145                 150                 155                 160

Leu Thr Ala Phe Ile Arg Glu Lys Lys Thr Ser Trp Lys Asn Gln Met
                165                 170                 175

Glu Pro Glu Arg Cys Arg Ile Gln Thr Glu Phe Asn Gln Leu Arg Asn
            180                 185                 190

Ile Leu Asp Arg Val Glu Gln Arg Glu Leu Lys Lys Leu Glu Gln Glu
        195                 200                 205

Glu Lys Lys Gly Leu Arg Ile Ile Glu Glu Ala Glu Asn Asp Leu Val
    210                 215                 220

His Gln Thr Gln Ser Leu Arg Glu Leu Ile Ser Asp Leu Glu Arg Arg
225                 230                 235                 240

Cys Gln Gly Ser Thr Met Glu Leu Leu Gln Asp Val Ser Asp Val Thr
                245                 250                 255

Glu Arg Ser Glu Phe Trp Thr Leu Arg Lys Pro Glu Ala Leu Pro Thr
            260                 265                 270

Lys Leu Arg Ser Met Phe Arg Ala Pro Asp Leu Lys Arg Met Leu Arg
        275                 280                 285

Val Cys Arg Glu Leu Thr Asp Val Gln Ser Tyr Trp Val Asp Val Thr
    290                 295                 300

Leu Asn Pro His Thr Ala Asn Leu Asn Leu Val Leu Ala Lys Asn Arg
305                 310                 315                 320

Arg Gln Val Arg Phe Val Gly Ala Lys Val Ser Gly Pro Ser Cys Leu
```

```
                        325                 330                 335
Glu Lys His Tyr Asp Cys Ser Val Leu Gly Ser Gln His Phe Ser Ser
            340                 345                 350

Gly Lys His Tyr Trp Glu Val Asp Val Ala Lys Lys Thr Ala Trp Ile
            355                 360                 365

Leu Gly Val Cys Ser Asn Ser Leu Gly Pro Thr Phe Ser Phe Asn His
            370                 375                 380

Phe Ala Gln Asn His Ser Ala Tyr Ser Arg Tyr Gln Pro Gln Ser Gly
385                 390                 395                 400

Tyr Trp Val Ile Gly Leu Gln His Asn His Glu Tyr Arg Ala Tyr Glu
                405                 410                 415

Asp Ser Ser Pro Ser Leu Leu Leu Ser Met Thr Val Pro Pro Arg Arg
            420                 425                 430

Val Gly Val Phe Leu Asp Tyr Glu Ala Gly Thr Val Ser Phe Tyr Asn
            435                 440                 445

Val Thr Asn His Gly Phe Pro Ile Tyr Thr Phe Ser Lys Tyr Tyr Phe
            450                 455                 460

Pro Thr Thr Leu Cys Pro Tyr Phe Asn Pro Cys Asn Cys Val Ile Pro
465                 470                 475                 480

Met Thr Leu Arg Arg Pro Ser Ser
                485

<210> SEQ ID NO 21
<211> LENGTH: 2004
<212> TYPE: DNA
<213> ORGANISM: Homo sapiens

<400> SEQUENCE: 21
gagtgtgtga cccagccctt cccccgtggc caagcagaga gagtggcctt gaggaagcca      60
tagcagcagg accagcatgg cctctgctgc ctctgtgacc agcctggcag atgaagtcaa     120
ctgccccatc tgtcagggta ccctgaggga gccgtcact atcgactgcg ccacaacttt    180
ctgccgggcc tgccttaccc gctactgtga tacccaggc ccagacctgg aggagtcccc     240
tacttgccca ctctgcaaag aacccttccg tcctgggagc ttccggccca actggcagct    300
ggctaacgtg gtggagaaca ttgagcgcct ccagctggtg tccacactgg gtttgggaga    360
ggaggatgtc tgccaagagc acggagggaa gatctacttc ttctgtgagg atgatgagat    420
gcagttgtgc gtggtgtgcc gggaggctgg ggagcacgct acccacacca tgcgcttcct    480
ggaggatgca gcggctccct atagggaaca aatccataag tgtcttaaat gtctaagaaa    540
agagagagag gagattcaag aaatccagtc aagagaaaat aaaaggatgc aagtcctcct    600
gactcaggtg tccaccaaga acaacaggt gatttctgag ttcgcacacc tgaggaagtt     660
tctagaggaa cagcagagca tcctcttagc acaattggag agccaggatg ggacatcttt    720
gaggcaacgg gatgaatttg atttgctggt tgctgggag atctgccggt ttagtgctct     780
tattgaagaa ctggaggaga gaatgagag gccagcaagg gagctcctga cggacatcag    840
aagcactcta ataagatgtg aaaccagaaa gtgccggaaa ccgtggctg tgtcgcaga     900 gctgggccag aggattcggg actttcccca gcaggccctc ccgctgcaga gggagatgaa    960
gatgtttctg gaaaaactat gctttgagtt ggactatgag ccagctcaca tttctctaga   1020
ccctcagact tcccacccca agctcctctt gtccgaggac caccagcgag ctcagttctc    1080
ctcaaaatgg cagaactcac cagacaaccc cagcgtttt gaccgggcca cctgtgttct    1140
ggcccacact ggcatcacag gggggagaca cacgtgggtg gtgagtatag acctggccca   1200
```

-continued

```
tggggcgagc tgcaccgtgg gcgtggtgag cgaggatgtg cagcggaagg gggagcttcg    1260
gctgcggcca aggaggggg tgtgggctgt gaggctggct tggggcttcg tctcggctct    1320
gggctccttc cccacacggc tgaccctgaa ggagcagccc cggcaggtga gggtgtctct    1380
tgactatgag gtgggctggg tgaccttcac caacgctgtc acccgagagc ccatctacac    1440
cttcactgcc tccttcacta ggaaggtcat tcccttcttt gggctctggg gccgagggtc    1500
cagtttctcc ctgagctcct gagaaggagc agttacctac tctcctctaa gtacaggact    1560
cattcaaccc agtaccatgt ggcttgatcc ctggctgaat cacctggatg actcgggata    1620
gaaatgactg ctttagaaga tgggatgggg tcggtggta agggatagaa gagaggactc    1680
tcaatctact gatcaagtcc tttccccaat gcccagtgga tggccagggt acctggggac    1740
tcaggctgct gccagttctg ctcaccacca tccgtgcttg gcacagaagt agctgcatag    1800
aaagagcact ggatttgaag tcagaagacc tggttcttga accagcctgt caaccagttg    1860
tatgacttta acaaggcat ctcacctctt ttcatcttgt tttcttccaa taatgttaga    1920
gttcatgtaa tcacattctc tagaaccatt tagtttgtgt taactatgaa ccaagcagtg    1980
tggtgggcca ctggtggact tgga                                          2004
```

<210> SEQ ID NO 22
<211> LENGTH: 481
<212> TYPE: PRT
<213> ORGANISM: Homo sapiens

<400> SEQUENCE: 22

```
Met Ala Ser Ala Ala Ser Val Thr Ser Leu Ala Asp Glu Val Asn Cys
 1               5                  10                  15

Pro Ile Cys Gln Gly Thr Leu Arg Glu Pro Val Thr Ile Asp Cys Gly
                20                  25                  30

His Asn Phe Cys Arg Ala Cys Leu Thr Arg Tyr Cys Glu Ile Pro Gly
            35                  40                  45

Pro Asp Leu Glu Glu Ser Pro Thr Cys Pro Leu Cys Lys Glu Pro Phe
        50                  55                  60

Arg Pro Gly Ser Phe Arg Pro Asn Trp Gln Leu Ala Asn Val Val Glu
65                  70                  75                  80

Asn Ile Glu Arg Leu Gln Leu Val Ser Thr Leu Gly Leu Gly Glu Glu
                85                  90                  95

Asp Val Cys Gln Glu His Gly Gly Lys Ile Tyr Phe Phe Cys Glu Asp
            100                 105                 110

Asp Glu Met Gln Leu Cys Val Val Cys Arg Glu Ala Gly Glu His Ala
        115                 120                 125

Thr His Thr Met Arg Phe Leu Glu Asp Ala Ala Ala Pro Tyr Arg Glu
    130                 135                 140

Gln Ile His Lys Cys Leu Lys Cys Leu Arg Lys Glu Arg Glu Glu Ile
145                 150                 155                 160

Gln Glu Ile Gln Ser Arg Glu Asn Lys Arg Met Gln Val Leu Leu Thr
                165                 170                 175

Gln Val Ser Thr Lys Arg Gln Gln Val Ile Ser Glu Phe Ala His Leu
            180                 185                 190

Arg Lys Phe Leu Glu Glu Gln Gln Ser Ile Leu Leu Ala Gln Leu Glu
        195                 200                 205

Ser Gln Asp Gly Asp Ile Leu Arg Gln Arg Asp Glu Phe Asp Leu Leu
    210                 215                 220

Val Ala Gly Glu Ile Cys Arg Phe Ser Ala Leu Ile Glu Glu Leu Glu
225                 230                 235                 240
```

Glu Lys Asn Glu Arg Pro Ala Arg Glu Leu Leu Thr Asp Ile Arg Ser
            245                 250                 255

Thr Leu Ile Arg Cys Glu Thr Arg Lys Cys Arg Lys Pro Val Ala Val
            260                 265                 270

Ser Pro Glu Leu Gly Gln Arg Ile Arg Asp Phe Pro Gln Gln Ala Leu
            275                 280                 285

Pro Leu Gln Arg Glu Met Lys Met Phe Leu Glu Lys Leu Cys Phe Glu
            290                 295                 300

Leu Asp Tyr Glu Pro Ala His Ile Ser Leu Asp Pro Gln Thr Ser His
305                 310                 315                 320

Pro Lys Leu Leu Leu Ser Glu Asp His Gln Arg Ala Gln Phe Ser Ser
            325                 330                 335

Lys Trp Gln Asn Ser Pro Asp Asn Pro Gln Arg Phe Asp Arg Ala Thr
            340                 345                 350

Cys Val Leu Ala His Thr Gly Ile Thr Gly Gly Arg His Thr Trp Val
            355                 360                 365

Val Ser Ile Asp Leu Ala His Gly Ala Ser Cys Thr Val Gly Val Val
            370                 375                 380

Ser Glu Asp Val Gln Arg Lys Gly Glu Leu Arg Leu Arg Pro Glu Glu
385                 390                 395                 400

Gly Val Trp Ala Val Arg Leu Ala Trp Gly Phe Val Ser Ala Leu Gly
            405                 410                 415

Ser Phe Pro Thr Arg Leu Thr Leu Lys Glu Gln Pro Arg Gln Val Arg
            420                 425                 430

Val Ser Leu Asp Tyr Glu Val Gly Trp Val Thr Phe Thr Asn Ala Val
            435                 440                 445

Thr Arg Glu Pro Ile Tyr Thr Phe Thr Ala Ser Phe Thr Arg Lys Val
            450                 455                 460

Ile Pro Phe Phe Gly Leu Trp Gly Arg Gly Ser Ser Phe Ser Leu Ser
465                 470                 475                 480

Ser

<210> SEQ ID NO 23
<211> LENGTH: 3033
<212> TYPE: DNA
<213> ORGANISM: Homo sapiens

<400> SEQUENCE: 23
gagtgtgtga cccagcccstt cccccgtggc caagcagaga gagtggcctt gaggaagcca      60
tagcagcagg accagcatgg cctctgctgc ctctgtgacc agcctggcag atgaagtcaa     120
ctgccccatc tgtcagggta ccctgaggga gccggtcact atcgactgcg ccacaacttt     180
ctgccgggcc tgccttaccc gctactgtga taccaggc ccagacctgg aggagtcccc       240
tacttgccca ctctgcaaag aaccctccg tcctgggagc ttccggccca actggcagct     300
ggctaacgtg gtggagaaca ttgagcgcct ccagctggtg tccacactgg gtttgggaga     360
ggaggatgtc tgccaagagc acggaggaa gatctacttc ttctgtgagg atgatgagat     420
gcagttgtgc gtggtgtgcc gggaggctgg ggagcacgct acccacacca tgcgcttcct     480
ggaggatgca gcggctccct atagggaaca aatccataag tgtcttaaat gtctaagaaa     540
agagagagag gagattcaag aaatccagtc aagaaaaaat aaaaggatgc aagtcctcct     600
gactcaggtg tccaccaaga gacaacaggt gatttctgag ttcgcacacc tgaggaagtt     660
tctagaggaa cagcagagca tcctcttagc acaattggag agccaggatg gggacatctt     720

```
gaggcaacgg gatgaatttg atttgctggt tgctggggag atctgccggt ttagtgctct    780
tattgaagaa ctggaggaga agaatgagag gccagcaagg gagctcctga cggacatcag    840
aagcactcta ataagatgtg aaaccagaaa gtgccggaaa ccggtggctg tgtcgccaga    900
gctgggccag aggattcggg actttcccca gcaggccctc ccgctgcaga gggagatgaa    960
gatgtttctg gaaaaactat gctttgagtt ggactatgag ccagctcaca tttctctaga   1020
ccctcagact tcccacccca agctcctctt gtccgaggac caccagcgag ctcagttctc   1080
ctacaaatgg cagaactcac cagacaaccc ccagcgtttt gaccgggcca cctgtgttct   1140
ggcccacact ggcatcacag gggggagaca cacgtgggtg tggatggcca gggtacctgg   1200
ggactcaggc ggctgccagt tctgctcacc accatccgtg cttggcacag aagtagctgc   1260
atagaaagag cactggattt gaagtcagaa gacctgggtt cttgaaccag cctgtcaacc   1320
agttgtatga ctttaaacaa ggcatctcac ctcttttcat cttgttttct tccaataatg   1380
ttagagttca tgtaatcaca ttctctagaa ccatttagtt tgtgttaact atgaaccaag   1440
cagtgtggtg gccactggtg acttgaaaat atagagaaaa aaaaaacctg ctctatatct   1500
gaaagagctc ttgggaagac agagaaacat aaagaggaaa ttacagcaca gtgtggtggg   1560
tgttacggga agtccaaccc cagcattatg ggagttcagg ggaaggggca tagcccagcc   1620
tggaaggaga gggtgagtgg gggatggctt tctgaaaagg gtggtctaaa ggatgcctat   1680
ggtcaatagg gaaaagaggg gaagaagcat cttaagaaga ggaaacagca gagaactggc   1740
tggatgacct gtgactctgg agcactgggt tgtctccatt gtcattatgg gcagatgtgt   1800
gccatcccca gccgacgcca ctcactgcct ccttcctcct ggtgttgcca cttctgggtg   1860
agattaaggt gcagggcctg ggggcaggag gacataaggt atagccataa atcataaccc   1920
agggaccaca ctcaacccta gggaaattgt cttcctgatc agttgattac catctgaggt   1980
caagaaatga gatagtggga gcaaatgggt cacaaatagc tcagctgtgg gctcagaaac   2040
tgctaggtaa aagaattcca gaaggaggcc agggcataag ttggatgacc tatgaacttt   2100
agtctaaaga attgagacta ccgtaattga gactactgta gtgacatctg agaaatggga   2160
tggaagagtg accatgtttt attttcttgt tcttgtcact attgtatttt attttgcata   2220
atcatgccct tcactgacag tctccttaac atcatctgtt tactctgctc agtgtaaact   2280
acaatgctct gtcatctccc tactgggtct cctggggagga gggagccat ccagggtgca   2340
aactcaaagg cagagggcac agcgtgctta ggcccaagct tagaattcaa ttgagaagtt   2400
ctgttgttca tccttacctc agcaggtaga aagaggtgg agatcagaag ccagggatta   2460
gagattgaat tgctttccct gggagtgtgc agtatctcat taaaatgttg tatattcaaa   2520
aaaatacaga cacacacaag tgcctatata atgataaaac atatccaaag cacccaaacc   2580
tgtgattcca gaaaagtaga tcctattttt gtttattttt attggcttta gctgtgtctt   2640
ttgaaaggac tattatcctc taaaatgtat gtgtatgaag atcctggctt gcagctcggg   2700
agctttacac accttgtgtc actttatctt ggtaacgagc caagatcatg caaccagttc   2760
atccatgtct gacccaagag ctcttaactg ctatgctgca ctgcctcatt cagagataga   2820
tgcctgcatg ggtcctggcg attatttttaa tgctggctac acccccacag gtgacttgga   2880
ttcagaaata caattatat ttcttctttt taaattgttt tattttattt ttcttttaat   2940
agttatatgt cagtgagaac aatttatatg tcttacactg agaaataaaa ctgctcataa   3000
gtgaaaaaaa aaaaaaaaaa aaaaaaaaaa aaa                                3033
```

<210> SEQ ID NO 24

```
<211> LENGTH: 395
<212> TYPE: PRT
<213> ORGANISM: Homo sapiens

<400> SEQUENCE: 24

Met Ala Ser Ala Ala Ser Val Thr Ser Leu Ala Asp Glu Val Asn Cys
 1               5                  10                  15

Pro Ile Cys Gln Gly Thr Leu Arg Glu Pro Val Thr Ile Asp Cys Gly
            20                  25                  30

His Asn Phe Cys Arg Ala Cys Leu Thr Arg Tyr Cys Glu Ile Pro Gly
        35                  40                  45

Pro Asp Leu Glu Glu Ser Pro Thr Cys Pro Leu Cys Lys Glu Pro Phe
 50                  55                  60

Arg Pro Gly Ser Phe Arg Pro Asn Trp Gln Leu Ala Asn Val Val Glu
 65                  70                  75                  80

Asn Ile Glu Arg Leu Gln Leu Val Ser Thr Leu Gly Leu Gly Glu Glu
                85                  90                  95

Asp Val Cys Gln Glu His Gly Gly Lys Ile Tyr Phe Phe Cys Glu Asp
            100                 105                 110

Asp Glu Met Gln Leu Cys Val Val Cys Arg Glu Ala Gly Glu His Ala
        115                 120                 125

Thr His Thr Met Arg Phe Leu Glu Asp Ala Ala Ala Pro Tyr Arg Glu
    130                 135                 140

Gln Ile His Lys Cys Leu Lys Cys Leu Arg Lys Arg Glu Glu Ile
145                 150                 155                 160

Gln Glu Ile Gln Ser Arg Lys Asn Lys Arg Met Gln Val Leu Leu Thr
                165                 170                 175

Gln Val Ser Thr Lys Arg Gln Gln Val Ile Ser Glu Phe Ala His Leu
            180                 185                 190

Arg Lys Phe Leu Glu Glu Gln Gln Ser Ile Leu Leu Ala Gln Leu Glu
        195                 200                 205

Ser Gln Asp Gly Asp Ile Leu Arg Gln Arg Asp Glu Phe Asp Leu Leu
    210                 215                 220

Val Ala Gly Glu Ile Cys Arg Phe Ser Ala Leu Ile Glu Glu Leu Glu
225                 230                 235                 240

Glu Lys Asn Glu Arg Pro Ala Arg Glu Leu Leu Thr Asp Ile Arg Ser
                245                 250                 255

Thr Leu Ile Arg Cys Glu Thr Arg Lys Cys Arg Lys Pro Val Ala Val
            260                 265                 270

Ser Pro Glu Leu Gly Gln Arg Ile Arg Asp Phe Pro Gln Gln Ala Leu
        275                 280                 285

Pro Leu Gln Arg Glu Met Lys Met Phe Leu Glu Lys Leu Cys Phe Glu
    290                 295                 300

Leu Asp Tyr Glu Pro Ala His Ile Ser Leu Asp Pro Gln Thr Ser His
305                 310                 315                 320

Pro Lys Leu Leu Leu Ser Glu Asp His Gln Arg Ala Gln Phe Ser Tyr
                325                 330                 335

Lys Trp Gln Asn Ser Pro Asp Asn Pro Gln Arg Phe Asp Arg Ala Thr
            340                 345                 350

Cys Val Leu Ala His Thr Gly Ile Thr Gly Gly Arg His Thr Trp Val
        355                 360                 365

Trp Met Ala Arg Val Pro Gly Asp Ser Gly Gly Cys Gln Phe Cys Ser
    370                 375                 380

Pro Pro Ser Val Leu Gly Thr Glu Val Ala Ala
385                 390                 395
```

<210> SEQ ID NO 25
<211> LENGTH: 4454
<212> TYPE: DNA
<213> ORGANISM: Homo sapiens

<400> SEQUENCE: 25

| | | | | | |
|---|---|---|---|---|---|
| gtggagatga | atggcgggcg | cggcgaccgg | gagccggacc | cctgggaggt | cggagcttgt | 60 |
| cgagggatgc | ggctggcgct | gcccggagca | tggcgaccgc | gtggctgagc | tcttctgtcg | 120 |
| ccgctgccgc | cgctgcgtgt | gcgcgctttg | cccggtgctg | ggcgcgcacc | gtggccaccc | 180 |
| tgtgggcctg | cgctggagg | cagcggtgca | cgtgcagaaa | ctcagccaag | aatgtttaaa | 240 |
| gcagctggca | atcaagaagc | agcagcacat | tgacaacata | acccagatag | aagatgccac | 300 |
| cgagaagctc | aaggctaatg | cagagtcaag | taaaacctgg | ctgaagggga | aattcactga | 360 |
| actcagatta | ctacttgacg | aagaggaagc | gctggccaag | aaattcattg | ataaaaacac | 420 |
| gcagcttacc | ctccaggtgt | acaggaaaca | agctgactct | tgcagagagc | aacttgacat | 480 |
| catgaatgat | ctctccaaca | gggtctggag | tatcagccag | gagcccgatc | ctgtccagag | 540 |
| gcttcaggca | tacacggcca | ccgagcagga | gatgcagcag | cagatgagcc | tcggggagct | 600 |
| gtgccatccc | gtgcccctct | cttttgagcc | cgtcaagagc | ttctttaagg | gcctcgtgga | 660 |
| agccgtggag | agtacattac | agacgccatt | ggacattcgc | cttaaggaaa | gcataaactg | 720 |
| ccagctctca | gacccttcca | gcaccaagcc | aggtaccttg | ttgaaaacca | gcccctcacc | 780 |
| agagcgatcg | ctattgctga | atacgcgcg | cacgcccacg | ctggatcctg | acacgatgca | 840 |
| cgcgcgcctg | cgcctgtccg | ccgatcgcct | gacggtgcgc | tgcggcctgc | tgggcagcct | 900 |
| ggggcccgtg | cccgtgctgc | ggttcgacgc | gctctggcaa | gtgctggctc | gtgactgctt | 960 |
| cgccaccggc | cgccactact | gggaggttga | cgtgcaggag | gcgggcgccg | gctggtgggt | 1020 |
| gggcgcggcc | tacgcctccc | ttcggcgccg | cggggcctcg | gccgccgccc | gctgggctg | 1080 |
| caaccgccag | tcctggtgcc | tcaagcgcta | cgaccttgag | tactgggcct | tccacgacgg | 1140 |
| ccagcgcagc | cgcctgcggc | cccgcgacga | cctcgaccgg | ctcggcgtct | tcctggacta | 1200 |
| cgaggccggc | gtcctcgcct | tctacgacgt | gacgggcggc | atgagccacc | tgcatacctt | 1260 |
| ccgcgccacg | ttccaggagc | cgctctaccc | ggccctgcgg | ctctgggagg | gggccatcag | 1320 |
| catccccgg | ctgccctagg | ggccaggacc | ggcgtgacag | cctccaggta | cgccgcagct | 1380 |
| gcccagtctc | gcctaatcta | cctagatcag | cgtggctggt | ccccttactg | cctgcttctt | 1440 |
| agggccctct | ccctgcccca | gctttccccg | accaatcacg | cctacagtgc | tttgaaggtt | 1500 |
| tcctctccta | ggctagtttc | aaacaggcc | taaacaagtc | tgctgctgcc | ctctcatcag | 1560 |
| acctccgcac | cctcacccca | ccatcactta | aactacttta | atccagttcc | ttcaaagtga | 1620 |
| taccccaca | ggtaagccct | cagcatcctg | aatacatcat | ccgcagcctg | ggaaccttct | 1680 |
| ccctcgtaca | gcacaggaac | ctgacacata | gtaggcacac | agtaaacgtt | tgtgaatgaa | 1740 |
| tgggagtcat | ccagtcctga | ctcttctgtc | tcttgaggtc | ccttgaatct | tccgcttcct | 1800 |
| ccccaccgat | ttcagcgtgt | ccacatcaca | gctccctcca | gaagctgcaa | gagcttctta | 1860 |
| gcagttcctg | gtctgaaccc | tctcccagtc | ctcatcttcc | accctaaaac | tagagtgatc | 1920 |
| ttcctaaaac | ttcacttaac | ccctcagcta | tgaaaaggct | tccaggagtt | tccatgaaat | 1980 |
| aacaaaaaaa | aatacaagcg | cctcacctta | gcattcaagg | cttgtctagt | ctgcccaaaa | 2040 |
| ttacttatcc | tcacctagct | cctaccactc | ttccttagaga | ctctccagtc | agaaatgtgt | 2100 |
| cgcatagttc | cacctccaca | cctctctgct | gccagcacat | tcatgcagaa | aagtcttttc | 2160 |

```
acctgtctca gtcttccgca ggcttacctg cgccaggaag tctaaccaag gaacaagaat   2220
ctcactatca gagccacaaa tctgggacct gtctttccaa ctaaattgga ggctttggaa   2280
gggcagcttt gtcctatact ctctccaccc tgaaaagttc ccagaaagcc ccttccctcc   2340
caagcagtga attaataacc agcaggtgcc tatcactgag taacagaaga gctgagttag   2400
gcgggcctca caggtcaccc agccagatct catctgggga gtctgaggtc ctgaaagaaa   2460
gcagagctgc gtaaagttac cccggggtga tatagggggg ccagacgtgt gccccgttca   2520
cccaccccca ggcaagcatc tgacctgtcc cctggcccag ccttaggcc cagctttcaa    2580 cctgcttact catttctcag ggattttggg aaggaatca gcaggtgaca gttgctaagc    2640
aaccaaaggg cgtggtgttt cccaactgtc ttgggacaaa aagggtaaga gcacccttag   2700
atccagatgt tgccaaggaa acccagagtg cccagctgtc tggaatgaag tgacagaggt   2760
agaaaacagt aggccctcac aggaggccac cttcgctagc agggagtggg aggcttcttt   2820
ccagggattt gtgtctccgt tctgaaggtt ctgcgtcctg ttttgtcaat tccctagacg   2880
gttttgaagt tatattctgt taaagcatct tcataggtgc ttggtgggag gccaaggtcg   2940
ccgaatcctc gtggtttaaa tagactttca gtgcattagt ttgaaccata taaaactgac   3000
aattttcaat agttttgag ttaaaaatgg cacttttgat atgagacaat gtagcagaat    3060
accaggcaga cagaaccttg caaacacctt aacttctaac caaagacttt aaaactctgg   3120
ctggacagag ttttaagcac tatgctgcag gaatcctgag aaaagggga attaattct    3180 attaggaatg gcccaaactg aattgtgaca ggcagagggt gttcctgaca gagggaagat   3240
gaatacactt gaccccaaca tttctgccca tccctgatga ccaagacctc ttcccagacc   3300
cacagctgca ggggccaagt aataacagct cttaatagtt tataatgcac tgttttaatg   3360
ctttacgact aaactcatct gatcctttca tcagccctag agggtagaaa gttttcccaa   3420
ttctacacat ggcaaaatgg agacccgag tcacttgccc aaggtcgcac agctagtggt    3480
ggagctggag tctgggccca ggctgtgagt tccaggtctg tgctcatggc caccaggcca   3540
tactgctcag ggtgaatgca gctggtctct ggccagtgcc tggtgctctg gcccctctcg   3600
tggagctact gcccatgatg cttcctagt gcctggttac tctgcgagac ttgagtctac    3660
ctttggactg ccttccttgg gggtctgaga tgaggcctta tggcccagag gggaacttga   3720
ttcaaaaatt tgggattcat gtagcagaga cagagctaga ctgtaaaggt cacaaactag   3780
ctgtgtcaag gcccgtgata gccagaaagc ggcagtttca gtccatatca attgtgtgac   3840
cagggctagt cacttttttac ttctcagtgc catctataaa atggggataa tagcactacc   3900
taccaagtgc tgtgaggctc aaatgagcca aaggttataa acttgcctta aaactatagt   3960
cctatacaaa aattagctgg gcgtggtggt gcatgcctgt aatcccagct actagggagg   4020
ctgaggcaag agagttgctt gaacccagga ggcggagatt gcagtgagct gagattgcac   4080
cactgcactc cagcctgggg acagagcaag actcttgtct caaaaaaaac aaaaaaaaca   4140
tatatactgc tgtatcatgc caggatttat cagcattccc aagggagctt gcacggtact   4200
gaccgagtgc tgagactact ggtattccca gctgccatgt ggcagcagca ggagctacta   4260
gaatattctc agcacaggaa tgaggcttcc ttggtttcca tgtctgtaag ggttactgat   4320
cacttacctt cttctctttc agacttgaat ctgtagacat ttctttattg atatggcaaa   4380
ttgcttgcag atattttaa atgacagcaa ttttctaata tttggtttaa taaaatgtga   4440
ataatgtccc tttt                                                    4454
```

<210> SEQ ID NO 26
<211> LENGTH: 442
<212> TYPE: PRT
<213> ORGANISM: Homo sapiens

<400> SEQUENCE: 26

```
Met Ala Gly Ala Ala Thr Gly Ser Arg Thr Pro Gly Arg Ser Glu Leu
 1               5                  10                  15

Val Glu Gly Cys Gly Trp Arg Cys Pro Glu His Gly Asp Arg Val Ala
             20                  25                  30

Glu Leu Phe Cys Arg Arg Cys Arg Arg Cys Val Cys Ala Leu Cys Pro
         35                  40                  45

Val Leu Gly Ala His Arg Gly His Pro Val Gly Leu Ala Leu Glu Ala
     50                  55                  60

Ala Val His Val Gln Lys Leu Ser Gln Glu Cys Leu Lys Gln Leu Ala
 65                  70                  75                  80

Ile Lys Lys Gln Gln His Ile Asp Asn Ile Thr Gln Ile Glu Asp Ala
                 85                  90                  95

Thr Glu Lys Leu Lys Ala Asn Ala Glu Ser Ser Lys Thr Trp Leu Lys
            100                 105                 110

Gly Lys Phe Thr Glu Leu Arg Leu Leu Leu Asp Glu Glu Ala Leu
            115                 120                 125

Ala Lys Lys Phe Ile Asp Lys Asn Thr Gln Leu Thr Leu Gln Val Tyr
    130                 135                 140

Arg Glu Gln Ala Asp Ser Cys Arg Glu Gln Leu Asp Ile Met Asn Asp
145                 150                 155                 160

Leu Ser Asn Arg Val Trp Ser Ile Ser Gln Glu Pro Asp Pro Val Gln
                165                 170                 175

Arg Leu Gln Ala Tyr Thr Ala Thr Glu Gln Glu Met Gln Gln Met
            180                 185                 190

Ser Leu Gly Glu Leu Cys His Pro Val Pro Leu Ser Phe Glu Pro Val
            195                 200                 205

Lys Ser Phe Phe Lys Gly Leu Val Glu Ala Val Glu Ser Thr Leu Gln
    210                 215                 220

Thr Pro Leu Asp Ile Arg Leu Lys Glu Ser Ile Asn Cys Gln Leu Ser
225                 230                 235                 240

Asp Pro Ser Ser Thr Lys Pro Gly Thr Leu Leu Lys Thr Ser Pro Ser
                245                 250                 255

Pro Glu Arg Ser Leu Leu Leu Lys Tyr Ala Arg Thr Pro Thr Leu Asp
            260                 265                 270

Pro Asp Thr Met His Ala Arg Leu Arg Leu Ser Ala Asp Arg Leu Thr
            275                 280                 285

Val Arg Cys Gly Leu Leu Gly Ser Leu Gly Pro Val Pro Val Leu Arg
    290                 295                 300

Phe Asp Ala Leu Trp Gln Val Leu Ala Arg Asp Cys Phe Ala Thr Gly
305                 310                 315                 320

Arg His Tyr Trp Glu Val Asp Val Gln Glu Ala Gly Ala Gly Trp Trp
                325                 330                 335

Val Gly Ala Ala Tyr Ala Ser Leu Arg Arg Gly Ala Ser Ala Ala
            340                 345                 350

Ala Arg Leu Gly Cys Asn Arg Gln Ser Trp Cys Leu Lys Arg Tyr Asp
    355                 360                 365

Leu Glu Tyr Trp Ala Phe His Asp Gly Gln Arg Ser Arg Leu Arg Pro
    370                 375                 380

Arg Asp Asp Leu Asp Arg Leu Gly Val Phe Leu Asp Tyr Glu Ala Gly
```

```
                385                 390                 395                 400
Val Leu Ala Phe Tyr Asp Val Thr Gly Gly Met Ser His Leu His Thr
                        405                 410                 415

Phe Arg Ala Thr Phe Gln Glu Pro Leu Tyr Pro Ala Leu Arg Leu Trp
                        420                 425                 430

Glu Gly Ala Ile Ser Ile Pro Arg Leu Pro
                        435                 440

<210> SEQ ID NO 27
<211> LENGTH: 1479
<212> TYPE: DNA
<213> ORGANISM: Homo sapiens

<400> SEQUENCE: 27
gtggagatga atggcgggcg cggcgaccgg gagccggacc cctgggaggt cggagcttgt      60
cgagggatgc ggctggcgct gcccggagca tggcgaccgc gtggctgagc tcttctgtcg     120
ccgctgccgc cgctgcgtgt gcgcgctttg cccggtgctg ggcgcgcacc gtggccaccc     180
tgtgggcctg gcgctggagg cagcggtgca cgtgcagaaa ctcagccaag aatgtttaaa     240
gcagctggca atcaagaagc agcagcacat tgacaacata acccagatag aagatgccac     300
cgagaagctc aaggctaatg cagagtcaag taaaacctgg ctgaagggga aattcactga     360
actcagatta ctacttgacg aagaggaagc gctggccaag aaattcattg ataaaaacac     420
gcagcttacc ctccaggtgt acagggaaca agctgactct tgcagagagc aacttgacat     480
catgaatgat ctctccaaca gggtctggag tatcagccag gagcccgatc ctgtccagag     540
gcttcaggca tacacggcca ccgagcagga gatgcagcag cagatgagcc tcggggagct     600
gtgccatccc gtgcccctct cttttgagcc cgtcaagagc ttctttaagg gcctcgtgga     660
agccgtggag agtacattac agacgccatt ggacattcgc cttaaggaaa gcataaactg     720
ccagctctca gacccttcca gcaccaagcc aggtaccttg ttgaaaacca gcccctcacc     780
agagcgatcg ctattgctga aatacgcgcg cacgcccacg ctggatcctg acacgatgca     840
cgcgcgcctg cgcctgtccg ccgatcgcct gacggtgcgc tgcggcctgc tgggcagcct     900
ggggcccgtg cccgtgctgc ggttcgacgc gctctggcaa gtgctggctc gtgactgctt     960
cgccaccggc cgccactact gggaggttga cgtgcaggag gcgggcgccg gctggtgggt    1020
gggcgcggcc tacgcctccc ttcggcgccg cggggcctcg gccgccgccc gctgggctg     1080 caaccgccag tcctggtgcc tcaagcgcta cgaccttgag tactgggcct tccacgacgg    1140
ccagcgcagc cgcctgcggc cccgcgacga cctcgaccgg ctcggcgtct tcctggacta    1200
cgaggccggc gtcctcgcct tctacgacgt gacgggcggc atgagccacc tgcataccett    1260 ccgcgccacg ttccaggagc cgctctaccc ggccctgcgg ctctgggagg gggccatcag    1320
catcccccgg ctgccctagg ggccaggacc ggcgtgacag cctccagact tgaatctgta    1380
gacatttctt tattgatatg gcaaattgct tgcagatatt tttaaatgac agcaattttc    1440
taatatttgg tttaataaaa tgtgaataat gtcccttt                            1479

<210> SEQ ID NO 28
<211> LENGTH: 442
<212> TYPE: PRT
<213> ORGANISM: Homo sapiens

<400> SEQUENCE: 28

Met Ala Gly Ala Ala Thr Gly Ser Arg Thr Pro Gly Arg Ser Glu Leu
  1               5                  10                  15
```

-continued

```
Val Glu Gly Cys Gly Trp Arg Cys Pro Glu His Gly Asp Arg Val Ala
             20                  25                  30
Glu Leu Phe Cys Arg Arg Cys Arg Cys Val Cys Ala Leu Cys Pro
         35                  40                  45
Val Leu Gly Ala His Arg Gly His Pro Val Gly Leu Ala Leu Glu Ala
 50                  55                  60
Ala Val His Val Gln Lys Leu Ser Gln Glu Cys Leu Lys Gln Leu Ala
 65                  70                  75                  80
Ile Lys Lys Gln Gln His Ile Asp Asn Ile Thr Gln Ile Glu Asp Ala
                 85                  90                  95
Thr Glu Lys Leu Lys Ala Asn Ala Glu Ser Ser Lys Thr Trp Leu Lys
             100                 105                 110
Gly Lys Phe Thr Glu Leu Arg Leu Leu Leu Asp Glu Glu Ala Leu
         115                 120                 125
Ala Lys Lys Phe Ile Asp Lys Asn Thr Gln Leu Thr Leu Gln Val Tyr
         130                 135                 140
Arg Glu Gln Ala Asp Ser Cys Arg Glu Gln Leu Asp Ile Met Asn Asp
145                 150                 155                 160
Leu Ser Asn Arg Val Trp Ser Ile Ser Gln Glu Pro Asp Pro Val Gln
                 165                 170                 175
Arg Leu Gln Ala Tyr Thr Ala Thr Glu Gln Glu Met Gln Gln Met
             180                 185                 190
Ser Leu Gly Glu Leu Cys His Pro Val Pro Leu Ser Phe Glu Pro Val
         195                 200                 205
Lys Ser Phe Phe Lys Gly Leu Val Glu Ala Val Glu Ser Thr Leu Gln
         210                 215                 220
Thr Pro Leu Asp Ile Arg Leu Lys Glu Ser Ile Asn Cys Gln Leu Ser
225                 230                 235                 240
Asp Pro Ser Ser Thr Lys Pro Gly Thr Leu Leu Lys Thr Ser Pro Ser
                 245                 250                 255
Pro Glu Arg Ser Leu Leu Leu Lys Tyr Ala Arg Thr Pro Thr Leu Asp
             260                 265                 270
Pro Asp Thr Met His Ala Arg Leu Arg Leu Ser Ala Arg Leu Thr
         275                 280                 285
Val Arg Cys Gly Leu Leu Gly Ser Leu Gly Pro Val Pro Val Leu Arg
         290                 295                 300
Phe Asp Ala Leu Trp Gln Val Leu Ala Arg Asp Cys Phe Ala Thr Gly
305                 310                 315                 320
Arg His Tyr Trp Glu Val Asp Val Gln Glu Ala Gly Ala Gly Trp Trp
                 325                 330                 335
Val Gly Ala Ala Tyr Ala Ser Leu Arg Arg Arg Gly Ala Ser Ala Ala
             340                 345                 350
Ala Arg Leu Gly Cys Asn Arg Gln Ser Trp Cys Leu Lys Arg Tyr Asp
         355                 360                 365
Leu Glu Tyr Trp Ala Phe His Asp Gly Gln Arg Ser Arg Leu Arg Pro
         370                 375                 380
Arg Asp Asp Leu Asp Arg Leu Gly Val Phe Leu Asp Tyr Glu Ala Gly
385                 390                 395                 400
Val Leu Ala Phe Tyr Asp Val Thr Gly Gly Met Ser His Leu His Thr
                 405                 410                 415
Phe Arg Ala Thr Phe Gln Glu Pro Leu Tyr Pro Ala Leu Arg Leu Trp
             420                 425                 430
Glu Gly Ala Ile Ser Ile Pro Arg Leu Pro
         435                 440
```

<210> SEQ ID NO 29
<211> LENGTH: 1789
<212> TYPE: DNA
<213> ORGANISM: Homo sapiens

<400> SEQUENCE: 29

```
cggaggaggt ggagatgaat ggcgggcgcg gcgaccggga gccggacccc tgggaggtcg    60
gagcttgtcg agggatgcgg ctggcgctgc ccggagcatg gcgaccgcgt ggctgagctc   120
ttctgtcgcc gctgccgccg ctgcgtgtgc gcgctttgcc cggtgctggg cgcgcaccgt   180
ggccaccctg tgggcctggc gctggaggca gcggtgcacg tgcagaaact cagccaagaa   240
tgtttaaagc agctggcaat caagaagcag cagcacattg acaacataac ccagatagaa   300
gatgccaccg agaagctcaa ggctaatgca gagtcaagta aaacctggct gaaggggaaa   360
ttcactgaac tcagattact acttgacgaa gaggaagcgc tggccaagaa attcattgat   420
aaaaacacgc agcttaccct ccaggtgtac agggaacaag ctgactcttg cagagagcaa   480
cttgacatca tgaatgatct ctccaacagg gtctggagta tcagccagga gcccgatcct   540
gtccagaggc ttcaggcata cacggccacc gagcaggaga tgcagcagca gatgagcctc   600
ggggagctgt gccatcccgt gcccctctcc tttgagcccg tcaagagctt ctttaagggc   660
ctcgtggaag ccgtggagag tacattacag acgccattgg acattcgcct taaggaaagc   720
ataaactgcc agctctcaga cccttccagc accaagccag gtaccttgtt gaaaaccagc   780
ccctcaccag agcgatcgct attgctgaaa tacgcgcgca cgcccacgct ggatcctgac   840
acgatgcacg cgcgcctgcg cctgtccgcc gatcgcctga cggtgcgctg cggcctgctg   900
ggcagcctgg ggccgtgcc cgtgctgcgg ttcgacgcgc tctggcaagt gctggctcgt   960
gactgcttcg ccaccggccg ccactactgg gaggttgacg tgcaggaggc gggcgccggc  1020
tggtgggtgg gcgcggccta cgcctcccct cggcgccgcg gggcctcggc cgccgcccgc  1080
ctgggctgca accgccagtc ctggtgcctc aagcgctacg accttgagta ctgggccttc  1140
cacgacggcc agcgcagccg cctgcggccc cgcgacgacc tcgaccggct cggcgtcttc  1200
ctggactacg aggccggcgt cctcgccttc tacgacgtga cgggcggcat gagccacctg  1260
cataccttcc gcgccacgtt ccaggagccg ctctacccgg ccctgcggct ctgggagggg  1320
gccatcagca tcccccggct gccctagggg ccaggaccgg cgtgacagcc tccagaatgt  1380
catggaagca gaatcgtaca gtatgttccc ttctgcatat gctgctttct cactcagcat  1440
catttccttg agatgcatcc aggctgctgc acgcatcaat agttcattcc tggctgggcg  1500
cggtggctca cgcctgtaat cccagcgctt tgggaggccg atgtgggtgg atcacaaggt  1560
caggagtttg agactagcct ggccaagatg gtgaaacccc atctctgcaa aaaatacaaa  1620
aattagccgg gcaccatggc atgtgcctgt aatcccctgct actcaggagg ctgaggaagg  1680
agaatcactt gaacccgggc agcggaggtt gcagtgagcc gagatcacac cactgcactc  1740
cagcctgggc aatagagtga gactccgttt caaaaaaaaa aaaaaaaaa                1789
```

<210> SEQ ID NO 30
<211> LENGTH: 442
<212> TYPE: PRT
<213> ORGANISM: Homo sapiens

<400> SEQUENCE: 30

```
Met Ala Gly Ala Ala Thr Gly Ser Arg Thr Pro Gly Arg Ser Glu Leu
 1               5                  10                  15
```

-continued

```
Val Glu Gly Cys Gly Trp Arg Cys Pro Glu His Gly Asp Arg Val Ala
         20                  25                  30
Glu Leu Phe Cys Arg Arg Cys Arg Cys Val Cys Ala Leu Cys Pro
     35                  40                  45
Val Leu Gly Ala His Arg Gly His Pro Val Gly Leu Ala Leu Glu Ala
 50                  55                  60
Ala Val His Val Gln Lys Leu Ser Gln Glu Cys Leu Lys Gln Leu Ala
 65                  70                  75                  80
Ile Lys Lys Gln Gln His Ile Asp Asn Ile Thr Gln Ile Glu Asp Ala
                 85                  90                  95
Thr Glu Lys Leu Lys Ala Asn Ala Glu Ser Ser Lys Thr Trp Leu Lys
             100                 105                 110
Gly Lys Phe Thr Glu Leu Arg Leu Leu Leu Asp Glu Glu Ala Leu
         115                 120                 125
Ala Lys Lys Phe Ile Asp Lys Asn Thr Gln Leu Thr Leu Gln Val Tyr
     130                 135                 140
Arg Glu Gln Ala Asp Ser Cys Arg Glu Gln Leu Asp Ile Met Asn Asp
145                 150                 155                 160
Leu Ser Asn Arg Val Trp Ser Ile Ser Gln Glu Pro Asp Pro Val Gln
                 165                 170                 175
Arg Leu Gln Ala Tyr Thr Ala Thr Glu Gln Glu Met Gln Gln Met
             180                 185                 190
Ser Leu Gly Glu Leu Cys His Pro Val Pro Leu Ser Phe Glu Pro Val
         195                 200                 205
Lys Ser Phe Phe Lys Gly Leu Val Glu Ala Val Glu Ser Thr Leu Gln
     210                 215                 220
Thr Pro Leu Asp Ile Arg Leu Lys Glu Ser Ile Asn Cys Gln Leu Ser
225                 230                 235                 240
Asp Pro Ser Ser Thr Lys Pro Gly Thr Leu Leu Lys Thr Ser Pro Ser
                 245                 250                 255
Pro Glu Arg Ser Leu Leu Leu Lys Tyr Ala Arg Thr Pro Thr Leu Asp
             260                 265                 270
Pro Asp Thr Met His Ala Arg Leu Arg Leu Ser Ala Asp Arg Leu Thr
         275                 280                 285
Val Arg Cys Gly Leu Leu Gly Ser Leu Gly Pro Val Pro Val Leu Arg
     290                 295                 300
Phe Asp Ala Leu Trp Gln Val Leu Ala Arg Asp Cys Phe Ala Thr Gly
305                 310                 315                 320
Arg His Tyr Trp Glu Val Asp Val Gln Glu Ala Gly Ala Gly Trp Trp
                 325                 330                 335
Val Gly Ala Ala Tyr Ala Ser Leu Arg Arg Arg Gly Ala Ser Ala Ala
             340                 345                 350
Ala Arg Leu Gly Cys Asn Arg Gln Ser Trp Cys Leu Lys Arg Tyr Asp
         355                 360                 365
Leu Glu Tyr Trp Ala Phe His Asp Gly Gln Arg Ser Arg Leu Arg Pro
     370                 375                 380
Arg Asp Asp Leu Asp Arg Leu Gly Val Phe Leu Asp Tyr Glu Ala Gly
385                 390                 395                 400
Val Leu Ala Phe Tyr Asp Val Thr Gly Gly Met Ser His Leu His Thr
                 405                 410                 415
Phe Arg Ala Thr Phe Gln Glu Pro Leu Tyr Pro Ala Leu Arg Leu Trp
             420                 425                 430
Glu Gly Ala Ile Ser Ile Pro Arg Leu Pro
         435                 440
```

<210> SEQ ID NO 31
<211> LENGTH: 3693
<212> TYPE: DNA
<213> ORGANISM: Homo sapiens

<400> SEQUENCE: 31

| | | | | | |
|---|---|---|---|---|---|
| gtggagatga | atggcgggcg | cggcgaccgg | gagccggacc | cctgggaggt | cggagcttgt | 60 |
| cgagggatgc | ggctggcgct | gcccggagca | tggcgaccgc | gtggctgagc | tcttctgtcg | 120 |
| ccgctgccgc | cgctgcgtgt | gcgcgctttg | cccggtgctg | ggcgcgcacc | gtggccaccc | 180 |
| tgtgggcctg | gcgctggagg | cagcggtgca | cgtgcagaaa | ctcagccaag | aatgtttaaa | 240 |
| gcagctggca | atcaagaagc | agcagcacat | tgacaacata | acccagatag | aagatgccac | 300 |
| cgagaagctc | aaggctaatg | cagagtcaag | taaaacctgg | ctgaagggga | aattcactga | 360 |
| actcagatta | ctacttgacg | aagaggaagc | gctggccaag | aaattcattg | ataaaaacac | 420 |
| gcagcttacc | ctccaggtgt | acaggaaaca | agctgactct | gcagagagc | aacttgacat | 480 |
| catgaatgat | ctctccaaca | gggtctggag | tatcagccag | gagcccgatc | ctgtccagag | 540 |
| gcttcaggca | tacacggcca | ccgagcagga | gatgcagcag | cagatgagcc | tcggggagct | 600 |
| gtgccatccc | gtgcccctct | cttttgagcc | cgtcaagagc | ttctttaagg | gcctcgtgga | 660 |
| agccgtggag | agtacattac | agacgccatt | ggacattcgc | cttccccga | ccaatcacgc | 720 |
| ctacagtgct | ttgaaggttt | cctctcctag | gctagtttca | aacaggccct | aaacaagtct | 780 |
| gctgctgccc | tctcatcaga | cctccgcacc | ctcaccccac | catcacttaa | actactttaa | 840 |
| tccagttcct | tcaaagtgat | accccacag | gtaagccctc | agcatcctga | atacatcatc | 900 |
| cgcagcctgg | gaaccttctc | cctcgtacag | cacaggaacc | tgacacatag | taggcacaca | 960 |
| gtaaacgttt | gtgaatgaat | gggagtcatc | cagtcctgac | tcttctgtct | cttgaggtcc | 1020 |
| cttgaatctt | ccgcttcctc | cccaccgatt | tcagcgtgtc | cacatcacag | ctccctccag | 1080 |
| aagctgcaag | agcttcttag | cagttcctgg | tctgaaccct | ctcccagtcc | tcatcttcca | 1140 |
| ccctaaaact | agagtgatct | tcctaaaact | tcacttaacc | cctcagctat | gaaaaggctt | 1200 |
| ccaggagttt | ccatgaaata | caaaaaaaaa | atacaagcgc | ctcaccttag | cattcaaggc | 1260 |
| ttgtctagtc | tgcccaaaat | tacttatcct | cacctagctc | ctaccactct | tcttagagac | 1320 |
| tctccagtca | gaaatgtgtc | gcatagttcc | acctccacac | ctctctgctg | ccagcacatt | 1380 |
| catgcagaaa | agtctttca | cctgtctcag | tcttccgcag | gcttacctgc | gccaggaagt | 1440 |
| ctaaccaagg | aacaagaatc | tcactatcag | agccacaaat | ctgggacctg | tctttccaac | 1500 |
| taaattggag | gctttggaag | ggcagctttg | tcctatactc | tctccaccct | gaaaagttcc | 1560 |
| cagaaagccc | cttccctccc | aagcagtgaa | ttaataacca | gcaggtgcct | atcactgagt | 1620 |
| aacagaagag | ctgagttagg | cgggcctcac | aggtcaccca | gccagatctc | atctggggag | 1680 |
| tctgaggtcc | tgaaagaaag | cagagctgcg | taaagttacc | ccggggtgat | atagggggc | 1740 |
| cagacgtgtg | ccccgttcac | ccaccccag | gcaagcatct | gacctgtccc | ctggcccagc | 1800 |
| ccttaggccc | agctttcaac | ctgcttactc | atttctcagg | ggattttggg | aaggaatcag | 1860 |
| caggtgacag | ttgctaagca | accaaagggc | gtggtgtttc | ccaactgtct | tgggacaaaa | 1920 |
| agggtaagag | cacccttaga | tccagatgtt | gccaaggaaa | cccagagtgc | ccagctgtct | 1980 |
| ggaatgaagt | gacagaggta | gaaaacagta | ggccctcaca | ggaggccacc | ttcgctagca | 2040 |
| gggagtggga | ggcttctttc | cagggatttg | tgtctccgtt | ctgaaggttc | tgcgtcctgt | 2100 |
| tttgtcaatt | ccctagacgg | ttttgaagtt | atattctgtt | aaagcatctt | cataggtgct | 2160 |

```
tggtgggagg ccaaggtcgc cgaatcctcg tggtttaaat agactttcag tgcattagtt    2220
tgaaccatat aaaactgaca attttcaata gttttttgagt taaaaatggc acttttgata    2280
tgagacaatg tagcagaata ccaggcagac agaaccttgc aaacacctta acttctaacc    2340
aaagacttta aaactctggc tggacagagt tttaagcact atgctgcagg aatcctgaga    2400
aaaaggggaa attaattcta ttaggaatgg cccaaactga attgtgacag gcagagggtg    2460
ttcctgacag agggaagatg aatacacttg accccaacat ttctgcccat ccctgatgac    2520
caagacctct tcccagaccc acagctgcag gggccaagta ataacagctc ttaatagttt    2580
ataatgcact gttttaatgc tttacgacta aactcatctg atcctttcat cagccctaga    2640
gggtagaaag ttttcccaat tctacacatg caaaatgga gacccagagt cacttgccca     2700
aggtcgcaca gctagtggtg gagctggagt ctgggcccag gctgtgagtt ccaggtctgt    2760
gctcatggcc accaggccat actgctcagg gtgaatgcag ctggtctctg gccagtgcct    2820
ggtgctctgg cccctctcgt ggagctactg cccatgatgc tttcctagtg cctggttact    2880
ctgcgagact tgagtctacc tttggactgc cttccttggg ggtctgagat gaggccttat    2940
ggcccagagg ggaacttgat tcaaaaattt gggattcatg tagcagagac agagctagac    3000
tgtaaaggtc acaaactagc tgtgtcaagg cccgtgatag ccagaaagcg gcagtttcag    3060
tccatatcaa ttgtgtgacc agggctagtc acttttttact tctcagtgcc atctataaaa    3120
tggggataat agcactacct accaagtgct gtgaggctca aatgagccaa aggttataaa    3180
cttgccttaa aactatagtc ctatacaaaa attagctggg cgtggtggtg catgcctgta    3240
atcccagcta ctagggaggc tgaggcaaga gagttgcttg aacccaggag gcggagattg    3300
cagtgagctg agattgcacc actgcactcc agcctgggga cagagcaaga ctcttgtctc    3360
aaaaaaaaca aaaaaaacat atatactgct gtatcatgcc aggatttatc agcattccca    3420
agggagcttg cacggtactg accgagtgct gagactactg gtattcccag ctgccatgtg    3480
gcagcagcag gagctactag aatattctca gcacaggaat gaggcttcct tggtttccat    3540
gtctgtaagg gttactgatc acttaccttc ttctcttttca gacttgaatc tgtagacatt    3600
tcttttattga tatggcaaat tgcttgcaga tattttttaaa tgacagcaat tttctaatat    3660
ttggtttaat aaaatgtgaa taatgtccct ttt                                 3693
```

<210> SEQ ID NO 32
<211> LENGTH: 253
<212> TYPE: PRT
<213> ORGANISM: Homo sapiens

<400> SEQUENCE: 32

Met Ala Gly Ala Ala Thr Gly Ser Arg Thr Pro Gly Arg Ser Glu Leu
 1               5                   10                  15

Val Glu Gly Cys Gly Trp Arg Cys Pro Glu His Gly Asp Arg Val Ala
            20                  25                  30

Glu Leu Phe Cys Arg Arg Cys Arg Arg Cys Val Cys Ala Leu Cys Pro
        35                  40                  45

Val Leu Gly Ala His Arg Gly His Pro Val Gly Leu Ala Leu Glu Ala
    50                  55                  60

Ala Val His Val Gln Lys Leu Ser Gln Glu Cys Leu Lys Gln Leu Ala
65                  70                  75                  80

Ile Lys Lys Gln Gln His Ile Asp Asn Ile Thr Gln Ile Glu Asp Ala
                85                  90                  95

Thr Glu Lys Leu Lys Ala Asn Ala Glu Ser Ser Lys Thr Trp Leu Lys

```
                     100                 105                 110
Gly Lys Phe Thr Glu Leu Arg Leu Leu Leu Asp Glu Glu Ala Leu
            115                 120                 125

Ala Lys Lys Phe Ile Asp Lys Asn Thr Gln Leu Thr Leu Gln Val Tyr
130                 135                 140

Arg Glu Gln Ala Asp Ser Cys Arg Glu Gln Leu Asp Ile Met Asn Asp
145                 150                 155                 160

Leu Ser Asn Arg Val Trp Ser Ile Ser Gln Glu Pro Asp Pro Val Gln
                165                 170                 175

Arg Leu Gln Ala Tyr Thr Ala Thr Glu Gln Glu Met Gln Gln Met
            180                 185                 190

Ser Leu Gly Glu Leu Cys His Pro Val Pro Leu Ser Phe Glu Pro Val
            195                 200                 205

Lys Ser Phe Phe Lys Gly Leu Val Glu Ala Val Glu Ser Thr Leu Gln
            210                 215                 220

Thr Pro Leu Asp Ile Arg Leu Ser Pro Thr Asn His Ala Tyr Ser Ala
225                 230                 235                 240

Leu Lys Val Ser Ser Pro Arg Leu Val Ser Asn Arg Pro
                245                 250

<210> SEQ ID NO 33
<211> LENGTH: 1937
<212> TYPE: DNA
<213> ORGANISM: Homo sapiens

<400> SEQUENCE: 33
ggaaactgaa agtgaaatag ggagctggct accagcgttg agttgccctg taaagccaaa       60
ccccctaaag gtctccacac tgctgtttaa cggcacactt gacaatggct tcagcagcac      120
gcttgacaat gatgtgggag gaggtcacat gccctatctg cctggacccc ttcgtggagc      180
ctgtgagcat cgagtgtggc cacagcttct gccaggaatg catctctcag gttgggaaag      240
gtgggggcag cgtctgtcct gtgtgccggc agcgctttct gctcaagaat ctccggccca      300
atcgacagct agccaacatg gtgaacaacc ttaaagaaat cagccaggag ccagagagg       360 gcacacaggg ggaacggtgt gcagtgcatg gagagagact tcacctgttc tgtgagaaag      420
atgggaaggc cctttgctgg gtatgtgccc agtctcggaa acaccgtgac cacgccatgg      480
tccctcttga ggaggctgca caggagtacc aggagaagct ccaggtggca ttaggggaac      540
tgagaagaaa gcaggagttg gctgagaagt tggaagtgga aattgcaata aagagagcag      600
actggaagaa aacagtggaa acacagaaat ctaggattca cgcagagttt gtgcagcaaa      660
aaaacttcct ggttgaagaa aacagaggc agctgcagga gctggagaag gatgagaggg      720
agcagctgag aatcctgggg gagaaagagg ccaagctggc ccagcagagc caggccctac      780
aggagctcat ctcagagcta gatcgaaggt gccacagctc agcactgaa ctgctgcagg       840 aggtgataat tgtcctggaa aggagtgagt cctggaacct gaaggacctg gatattacct      900
ctccagaact caggagtgtg tgccatgtgc cagggctgaa gaagatgctg aggacatgtg      960
cagtccacat cactctggat ccagacacag ccaatccgtg gctgatactt tcagaagatc     1020
ggagacaagt gaggcttgga gacacccagc agagcatacc tggaaatgaa gagagatttg     1080
atagttatcc tatggtcctg ggtgcccagc actttcactc tggaaaacat tactgggagg     1140
tagatgtgac aggaaaggag gcctgggacc tgggtgtctg cagagactct gtgcgcagga     1200
aggggcactt tttgcttagt tccaagagtg gcttctggaa aatttggttg tggaacaaac     1260
aaaaatatga ggctggcacc tacccccaga ctcccctcca ccttcaggtg cctccatgcc     1320
```

-continued

```
aagttgggat tttcctggac tatgaggctg gcatggtctc cttctacaac atcactgacc    1380
atggctccct catctactcc ttctctgaat gtgcctttac aggacctctg cggcccttct    1440
tcagtcctgg tttcaatgat ggaggaaaaa acacagcccc tctaaccctc tgtccactga    1500
atattggatc acaaggatcc actgactatt gatggctttc tctggacact gccactctcc    1560
ccattggcac cgcttctcag ccacaaaccc tgcctctttt ccccatgaac tctgaaccac    1620
ctttgtctct gcagaggcat ccggatccca gcaagcgagc tttagcaggg aagtcacttc    1680
accatcaaca ttcctgcccc agatggcttt gtgattccct ccagtgaagc agcctcctta    1740
tatttggccc aaactcatct tgatcaacca aaaacatgtt tctgccttct ttatgggact    1800
taagttttttt ttttctcctc tccatctcta ggatgtcgtc tttggtgaga tctctattat    1860
atcttgtatg gtttgcaaaa gggcttccta aaataaaaa ataaaattta aaaaactgtg    1920
aaaaaaaaaa aaaaaaa                                                  1937
```

<210> SEQ ID NO 34
<211> LENGTH: 475
<212> TYPE: PRT
<213> ORGANISM: Homo sapiens

<400> SEQUENCE: 34

```
Met Ala Ser Ala Ala Arg Leu Thr Met Met Trp Glu Glu Val Thr Cys
 1               5                   10                  15
Pro Ile Cys Leu Asp Pro Phe Val Glu Pro Val Ser Ile Glu Cys Gly
            20                  25                  30
His Ser Phe Cys Gln Glu Cys Ile Ser Gln Val Gly Lys Gly Gly Gly
        35                  40                  45
Ser Val Cys Pro Val Cys Arg Gln Arg Phe Leu Leu Lys Asn Leu Arg
    50                  55                  60
Pro Asn Arg Gln Leu Ala Asn Met Val Asn Asn Leu Lys Glu Ile Ser
65                  70                  75                  80
Gln Glu Ala Arg Glu Gly Thr Gln Gly Glu Arg Cys Ala Val His Gly
                85                  90                  95
Glu Arg Leu His Leu Phe Cys Glu Lys Asp Gly Lys Ala Leu Cys Trp
            100                 105                 110
Val Cys Ala Gln Ser Arg Lys His Arg Asp His Ala Met Val Pro Leu
        115                 120                 125
Glu Glu Ala Ala Gln Glu Tyr Gln Glu Lys Leu Gln Val Ala Leu Gly
    130                 135                 140
Glu Leu Arg Arg Lys Gln Glu Leu Ala Glu Lys Leu Glu Val Glu Ile
145                 150                 155                 160
Ala Ile Lys Arg Ala Asp Trp Lys Lys Thr Val Glu Thr Gln Lys Ser
                165                 170                 175
Arg Ile His Ala Glu Phe Val Gln Gln Lys Asn Phe Leu Val Glu Glu
            180                 185                 190
Glu Gln Arg Gln Leu Gln Glu Leu Glu Lys Asp Glu Arg Glu Gln Leu
        195                 200                 205
Arg Ile Leu Gly Glu Lys Glu Ala Lys Leu Ala Gln Gln Ser Gln Ala
    210                 215                 220
Leu Gln Glu Leu Ile Ser Glu Leu Asp Arg Arg Cys His Ser Ser Ala
225                 230                 235                 240
Leu Glu Leu Leu Gln Glu Val Ile Ile Val Leu Glu Arg Ser Glu Ser
                245                 250                 255
Trp Asn Leu Lys Asp Leu Asp Ile Thr Ser Pro Glu Leu Arg Ser Val
```

-continued

```
                 260                 265                 270
Cys His Val Pro Gly Leu Lys Lys Met Leu Arg Thr Cys Ala Val His
                275                 280                 285
Ile Thr Leu Asp Pro Asp Thr Ala Asn Pro Trp Leu Ile Leu Ser Glu
290                 295                 300
Asp Arg Arg Gln Val Arg Leu Gly Asp Thr Gln Ser Ile Pro Gly
305                 310                 315                 320
Asn Glu Glu Arg Phe Asp Ser Tyr Pro Met Val Leu Gly Ala Gln His
                325                 330                 335
Phe His Ser Gly Lys His Tyr Trp Glu Val Asp Val Thr Gly Lys Glu
                340                 345                 350
Ala Trp Asp Leu Gly Val Cys Arg Asp Ser Val Arg Arg Lys Gly His
                355                 360                 365
Phe Leu Leu Ser Ser Lys Ser Gly Phe Trp Thr Ile Trp Leu Trp Asn
                370                 375                 380
Lys Gln Lys Tyr Glu Ala Gly Thr Tyr Pro Gln Thr Pro Leu His Leu
385                 390                 395                 400
Gln Val Pro Pro Cys Gln Val Gly Ile Phe Leu Asp Tyr Glu Ala Gly
                405                 410                 415
Met Val Ser Phe Tyr Asn Ile Thr Asp His Gly Ser Leu Ile Tyr Ser
                420                 425                 430
Phe Ser Glu Cys Ala Phe Thr Gly Pro Leu Arg Pro Phe Phe Ser Pro
                435                 440                 445
Gly Phe Asn Asp Gly Lys Asn Thr Ala Pro Leu Thr Leu Cys Pro
                450                 455                 460
Leu Asn Ile Gly Ser Gln Gly Ser Thr Asp Tyr
465                 470                 475

<210> SEQ ID NO 35
<211> LENGTH: 2815
<212> TYPE: DNA
<213> ORGANISM: Homo sapiens

<400> SEQUENCE: 35
gaattcggca cgagctcttc tcccctgatt caagactcct ctgctttgga ctgaagcact    60
gcaggagttt gtgaccaaga acttcaagag tcaagacaga aggaagccaa gggagcagtg   120
caatggattt ctcagtaaag gtagacatag agaaggaggt gacctgcccc atctgcctgg   180
agctcctgac agaacctctg agcctagatt gtggccacag cttctgccaa gcctgcatca   240
ctgcaaagat caaggagtca gtgatcatct caagagggga aagcagctgt cctgtgtgtc   300
agaccagatt ccagcctggg aacctccgac ctaatcggca tctggccaac atagttgaga   360
gagtcaaaga ggtcaagatg agcccacagg aggggcagaa gagagatgtc tgtgagcacc   420
atggaaaaaa actccagatc ttctgtaagg aggatggaaa agtcatttgc tgggtttgtg   480
aactgtctca ggaacaccaa ggtcaccaaa cattccgcat aaacgaggtg gtcaaggaat   540
gtcaggaaaa gctgcaggta gccctgcaga ggctgataaa ggaggatcaa gaggctgaga   600
agctggaaga tgacatcaga caagagagaa ccgcctggaa gatcgagaga cagaagattc   660
tgaaagggtt caatgaaatg agagtcatct tggacaatga ggagcagaga gagctgcaaa   720
agctggagga aggtgaggtg aatgtgctgg acaacctggc agcagctaca gaccagctgg   780
tccagcagag gcaggatgcc agcacgctca tctcagatct ccagcggagg ttgacgggat   840
cgtcagtaga gatgctgcag gatgtgattg acgtcatgaa aaggagtgaa agctggacat   900
tgaagaagcc aaaatctgtt tccaagaaac taaagagtgt attccgagta ccagatctga   960
```

```
gtgggatgct gcaagttctt aaagagctga cagatgtcca gtactactgg gtggacgtga    1020
tgctgaatcc aggcagtgcc acttcgaatg ttgctatttc tgtggatcag agacaagtga    1080
aaactgtacg cacctgcaca tttaagaatt caaatccatg tgattttcct gcttttggtg    1140
tcttcggctg ccaatatttc tcttcgggga aatattactg ggaagtagat gtgtctggaa    1200
agattgcctg gatcctgggc gtacacagta aataagtag tctgaataaa aggaagagct    1260
ctgggtttgc ttttgatcca agtgtaaatt attcaaaagt ttactccaga tatagacctc    1320
aatatggcta ctgggttata ggattacaga atacatgtga atataatgct tttgaggact    1380
cctcctcttc tgatcccaag gttttgactc tctttatggc tgtgctccct gtcgtattgg    1440
ggttttccta gactatgagg caggcattgt ctcattttc aatgtcacaa accacggagc    1500
actcatctac aagttctctg gatgtcgctt ttctcgacct gcttatccgt atttcaatcc    1560
ttggaactgc ctagtcccca tgactgtgtg cccaccgagc tcctgagtgt tctcattcct    1620
ttacccactt ctgcatagta gcccttgtgc tgagactcag attctgcacc tgagttcatc    1680
tctactgaga ccatctcttc ctttctttcc ccttctttta cttagaatgt ctttgtattc    1740
atttgctagg gcttccatag caaagcatca tagattgctg atttaaactg taattgtatt    1800
gccgtactgt gggctggaaa tcccaaatct agattccagc agagttggtt ctttctgagg    1860
tctgcaagga agggctctgt tccatgcctc tctccttggc ttgtagaagg catcttgtcc    1920
ctatgactct tcacattgtc tttatgtaca tctctgtgcc caagttttcc cttttatta    1980 agacaccagt catactggct cagggcccac cgctaatgcc ttaatgaaat cattttaaca    2040
ttatattctc tacaaagacc ttatttccaa ataagataat atttggaggt attgggaata    2100
aaatttgagg aaggcacgat ttcactcata acaatcttac cctttcttgc aagagatgct    2160
tgtacattat tttcctaata ccttggtttc actagtagta aacattatta ttttttttat    2220
atttgcaaag gaaacatatc taatccttcc tatagaaaga acagtattgc tgtaattcct    2280
tttcttttct tcctcatttc ctctgcccct taaaagattg aagaaagaga aacttgtcaa    2340
ctcatatcca cgttatctag caaaagtcat aagaatctat cactaagtaa tgtatccttc    2400
agaatgtgtt ggtttaccag tgacacccca tattcatcac aaaattaaag caagaagtcc    2460
atagtaattt atttgctaat agtggatttt taatgctcag agtttctgag gtcaaatttt    2520 atctttttcac ttacaagctc tatgatctta ataatttac ttaatgtatt ttggtgtatt    2580
ttcctcaaat taatattggt gttcaagact atatctaatt cctctgatca ctttgagaaa    2640 caaacttta ttaaatgtaa ggcacttttc tatgaatttt aaatataaaa ataaatattg    2700
ttctgattat tactgaaaag atgtcagcca tttcaatgtc ttgggaaaca attttttgtt    2760
tttgttctgt tttcttttg cttcaataaa acaatagctg gctctaaaaa aaaaa          2815
```

<210> SEQ ID NO 36
<211> LENGTH: 442
<212> TYPE: PRT
<213> ORGANISM: Homo sapiens

<400> SEQUENCE: 36

```
Met Asp Phe Ser Val Lys Val Asp Ile Glu Lys Glu Val Thr Cys Pro
  1               5                  10                  15

Ile Cys Leu Glu Leu Leu Thr Glu Pro Leu Ser Leu Asp Cys Gly His
                 20                  25                  30

Ser Phe Cys Gln Ala Cys Ile Thr Ala Lys Ile Lys Glu Ser Val Ile
             35                  40                  45
```

```
Ile Ser Arg Gly Glu Ser Ser Cys Pro Val Cys Gln Thr Arg Phe Gln
 50                  55                  60

Pro Gly Asn Leu Arg Pro Asn Arg His Leu Ala Asn Ile Val Glu Arg
 65                  70                  75                  80

Val Lys Glu Val Lys Met Ser Pro Gln Glu Gly Gln Lys Arg Asp Val
                 85                  90                  95

Cys Glu His His Gly Lys Lys Leu Gln Ile Phe Cys Lys Glu Asp Gly
                100                 105                 110

Lys Val Ile Cys Trp Val Cys Glu Leu Ser Gln Glu His Gln Gly His
            115                 120                 125

Gln Thr Phe Arg Ile Asn Glu Val Val Lys Glu Cys Gln Glu Lys Leu
        130                 135                 140

Gln Val Ala Leu Gln Arg Leu Ile Lys Glu Asp Gln Glu Ala Glu Lys
145                 150                 155                 160

Leu Glu Asp Asp Ile Arg Gln Glu Arg Thr Ala Trp Lys Ile Glu Arg
                165                 170                 175

Gln Lys Ile Leu Lys Gly Phe Asn Glu Met Arg Val Ile Leu Asp Asn
            180                 185                 190

Glu Glu Gln Arg Glu Leu Gln Lys Leu Glu Gly Gly Val Asn Val
        195                 200                 205

Leu Asp Asn Leu Ala Ala Ala Thr Asp Gln Leu Val Gln Gln Arg Gln
210                 215                 220

Asp Ala Ser Thr Leu Ile Ser Asp Leu Gln Arg Arg Leu Thr Gly Ser
225                 230                 235                 240

Ser Val Glu Met Leu Gln Asp Val Ile Asp Val Met Lys Arg Ser Glu
                245                 250                 255

Ser Trp Thr Leu Lys Lys Pro Lys Ser Val Ser Lys Lys Leu Lys Ser
            260                 265                 270

Val Phe Arg Val Pro Asp Leu Ser Gly Met Leu Gln Val Leu Lys Glu
        275                 280                 285

Leu Thr Asp Val Gln Tyr Tyr Trp Val Asp Val Met Leu Asn Pro Gly
        290                 295                 300

Ser Ala Thr Ser Asn Val Ala Ile Ser Val Asp Gln Arg Gln Val Lys
305                 310                 315                 320

Thr Val Arg Thr Cys Thr Phe Lys Asn Ser Asn Pro Cys Asp Phe Ser
                325                 330                 335

Ala Phe Gly Val Phe Gly Cys Gln Tyr Phe Ser Ser Gly Lys Tyr Tyr
            340                 345                 350

Trp Glu Val Asp Val Ser Gly Lys Ile Ala Trp Ile Leu Gly Val His
        355                 360                 365

Ser Lys Ile Ser Ser Leu Asn Lys Arg Lys Ser Ser Gly Phe Ala Phe
        370                 375                 380

Asp Pro Ser Val Asn Tyr Ser Lys Val Tyr Ser Arg Tyr Arg Pro Gln
385                 390                 395                 400

Tyr Gly Tyr Trp Val Ile Gly Leu Gln Asn Thr Cys Glu Tyr Asn Ala
                405                 410                 415

Phe Glu Asp Ser Ser Ser Ser Asp Pro Lys Val Leu Thr Leu Phe Met
            420                 425                 430

Ala Val Leu Pro Val Val Leu Gly Phe Ser
        435                 440

<210> SEQ ID NO 37
<211> LENGTH: 2984
<212> TYPE: DNA
<213> ORGANISM: Homo sapiens
```

<400> SEQUENCE: 37

```
gttttacgct gccgccggca tccgctcgga cgcggccacg ttgtcttgcg cgctttgccc      60
gcctggccct gggactctga ccctcggcta ccctttcctg ccccactagc gtggccgcga     120
gcctcggtga gccggccgta ttcccgctct cgcttagggg gcacaggcgc aggcatcggc     180
ccggccactc caagccttcg gtgcgcgggc gcgtctggga tacggcccg ggaggcgccg      240
ccctccgtcc gcccggtgcc tctcaggaac agcgaaccgg agagagcgcc ggagagttgg     300
gctcagtgcg gagctcggcg ccggggccca tgcccgtgcg cccccgcagg ccggcgccat     360
ggcctccggg agtgtggccg agtgcctgca gcaggagacc cctgccccg tgtgcctgca     420
gtacttcgca gagcccatga tgctcgactg cggccataac atctgttgcg cgtgcctcgc     480
ccgctgctgg ggcacggcag agactaacgt gtcgtgcccg cagtgccggg agaccttccc     540
gcagaggcac atgcggccca accggcacct ggccaacgtg acccaactgg taaagcagct     600
gcgcaccgag cggccgtcgg ggcccggcgg cgagatgggc gtgtgcgaga agcaccgcga     660
gccctgaag ctgtactgcg aggaggacca gatgcccatc tgcgtggtgt gcgaccgctc      720
ccgcgagcac cgcggccaca gcgtgctgcc gctcgaggag gcggtggagg gcttcaagga     780
gcaaatccag aaccagctcg accatttaaa aagagtgaaa gatttaaaga agagacgtcg     840
ggcccagggg gaacaggcac gagctgaact cttgagccta cccagatgg agagggagaa      900
gattgtttgg gagtttgagc agctgtatca ctccttaaag gagcatgagt atcgcctcct     960
ggcccgcctt gaggagctag acttggccat ctacaatagc atcaatggtg ccatcaccca    1020
gttctcttgc aacatctccc acctcagcag cctgatcgct cagctagaag agaagcagca    1080
gcagcccacc agggagctcc tgcaggacat tggggacaca ttgagcaggg ctgaaagaat    1140
caggattcct gaaccttgga tcacacctcc agatttgcaa gagaaaatcc acattttgc     1200
ccaaaaatgt ctattcttga cggagagtct aaagcagttc acagaaaaaa tgcagtcaga    1260
tatggagaaa atccaagaat taagagaggc tcagttatac tcagtggacg tgactctgga    1320
cccagacacg gcctacccca gcctgatcct ctctgataat ctgcggcaag tgcggtacag    1380
ttacctccaa caggacctgc ctgacaaccc cgagaggttc aatctgtttc cctgtgtctt    1440
gggctctcca tgcttcatcg ccgggagaca ttattgggag gtagaggtgg gagataaagc    1500
caagtggacc ataggtgtct gtgaagactc agtgtgcaga aaaggtggag taacctcagc    1560
cccccagaat ggattctggg cagtgtcttt gtggtatggg aaagaatatt gggctcttac    1620
ctccccaatg actgccctac ccctgcggac cccgctccag cgggtgggga ttttcttgga    1680
ctatgatgct ggtgaggtct ccttctacaa cgtgacagag aggtgtcaca ccttcacttt    1740
ctctcatgct accttttgtg ggcctgtccg gccctacttc agtctgagtt actcgggagg    1800
gaaaagtgca gctcctctga tcatctgccc catgagtggg atagatgggt tttctggcca    1860
tgttgggaat catggtcatt ccatggagac ctccccttga ggaggtgaat tcaggccaaa    1920
agggctgttg gctgtaatcc tacgccaggc acaaggcatc ttgttgcctt gccacgtcct    1980
gtcacagctg ggtatcctta ccatgttcca cgccttgca gtgggagaca ggatgtccat     2040
gttctctacc atccttttcc ttcccatgca gattgtgaaa tgtaatgaga tgtatcaaga    2100
catcctagaa ataaaaacca gatgtccacc tccagtgttt catactttct ggttttacac    2160
atcgctggag ggataaagag tatggataat ctttggattt ggagagccgt tcaagatact    2220
tccagcttct tggctcagcc tggcttcctc tggttcagcc ccacataatg attatgcta     2280
tttgctgtca tttctgggct agggctcctt tctaacaacc tagactggaa taaggccctg    2340
```

-continued

```
tcagcatggc tcccttatc ccagttttcc gtctgggaac agtacctctg cccctgattc    2400
ccaatgtgcc atagttttat taactccatt aaagaagcct gtatgtgttt tggttagtta    2460
cagttatttt acaataatgg tgggtaatgg ccccacctct gttatgagat aatgttctaa    2520
tcaatgtctc tgcctttgta tcttttctga gggctttgtc tgttctcttc attctaatga    2580
aaggtgtatt ctagtgctgg gtgcatatca tccaggataa tattctgccc aactccatcc    2640
tctgttacta gatcccttac cagtcacatt tgtggactgg tggccagtcg tataccatcc    2700
ctggaaggat tctgggacaa tattccaggg attcattgac ttcttggctc cttttctcca    2760
tttcctttgg gggaagggggg aattgaccat gcttaagtgc atcctatcaa ggggcagctc    2820
cgtccccatg gccattggat catgagacac tcgaagtcag aaggctgggg cagatcactt    2880
caagcaagcc cccatgatgg ttctcagtcc tgcttctctg tgggtacgtg ccctctgtt    2940 taaaaataaa ctgaatatgg atgtttaaaa aaaaaaaaa aaaa                      2984
```

<210> SEQ ID NO 38
<211> LENGTH: 513
<212> TYPE: PRT
<213> ORGANISM: Homo sapiens

<400> SEQUENCE: 38

```
Met Ala Ser Gly Ser Val Ala Glu Cys Leu Gln Gln Glu Thr Thr Cys
 1               5                  10                  15

Pro Val Cys Leu Gln Tyr Phe Ala Glu Pro Met Met Leu Asp Cys Gly
            20                  25                  30

His Asn Ile Cys Cys Ala Cys Leu Ala Arg Cys Trp Gly Thr Ala Glu
        35                  40                  45

Thr Asn Val Ser Cys Pro Gln Cys Arg Glu Thr Phe Pro Gln Arg His
    50                  55                  60

Met Arg Pro Asn Arg His Leu Ala Asn Val Thr Gln Leu Val Lys Gln
65                  70                  75                  80

Leu Arg Thr Glu Arg Pro Ser Gly Pro Gly Gly Glu Met Gly Val Cys
                85                  90                  95

Glu Lys His Arg Glu Pro Leu Lys Leu Tyr Cys Glu Glu Asp Gln Met
            100                 105                 110

Pro Ile Cys Val Val Cys Asp Arg Ser Arg Glu His Arg Gly His Ser
        115                 120                 125

Val Leu Pro Leu Glu Glu Ala Val Glu Gly Phe Lys Glu Gln Ile Gln
    130                 135                 140

Asn Gln Leu Asp His Leu Lys Arg Val Lys Asp Leu Lys Lys Arg Arg
145                 150                 155                 160

Arg Ala Gln Gly Glu Gln Ala Arg Ala Glu Leu Leu Ser Leu Thr Gln
                165                 170                 175

Met Glu Arg Glu Lys Ile Val Trp Glu Phe Glu Gln Leu Tyr His Ser
            180                 185                 190

Leu Lys Glu His Glu Tyr Arg Leu Leu Ala Arg Leu Glu Glu Leu Asp
        195                 200                 205

Leu Ala Ile Tyr Asn Ser Ile Asn Gly Ala Ile Thr Gln Phe Ser Cys
    210                 215                 220

Asn Ile Ser His Leu Ser Ser Leu Ile Ala Gln Leu Glu Glu Lys Gln
225                 230                 235                 240

Gln Gln Pro Thr Arg Glu Leu Leu Gln Asp Ile Gly Asp Thr Leu Ser
                245                 250                 255

Arg Ala Glu Arg Ile Arg Ile Pro Glu Pro Trp Ile Thr Pro Pro Asp
```

```
                260                 265                 270
Leu Gln Glu Lys Ile His Ile Phe Ala Gln Lys Cys Leu Phe Leu Thr
            275                 280                 285
Glu Ser Leu Lys Gln Phe Thr Glu Lys Met Gln Ser Asp Met Glu Lys
        290                 295                 300
Ile Gln Glu Leu Arg Glu Ala Gln Leu Tyr Ser Val Asp Val Thr Leu
305                 310                 315                 320
Asp Pro Asp Thr Ala Tyr Pro Ser Leu Ile Leu Ser Asn Leu Arg
                325                 330                 335
Gln Val Arg Tyr Ser Tyr Leu Gln Gln Asp Leu Pro Asp Asn Pro Glu
            340                 345                 350
Arg Phe Asn Leu Phe Pro Cys Val Leu Gly Ser Pro Cys Phe Ile Ala
                355                 360                 365
Gly Arg His Tyr Trp Glu Val Glu Val Gly Asp Lys Ala Lys Trp Thr
            370                 375                 380
Ile Gly Val Cys Glu Asp Ser Val Cys Arg Lys Gly Gly Val Thr Ser
385                 390                 395                 400
Ala Pro Gln Asn Gly Phe Trp Ala Val Ser Leu Trp Tyr Gly Lys Glu
                405                 410                 415
Tyr Trp Ala Leu Thr Ser Pro Met Thr Ala Leu Pro Leu Arg Thr Pro
            420                 425                 430
Leu Gln Arg Val Gly Ile Phe Leu Asp Tyr Asp Ala Gly Glu Val Ser
                435                 440                 445
Phe Tyr Asn Val Thr Glu Arg Cys His Thr Phe Thr Phe Ser His Ala
            450                 455                 460
Thr Phe Cys Gly Pro Val Arg Pro Tyr Phe Ser Leu Ser Tyr Ser Gly
465                 470                 475                 480
Gly Lys Ser Ala Ala Pro Leu Ile Ile Cys Pro Met Ser Gly Ile Asp
                485                 490                 495
Gly Phe Ser Gly His Val Gly Asn His Gly His Ser Met Glu Thr Ser
            500                 505                 510
Pro

<210> SEQ ID NO 39
<211> LENGTH: 2704
<212> TYPE: DNA
<213> ORGANISM: Homo sapiens

<400> SEQUENCE: 39
gttttacgct gccgccggca tccgctcgga cgcggccacg ttgtcttgcg cgctttgccc      60
gcctggccct gggactctga ccctcggcta ccctttcctg ccccactagc gtggccgcga     120
gcctcggtga gccggccgta ttcccgctct cgcttagggg gcacaggcgc aggcatcggc     180
ccggccactc caagccttcg gtgcgcgggc gcgtctggga tacggccccg ggaggcgccg     240
ccctccgtcc gcccggtgcc tctcaggaac agcgaaccgg agagagcgcc ggagagttgg     300
gctcagtgcg gagctcggcg ccggggccca tgcccgtgcg cccccgcagg ccggcgccat     360
ggcctccggg agtgtggccg agtgcctgca gcaggagacc acctgccccg tgtgcctgca     420
gtacttcgca gagcccatga tgctcgactg cggccataac atctgttgcg cgtgcctcgc     480
ccgctgctgg ggcacggcag agactaacgt gtcgtgcccg cagtgccggg agaccttccc     540
gcagaggcac atgcggccca accggcacct ggccaacgtg acccaactgg taaagcagct     600
gcgcaccgag cggccgtcgg ggcccggcgg cgagatgggc gtgtgcgaga agcaccgcga     660 gccccctgaag ctgtactgcg aggaggacca gatgcccatc tgcgtggtgt gcgaccgctc     720
```

```
ccgcgagcac cgcggccaca gcgtgctgcc gctcgaggag gcggtggagg gcttcaagga    780
gcaaatccag aaccagctcg accatttaaa aagagtgaaa gatttaaaga agagacgtcg    840
ggcccagggg gaacaggcac gagctgaact cttgagccta acccagatgg agagggagaa    900
gattgtttgg gagtttgagc agctgtatca ctccttaaag gagcatgagt atcgcctcct    960
ggcccgcctt gaggagctag acttggccat ctacaatagc atcaatggtg ccatcaccca   1020
gttctcttgc aacatctccc acctcagcag cctgatcgct cagctagaag agaagcagca   1080
gcagcccacc agggagctcc tgcaggacat tggggacaca ttgagcaggg ctgaaagaat   1140
caggattcct gaaccttgga tcacacctcc agatttgcaa gagaaaatcc acattttgc    1200 ccaaaaatgt ctattcttga cggagagtct aaagcagttc acagaaaaaa tgcagtcaga   1260
tatggagaaa atccaagaat taagagaggc tcagttatac tcagtggacg tgactctgga   1320
cccagacacg gcctaccccca gcctgatcct ctctgataat ctgcggcaag tgcggtacag   1380
ttacctccaa caggacctgc ctgacaaccc cgagaggtct ccttctacaa cgtgacagag   1440
aggtgtcaca ccttcacttt ctctcatgct accttttgtg ggcctgtccg ccctacttc    1500 agtctgagtt actcgggagg gaaaagtgca gctcctctga tcatctgccc catgagtggg   1560
atagatgggt tttctggcca tgttgggaat catggtcatt ccatggagac ctccccttga   1620
ggaggtgaat tcaggccaaa agggctgttg gctgtaatcc tacgccaggc acaaggcatc   1680
ttgttgcctt gccacgtcct gtcacagctg gtatcctta ccatgttcca cgcccttgca    1740
gtgggagaca ggatgtccat gttctctacc atccttttcc ttcccatgca gattgtgaaa   1800
tgtaatgaga tgtatcaaga catcctagaa ataaaaacca gatgtccacc tccagtgttt   1860
catactttct ggttttacac atcgctggag ggataaagag tatggataat ctttggattt   1920
ggagagccgt tcaagatact tccagcttct tggctcagcc tggcttcctc tggttcagcc   1980
ccacataatg attatggcta tttgctgtca tttctgggct agggctcctt tctaacaacc   2040
tagactggaa taaggccctg tcagcatggc tccctttatc ccagttttcc gtctgggaac   2100
agtacctctg cccctgattc ccaatgtgcc atagttttat taactccatt aaagaagcct   2160
gtatgtgttt tggttagtta cagttatttt acaataatgg tgggtaatgg ccccacctct   2220
gttatgagat aatgttctaa tcaatgtctc tgcctttgta tctttcctga gggctttgtc   2280
tgttctcttc attctaatga aggtgtatt ctagtgctgg gtgcatatca tccaggataa    2340
tattctgccc aactccatcc tctgttacta gatcccttac cagtcacatt tgtggactgg   2400
tggccagtcg tataccatcc ctggaaggat tctgggacaa tattccaggg attcattgac   2460
ttcttggctc ctttctcca tttcctttgg gggaagggg aattgaccat gcttaagtgc     2520
atcctatcaa ggggcagctc cgtccccatg gccattggat catgagacac tcgaagtcag   2580
aaggctgggg cagatcactt caagcaagcc cccatgatgg ttctcagtcc tgcttctctg   2640
tgggtacgtg cccctctgtt taaaaataaa ctgaatatgg atgtttaaaa aaaaaaaaa    2700 aaaa                                                                 2704
```

<210> SEQ ID NO 40
<211> LENGTH: 358
<212> TYPE: PRT
<213> ORGANISM: Homo sapiens

<400> SEQUENCE: 40

Met Ala Ser Gly Ser Val Ala Glu Cys Leu Gln Gln Glu Thr Thr Cys
1               5                   10                  15

```
Pro Val Cys Leu Gln Tyr Phe Ala Glu Pro Met Met Leu Asp Cys Gly
        20                  25                  30

His Asn Ile Cys Cys Ala Cys Leu Ala Arg Cys Trp Gly Thr Ala Glu
            35                  40                  45

Thr Asn Val Ser Cys Pro Gln Cys Arg Glu Thr Phe Pro Gln Arg His
 50                  55                  60

Met Arg Pro Asn Arg His Leu Ala Asn Val Thr Gln Leu Val Lys Gln
 65                  70                  75                  80

Leu Arg Thr Glu Arg Pro Ser Gly Pro Gly Gly Glu Met Gly Val Cys
                 85                  90                  95

Glu Lys His Arg Glu Pro Leu Lys Leu Tyr Cys Glu Glu Asp Gln Met
            100                 105                 110

Pro Ile Cys Val Val Cys Asp Arg Ser Arg Glu His Arg Gly His Ser
            115                 120                 125

Val Leu Pro Leu Glu Glu Ala Val Glu Gly Phe Lys Glu Gln Ile Gln
130                 135                 140

Asn Gln Leu Asp His Leu Lys Arg Val Lys Asp Leu Lys Lys Arg Arg
145                 150                 155                 160

Arg Ala Gln Gly Glu Gln Ala Arg Ala Glu Leu Leu Ser Leu Thr Gln
                165                 170                 175

Met Glu Arg Glu Lys Ile Val Trp Glu Phe Glu Gln Leu Tyr His Ser
            180                 185                 190

Leu Lys Glu His Glu Tyr Arg Leu Leu Ala Arg Leu Glu Glu Leu Asp
            195                 200                 205

Leu Ala Ile Tyr Asn Ser Ile Asn Gly Ala Ile Thr Gln Phe Ser Cys
210                 215                 220

Asn Ile Ser His Leu Ser Ser Leu Ile Ala Gln Leu Glu Glu Lys Gln
225                 230                 235                 240

Gln Gln Pro Thr Arg Glu Leu Leu Gln Asp Ile Gly Asp Thr Leu Ser
                245                 250                 255

Arg Ala Glu Arg Ile Arg Ile Pro Glu Pro Trp Ile Thr Pro Pro Asp
            260                 265                 270

Leu Gln Glu Lys Ile His Ile Phe Ala Gln Lys Cys Leu Phe Leu Thr
            275                 280                 285

Glu Ser Leu Lys Gln Phe Thr Glu Lys Met Gln Ser Asp Met Glu Lys
290                 295                 300

Ile Gln Glu Leu Arg Glu Ala Gln Leu Tyr Ser Val Asp Val Thr Leu
305                 310                 315                 320

Asp Pro Asp Thr Ala Tyr Pro Ser Leu Ile Leu Ser Asp Asn Leu Arg
                325                 330                 335

Gln Val Arg Tyr Ser Tyr Leu Gln Gln Asp Leu Pro Asp Asn Pro Glu
            340                 345                 350

Arg Ser Pro Ser Thr Thr
        355

<210> SEQ ID NO 41
<211> LENGTH: 2290
<212> TYPE: DNA
<213> ORGANISM: Homo sapiens

<400> SEQUENCE: 41
cttcacctct tcaaccagga gccgagattt ctgttgctct gaagccatcc agggtctttt      60
aaccagaaga gagaggagag cctcaggagt taggaccaga agaagccagg gaagcagtgc     120
aatggcttca aaaatcttgc ttaacgtaca agaggaggtg acctgtccca tctgcctgga     180
```

```
gctgttgaca gaacccttga gtctagactg tggccacagc ctctgccgag cctgcatcac    240
tgtgagcaac aaggaggcag tgaccagcat gggaggaaaa agcagctgtc ctgtgtgtgg    300
tatcagttac tcatttgaac atctacaggc taatcagcat ctggccaaca tagtggagag    360
actcaaggag gtcaagttga gcccagacaa tgggaagaag agagatctct gtgatcatca    420
tggagagaaa ctcctactct tctgtaagga ggataggaaa gtcatttgct ggctttgtga    480
gcggtctcag gagcaccgtg gtcaccacac agtcctcacg gaggaagtat tcaaggaatg    540
tcaggagaaa ctccaggcag tcctcaagag gctgaagaag gaagaggagg aagctgagaa    600
gctggaagct gacatcagag aagagaaaac ttcctggaag tatcaggtac aaactgagag    660
acaaaggata caaacagaat ttgatcagct tagaagcatc ctaaataatg aggagcagag    720
agagctgcaa agattggaag aagaagaaaa gaagacgctg gataagtttg cagaggctga    780
ggatgagcta gttcagcaga agcagttggt gagagagctc atctcagatg tggagtgtcg    840
gagtcagtgg tcaacaatgg agctgctgca ggacatgagt ggaatcatga atggagtga    900 gatctggagg ctgaaaaagc caaaaatggt ttccaagaaa ctgaagactg tattccatgc    960
tccagatctg agtaggatgc tgcaaatgtt tagagaactg acagctgtcc ggtgctactg   1020
ggtggatgtc acactgaatt cagtcaacct aaatttgaat cttgtccttt cagaagatca   1080
gagacaagtg atatctgtgc aatttggcc ttttcagtgt tataattatg gtgtcttggg    1140
atcccaatat ttctcctctg ggaaacatta ctgggaagtg gacgtgtcca agaaaactgc   1200
ctggatcctg ggggtatact gtagaacata ttcccgccat atgaagtatg ttgttagaag   1260
atgtgcaaat cgtcaaaatc tttacaccaa atacagacct ctatttggct actgggttat   1320
agggttacag aataaatgta agtatggtgt ctttgaagag tctttgtcct ctgatcccga   1380
ggttttgact ctctccatgg ctgtgcctcc ctgccgtgtt ggggttttcc tcgactatga   1440
agcaggcatt gtctcatttt tcaatgtcac aagccatggc tccctcattt acaagttctc   1500
taaatgttgc ttttctcagc ctgtttatcc atatttcaat ccttggaact gtccagctcc   1560
catgactcta tgcccaccaa gctcttgaat tttctcattt cttcacctac aaccctttgt   1620
ctcgacttat ctcctgcaac tgactcatct gcaacattca caccattgct tccttgtggt   1680
ttcccttctt tagaactttt actcatcctt gagatgtatg gtgtatttgg cttgagttat   1740
gagagatgct tatttattca tttactcttt ttcatatttt cagagaaagt tacctaatcc   1800
ctcctaaaga cacagcagta tgggtataac atccttgcct tcccatttat ccatgtttca   1860
ctttatcact gatgtgaaga ggcccaaagc ctgttagcca ccatccatgc tacctaggta   1920
gtccatagga accaccccca tgaccaccac caacatcaac taaaggttct tggagggtat   1980
gtcagtgtgt tgctcaggat accccaggta catcaaggaa tcaaggagag gaaaatatga   2040
gcaatatgtg tattcagagt gaagatttta tgtccagagt atttgagctc aaaccttgcc   2100
tgttgttttc taatcatgat gaatactttc tcagtttctt tttcctgaaa tataaattgg   2160
gatttaagac tgtacctaac tattaagatc actgtgtaaa actaagtgtc tctaaatgta   2220
atgcatcgat ttagtgtctg gaacataata aatatttgct ctcatgattg ctaaaaaaaa   2280
aaaaaaaaa                                                          2290
```

<210> SEQ ID NO 42
<211> LENGTH: 488
<212> TYPE: PRT
<213> ORGANISM: Homo sapiens

<400> SEQUENCE: 42

```
Met Ala Ser Lys Ile Leu Leu Asn Val Gln Glu Val Thr Cys Pro
 1               5                  10                  15

Ile Cys Leu Glu Leu Leu Thr Glu Pro Leu Ser Leu Asp Cys Gly His
                 20                  25                  30

Ser Leu Cys Arg Ala Cys Ile Thr Val Ser Asn Lys Glu Ala Val Thr
             35                  40                  45

Ser Met Gly Gly Lys Ser Ser Cys Pro Val Cys Gly Ile Ser Tyr Ser
     50                  55                  60

Phe Glu His Leu Gln Ala Asn Gln His Leu Ala Asn Ile Val Glu Arg
65                  70                  75                  80

Leu Lys Glu Val Lys Leu Ser Pro Asp Asn Gly Lys Lys Arg Asp Leu
                 85                  90                  95

Cys Asp His His Gly Glu Lys Leu Leu Leu Phe Cys Lys Glu Asp Arg
             100                 105                 110

Lys Val Ile Cys Trp Leu Cys Glu Arg Ser Gln Glu His Arg Gly His
             115                 120                 125

His Thr Val Leu Thr Glu Glu Val Phe Lys Glu Cys Gln Glu Lys Leu
     130                 135                 140

Gln Ala Val Leu Lys Arg Leu Lys Lys Glu Glu Glu Ala Glu Lys Lys
145                 150                 155                 160

Leu Glu Ala Asp Ile Arg Glu Glu Lys Thr Ser Trp Lys Tyr Gln Val
                 165                 170                 175

Gln Thr Glu Arg Gln Arg Ile Gln Thr Glu Phe Asp Gln Leu Arg Ser
             180                 185                 190

Ile Leu Asn Asn Glu Glu Gln Arg Glu Leu Gln Arg Leu Glu Glu Glu
             195                 200                 205

Glu Lys Lys Thr Leu Asp Lys Phe Ala Glu Ala Glu Asp Glu Leu Val
     210                 215                 220

Gln Gln Lys Gln Leu Val Arg Glu Leu Ile Ser Asp Val Glu Cys Arg
225                 230                 235                 240

Ser Gln Trp Ser Thr Met Glu Leu Leu Gln Asp Met Ser Gly Ile Met
                 245                 250                 255

Lys Trp Ser Glu Ile Trp Arg Leu Lys Lys Pro Lys Met Val Ser Lys
             260                 265                 270

Lys Leu Lys Thr Val Phe His Ala Pro Asp Leu Ser Arg Met Leu Gln
             275                 280                 285

Met Phe Arg Glu Leu Thr Ala Val Arg Cys Tyr Trp Val Asp Val Thr
     290                 295                 300

Leu Asn Ser Val Asn Leu Asn Leu Asn Leu Val Leu Ser Glu Asp Gln
305                 310                 315                 320

Arg Gln Val Ile Ser Val Pro Ile Trp Pro Phe Gln Cys Tyr Asn Tyr
                 325                 330                 335

Gly Val Leu Gly Ser Gln Tyr Phe Ser Ser Gly Lys His Tyr Trp Glu
             340                 345                 350

Val Asp Val Ser Lys Lys Thr Ala Trp Ile Leu Gly Val Tyr Cys Arg
             355                 360                 365

Thr Tyr Ser Arg His Met Lys Tyr Val Val Arg Cys Ala Asn Arg
     370                 375                 380

Gln Asn Leu Tyr Thr Lys Tyr Arg Pro Leu Phe Gly Tyr Trp Val Ile
385                 390                 395                 400

Gly Leu Gln Asn Lys Cys Lys Tyr Gly Val Phe Glu Glu Ser Leu Ser
                 405                 410                 415

Ser Asp Pro Glu Val Leu Thr Leu Ser Met Ala Val Pro Pro Cys Arg
             420                 425                 430
```

```
Val Gly Val Phe Leu Asp Tyr Glu Ala Gly Ile Val Ser Phe Phe Asn
        435                 440                 445

Val Thr Ser His Gly Ser Leu Ile Tyr Lys Phe Ser Lys Cys Cys Phe
    450                 455                 460

Ser Gln Pro Val Tyr Pro Tyr Phe Asn Pro Trp Asn Cys Pro Ala Pro
465                 470                 475                 480

Met Thr Leu Cys Pro Pro Ser Ser
                485
```

<210> SEQ ID NO 43
<211> LENGTH: 2223
<212> TYPE: DNA
<213> ORGANISM: Homo sapiens

<400> SEQUENCE: 43

| | | | | | |
|---|---|---|---|---|---|
| cttcacctct | tcaaccagga | gccgagattt | ctgttgctct | gaagccatcc | agggtctttt | 60 |
| aaccagaaga | gagaggagag | cctcaggagt | taggaccaga | agaagccagg | gaagcagtgc | 120 |
| aatggcttca | aaatcttgc | ttaacgtaca | agaggaggtg | acctgtccca | tctgcctgga | 180 |
| gctgttgaca | gaacccttga | gtctagactg | tggccacagc | ctctgccgag | cctgcatcac | 240 |
| tgtgagcaac | aaggaggcag | tgaccagcat | gggaggaaaa | agcagctgtc | ctgtgtgtgg | 300 |
| tatcagttac | tcatttgaac | atctacaggc | taatcagcat | ctggccaaca | tagtggagag | 360 |
| actcaaggag | gtcaagttga | gcccagacaa | tgggaagaag | agagatctct | gtgatcatca | 420 |
| tggagagaaa | ctcctactct | tctgtaagga | ggataggaag | tattcaagga | atgtcaggag | 480 |
| aaactccagg | cagtcctcaa | gaggctgaag | aaggaagagg | aggaagctga | gaagctggaa | 540 |
| gctgacatca | gagaagagaa | aacttcctgg | aagtatcagg | tacaaactga | gagacaaagg | 600 |
| atacaaacag | aatttgatca | gcttagaagc | atcctaaata | tgaggagca | gagagagctg | 660 |
| caaagattgg | aagaagaaga | aaagaagacg | ctggataagt | ttgcagaggc | tgaggatgag | 720 |
| ctagttcagc | agaagcagtt | ggtgagagag | ctcatctcag | atgtggagtg | tcggagtcag | 780 |
| tggtcaacaa | tggagctgct | gcaggacatg | agtggaatca | tgaaatggag | tgagatctgg | 840 |
| aggctgaaaa | agccaaaaat | ggtttccaag | aaactgaaga | ctgtattcca | tgctccagat | 900 |
| ctgagtagga | tgctgcaaat | gtttagagaa | ctgacagctg | tccggtgcta | ctgggtggat | 960 |
| gtcacactga | attcagtcaa | cctaaatttg | aatcttgtcc | tttcagaaga | tcagagacaa | 1020 |
| gtgatatctg | tgccaatttg | gccttttcag | tgttataatt | atggtgtctt | gggatcccaa | 1080 |
| tatttctcct | ctgggaaaca | ttactgggaa | gtggacgtgt | ccaagaaaac | tgcctggatc | 1140 |
| ctgggggtat | actgtagaac | atattcccgc | catatgaagt | atgttgttag | aagatgtgca | 1200 |
| aatcgtcaaa | atctttacac | caaatacaga | cctctatttg | gctactgggt | tataggtta | 1260 |
| cagaataaaa | gtaagtatgg | tgtctttgaa | gagtcttttgt | cctctgatcc | cgaggttttg | 1320 |
| actctctcca | tggctgtgcc | tccctgccgt | gttgggttt | cctcgactta | tgaagcaggc | 1380 |
| attgtctcat | ttttcaatgt | cacaagccat | ggctccctca | tttacaagtt | ctctaaatgt | 1440 |
| tgcttttctc | agcctgttta | tccatatttc | aatccttgga | actgtccagc | tcccatgact | 1500 |
| ctatgcccac | caagctcttg | aattttctca | tttcttcacc | tacaacccctt | tgtctcgact | 1560 |
| tatctcctgc | aactgactca | tctgcaacat | tcacaccatt | gcttccttgt | ggtttccctt | 1620 |
| ctttagaact | tttactcatc | cttgagatgt | atggtgtatt | tggcttgagt | tatgagagat | 1680 |
| gcttatttat | tcatttactc | tttttcatat | tttcagagaa | agttacctaa | tccctcctaa | 1740 |
| agacacagca | gtatgggtat | aacatccttg | ccttcccatt | tatccatgtt | tcactttatc | 1800 |

-continued

```
actgatgtga agaggcccaa agcctgttag ccaccatcca tgctacctag gtagtccata    1860
ggaaccaccc ccatgaccac caccaacatc aactaaaggt tcttggaggg tatgtcagtg    1920
tgttgctcag gatacccag gtacatcaag gaatcaagga gaggaaaata tgagcaatat     1980
gtgtattcag agtgaagatt ttatgtccag agtatttgag ctcaaacctt gcctgttgtt    2040
ttctaatcat gatgaatact ttctcagttt cttttttcctg aaatataaat tgggatttaa   2100
gactgtacct aactattaag atcactgtgt aaaactaagt gtctctaaat gtaatgcatc    2160
gatttagtgt ctggaacata ataaatattt gctctcatga ttgctaaaaa aaaaaaaaa     2220 aaa                                                                  2223
```

<210> SEQ ID NO 44
<211> LENGTH: 243
<212> TYPE: PRT
<213> ORGANISM: Homo sapiens

<400> SEQUENCE: 44

```
Met Glu Leu Leu Gln Asp Met Ser Gly Ile Met Lys Trp Ser Glu Ile
 1               5                  10                  15

Trp Arg Leu Lys Lys Pro Lys Met Val Ser Lys Lys Leu Lys Thr Val
                20                  25                  30

Phe His Ala Pro Asp Leu Ser Arg Met Leu Gln Met Phe Arg Glu Leu
            35                  40                  45

Thr Ala Val Arg Cys Tyr Trp Val Asp Val Thr Leu Asn Ser Val Asn
        50                  55                  60

Leu Asn Leu Asn Leu Val Leu Ser Glu Asp Gln Arg Gln Val Ile Ser
65                  70                  75                  80

Val Pro Ile Trp Pro Phe Gln Cys Tyr Asn Tyr Gly Val Leu Gly Ser
                85                  90                  95

Gln Tyr Phe Ser Ser Gly Lys His Tyr Trp Glu Val Asp Val Ser Lys
            100                 105                 110

Lys Thr Ala Trp Ile Leu Gly Val Tyr Cys Arg Thr Tyr Ser Arg His
        115                 120                 125

Met Lys Tyr Val Val Arg Arg Cys Ala Asn Arg Gln Asn Leu Tyr Thr
    130                 135                 140

Lys Tyr Arg Pro Leu Phe Gly Tyr Trp Val Ile Gly Leu Gln Asn Lys
145                 150                 155                 160

Cys Lys Tyr Gly Val Phe Glu Glu Ser Leu Ser Ser Asp Pro Glu Val
                165                 170                 175

Leu Thr Leu Ser Met Ala Val Pro Pro Cys Arg Val Gly Val Phe Leu
            180                 185                 190

Asp Tyr Glu Ala Gly Ile Val Ser Phe Phe Asn Val Thr Ser His Gly
        195                 200                 205

Ser Leu Ile Tyr Lys Phe Ser Lys Cys Cys Phe Ser Gln Pro Val Tyr
    210                 215                 220

Pro Tyr Phe Asn Pro Trp Asn Cys Pro Ala Pro Met Thr Leu Cys Pro
225                 230                 235                 240

Pro Ser Ser
```

<210> SEQ ID NO 45
<211> LENGTH: 944
<212> TYPE: DNA
<213> ORGANISM: Homo sapiens

<400> SEQUENCE: 45

-continued

```
gagagggagag cctcaggagt taggaccaga agaagccagg gaagcagtgc aatggcttca      60
aaaatcttgc ttaacgtaca agaggaggtg acctgtccca tctgcctgga gctgttgaca     120
gaacccttga gtctagactg tggccacagc ctctgccgag cctgcatcac tgtgagcaac     180
aaggaggcag tgaccagcat gggaggaaaa agcagctgtc ctgtgtgtgg tatcagttac     240
tcatttgaac atctacaggc taatcagcat ctggccaaca tagtggagag actcaaggag     300
gtcaagttga gcccagacaa tgggaagaag agagatctct gtgatcatca tggagagaaa     360
ctcctactct tctgtaagga ggataggaaa gtcatttgct ggctttgtga gcggtctcag     420
gagcaccgtg gtcaccacac agtcctcacg gaagaagtat tcaaggaatg tcaggagaaa     480
ctccaggcag tcctcaagag gctgaagaag gaagaggagg aagctgagaa gctggaagct     540
gacatcagag aagagaaaac ttcctggaag tatcaggtac aaactgagag acaaaggata     600
caaacagaat ttgatcagct tagaagcatc ctaaataatg aggagcagag agagctgcaa     660
agattggaag aagaagaaaa gaagacgctg gataagtttg cagaggctga ggatgagcta     720
gttcagcaga gcagttggt gagagagctc atctcagatg tggagtgtcg gagtcagtgg     780
tcaacaatgg agctgctgca ggacatgagt ggaatcatga atggtgcgt atgggtggcc     840 acgagtggtg cttgtgagtt ataaagaagt gtttgtagct attagagtta tttggtggtc     900
aattggaata aaaatctcc cagagtagta aaaaaaaaa aaaa                        944
```

<210> SEQ ID NO 46
<211> LENGTH: 270
<212> TYPE: PRT
<213> ORGANISM: Homo sapiens

<400> SEQUENCE: 46

```
Met Ala Ser Lys Ile Leu Leu Asn Val Gln Glu Glu Val Thr Cys Pro
 1               5                  10                  15

Ile Cys Leu Glu Leu Leu Thr Glu Pro Leu Ser Leu Asp Cys Gly His
                20                  25                  30

Ser Leu Cys Arg Ala Cys Ile Thr Val Ser Asn Lys Glu Ala Val Thr
            35                  40                  45

Ser Met Gly Gly Lys Ser Ser Cys Pro Val Cys Gly Ile Ser Tyr Ser
        50                  55                  60

Phe Glu His Leu Gln Ala Asn Gln His Leu Ala Asn Ile Val Glu Arg
    65                  70                  75                  80

Leu Lys Glu Val Lys Leu Ser Pro Asp Asn Gly Lys Lys Arg Asp Leu
                85                  90                  95

Cys Asp His His Gly Glu Lys Leu Leu Leu Phe Cys Lys Glu Asp Arg
            100                 105                 110

Lys Val Ile Cys Trp Leu Cys Glu Arg Ser Gln Glu His Arg Gly His
        115                 120                 125

His Thr Val Leu Thr Glu Glu Val Phe Lys Glu Cys Gln Glu Lys Leu
    130                 135                 140

Gln Ala Val Leu Lys Arg Leu Lys Lys Glu Glu Glu Glu Ala Glu Lys
145                 150                 155                 160

Leu Glu Ala Asp Ile Arg Glu Glu Lys Thr Ser Trp Lys Tyr Gln Val
                165                 170                 175

Gln Thr Glu Arg Gln Arg Ile Gln Thr Glu Phe Asp Gln Leu Arg Ser
            180                 185                 190

Ile Leu Asn Asn Glu Glu Gln Arg Glu Leu Gln Arg Leu Glu Glu Glu
        195                 200                 205

Glu Lys Lys Thr Leu Asp Lys Phe Ala Glu Ala Glu Asp Glu Leu Val
```

```
           210                 215                 220
Gln Gln Lys Gln Leu Val Arg Glu Leu Ile Ser Asp Val Glu Cys Arg
225                 230                 235                 240

Ser Gln Trp Ser Thr Met Glu Leu Leu Gln Asp Met Ser Gly Ile Met
                245                 250                 255

Lys Trp Cys Val Trp Val Ala Thr Ser Gly Ala Cys Glu Leu
                260                 265                 270

<210> SEQ ID NO 47
<211> LENGTH: 2990
<212> TYPE: DNA
<213> ORGANISM: Homo sapiens

<400> SEQUENCE: 47
```

| | | | | | |
|---|---|---|---|---|---|
| gcggttcctc | taggaaaatt | cctttgtgca | gatcaggccc | gtggattggt | gagtgaatcc | 60 |
| taaccacgtc | ttccctggcc | tgtcttcact | cttctcccca | gaatcaccac | ttctgcactg | 120 |
| gtgtctgaag | gtgtattgag | tgattttgtg | gagggcagaa | gtaggaagtc | tttgggacaa | 180 |
| aactgtattt | accttgggat | ctgtgaacaa | gaggaacctc | agcagccagg | acaggcagga | 240 |
| gcagtggaat | agctactatg | gcttctggaa | tcctggttaa | tgtaaaggag | gaggtgacct | 300 |
| gccccatctg | cctggaactc | ctgacacaac | ccctgagcct | ggactgcggc | cacagcttct | 360 |
| gccaagcatg | cctcactgca | aaccacaaga | agtccatgct | agacaaagga | gagagtagct | 420 |
| gccctgtgtg | ccggatcagt | taccagcctg | agaacatacg | gcctaatcgg | catgtagcca | 480 |
| acttagtgga | gaagctcagg | gaggtcaagt | tgagcccaga | ggggcagaaa | gttgatcatt | 540 |
| gtgcacgcca | tggagagaaa | cttctactct | tctgtcagga | ggacgggaag | gtcatttgct | 600 |
| ggctttgtga | gcggtctcag | gagcaccgtg | gtcaccacac | gttccccaca | gaggaggttg | 660 |
| cccaggagta | ccaagtgaag | ctccaggcag | ctctggagat | gctgaggcag | aagcagcagg | 720 |
| aagctgaaga | gttggaagct | gacatcagag | aagagaaagc | ttcctggaag | actcaaatac | 780 |
| agtatgacaa | aaccaacgtc | ttggcagatt | ttgagcaact | gagagacatc | ctggactggg | 840 |
| aggagagcaa | tgagctgcaa | aacctggaga | aggaggagga | agacattctg | aaaagcctta | 900 |
| cgaactctga | aactgagatg | gtgcagcaga | cccagtccct | gagagagctc | atctcagatc | 960 |
| tggagcatcg | gctgcagggg | tcagtgatgg | agctgcttca | gggtgtggat | ggcgtcataa | 1020 |
| aaaggacgga | gaacgtgacc | ttgaagaagc | cagaaacttt | tccaaaaaat | caaaggagag | 1080 |
| tgtttcgagc | tcctgatctg | aaaggaatgc | tagaagtgtt | tagagagctg | acagatgtcc | 1140 |
| gacgctactg | ggttgatgtg | acagtggctc | caaacaacat | ttcatgtgct | gtcatttctg | 1200 |
| aagataagag | acaagtgagc | tctccgaaac | cacagataat | atatgggca | cgagggacaa | 1260 |
| gataccagac | atttgtgaat | tcaattatt | gtactggcat | cctgggctct | caaagtatca | 1320 |
| catcagggaa | acattactgg | gaggtagacg | tgtccaagaa | aactgcttgg | atcctggggg | 1380 |
| tatgtgctgg | cttccaacct | gatgcaatgt | gtaatattga | aaaaaatgaa | aattatcaac | 1440 |
| ctaaatacgg | ctactgggtt | atagggttag | aggaaggagt | taaatgtagt | gctttccagg | 1500 |
| atagttcctt | ccatactcct | tctgttcctt | tcattgtgcc | cctctctgtg | attatttgtc | 1560 |
| ctgatcgtgt | tggagttttc | ctagactatg | aggcttgcac | tgtctcattc | ttcaatatca | 1620 |
| caaaccatgg | atttctcatc | tataagtttt | ctcactgttc | ttttttctcag | cctgtatttc | 1680 |
| catatttaaa | tcctagaaaa | tgtggagtcc | ccatgactct | gtgctcacca | agctcttgaa | 1740 |
| ccttcttaca | cactcagccc | cttctgtaca | gcacctcttg | tccaggtgca | tctcatacac | 1800 |
| ctgaactcat | ttgcatcatt | ttaaccatct | tttccttgct | gtctcccttc | tttctatttg | 1860 |

-continued

```
aacgtccttc actcatcagt aaaatgtaat aattgccttg tgccatattg tccccaatat    1920
tttattgaca tttgatagca attttttca tcattttccg tactcctaag gaaaactgac    1980
ctatacctca taaaatgaga ccgctattta ggtattactt ctgccagata tttatcaccc    2040
aattgcctct gacactgact aagaagatga agaaaagctt ttcaacagcc tttctatatc    2100
atcgtgtgat aattgttcac caatgaatga gtccttagcc ctgtgtcagt ttaccctcga    2160
tgcccttatt tgtgagttaa agagaaaata tcataaatgg tatactctta agtatagagg    2220
ttttgtatct agaggatctc agttcaactc ctgtctctcc atataccagc agtgtaactg    2280
tgaataacat acttaaatgg ctgtgcttat ttcctttct tttctttttt ctttttttt    2340 tttttgaga tgaagttttg ctcttgttcc ccaggctgga gtgcaatggc acgatctcgg    2400
ttcactgcaa cctccacctc tcagattcaa gcaattctcc tgcctcagcc tcccaagtag    2460
ctgggattac aggtgcccac caccacccct ggctaaattt gtattttcag tagagacggg    2520
gtttccccat gttggttagg ctcgtctaga acctctgacc tcaggtgatc cacccgcctc    2580
ggcctcccaa agtgctggga ttacaggcgt gagccacggc gcccagcctg tgcttatttt    2640
cttaaaataa ttttgtatt aaaaacttca cattaaataa gtgctaatgt tttattgcat    2700
agtagggtga ctagagttaa caataaccta ttgcatatat tttgaaatag ctagaagaga    2760
ggattttgaa agttctcaac acaaagaaac gacacatatt tgaggtgatg gatatgctaa    2820
ttaccctggt tcggttatta cgcaatgtat acatgtatca aaacatcaca ctgtaccaca    2880
taaatatgta tatttattat ttgtcaatta aaagcaaaat aaaacaaaaa accttcatct    2940
aatactttgg atcattgtga aaaataaat tcctgaagta taaagcatct                2990
```

<210> SEQ ID NO 48
<211> LENGTH: 493
<212> TYPE: PRT
<213> ORGANISM: Homo sapiens

<400> SEQUENCE: 48

```
Met Ala Ser Gly Ile Leu Val Asn Val Lys Glu Glu Val Thr Cys Pro
 1               5                  10                  15

Ile Cys Leu Glu Leu Leu Thr Gln Pro Leu Ser Leu Asp Cys Gly His
             20                  25                  30

Ser Phe Cys Gln Ala Cys Leu Thr Ala Asn His Lys Lys Ser Met Leu
         35                  40                  45

Asp Lys Gly Glu Ser Ser Cys Pro Val Cys Arg Ile Ser Tyr Gln Pro
     50                  55                  60

Glu Asn Ile Arg Pro Asn Arg His Val Ala Asn Leu Val Glu Lys Leu
 65                  70                  75                  80

Arg Glu Val Lys Leu Ser Pro Glu Gly Gln Lys Val Asp His Cys Ala
                 85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Pro Thr Glu Glu Val Ala Gln Glu Tyr Gln Val Lys Leu Gln Ala
    130                 135                 140

Ala Leu Glu Met Leu Arg Gln Lys Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175
```

```
Asp Lys Thr Asn Val Leu Ala Asp Phe Glu Gln Leu Arg Asp Ile Leu
            180                 185                 190
Asp Trp Glu Ser Asn Glu Leu Gln Asn Leu Glu Lys Glu Glu
        195                 200                 205
Asp Ile Leu Lys Ser Leu Thr Asn Ser Glu Thr Glu Met Val Gln Gln
        210                 215                 220
Thr Gln Ser Leu Arg Glu Leu Ile Ser Asp Leu Glu His Arg Leu Gln
225                 230                 235                 240
Gly Ser Val Met Glu Leu Leu Gln Gly Val Asp Gly Val Ile Lys Arg
                245                 250                 255
Thr Glu Asn Val Thr Leu Lys Lys Pro Glu Thr Phe Pro Lys Asn Gln
            260                 265                 270
Arg Arg Val Phe Arg Ala Pro Asp Leu Lys Gly Met Leu Glu Val Phe
        275                 280                 285
Arg Glu Leu Thr Asp Val Arg Arg Tyr Trp Val Asp Val Thr Val Ala
        290                 295                 300
Pro Asn Asn Ile Ser Cys Ala Val Ile Ser Glu Asp Lys Arg Gln Val
305                 310                 315                 320
Ser Ser Pro Lys Pro Gln Ile Ile Tyr Gly Ala Arg Gly Thr Arg Tyr
                325                 330                 335
Gln Thr Phe Val Asn Phe Asn Tyr Cys Thr Gly Ile Leu Gly Ser Gln
            340                 345                 350
Ser Ile Thr Ser Gly Lys His Tyr Trp Glu Val Asp Val Ser Lys Lys
        355                 360                 365
Thr Ala Trp Ile Leu Gly Val Cys Ala Gly Phe Gln Pro Asp Ala Met
        370                 375                 380
Cys Asn Ile Glu Lys Asn Glu Asn Tyr Gln Pro Lys Tyr Gly Tyr Trp
385                 390                 395                 400
Val Ile Gly Leu Glu Glu Gly Val Lys Cys Ser Ala Phe Gln Asp Ser
                405                 410                 415
Ser Phe His Thr Pro Ser Val Pro Phe Ile Val Pro Leu Ser Val Ile
            420                 425                 430
Ile Cys Pro Asp Arg Val Gly Val Phe Leu Asp Tyr Glu Ala Cys Thr
        435                 440                 445
Val Ser Phe Phe Asn Ile Thr Asn His Gly Phe Leu Ile Tyr Lys Phe
        450                 455                 460
Ser His Cys Ser Phe Ser Gln Pro Val Phe Pro Tyr Leu Asn Pro Arg
465                 470                 475                 480
Lys Cys Gly Val Pro Met Thr Leu Cys Ser Pro Ser Ser
                485                 490

<210> SEQ ID NO 49
<211> LENGTH: 1539
<212> TYPE: DNA
<213> ORGANISM: Homo sapiens

<400> SEQUENCE: 49
cacgagggtg aacaagagga acctcagcag ccaggacagg caggagcagt ggaatagcta      60
ctatggcttc tggaatcctg gttaatgtaa aggaggaggt gacctgcccc atctgcctgg     120
aactcctgac acaaccctg agcctggact gcggccacag cttctgccaa gcatgcctca     180
ctgcaaacca caagaagtcc atgctagaca aggagagag tagctgccct gtgtgccgga     240
tcagttacca gcctgagaac atacggccta tcggcatgt agccaacata gtggagaagc     300
tcagggaggt caagttgagc ccagaggggc agaaagttga tcattgtgca cgccatggag     360
```

-continued

```
agaaacttct actcttctgt caggaggacg ggaaggtcat tgctggctt tgtgagcggt      420
ctcaggagca ccgtggtcac cacacgttcc tcacagagga ggttgcccgg gagtaccaag      480
tgaagctcca ggcagctctg gagatgctga ggcagaagca gcaggaagct gaagagttgg      540
aagctgacat cagagaagag aaagcttcct ggaagactca aatacagtat gacaaaacca      600
acgtcttggc agattttgag caactgagag acatcctgga ctgggaggag agcaatgagc      660
tgcaaaacct ggagaaggag gaggaagaca ttctgaaaag ccttacgaac tctgaaactg      720
agatggtgca gcagacccag tccctgagag agctcatctc agatctggag catcggctgc      780
aggggtcagt gatggagctg cttcagggtg tggatggcgt cataaaaagg acggagaacg      840
tgaccttgaa gaagccagaa acttttccaa aaaatcaaag gagagtgttt cgagctcctg      900
atctgaaagg aatgctagaa gtgtttagag agctgacaga tgtccgacgc tactgggttg      960
atgtgacagt ggctccaaac aacatttcat gtgctgtcat ttctgaagat aagagacaag     1020
tgagctctcc gaaaccacag ataatatatg gggcacgagg acaagatac cagacatttg      1080
tgaatttcaa ttattgtact ggcatcctgg gctctcaaag tatcacatca gggaaacatt     1140
actgggaggt agacgtgtcc aagaaaactg cttggatcct gggggtatgt gctggcttcc     1200
aacctgatgc aatgtgtaat attgaaaaaa aaagattat gattctcctt ccaagacaca      1260
cataacttac ccctccttat aacttctaaa caaggttcct cccagttttc tctcaagtct     1320
ttatcaagat ttctctcata tcacaataa agttacatta tatcccttag ctgacctgtt       1380
aattttttcta cagttgatgt gacagtggct ccaaacaaca tttcatgtgc tgtcatttct     1440
gaagataaga gacaagtgag ctctccgaaa ccacagataa tatatgggggc acgagggaca     1500
agataccaga catttgtgaa tttcaattat tgtactggc                             1539
```

<210> SEQ ID NO 50
<211> LENGTH: 400
<212> TYPE: PRT
<213> ORGANISM: Homo sapiens

<400> SEQUENCE: 50

```
Met Ala Ser Gly Ile Leu Val Asn Val Lys Glu Glu Val Thr Cys Pro
  1               5                  10                  15
Ile Cys Leu Glu Leu Leu Thr Gln Pro Leu Ser Leu Asp Cys Gly His
                 20                  25                  30
Ser Phe Cys Gln Ala Cys Leu Thr Ala Asn His Lys Lys Ser Met Leu
             35                  40                  45
Asp Lys Gly Glu Ser Ser Cys Pro Val Cys Arg Ile Ser Tyr Gln Pro
         50                  55                  60
Glu Asn Ile Arg Pro Asn Arg His Val Ala Asn Ile Val Glu Lys Leu
 65                  70                  75                  80
Arg Glu Val Lys Leu Ser Pro Glu Gly Gln Lys Val Asp His Cys Ala
                 85                  90                  95
Arg His Gly Glu Lys Leu Leu Leu Phe Cys Gln Glu Asp Gly Lys Val
            100                 105                 110
Ile Cys Trp Leu Cys Glu Arg Ser Gln Glu His Arg Gly His His Thr
            115                 120                 125
Phe Leu Thr Glu Glu Val Ala Arg Glu Tyr Gln Val Lys Leu Gln Ala
        130                 135                 140
Ala Leu Glu Met Leu Arg Gln Lys Gln Gln Glu Ala Glu Glu Leu Glu
145                 150                 155                 160
Ala Asp Ile Arg Glu Glu Lys Ala Ser Trp Lys Thr Gln Ile Gln Tyr
                165                 170                 175
```

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Val Thr Val Ala
290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
370                 375                 380

Cys Asn Ile Glu Lys Lys Arg Phe Met Ile Leu Leu Pro Arg His Thr
385                 390                 395                 400

<210> SEQ ID NO 51
<211> LENGTH: 1686
<212> TYPE: DNA
<213> ORGANISM: Homo sapiens

<400> SEQUENCE: 51
gcggttcctc taggaaaatt cctttgtgca gatcaggccc gtggattggt gagtgaatcc      60
taaccacgtc ttccctggcc tgtcttcact cttctcccca gaatcaccac ttctgcactg     120
gtgtctgaag gtgtattgag tgattttgtg gagggcagaa gtaggaagtc tttgggacaa     180 aactgtatt acccttgggat ctgtgaacaa gaggaacctc agcagccagg acaggcagga     240
gcagtggaat agctactatg gcttctggaa tcctggttaa tgtaaaggag gaggtgacct     300
gccccatctg cctggaactc ctgacacaac ccctgagcct ggactgcggc cacagcttct     360
gccaagcatg cctcactgca aaccacaaga agtccatgct agacaaagga gagagtagct     420
gccctgtgtg ccggatcagt taccagcctg agaacatacg gcctaatcgg catgtagcca     480
acatagtgga gaagctcagg gaggtcaagt tgagcccaga ggggcagaaa gttgatcatt     540
gtgcacgcca tggagagaaa cttctactct tctgtcagga ggacgggaag gtcatttgct     600
ggctttgtga gcggtctcag gagcaccgtg gtcaccacac gttcctcaca gaggaggttg     660
cccaggagta ccaagtgaag ctccaggcag ctctggagat gctgaggcag aagcagcagg     720
aagctgaaga gttggaagct gacatcagag aagagaaagc ttcctggaag actcaaatac     780
agtatgacaa aaccaacgtc ttggcagatt ttgagcaact gagagacatc ctggactggg     840
aggagagcaa tgagctgcaa aacctggaga aggaggagga agacattctg aaaagcctta     900

```
cgaactctga aactgagatg gtgcagcaga cccagtccct gagagagctc atctcagatc    960
tggagcatcg gctgcagggg tcagtgatgg agctgcttca gggtgtggat ggcgtcataa   1020
aaaggacgga gaacgtgacc ttgaagaagc cagaaacttt tccaaaaaat caaaggagag   1080
tgtttcgagc tcctgatctg aaaggaatgc tagaagtgtt tagagagctg acagatgtcc   1140
gacgctactg gggtaaggag aagtcacatt atcataagcc accctgcggc ttatcattat   1200
tattatcttt atcttttaga attttatgtt ctctattagg ctcatgtttt aagatttatg   1260
attctccttc caagacacac ataacttacc cctccttata acttctaaac aaggttcctc   1320
ccagttttct ctcaagtctt tatcaagatt tctctcatat cacaaataaa gttacattat   1380
atcccttagc tgacctgtta attttttctac agttgatgtg acagtggctc caaacaacat   1440
ttcatgtgct gtcatttctg aagataagag acaagtgagc tctccgaaac cacagataat   1500
atatggggca cgaggggacaa gataccagac atttgtgaat ttcaattatt gtactggcat   1560
cctgggctct caaagtatca catcagggaa acattactgg gagtagacg tgtccaagaa   1620
aactgcttgg atcctggggg tatgtgctgg cttccaacct gatgcaatgt gtaatattga   1680
aaaaaa                                                              1686
```

<210> SEQ ID NO 52
<211> LENGTH: 347
<212> TYPE: PRT
<213> ORGANISM: Homo sapiens

<400> SEQUENCE: 52

```
Met Ala Ser Gly Ile Leu Val Asn Val Lys Glu Glu Val Thr Cys Pro
  1               5                  10                  15
Ile Cys Leu Glu Leu Leu Thr Gln Pro Leu Ser Leu Asp Cys Gly His
             20                  25                  30
Ser Phe Cys Gln Ala Cys Leu Thr Ala Asn His Lys Lys Ser Met Leu
         35                  40                  45
Asp Lys Gly Glu Ser Ser Cys Pro Val Cys Arg Ile Ser Tyr Gln Pro
     50                  55                  60
Glu Asn Ile Arg Pro Asn Arg His Val Ala Asn Ile Val Glu Lys Leu
 65                  70                  75                  80
Arg Glu Val Lys Leu Ser Pro Glu Gly Gln Lys Val Asp His Cys Ala
                 85                  90                  95
Arg His Gly Glu Lys Leu Leu Leu Phe Cys Gln Glu Asp Gly Lys Val
            100                 105                 110
Ile Cys Trp Leu Cys Glu Arg Ser Gln Glu His Arg Gly His His Thr
        115                 120                 125
Phe Leu Thr Glu Glu Val Ala Gln Glu Tyr Gln Val Lys Leu Gln Ala
    130                 135                 140
Ala Leu Glu Met Leu Arg Gln Lys Gln Gln Glu Ala Glu Glu Leu Glu
145                 150                 155                 160
Ala Asp Ile Arg Glu Glu Lys Ala Ser Trp Lys Thr Gln Ile Gln Tyr
                165                 170                 175
Asp Lys Thr Asn Val Leu Ala Asp Phe Glu Gln Leu Arg Asp Ile Leu
            180                 185                 190
Asp Trp Glu Glu Ser Asn Glu Leu Gln Asn Leu Glu Lys Glu Glu Glu
        195                 200                 205
Asp Ile Leu Lys Ser Leu Thr Asn Ser Glu Thr Glu Met Val Gln Gln
    210                 215                 220
Thr Gln Ser Leu Arg Glu Leu Ile Ser Asp Leu Glu His Arg Leu Gln
```

```
                    225                 230                 235                 240
Gly Ser Val Met Glu Leu Leu Gln Gly Val Asp Gly Val Ile Lys Arg
                245                 250                 255
Thr Glu Asn Val Thr Leu Lys Lys Pro Glu Thr Phe Pro Lys Asn Gln
            260                 265                 270
Arg Arg Val Phe Arg Ala Pro Asp Leu Lys Gly Met Leu Glu Val Phe
        275                 280                 285
Arg Glu Leu Thr Asp Val Arg Arg Tyr Trp Gly Lys Glu Lys Ser His
    290                 295                 300
Tyr His Lys Pro Pro Cys Gly Leu Ser Leu Leu Ser Leu Ser Phe
305                 310                 315                 320
Arg Ile Leu Cys Ser Leu Leu Gly Ser Cys Phe Lys Ile Tyr Asp Ser
                325                 330                 335
Pro Ser Lys Thr His Ile Thr Tyr Pro Ser Leu
                340                 345

<210> SEQ ID NO 53
<211> LENGTH: 1782
<212> TYPE: DNA
<213> ORGANISM: Homo sapiens

<400> SEQUENCE: 53
gcggttcctc taggaaaatt cctttgtgca gatcaggccc gtggattggt gagtgaatcc      60
taaccacgtc ttccctggcc tgtcttcact cttctcccca gaatcaccac ttctgcactg     120
gtgtctgaag gtgtattgag tgattttgtg gagggcagaa gtaggaagtc tttgggacaa     180
aactgtattt accttgggat ctgtgaacaa gaggaacctc agcagccagg acaggcagga     240
gcagtggaat agctactatg gcttctggaa tcctggttaa tgtaaaggag gaggtgacct     300
gccccatctg cctggaactc ctgacacaac ccctgagcct ggactgcggc cacagcttct     360
gccaagcatg cctcactgca aaccacaaga agtccatgct agacaaagga gagagtagct     420
gccctgtgtg ccggatcagt taccagcctg agaacatacg gcctaatcgg catgtagcca     480
acatagtgga gaagctcagg gaggtcaagt tgagcccaga ggggcagaaa gttgatcatt     540
gtgcacgcca tggagagaaa cttctactct tctgtcagga ggacgggaag gtcatttgct     600
ggctttgtga gcggtctcag gagcaccgtg gtcaccacac gttcctcaca gaggaggttg     660
cccaggagta ccaagtgaag ctccaggcag ctctggagat gctgaggcag aagcagcagg     720
aagctgaaga gttggaagct gacatcagag aagagaaagc ttcctggaag actcaaatac     780
agtatgacaa aaccaacgtc ttggcagatt ttgagcaact gagagacatc ctggactggg     840
aggagagcaa tgagctgcaa aacctggaga aggaggagga agacattctg aaaagcctta     900
cgaactctga aactgagatg gtgcagcaga cccagtccct gagagagctc atctcagatc     960
tggagcatcg gctgcagggg tcagtgatgg agctgcttca gggtgtggat ggcgtcataa    1020
aaaggacgga gaacgtgacc ttgaagaagc cagaaacttt ccaaaaaat caaaggagag    1080
tgtttcgagc tcctgatctg aaaggaatgc tagaagtgtt tagagagctg acagatgtcc    1140
gacgctactg gggctggagt gcaatggcac gatctcggtt cactgcaacc tccacctctc    1200
agattcaagc aattctcctg cctcagcctc ccaagtagct gggattacag gtgccacca    1260
ccaccctgg ctaaatttgt attttcagta gagacggggt ttccccatgt tggttaggct    1320
cgtctagaac ctctgacctc aggtgatcca cccgcctcgg cctcccaaag tgctgggatt    1380
acaggcgtga gccacggcgc ccagcctgtg cttatttct taaataatt tttgtattaa    1440
aaacttcaca ttaaataagt gctaatgttt tattgcatag tagggtgact agagttaaca    1500
```

-continued

```
ataacctatt gcatatattt tgaaatagct agaagagagg attttgaaag ttctcaacac    1560
aaagaaatga cacatatttg aggtgatgga tatgctaatt accctggttc ggttattacg    1620
caatgtatac atgtatcaaa acatcacact gtaccacata aatatgtata tttattattt    1680
gtcaattaaa agcaaaataa aacaaaaaac cttcatctaa tactttggat cattgtgaaa    1740
aaataaattc ctgaagtata agaaaaaaaa aaaaaaaaa aa                        1782
```

<210> SEQ ID NO 54
<211> LENGTH: 326
<212> TYPE: PRT
<213> ORGANISM: Homo sapiens

<400> SEQUENCE: 54

```
Met Ala Ser Gly Ile Leu Val Asn Val Lys Glu Glu Val Thr Cys Pro
  1               5                  10                  15

Ile Cys Leu Glu Leu Leu Thr Gln Pro Leu Ser Leu Asp Cys Gly His
                 20                  25                  30

Ser Phe Cys Gln Ala Cys Leu Thr Ala Asn His Lys Lys Ser Met Leu
             35                  40                  45

Asp Lys Gly Glu Ser Ser Cys Pro Val Cys Arg Ile Ser Tyr Gln Pro
         50                  55                  60

Glu Asn Ile Arg Pro Asn Arg His Val Ala Asn Ile Val Glu Lys Leu
 65                  70                  75                  80

Arg Glu Val Lys Leu Ser Pro Glu Gly Gln Lys Val Asp His Cys Ala
                 85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Gln Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Gly Trp Ser Ala Met Ala
    290                 295                 300

Arg Ser Arg Phe Thr Ala Thr Ser Thr Ser Gln Ile Gln Ala Ile Leu
305                 310                 315                 320

Leu Pro Gln Pro Pro Lys
```

325

<210> SEQ ID NO 55
<211> LENGTH: 2795
<212> TYPE: DNA
<213> ORGANISM: Homo sapiens

<400> SEQUENCE: 55

| | | | | | | |
|---|---|---|---|---|---|---|
| cacgagggtg | aacaagagga | acctcagcag | ccaggacagg | caggagcagt | ggaatagcta | 60 |
| ctatggcttc | tggaatcctg | gttaatgtaa | aggaggaggt | gacctgcccc | atctgcctgg | 120 |
| aactcctgac | acaacccctg | agcctggact | gcggccacag | cttctgccaa | gcatgcctca | 180 |
| ctgcaaacca | caagaagtcc | atgctagaca | aggagagag | tagctgccct | gtgtgccgga | 240 |
| tcagttacca | gcctgagaac | atacggccta | atcggcatgt | agccaacata | gtggagaagc | 300 |
| tcagggaggt | caagttgagc | ccagaggggc | agaaagttga | tcattgtgca | cgccatggag | 360 |
| agaaacttct | actcttctgt | caggaggacg | ggaaggtcat | ttgctggctt | tgtgagcggt | 420 |
| ctcaggagca | ccgtggtcac | cacacgttcc | tcacagagga | ggttgcccgg | gagtaccaag | 480 |
| tgaagctcca | ggcagctctg | gagatgctga | ggcagaagca | gcaggaagct | gaagagttgg | 540 |
| aagctgacat | cagagaagag | aaagcttcct | ggaagactca | aatacagtat | gacaaaacca | 600 |
| acgtcttggc | agattttgag | caactgagag | acatcctgga | ctgggaggag | agcaatgagc | 660 |
| tgcaaaacct | ggagaaggag | gaggaagaca | ttctgaaaag | ccttacgaac | tctgaaactg | 720 |
| agatggtgca | gcagacccag | tccctggaga | agctcatctc | agatctggag | catcggctgc | 780 |
| aggggtcagt | gatggagctg | cttcaggacg | gagaacgtga | ccttgaagaa | gccagaaact | 840 |
| tttccaaaaa | atcaaggag | agtgtttcga | gctcctgatc | tgaaggaat | gctagaagtg | 900 |
| tttagagagc | tgacagatgt | ccgacgctac | tgggttgatg | tgacagtggc | tccaaacaac | 960 |
| atttcatgtg | ctgtcatttc | tgaagataag | agacaagtga | gctctccgaa | accacagata | 1020 |
| atatatgggg | cacgagggac | aagataccag | acatttgtga | atttcaatta | ttgtactggc | 1080 |
| atcctgggct | ctcaaagtat | cacatcaggg | aaacattact | gggaggtaga | cgtgtccaag | 1140 |
| aaaactgctt | ggatcctggg | ggtatgtgct | ggcttccaac | ctgatgcaat | gtgtaatatt | 1200 |
| gaaaaaaatg | aaaattatca | acctaaatac | ggctactggg | ttatagggtt | agaggaagga | 1260 |
| gttaaatgta | gtgctttcca | ggatagttcc | ttccatactc | cttctgttcc | tttcattgtg | 1320 |
| cccctctctg | tgattatttg | tcctgatcgt | gttggagttt | tcctagacta | tgaggcttgc | 1380 |
| actgtctcat | tcttcaatat | cacaaaccat | ggatttctca | tctataagtt | ttctcactgt | 1440 |
| tctttttctc | agcctgtatt | tccatattta | aatcctagaa | aatgtggagt | ccccatgact | 1500 |
| ctgtgctcac | caagctcttg | aaccttctta | cacactcagc | cccttctgta | cagcacctct | 1560 |
| tgtccaggtg | catctcatac | acctgaactc | atttgcatca | ttttaaccat | cttttccttg | 1620 |
| ctgtctccct | tctttctatt | tgaacgtcct | tcactcatca | gtaaaatgta | ataattgcct | 1680 |
| tgtgccatat | tgtccccaat | attttattga | catttgatag | caattttttt | catcattttc | 1740 |
| cgtactccta | aggaaaactg | acctatacct | cataaaatga | gaccgctatt | taggtattac | 1800 |
| ttctgccaga | tatttatcac | ccaattgcct | ctgacactga | ctaagaagat | gaagaaaagc | 1860 |
| ttttcaacag | cctttctata | tcatcgtgtg | ataattgttc | accaatgaat | gagtccttag | 1920 |
| ccctgtgtca | gtttacccctc | gatgcccttta | tttgtgagtt | aaagagaaaa | tatcataaat | 1980 |
| ggtatactct | taagtataga | ggttttgtat | ctagaggatc | tcagttcaac | tcctgtctct | 2040 |
| ccatatacca | gcagtgtaac | tgtgaataac | atacttaaat | ggctgtgctt | atttcctttt | 2100 |

```
ctttctttt tctttttt tttttttg agatgaagtt ttgctcttgt tccccaggct    2160
ggagtgcaat ggcacgatct cggttcactg caacctccac ctctcagatt caagcaattc    2220
tcctgcctca gcctcccaag tagctgggat tacaggtgcc caccaccacc cctggctaaa    2280
tttgtatttt cagtagagac gggggtttccc catgttggtt aggctcgtct agaacctctg    2340
acctcaggtg atccacccgc ctcggcctcc caaagtgctg ggattacagg cgtgagccac    2400
ggcgcccagc ctgtgcttat tttcttaaaa taattttgt attaaaaact tcacattaaa    2460
taagtgctaa tgtttattg catagtaggg tgactagagt taacaataac ctattgcata    2520 tatttgaaa tagctagaag agaggatttt gaaagttctc aacacaaaga aatgacacat    2580
atttgaggtg atggatatgc taattaccct ggttcggtta ttacgcaatg tatacatgta    2640
tcaaaacatc acactgtacc acataaatat gtatatttat tatttgtcaa ttaaaagcaa    2700
aataaaacaa aaaaccttca tctaatactt tggatcattg tgaaaaaata aattcctgaa    2760
gtataaaaaa aaaaaaaaaa aaaaaaaaaa aaaaa    2795
```

<210> SEQ ID NO 56
<211> LENGTH: 271
<212> TYPE: PRT
<213> ORGANISM: Homo sapiens

<400> SEQUENCE: 56

```
Met Ala Ser Gly Ile Leu Val Asn Val Lys Glu Glu Val Thr Cys Pro
 1               5                  10                  15

Ile Cys Leu Glu Leu Leu Thr Gln Pro Leu Ser Leu Asp Cys Gly His
                20                  25                  30

Ser Phe Cys Gln Ala Cys Leu Thr Ala Asn His Lys Lys Ser Met Leu
            35                  40                  45

Asp Lys Gly Glu Ser Ser Cys Pro Val Cys Arg Ile Ser Tyr Gln Pro
        50                  55                  60

Glu Asn Ile Arg Pro Asn Arg His Val Ala Asn Ile Val Glu Lys Leu
    65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
                100                 105                 110

Ile Cys Trp Leu Cys Glu Arg Ser Gln Glu His Arg Gly His His Thr
            115                 120                 125

Phe Leu Thr Glu Glu Val Ala Arg Glu Tyr Gln Val Lys Leu Gln Ala
        130                 135                 140

Ala Leu Glu Met Leu Arg Gln Lys Gln Gln Glu Ala Glu Glu Leu Glu
    145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
                180                 185                 190

Asp Trp Glu Glu Ser Asn Glu Leu Gln Asn Leu Glu Lys Glu Glu Glu
            195                 200                 205

Asp Ile Leu Lys Ser Leu Thr Asn Ser Glu Thr Glu Met Val Gln Gln
        210                 215                 220

Thr Gln Ser Leu Arg Glu Leu Ile Ser Asp Leu Glu His Arg Leu Gln
    225                 230                 235                 240

Gly Ser Val Met Glu Leu Leu Gln Asp Gly Glu Arg Asp Leu Glu Glu
                245                 250                 255
```

```
Ala Arg Asn Phe Ser Lys Lys Ser Lys Glu Ser Val Ser Ser Ser
            260                 265                 270

<210> SEQ ID NO 57
<211> LENGTH: 101
<212> TYPE: PRT
<213> ORGANISM: HIV-1

<400> SEQUENCE: 57

Met Glu Pro Val Asp Pro Arg Leu Glu Pro Trp Lys His Pro Gly Ser
  1               5                  10                  15

Gln Pro Arg Thr Ser Cys Asn Asn Cys Tyr Cys Lys Lys Cys Cys Phe
             20                  25                  30

His Cys Gln Val Cys Phe Thr Lys Lys Gly Leu Gly Ile Ser Tyr Gly
         35                  40                  45

Arg Lys Lys Arg Arg Gln Arg Arg Thr Pro Gln Asp Ser Lys Asn
     50                  55                  60

His Gln Val Pro Leu Ser Lys Gln Pro Ala Ser Gln Pro Arg Gly Asp
 65                  70                  75                  80

Pro Thr Gly Pro Lys Glu Ser Lys Lys Lys Val Glu Arg Lys Ala Glu
                 85                  90                  95

Thr Asp Pro Glu Cys
            100

<210> SEQ ID NO 58
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 58
gcucagggag gucaaguugt ttttt                                         25

<210> SEQ ID NO 59
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 59
gagaaagcuu ccuggaagat ttttt                                         25

<210> SEQ ID NO 60
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 60
gccuuacgaa gucugaaact ttttt                                         25

<210> SEQ ID NO 61
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 61
ggagaguguu ucgagcucct ttttt                                         25
```

<210> SEQ ID NO 62
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 62
ccuucuuaca cacucagcct ttttt                                              25

<210> SEQ ID NO 63
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 63
cguccugcac ucaucagugt ttttt                                              25

<210> SEQ ID NO 64
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 64
cagccuuucu auaucaucgt ttttt                                              25

<210> SEQ ID NO 65
<211> LENGTH: 25
<212> TYPE: DNA
<213> ORGANISM: Artificial sequence
<220> FEATURE:
<223> OTHER INFORMATION: Synthetic oligonucleotides

<400> SEQUENCE: 65
cuccugucuc uccauguact ttttt                                              25

<210> SEQ ID NO 66
<211> LENGTH: 21
<212> TYPE: DNA
<213> ORGANISM: Artificial sequence
<220> FEATURE:
<223> OTHER INFORMATION: Synthetic oligonucleotides

<400> SEQUENCE: 66
augaacguga auugcucaau u                                                  21

<210> SEQ ID NO 67
<211> LENGTH: 556
<212> TYPE: DNA
<213> ORGANISM: Human TRIM5alpha genomic sequence exon 1

<400> SEQUENCE: 67
gaaaagggag attgagtggg aatgcctcta gttcccacgg ctcctcctgt gaacagcaca         60
gctacacggc ccggctgatt cattcagagg gcgggactca ccaggcccta cgtggagaaa        120
tgccattggc ccatagttta tctttcactt tcctgccctg agtgtgagca agaatttcct        180
gcggttcctc taggaaaatt cctttgtgca gatcaggccc gtggattggt gagtgaatcc        240
taaccacgtc tttccctggcc tgtcttcact cttctcccca gaatcaccac ttctgcactg        300
gtgtctgaag gtgtattgag tgattttgtg gagggcagaa gtaggaagtc tttgggacaa        360

```
aactgtattt accttggtga gtttaactta tctgaaaagc tgtgcggggg tggggaaaag    420
acacagttca cagacttctt gctgccagag ctgactgagg ggaacagagc cgcctggcgg    480
gcaggcagat ttgaaagaag ggagagcttt aaagtgaagg gctttgtttc ccgaaggctg    540 gttattttc catgct                                                     556

<210> SEQ ID NO 68
<211> LENGTH: 838
<212> TYPE: DNA
<213> ORGANISM: Human TRIM5alpha genomic sequence exon 2

<400> SEQUENCE: 68
gtatttaagg tgattatgaa aagcccttat taccaggtaa ccaaacacct tttcttattt     60
ctcccctttt tttgtcctta attattttca tcttgcccat tttctaattg tgcacaatca    120
atatcctttc tatttctacc tttcttactt ggtcccattt taaccttccc aatcatgcag    180
ggatctgtga acaagaggaa cctcagcagc caggacaggc aggagcagtg gaatagctac    240
tatggcttct ggaatcctgg ttaatgtaaa ggaggaggtg acctgcccca tctgcctgga    300
actcctgaca caacccctga gcctggactg cggccacagc ttctgccaag catgcctcac    360
tgcaaaccac aagaagtcca tgctagacaa aggagagagt agctgccctg tgtgccggat    420
cagttaccag cctgagaaca tacggcctaa tcggcatgta gccaacatag tggagaagct    480 caggggaggtc aagttgagcc cagaggggca gaaagttgat cattgtgcac gccatggaga    540
gaaacttcta ctcttctgtc aggaggacgg gaaggtcatt tgctggcttt gtgagcggtc    600
tcaggagcac cgtggtcacc acacgttcct cacagaggag gttgcccggg agtaccaagt    660
aagagactgg gatggaagga agagagggca gaaaatggga ccagatggaa aattttcact    720
ttgcctttga cattaactgc cttgtcatga tagacctgag acccgggatt attttttca    780 tgctatgctt aacttctgag gctttaagga tggttttttg catttcaccc aattacag     838

<210> SEQ ID NO 69
<211> LENGTH: 456
<212> TYPE: DNA
<213> ORGANISM: Human TRIM5alpha genomic sequence exon 3

<400> SEQUENCE: 69
gatgtaggga gcacattcac caatgtaagt tttcttccaa gtcatggatt ctcattgcca     60
ttctcacagt ttctgcaaat ttgtttcttc tgagatcaac ctgatttatt tcatgtttat    120
actctatcta ggtgctggaa aacctcatag cttgactatg gtgtgattcc tttctcacag    180
gtgaagctcc aggcagctct ggagatgctg aggcagaagc agcaggaagc tgaagagtta    240
gaagctgaca tcagagaaga gaaagcttcc tggaaggcaa gaggatgtgg ttcccgaagg    300
agttagctag aaatctgggc aggaccaggg gaaggagctt tcttcctctt tattccctga    360
catttgataa gtccagaagt catttgatta gtcctcttca tccttcccct gatggggtgt    420
ggtggctgag gagtgaatat gtcacagtga acacag                              456

<210> SEQ ID NO 70
<211> LENGTH: 591
<212> TYPE: DNA
<213> ORGANISM: Human TRIM5alpha genomic sequence exon 4

<400> SEQUENCE: 70
gtcattgttt taaaatgtca tgaaggaaaa gaaataggaa aaggcagctt tcctaagacc     60
tactctcctg ctactatgtc ccctccttgt gagaactccc caaaagaaac agctcctttt    120
```

-continued

| | |
|---|---|
| ctggctaaca gcctctgcct ggtagactga gtgcccctttt ctcttctctt atctctgaag | 180 |
| actcaaatac agtatgacaa aaccaacgtc ttggcagatt ttgagcaact gagagacatc | 240 |
| ctggactggg aggagagcaa tgagctgcaa aacctggaga aggaggagga agacattctg | 300 |
| aaaagcctta cgaactctga aactgagatg gtgcagcaga cccagtccct gagagagctc | 360 |
| atctcagatc tggagcatcg gctgcagggg tcagtgatgg agctgcttca ggtaaaaagt | 420 |
| ggaaagaagc ctgagcactg agattaaaga aaagtgaagg ctatttcctt ctctgcgttg | 480 |
| ctgtgctttt tctaatatta acaatgttct ctgcaggacc gcttttctga atcaattgct | 540 |
| gaagttataa gaataattga atgtagaagt agcaagagat aatcccattt t | 591 |

<210> SEQ ID NO 71
<211> LENGTH: 383
<212> TYPE: DNA
<213> ORGANISM: Human TRIM5alpha genomic sequence exon 5

<400> SEQUENCE: 71

| | |
|---|---|
| tggaaatctc acatgagtct tctgggatga ttgccttgag tcttatcttt gctttttttgt | 60 |
| ctttcacact gtcaccatct ccattctcag cacattagga accgggggaa atgtgatgaa | 120 |
| gctttataag tgaggagaga ctctttcttt cttaattgat gttttctctc ttcttcctag | 180 |
| ggtgtggatg gcgtcataaa aaggtatgtg tgggaggaca gagatggtcc ttttgtgcag | 240 |
| tgaggagaga tttatagcca ttagaattgt cctgggttta attagaataa acatctccc | 300 |
| agggcagaaa aatttcgata ttgtttttatc ataaatttct ggtcataaat cagcattcga | 360 |
| atgttctata actattaaga ata | 383 |

<210> SEQ ID NO 72
<211> LENGTH: 461
<212> TYPE: DNA
<213> ORGANISM: Human TRIM5alpha genomic sequence exon 6

<400> SEQUENCE: 72

| | |
|---|---|
| aaggcaaaca tgagaacatt ttgtttgcct ccagggtcaa gagtttgcac tctcccttct | 60 |
| caggatcccc aagaagagag ttcaagtgcc tcaatgggtt gaaatgatag gaagtcaggg | 120 |
| gtgttccacg gacacaaggt caaaggtttg gaagtttttt ttttttttt taattcttag | 180 |
| gacggagaac gtgaccttga agaagccaga aacttttcca aaaaatcaaa ggagagtgtt | 240 |
| tcgagctcct gatctgaaag gaatgctaga agtgtttaga ggtgaggaga gctagatcaa | 300 |
| caacagggtt atgaaattca gtggtgttaa gggtgctaaa tagggaagag ggtgcagttt | 360 |
| ccaaatatgg atagagggga taggggagga tagatattgt ctgctgctga tgggattata | 420 |
| tttaatggga aatggctagg tggctgtttc atctcatcat t | 461 |

<210> SEQ ID NO 73
<211> LENGTH: 387
<212> TYPE: DNA
<213> ORGANISM: Human TRIM5alpha genomic sequence exon 7

<400> SEQUENCE: 73

| | |
|---|---|
| tctgctgctg atgggattat atttaatggg aaatggctag gtggctgttt catctcatca | 60 |
| ttcagcaatt tactgcccta ccatagggca tacctactct ttccctaatc tggagagaaa | 120 |
| atgaatttca gtgctgactc ctttgtttgt attcaatatt gtgcattttt atcatttcag | 180 |
| agctgacaga tgtccgacgc tactgggta aggagaagtc acattatcat aagccaccct | 240 |
| gcggcttatc attattatta tctttatctt ttagaatttt atgttctcta ttaggctcat | 300 |

-continued

| | |
|---|---|
| gttttaagat ttatgattct ccttccaaga cacacataac ttacccctcc ttataacttc | 360 |
| taaacaaggt tcctcccagt tttctct | 387 |

<210> SEQ ID NO 74
<211> LENGTH: 2198
<212> TYPE: DNA
<213> ORGANISM: Human TRIM5alpha genomic sequence exon 8

<400> SEQUENCE: 74

| | |
|---|---|
| ctattaggct catgttttaa gatttatgat tctccttcca agacacacat aacttacccc | 60 |
| tccttataac ttctaaacaa ggttcctccc agtttttctct caagtctttta tcaagatttc | 120 |
| tctcatatca caaataaagt tacattatat cccttagctg acctgttaat ttttctacag | 180 |
| ttgatgtgac agtggctcca acaacatttt catgtgctgt catttctgaa gataagagac | 240 |
| aagtgagctc tccgaaacca cagataatat atggggcacg agggacaaga taccagacat | 300 |
| ttgtgaattt caattattgt actggcatcc tgggctctca agtatcaca tcagggaaac | 360 |
| attactggga ggtagacgtg tccaagaaaa ctgcttggat cctgggggta tgtgctggct | 420 |
| tccaacctga tgcaatgtgt aatattgaaa aaatgaaaaa ttatcaacct aaatacggct | 480 |
| actgggttat agggttagag gaaggagtta aatgtagtgc tttccaggat agttccttcc | 540 |
| atactccttc tgttcctttc attgtgcccc tctctgtgat tatttgtcct gatcgtgttg | 600 |
| gagttttcct agactatgag gcttgcactg tctcattctt caatatcaca aaccatggat | 660 |
| ttctcatcta taagttttct cactgttctt tttctcagcc tgtatttcca tatttaaatc | 720 |
| ctagaaaatg tggagtcccc atgactctgt gctcaccaag ctcttgaacc ttcttacaca | 780 |
| ctcagcccct tctgtacagc acctcttgtc caggtgcatc tcatacacct gaactcattt | 840 |
| gcatcatttt aaccatcttt tccttgctgt ctcccttctt tctatttgaa cgtccttcac | 900 |
| tcatcagtaa aatgtaataa ttgccttgtg ccatattgtc cccaatattt tattgacatt | 960 |
| tgatagcaat ttttttcatc attttccgta ctcctaagga aaactgacct atacctcata | 1020 |
| aaatgagacc gctatttagg tattacttct gccagatatt tatcacccaa ttgcctctga | 1080 |
| cactgactaa aagatgaag aaaagctttt caacagcctt tctatatcat cgtgtgataa | 1140 |
| ttgttcacca atgaatgagt ccttagccct gtgtcagttt accctcgatg cccttatttg | 1200 |
| tgagttaaag agaaaatatc ataaatggta tactcttaag tatagaggtt ttgtatctag | 1260 |
| aggatctcag ttcaactcct gtctctccat ataccagcag tgtaactgtg aataacatac | 1320 |
| ttaaatggct gtgcttattt cctttctctt tctttttttct ttttttttttt ttttgagatg | 1380 |
| aagtttttgct cttgttcccc aggctggagt gcaatggcac gatctcggtt cactgcaacc | 1440 |
| tccacctctc agattcaagc aattctcctg cctcagcctc caagtagct gggattacag | 1500 |
| gtgcccacca ccacccctgg ctaaatttgt attttcagta gagacggggt ttccccatgt | 1560 |
| tggttaggct cgtctagaac ctctgacctc aggtgatcca cccgcctcgg cctcccaaag | 1620 |
| tgctgggatt acaggcgtga gccacggcgc ccagcctgtg cttatttttct taaaataatt | 1680 |
| tttgtattaa aaacttcaca ttaaataagt gctaatgttt tattgcatag tagggtgact | 1740 |
| agagttaaca ataaccctatt gcatatattt tgaaatagct agaagagagg attttgaaag | 1800 |
| ttctcaacac aaagaaatga cacatatttg aggtgatgga tatgctaatt accctggttc | 1860 |
| ggttattacg caatgtatac atgtatcaaa acatcacact gtaccacata aatatgtata | 1920 |
| tttattattt gtcaattaaa agcaaataa aacaaaaaac cttcatctaa tactttggat | 1980 |
| cattgtgaaa aataaaattc ctgaagtata aagcatctat ctaagtgtct tgatctaata | 2040 |

```
agtacttgtt ctacaaatta ttgaaaaaca taaactctgt taatgtctca tggaacaggt    2100
tgtgccttca gggaaactag gattggattt actaaattct cattttttag atctcagata    2160
ctactgtcaa aatgacttca attctgcctt ctatatat                            2198

<210> SEQ ID NO 75
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 75
gccttacgaa gtctgaaac                                                 19

<210> SEQ ID NO 76
<211> LENGTH: 19
<212> TYPE: DNA
<213> ORGANISM: Artificial sequence
<220> FEATURE:
<223> OTHER INFORMATION: Synthetic oligonucleotides

<400> SEQUENCE: 76
ggttaacgaa gagcgaaac                                                 19
```

METHODS AND COMPOSITIONS FOR THE TREATMENT AND PREVENTION OF HIV INFECTION USING TRIM5α

RELATED APPLICATIONS

This application is a Divisional Application of U.S. Ser. No. 11/510,500, filed on Aug. 25, 2006, which is a Continuation of International Patent Application No. PCT/US2005/005458, filed on Feb. 17, 2005, which claims the benefit of priority to U.S. Provisional Application Ser. No. 60/548,139, filed on Feb. 25, 2004. The contents of each application are incorporated herein in their entirety by this reference.

GOVERNMENT FUNDING

Work described herein was supported, at least in part, by National Institutes of Health (NIH) under grants PO1 HL54785. The government has certain rights in this invention.

BACKGROUND OF THE INVENTION

The primate lentiviruses include the human immunodeficiency viruses types 1 and 2 (HIV-1 and HIV-2) and simian immunodeficiency viruses (SIVs) (Barre-Sinoussi, F., et al. (1983) Science 220:868-871; Clavel, F. (1987) AIDS 1:135-140; Daniel, M. D., et al. (1985) Science 228:1201-1204; Desrosiers, R. C. (1990) Ann. Rev. Immunol. 8: 557-578; Gallo, R. C, et al. (1984) Science 224:500-503). HIV-1 and HIV-2 infect humans, HIV-1-like viruses infect chimpanzees, and SIV variants infect African monkeys. Humans infected by HIV-1 and HIV-2 and Asian macaques infected by certain SIV strains often develop life-threatening immunodeficiency due to depletion of CD4-positive T lymphocytes (Fauci, A., et al. (1984) Ann. Int. Med. 100:91-106; Letvin, N. L., et al. (1985) Science 230:71-739, 19).

In humans, HIV infection causes Acquired Immunodeficiency Syndrome (AIDS), an incurable disease in which the body's immune system breaks down leaving the victim vulnerable to opportunistic infections, e.g., pneumonia, and certain cancers, e.g., Kaposi's Sarcoma. AIDS is a major global health problem. The Joint United Nations Programme on HIV/AIDS (UNAIDS) estimates that there are now over 34 million people living with HIV or AIDS worldwide, some 28.1 million of those infected individuals reside in impoverished sub-Saharan Africa. In the United States, approximately one out of every 500 people are infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide.

HIV and SIV tropism is determined by cell-type-specific and species-specific host factors. Following entry into the host cell, uncoating of the viral core, reverse transcription, nuclear access, and integration of the viral DNA into the host genome must occur to establish a permanent infection (Arts, E. J., and M. A. Wainberg. (1996) Adv. Virus Res. 46:97-163; Freed, E. O. (1998) Virology 251:1-15; Whitcomb, J. M., and S. H. Hughes. (1992) Annu. Rev. Cell. Biol. 8:275-306). Early, post-entry restrictions to retrovirus infection can determine tropism at the species level. HIV-1 encounters a post-entry block in Old World monkeys, whereas SIVmac is blocked in most New World monkey cells (Himathongkham, S., and P. A. Luciw. (1996) Virology 219:485-488; Hofmann, W., et al. (1999) J. Virol. 73:10020-10028; Shibata, R., et al. (1995) J. Gen. Virol. 76:2723-2730). These species-specific restrictions occur prior to or concurrent with reverse transcription; at most, low levels of early reverse transcripts are made in restricted cells (Cowan, S., et al. (2002) Proc. Natl. Acad. Sci. USA 99:11914-11919; Himathongkham, S., and P. A. Luciw. (1996) Virology 219:485-488; Munk, C, et al. (2002) Proc. Natl. Acad. Sci. USA 99:13843-13848; Shibata, R., et al. (1995) J. Gen. Virol. 76:2723-2730). The viral determinant of susceptibility to these blocks is the capsid protein (Cowan, S., et al. (2002) Proc. Natl. Acad. Sci. USA 99:11914-11919; Hatziioannou, T., et al. (2004) J. Virol. 78:6005-6012; Kootstra, N. A., et al. (2003) Proc. Natl. Acad. Sci. USA 200:1298-1303; Owens, C. M., et al. (2004) J. Virol. 78:5423-5437; Owens, C. M., et al. (2003) J. Virol. 77:726-731; Towers, G., et al. (2000) Proc. Natl. Acad. Sci. USA 97:12295-12299). The early restriction to HIV-1 and SIV is mediated by dominant host factors, the activity of which can be titrated by the introduction of virus-like particles containing proteolytically processed capsid proteins of the restricted viruses (Besnier, C, et al. (2002) Proc. Natl. Acad. Sci. USA 99:11920-11925; Bieniasz P. D. (2003) Trends Microbiol. 11:286-291; Cowan, S., et al. (2002) Proc. Natl. Acad. Sci. USA 99:11914-11919; Hatziioannou, T., et al. (2003) EMBO J. 22:385-394; Owens, C. M., et al. (2004) J. Virol. 78:5423-5437; Towers, G., et al. (2002) J. Virol. 76:2548-2550; Towers, G. J., et al. (2003) Nat. Med. 9:1138-1143). Thus, in the cells of specific monkey species, host restriction factors apparently interact, directly or indirectly, with the HIV-1 or SIV capsid and prevent its progression along the infectious pathway.

The identification of the factor(s) that mediate this blocking will shed light on the poorly understood series of events that govern the fate of retroviral capsids after entry, permit the development of animal models for the study of HIV-1 pathogenesis, treatment and prophylaxis, and suggest approaches to intervene in transmission or spread within the host.

SUMMARY OF THE INVENTION

The present invention is based, at least in part, on the identification of a novel member of the TRIM family of molecules. In particular, the invention is based on the identification of the rhesus monkey TRIM5α (TRIM5$α_{rh}$) molecule, a component of cellular cytoplasmic bodies. The present invention is also based, at least in part, on the discovery that TRIM5α specifically and efficiently prevents viral infection, e.g., lentiviral infection, e.g., SIV and/or HIV, e.g., HIV-1 infection and replication in cells, i.e., in both human and monkey cells.

Accordingly, one aspect of the present invention includes an isolated nucleic acid molecule comprising or consisting of the nucleotide sequence set forth in SEQ ID NO:1, or a complement thereof, and an isolated nucleic acid molecule which encodes a polypeptide comprising or consisting of the amino acid sequence set forth in SEQ ID NO:2, or a complement thereof.

In another aspect, the present invention includes an isolated nucleic acid molecule which encodes a TRIM5α polypeptide comprising a nucleotide sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the nucleotide sequence of SEQ ID NO:1, wherein percent identity is determined according to the LALIGN algorithm using a PAM120 weight residue table, a gap length penalty of 12 and a gap penalty of 4.

In a further aspect, the present invention provides an isolated nucleic acid molecule encoding a TRIM5α protein comprising amino acids 15-59, amino acid residues 321-346, and/or amino acids 297-497 of SEQ ID NO:2. The invention also includes an isolated nucleic acid molecule encoding a fusion protein comprising a TRIM5α fragment consisting essentially of amino acids 15-59, amino acid residues 321-346, and/or amino acids 297-497 of SEQ ID NO:2 and at least one non-TRIM5α polypeptide.

Furthermore, the invention provides an isolated protein comprising or consisting of the amino acid sequence set forth in SEQ ID NO:2. In another aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the amino acid sequence of SEQ ID NO:2, wherein percent identity is determined according to the LALIGN algorithm using a PAM120 weight residue table, a gap length penalty of 12 and a gap penalty of 4. In a further aspect, the invention provides an isolated protein comprising amino acids 15-59 and/or amino acids 297-497 of SEQ ID NO:2.

In a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 15-59 of SEQ ID NO:2, and having one or more of the following: glutamic acid (E) at amino acid residue 24, histidine (H) at amino acid residue 29, isoleucine (I) at amino acid residue 39, tyrosine (Y) at amino acid residue 49, and/or serine (R) at amino acid residue 54, and combinations thereof.

In one embodiment, the invention provides an isolated protein comprising an amino acid sequence which is at least 90% identical to amino acids 15-59 of SEQ ID NO:2. In another embodiment, the invention provides an isolated protein comprising an amino acid sequence which is at least 90% identical to amino acids 297-497 of SEQ ID NO:2. In another embodiment, the invention provides an isolated protein comprising an amino acid sequence which is at least 90% identical to amino acids 321-346 of SEQ ID NO:2. In yet another embodiment, the invention provides an isolated protein comprising an amino acid sequence which is at least 90% identical to amino acids 15-59 and/or amino acid residues 297-487 of SEQ ID NO:2.

In still a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 297-497 of SEQ ID NO:2, and having one or more of the following: leucine (L) at amino acid residue 305, threonine (T) at amino acid residue 307, histidine (H) at amino acid residue 312, alanine (A) at amino acid residue 316, arginine (R) at amino acid residue 325, asparagine (N) at amino acid residue 326, methionine (M) at amino acid residue 330, glutamine (Q) at amino acid residue 332, proline (P) at amino acid residue 334, leucine (L) at amino acid residue 337, phenylalanine (F) at amino acid residue 338, threonine (T) at amino acid residue 339, phenylalanine (F) at amino acid residue 340, leucine (L) at amino acid residue 343, threonine (T) at amino acid residue 344, valine (V) at amino acid residue 352, serine (S) at amino acid residue 373, serine (S) at amino acid residue 385, tyrosine (Y) at amino acid residue 389, glutamine (Q) at amino acid residue 393, glutamine (Q) at amino acid residue 409, tyrosine (Y) at amino acid residue 414, valine (V) at amino acid residue 416, glycine (G) at amino acid residue 420, serine (S) at amino acid residue 422, phenylalanine (F) at amino acid residue 426, alanine (A) at amino acid residue 427, valine (V) at amino acid residue 446, glutamine (Q) at amino acid residue 470, lysine (K) at amino acid residue 475, and/or threonine (T) at amino acid residue 487, and combinations thereof.

In still a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 286-371 of SEQ ID NO:2, and having one or more of the following: a D at amino acid residue 288, an M at amino acid residue 289, an A at amino acid residue 296, an L at amino acid residue 305, an T at amino acid residue 307, an H at amino acid residue 312, an A at amino acid residue 316, an R at amino acid residue 325, an N at amino acid residue 326, an M at amino acid residue 330, an Q at amino acid residue 332, an P at amino acid residue 334, an L at amino acid residue 337, an F at amino acid residue 338, an T at amino acid residue 339, an F at amino acid residue 340, an L at amino acid residue 343, an T at amino acid residue 344, and/or a V at amino acid residue 352, and combinations thereof.

In still a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9°A or more identical to amino acids 321-346 of SEQ ID NO:2, and having one or more of the following: an R at amino acid residue 325, an N at amino acid residue 326, an M at amino acid residue 330, an Q at amino acid residue 332, an P at amino acid residue 334, an L at amino acid residue 337, an F at amino acid residue 338, an T at amino acid residue 339, an F at amino acid residue 340, an L at amino acid residue 343, and/or an T at amino acid residue 344, and combinations thereof.

In still a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9°A or more identical to amino acids 323-332 of SEQ ID NO:2, and having one or more of the following: an R at amino acid residue 325, an N at amino acid residue 326, an M at amino acid residue 330, and/or an Q at amino acid residue 332, and combinations thereof.

In still a further aspect, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 323-328 of SEQ ID NO:2, and having one or more of the following: an R at amino acid residue 325, and/or an N at amino acid residue 326, and combinations thereof.

The present invention also includes methods for detecting the presence of a polypeptide of the invention in a sample comprising contacting the sample with an agent capable of specifically detecting the polypeptide such that the presence of the polypeptide is detected in the sample. In a related embodiment, the invention provides a method for detecting the presence of a nucleic acid molecule of the invention in a sample comprising contacting the sample with an agent capable of specifically detecting the nucleic acid molecule such that the presence of the nucleic acid molecule is detected in the sample.

The present invention also provides methods for modulating the activity of a TRIM5α polypeptide comprising contacting the polypeptide or a cell expressing the polypeptide with a compound which binds to the polypeptide in a sufficient concentration to modulate the activity of the polypeptide.

The present invention also includes screening assays which may be used to identify modulators of the TRIM molecules of the invention. In one aspect, the invention provides methods for identifying a compound which modulates TRIM5α expression or activity comprising contacting the TRIM5α protein or a cell expressing TRIM5α with a test compound, and determining the effect of the test compound on the expression or activity of TRIM5α.

In one embodiment, determining the effect of the test compound on the expression or activity of the TRIM5α a protein comprises determining a stimulatory effect. In another embodiment, determining the effect of the test compound on the expression or activity of the TRIM5α protein comprises determining an inhibitory effect.

In a further embodiment, the test compound is selected from the group consisting of a nucleic acid molecule, a peptide, a peptidomimetic, or a small molecule.

In yet another embodiment, the activity is modulation of HIV infection and/or replication, e.g., HIV-1 infection and/or replication, interaction of a TRIM5α protein with a TRIM5α binding partner, ubiquitination or signaling of ubiquitination, protein degradation or signaling of protein degradation, or binding to capsid protein, e.g., HIV-1 capsid protein.

In a further embodiment, the invention provides methods for identifying a compound which modulates TRIM expression or activity comprising contacting a cell which expresses TRIM with a test compound and determining the effect of the test compound on the expression or activity of the TRIM protein, where the activity is modulation of HIV infection, interaction of a TRIM protein with a TRIM binding partner, ubiquitination or signaling of ubiquitination, degradation or signaling of degradation, or binding to HIV capsid protein. In one embodiment, TRIM is a cytoplasmic TRIM polypeptide. In another embodiment, TRIM is TRIM 4, 5, 6, 10, 14, 21, 22, 27, or 34 or any isoform thereof. In a preferred embodiment, TRIM is TRIM5α, e.g., TRIM5α$_{rh}$ or TRIM5α$_{hu}$.

In another aspect, the invention provides methods for identifying a compound capable of treating or preventing HIV infection comprising assaying the ability of the compound to modulate TRIM expression or activity.

In a further aspect, the present invention provides methods of preventing and/or treating HIV infection and/or replication in a subject comprising administering to the subject a TRIM modulator. In one embodiment, TRIM is a cytoplasmic TRIM polypeptide. In another embodiment, TRIM is TRIM 4, 5, 6, 10, 14, 21, 22, 27, or 34 or any isoform thereof. In a preferred embodiment, TRIM is TRIM5α, e.g., TRIM5α$_{rh}$ or TRIM5α$_{hu}$, or fragments thereof.

In one embodiment, the TRIM modulator is administered in combination with at least one additional pharmaceutical used to treat and/or prevent a viral infection and/or replicaiton, e.g., HIV. Examples of pharmaceuticals used to treat or prevent an infectious disease or disorder, e.g., HIV infection, AIDS, and AIDS-related diseases include, without limitation, antiretroviral therapies, e.g., protease inhibitors, immuno-modulators, immunostimulants, antibiotics, antiprotozoal agents, antifungal agents, antiviral compounds, anticancer drugs, and other agents and treatments, and combinations thereof, that can be employed to treat or prevent an infectious disease or disorder, e.g., HIV infection, AIDS, and AIDS-related diseases or delay the progression thereof. Specific pharmaceuticals which may be used in combination with the modulators of the invention to treat and/or prevent HIV infection and or/replication, AIDS, and AIDS-related diseases, include, without limitation, Norvir, Kaletra, Nevirapine, Efavirenz, Delavirdine, Zidovudine, Didanosine, Zalcitabine, Stavudine, Lamivudine, Abacavir, Lamivudine+Zidovudine, Saquinavir, Ritonavir, Indinavir, Nelfinavir, Amprenavir, Lopinavir+Ritonavir, Azithromycin, Clarithromycin, Clindamycin; Ceftriaxone, Cefixime, Ciprofloxacin; Rifabutin, Trimethoprim/Sulphamethoxazole (IV); Pentamidine, Pyrimethamine, Sulfadiazine, Folinic acid, Acyclovir, Cidofovir, Ganciclovir, Forscarnet, Amphotericin B, Fluconazole, Itraconazole, Ketoconazole; Vinblastine, Etoposide, Bleomycin, and Vincristine.

In another embodiment, the TRIM modulator is administered in combination with at least one additional TRIM protein, or a modulator thereof. The additional TRIM protein may be a cytoplasmic TRIM protein, or a biologically active fragment thereof, e.g., TRIM 4, 5, 6, 10, 14, 21, 22, 27, or 34 or any isoform thereof.

In one embodiment, the TRIM modulator is a small molecule or a peptidomimetic. In still another embodiment, the TRIM modulator is capable of modulating TRIM polypeptide activity. In yet another embodiment, the TRIM modulator is a polypeptide. For example, the TRIM modulator may be a TRIM5α polypeptide comprising an amino acid sequence which is at least 90% identical to the amino acid sequence of SEQ ID NO:2 wherein said % identity is calculated using the ALIGN program for comparing amino acid sequences, a PAM120 weight residue table, a gap length penalty of 12, and a gap penalty of 4.

In another embodiment, the TRIM modulator is capable of modulating TRIM5 nucleic acid expression. For example, the TRIM modulator may comprise a nucleic acid molecule encoding a polypeptide comprising an amino acid sequence which is at least 90% identical to the amino acid sequence of SEQ ID NO:2, wherein said % identity is calculated using the ALIGN program for comparing amino acid sequences, a PAM120 weight residue table, a gap length penalty of 12, and a gap penalty of 4. The TRIM modulator can be administered using a gene therapy vector, e.g., a viral vector.

In another aspect, the invention provides methods of inhibiting HIV infection or replication in a cell population comprising administering said cells TRIM, e.g., TRIM5α. For example, the cell population may be present in a mucosal membrane of a subject. In one embodiment, the TRIM modulator is administered in combination with a basic peptide, e.g., a TAT peptide, that allows cell uptake. In another embodiment, the TRIM modulator is encapsulated in a liposome prior to administration. In still another embodiment, the TRIM modulator is administered using a gene therapy vector, e.g., a viral vector.

In yet another aspect, the invention provides methods of determining whether a subject is susceptible or resistant to infection by HIV comprising the steps of: obtaining a nucleic acid sample from the subject; and determining the identity of one or more nucleotides in polymorphic regions of a TRIM nucleic acid molecule which are associated with susceptibility or resistance to infection by HIV.

In a related aspect the invention provides methods of determining whether a subject is susceptible or resistant to infection by HIV comprising the steps of obtaining a TRIM5α protein sample from the subject; and determining the identity of one or more amino acids in polymorphic regions of a TRIM polypeptide molecule which are associated with susceptibility or resistance to infection by HIV.

In a further aspect, the invention provides methods of determining whether a subject is susceptible or resistant to infection by HIV comprising the steps of: obtaining a sample from the subject; and determining the ratio of TRIM5α to other TRIM5 isoforms in said sample.

In another aspect, the invention provides methods for identifying a TRIM protein capable of treating or preventing HIV infection comprising assaying the ability of TRIM protein to bind to an HIV capsid protein. In still another aspect, the invention provides methods for identifying a TRIM protein capable of treating or preventing HIV infection comprising providing an animal, e.g., a mouse wherein said TRIM protein has been disrupted; exposing the animal, e.g., mouse to HIV; and assaying the susceptibility of said mouse to HIV.

In one embodiment, the TRIM protein is at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the nucleotide sequence set forth as SEQ ID NO:2. In another embodiment, the TRIM protein comprises amino acid residues 15-59 of SEQ ID NO:2, amino acid residues 321-346, and/or amino acid residues 297-497 of SEQ ID NO:2, and combinations thereof.

BRIEF DESCRIPTION OF THE DRAWINGS

FIGS. 1A-1E depict that rhesus monkey TRIM5α$_{rh}$ preferentially blocks HIV-1 infection. A. The amino-acid sequences of rhesus monkey TRIM5α$_{rh}$ and human TRIM5α$_{hu}$ are aligned, with major domains delineated Amino-acid residues conserved among RING and B-box 2 domains are colored. B. HeLa cells transduced with the pLPCX-TRIM5α$_{rh}$(fl) vector expressing TRIM5α$_{rh}$ or an empty control vector (pLPCX) were selected in medium containing puromycin and incubated with $2 \times 10^4$ RT units HIV-1.GFP or $8 \times 10^3$ RT units MLV.GFP. Infected, GFP-positive cells were visualized by fluorescence microscopy. C. HeLa cells transduced with pLPCX-TRIM5α$_{rh}$(fl) expressing TRIM5α$_{rh}$ (open circle) or an empty control vector (filled circle) were incubated with various amounts of the indicated viruses expressing GFP, and GFP-positive cells counted by FACS. The results shown are typical of those obtained in at least three independent experiments. D. HeLa-CD4 cells transduced with the pLPCX-TRIM5α$_{rh}$(cds) vector expressing TRIM5α$_{rh}$ (open circle) or an empty control vector (filled circle) were incubated with $1 \times 10^4$ RT units of infectious HIV-1 or SHIV, as indicated. E. HeLa cells transduced with the pLPCX-TRIM5α$_{rh}$(fl) vector expressing TRIM5α$_{rh}$ (open circle) or an empty control vector (filled circle) were exposed to the indicated GFP-expressing viruses, and GFP-positive cells counted by FACS.

FIG. 8 depicts the nucleotide sequence of the human TRIM5α exons including approximately 200 base pairs of genomic sequence flanking each exon 5' and 3' The size of each exon is noted in parentheses. Coding sequences are in capital letters and bold, intronic sequences are in small letters, the putative start site (ATG) in exon 2 and the stop codon in exon 8 are italicized, the 3' untranslated region in exon 8 is underlined, and a putative interferon stimulating response element (ISRE) which is 33 base pairs upstream of the putative start site is underlined. Exon 1 and surrounding genomic sequence corresponds to SEQ ID NO:67; exon 2 and surrounding genomic sequence corresponds to SEQ ID NO:68; exon 3 and surrounding genomic sequence corresponds to SEQ ID NO:69; exon 4 and surrounding genomic sequence corresponds to SEQ ID NO:70; exon 5 and surrounding genomic sequence corresponds to SEQ ID NO:71; exon 6 and surrounding genomic sequence corresponds to SEQ ID NO:72; exon 7 and surrounding genomic sequence corresponds to SEQ ID NO:73; exon 8 and surrounding genomic sequence corresponds to SEQ ID NO:74.

DETAILED DESCRIPTION OF THE INVENTION

Figure 1B:
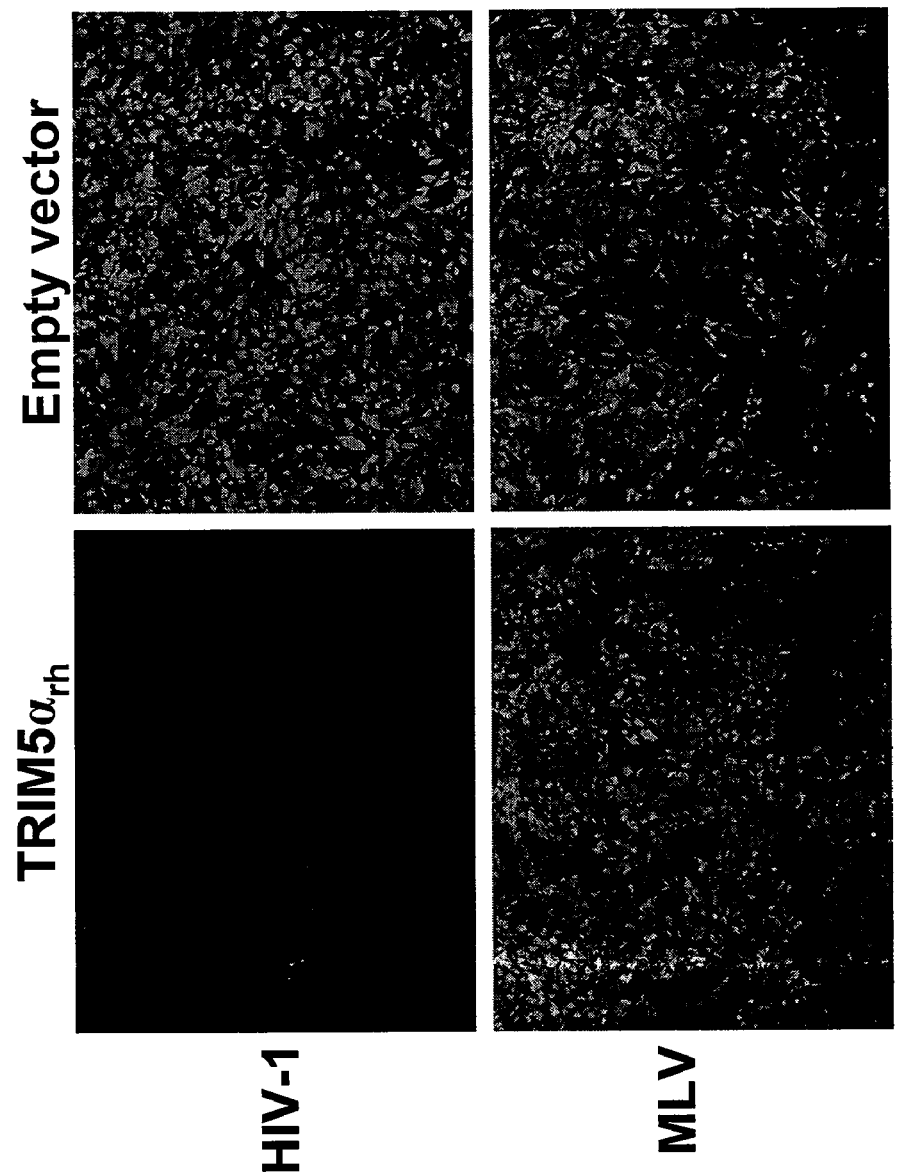

The present invention is based, at least in part, on the identification of a novel member of the TRIM family of molecules. In particular, the invention is based on the identification of the rhesus monkey TRIM5α (TRIM5α$_{rh}$) molecule, a component of cellular cytoplasmic bodies. The present invention is also based, at least in part, on the discovery that TRIM5α$_{rh}$ specifically and efficiently prevents viral infection and/or replication, e.g., lentiviral infection, e.g., HIV, e.g., HIV-1 infection and/or replication in cells, i.e., in both human and monkey cells. Thus, it has been determined that TRIM5α$_{rh}$ is a species-specific mediator of innate cellular resistance to HIV-1 infection and replication. Furthermore, it has been determined that the N-terminal RING domain of TRIM5α$_{rh}$ (amino acids 15-59 of SEQ ID NO:2) and the C-terminal B30.2 (SPRY) domain of TRIM5α$_{rh}$ (amino acids 297-479 of SEQ ID NO:2) contribute to the viral, e.g., HIV-1 inhibitory activity, of the TRIM5α$_{rh}$ protein (Stremlau, et al. (2004) *Nature*, 427:6977, incorporated in its entirety herein by reference). It has also been shown that one determinant of anti-viral potency, e.g., anti-HIV-1 potency is the B30.2 (SPRY) domain. Analysis of species-specific variation in TRIM5α has identified three variable regions (v1, v2, and v3) within the SPRY domain. Replacement of specific amino acids in the N-terminus of the TRIM5α$_{hu}$ SPRY v1 region with corresponding TRIM5α$_{rh}$ residue results in a TRIM5α molecule that restricts HIV-1. In addition, a specific amino acid substitution in the SPRY v1 domain of TRIM5α$_{hu}$ restricts simian immunodeficiency virus (SIV$_{mac}$).

Accordingly, in one aspect, the present invention provides methods and compositions for the treatment and/or prevention of viral infection and/or replication, e.g., HIV infection and/or replication, comprising administering a modulator of TRIM, e.g., cytoplasmic TRIM, e.g., TRIM5α, e.g., TRIM5α$_{rh}$, expression or activity. In one embodiment, the modulator is a TRIM protein, e.g., a cytoplasmic TRIM protein, such as TRIM5α, e.g., TRIM5α$_{rh}$, or a biologically active fragment thereof, e.g., a fragment comprising the RING domain and/or the SPRY domain, or a fragment thereof, such as for example a variable region of the SPRY domain, e.g., v1, v2 and/or v3, of a TRIM protein, e.g., a cytoplasmic TRIM protein, such as TRIM5α, e.g., TRIM5α$_{rh}$, a TRIM varaint, a TRIM mutant, or a chimeric protein comprising one or more TRIM proteins, e.g., a human TRIM protein and a rhesus monkey protein, or a TRIM protein and a non-TRIM protein. In another embodiment, the modulator is a nucleic acid molecule, a peptidomimetic, or a small molecule.

In another aspect, the present invention provides methods for identifying a compound which modulates TRIM, e.g., cytoplasmic TRIM, e.g., TRIM5α, e.g., TRIM5α$_{rh}$ expression or activity comprising contacting a cell which expresses TRIM, e.g., cytoplasmic TRIM, e.g., TRIM5α, e.g., TRIM5α$_{rh}$, with a test compound and determining the effect of the test compound on the expression or activity of the TRIM protein. In one embodiment, the TRIM activity is modulation of HIV infection and/or replication, interaction of a TRIM protein with a TRIM binding partner, ubiquitination or signaling of ubiquitination, protein degradation or signaling of protein degradation, or binding to a viral capsid protein.

In another aspect, the present invention also provides methods for identifying a compound capable of treating and/or preventing HIV infection and/or replication comprising assaying the ability of the compound to modulate TRIM protein, e.g., a cytoplasmic TRIM protein, such as TRIM5α, e.g., TRIM5α$_{rh}$ expression or activity.

The methods of the present invention are not limited to the use of TRIM5α$_{rh}$, but include additional members of the TRIM family, e.g., cytoplasmic TRIM molecules, e.g., TRIM 4, 6, 10, 14, 21, 22, 27, or 34, any isoform thereof, or any biologically active fragment thereof, which have a TRIM activity, e.g., modulation of HIV and/or SIV infection and/or replication, interaction of a TRIM protein with a TRIM binding partner, ubiquitination or signaling of ubiquitination, protein degradation or signaling of protein degradation, or binding to a viral capsid protein. Accordingly, the term "TRIM" includes TRIM5α, TRIM5α$_{rh}$, or any TRIM molecule, or biologically active fragment thereof, such as for example a RING domain or a SPRY domain, or a fragment of said domain, e.g., a variable region (v1, v2, and/or v3, preferably a cytoplasmic TRIM molecule, which has a TRIM activity as defined herein. The nucleotide and amino acid sequences of human TRIM4α are known and can be found in gi:15011939 (SEQ ID NO:15) and gi:14670266 (SEQ ID NO:16), respectively; the nucleotide and amino acid sequences of human TRIM4β are known and can be found in gi:15011940 (SEQ ID NO:17) and gi:15011941 (SEQ ID NO:18), respectively; the nucleotide and amino acid sequences of human TRIM6 are known and can be found in gi:18641348 (SEQ ID NO:19) and gi:18079262 (SEQ ID NO:20), respectively; the nucleotide and amino acid sequences of human TRIM10, isoform 1, are known and can be found in gi:16519562 (SEQ ID NO:21) and gi:5803147 (SEQ ID NO:22), respectively; the nucleotide and amino acid sequences of human TRIM10, isoform 2, are known and can be found in gi:16519560 (SEQ ID NO:23) and gi:16519561 (SEQ ID NO:24), respectively; the nucleotide and amino acid sequences of human TRIM14α, variant 1, are known and can be found in gi:15208662 (SEQ ID NO:25) and gi:15208663 (SEQ ID NO:26), respectively; the nucleotide and amino acid sequences of human TRIM14α, variant 2, are known and can be found in gi:15208664 (SEQ ID NO:27) and gi:15208665 (SEQ ID NO:28), respectively; the nucleotide and amino acid sequences of human TRIM14α, variant 3, are known and can be found in gi:15208666 (SEQ ID NO:29) and gi:15208667 (SEQ ID NO:30), respectively; the nucleotide and amino acid sequences of human TRIM14β are known and can be found in gi:15208668 (SEQ ID NO:31) and gi:15208669 (SEQ ID NO:32), respectively; the nucleotide and amino acid sequences of human TRIM21, also referred to as Sjogren syndrome antigen A1, are known and can be found in gi:15208659 (SEQ ID NO:33) and gi:15208660 (SEQ ID NO:34), respectively; the nucleotide and amino acid sequences of human TRIM22 are known and can be found in gi:15208661 (SEQ ID NO:35) and gi:5174699 (SEQ ID NO:36), respectively; the nucleotide and amino acid sequences of human TRIM27α are known and can be found in gi:17105396 (SEQ ID NO:37) and gi:5730009 (SEQ ID NO:38), respectively; the nucleotide and amino acid sequences of human TRIM27β are known and can be found in gi:18641280 (SEQ ID NO:39) and gi:15011933 (SEQ ID NO:40), respectively; the nucleotide and amino acid sequences of human TRIM34, isoform 1, are known and can be found in gi:18641341 (SEQ ID NO:41) and gi:18087807 (SEQ ID NO:42), respectively; the nucleotide and amino acid sequences of human TRIM34, isoform 2, are known and can be found in gi:18641342 (SEQ ID NO:43) and gi:18641343 (SEQ ID NO:44), respectively; the nucleotide and amino acid sequences of human TRIM34, isoform 3, are known and can be found in gi:18641344 (SEQ ID NO:45) and gi:18641345 (SEQ ID NO:46), respectively; the entire contents of all of which are incorporated herein by reference.

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., mouse or monkey polypeptides. Members of a family may also have common functional characteristics.

The tripartite motif (TRIM) protein family, also known as the RBCC family (Reddy, B. A., et al. (1992) *Trends Biochem. Sci.*, 17:344-345; Borden, K. L. (1998) *Biochem. Cell Biol.*, 76:351-358), refers to a family of proteins that are composed of three zinc-binding domains, a RING (R), a B-box type 1 (B1) and a B-box type 2 (B2), followed by a coiled-coil (CC) region (Reddy, B. A., et al. (1992) *Trends Biochem. Sci.* 17:344-345; Borden, K. L. (1998) *Biochem. Cell Biol.* 76:351-358). Thirty-seven members of the human TRIM family have been identified and shown to homodimerize, thus forming distinct cellular compartments which can often be localized in the cytoplasm (e.g., TRIM 1, 2, 3, 4, 5, 6, 9, 10, 12, 13, 14, 18, 20, 21, 22, 24, 25, 26, 27, 32, 34), the nucleus (e.g., TRIM8, 28), or both (e.g., TRIM7, 11, 23, 30, 31) (Reymond, A., et al. (2001) *EMBO J.* 20:2140-2151). In addition, some of the TRIM family members are clustered on CHR 6p21-23 and CHR 11p15, including, for example TRIM 5, 6, 21, 22, and 34, are more closely related to each other than to the other TRIMs, based on their sequence and therefore are preferred molecules for use in the methods of the present invention. There are multiple isoforms of each TRIM protein due to alternative splicing. For example, there are multiple isoforms of human TRIM5 in addition to TRIM5α, e.g., TRIM5α (nucleotide sequence, gi:14719417 (SEQ ID NO:47); amino acid sequence, gi:14719418 (SEQ ID NO:48)), TRIM5β (nucleotide sequence, gi: 12407382 (SEQ ID NO:49); amino acid sequence, gi:12407383 (SEQ ID NO:50)), TRIM5γ (nucleotide sequence, gi:15011943 (SEQ ID NO:51); amino acid sequence, gi:15011944 (SEQ ID NO:52)), TRIM5δ (nucleotide sequence, gi:15011945 (SEQ ID NO:53); amino acid sequence, gi:15011946 (SEQ ID NO:54)), and TRIM5ε (nucleotide sequence, gi:12407388 (SEQ ID NO:55); amino acid sequence, gi:12407389 (SEQ ID NO:56)) (gi:12407388); the contents of each of which are incorporated herein by reference.

As used interchangeably herein, a "TRIM activity," "biological activity of TRIM," or "functional activity of TRIM", refers to an activity exerted by a TRIM protein, polypeptide, biologically active fragment thereof, or nucleic acid molecule on a TRIM responsive cell or tissue, or on a TRIM protein substrate, as determined in vivo, or in vitro, according to standard techniques and methods described herein. In one embodiment, a TRIM activity is a direct activity, such as an association with a TRIM-target molecule. As used herein, a "target molecule" or "binding partner" is a molecule with which a TRIM protein binds or interacts in nature, such that TRIM-mediated function is achieved. A TRIM target molecule can be a non-TRIM molecule or a TRIM protein or polypeptide of the present invention, e.g., a capsid polypeptide, e.g., an HIV-1 capsid protein, e.g., p24. Alternatively, a TRIM activity is an indirect activity, such as a cellular signaling activity mediated by interaction of the TRIM protein with a TRIM5α ligand. The biological activities of TRIM are described herein. For example, the TRIM proteins of the present invention can have one or more of the following activities: modulation of viral infection and/or replication, e.g., HIV and/or SIV infection and/or replication, interaction of a TRIM protein with a TRIM binding partner, ubiquitination or signaling of ubiquitination, protein degradation or signaling of degradation of a protein, or binding to viral capsid protein, e.g., HIV capsid protein. Therefore, additional TRIM molecules having TRIM5α, e.g., anti-viral activity, e.g., TRIM5α$_{rh}$, may be identified by assaying the ability of TRIM protein to bind to an HIV capsid protein or restrict viral infection of a cell, thereby identifying a TRIM protein capable of treating or preventing HIV and/or SIV infection. Additional TRIM molecules having TRIM5α, e.g., anti-viral activity, e.g., TRIM5α$_{rh}$, may be also be identified by providing an animal, e.g., a mouse, wherein a particular TRIM protein has been disrupted, e.g., a knock-out mouse; exposing the animal to a virus, e.g., HIV, and assaying the susceptibility of the animal to the virus, e.g., HIV.

Furthermore, based on the discovery that the RING domain of TRIM5α$_{rh}$ (amino acids 15-59 of SEQ ID NO:2) and the B30.2 (SPRY) domain of TRIM5α$_{rh}$ (amino acids 297-479 of SEQ ID NO:2) contribute to the viral, e.g., HIV-1, inhibitory activity of the TRIM5α$_{rh}$ protein, TRIM proteins used in the methods of the invention preferably contain one or more of the following: a RING domain and/or a SPRY domain. As used herein, the term "RING domain" includes a protein domain having at least about 30-90 amino acid residues or preferably about 44 amino acid residues, and a RING domain mediated activity, e.g., ubiquitination or the inhibition of viral infection and/or replication. As used interchangeably herein, the term "SPRY domain" or "B30.2 domain" includes a protein domain having at least about 100-300 amino acid residues or preferably about 200 amino acid residues, and a SPRY domain mediated activity, e.g., promotion of protein-protein interactions and/or the inhibition of viral infection and/or replication. As used herein a "SPRY variable region" or "B30.2 variable region", such as v1, v2, and v3, is a subregion of the TRIM5α protein that has been shown to exhibit dramatic species-specific length and amino acid variation. The v1 subregion of the TRIM5α$_{rh}$ protein corresponds to amino acid residues 321-346 of SEQ ID NO:2.

Isolated TRIM polypeptides of the present invention have an amino acid sequence sufficiently identical to the amino acid sequence of SEQ ID NO:2 or are encoded by a nucleotide sequence sufficiently identical to SEQ ID NO:1. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid sequences which share common structural domains having at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identity to SEQ ID NO:2 or across the amino acid sequences comprising the RING and/or SPRY domain (amino acids 15-59 of SEQ ID NO:2 and amino acids 297-479 of SEQ ID NO:2, respectively), are defined herein as sufficiently identical. In a further embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the amino acid sequences comprising the RING and/or SPRY domain (amino acids 15-59 of SEQ ID NO:2 and amino acids 297-479 of SEQ ID NO:2, respectively), and having one or more of the amino acid residues specific to the TRIM5α$_{rh}$ protein as compared to the TRIM5α$_{hu}$ protein (see FIG. 1A, which contains an alignment of the amino acid sequences of the TRIM5α$_{rh}$ protein and the TRIM5α$_{hu}$ protein).

Furthermore, amino acid sequences which share at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identity to SEQ ID NO:2 and share a common functional activity, e.g., modulation of viral infection and/or replication, e.g., inhibition of HIV and/or SIV infection and/or replication, interaction of a TRIM protein with a TRIM binding partner, ubiquitination or signaling of ubiquitination, protein degradation or signaling of degradation of a protein, or binding to viral capsid protein, e.g., HIV capsid protein, are defined herein as sufficiently identical.

The nucleotide and amino acid sequences of the isolated rhesus monkey TRIM5α molecule are shown in SEQ ID NOs:1 and 2, respectively.

Various aspects of the invention are described in further detail in the following subsections:

I. Definitions

The term "lentivirus" refers to a genus of viruses of the family retroviridae that cause persistent infection that typically results in chronic, progressive, usually fatal disease. It includes the human immunodeficiency viruses (HIV), e.g., HIV-1, simian immunodeficiency virus (SIV), feline immunodeficiency virus, maedi/visna virus, caprine arthritis-encephalitis virus, and equine infectious anemia virus.

As used herein, the term "compound" includes compounds that modulate, e.g., up-modulate or stimulate and down-modulate or inhibit, the expression and/or activity of TRIM, e.g., cytoplasmic TRIM, e.g., TRIM5α. As used herein the term "inhibitor" or "inhibitory agent" includes agents which inhibit the expression and/or activity of a TRIM, e.g., cytoplasmic TRIM, e.g., TRIM5α. Exemplary inhibitors include antibodies, RNAi, compounds that mediate RNAi (e.g., siRNA), antisense RNA, dominant/negative mutants of molecules of the invention, peptides, peptidomimetics and/or small molecules.

The term "stimulator" or "stimulatory agent" includes agents, e.g., agonists, which increase the expression and/or activity of TRIM, e.g., cytoplasmic TRIM, e.g., TRIM5α. Exemplary stimulating agents include active protein and nucleic acid molecules, peptides and peptidomimetics of TRIM, e.g., cytoplasmic TRIM, e.g., TRIM5α. Modulatory agents also include naturally occurring modulators, e.g., modulators of expression such as, for example, interferons.

The agents of the invention can directly or indirectly modulate, i.e., increase or decrease, the expression and/or activity of TRIM, e.g., cytoplasmic TRIM, e.g., TRIM5α. Exemplary agents are described herein or can be identified using screening assays that select for such compounds, as described in detail below.

For screening assays of the invention, preferably, the "test compound or agent" screened includes molecules that are not known in the art to modulate TRIM activity and/or expression and/or restriction of HIV-1 infection and/or replication. Preferably, a plurality of agents are tested using the instant methods.

The term "library of test compounds" is intended to refer to a panel comprising a multiplicity of test compounds.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

As used herein, the term "contacting" (i.e., contacting a cell e.g. an immune cell, with a compound) is intended to include incubating the compound and the cell together in vitro (e.g., adding the compound to cells in culture) or administering the compound to a subject such that the compound and cells of the subject are contacted in vivo.

As used herein, the term "cell free composition" refers to an isolated composition which does not contain intact cells. Examples of cell free compositions include cell extracts and compositions containing isolated proteins.

As used herein, the term "compound" includes any agent, e.g., nucleic acid molecules, antisense nucleic acid molecule, peptide, peptidomimetic, small molecule, or other drug, which binds to TRIM, e.g., cytoplasmic TRIM, e.g., TRIM5α proteins or has a stimulatory or inhibitory effect on, for example, TRIM, e.g., cytoplasmic TRIM, e.g., TRIM5α expression or TRIM activity, binding affinity or stability. In one embodiment, the compound may modulate transcription of TRIM.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane, et al. 1998. *Science* 282: 63), and natural product extract libraries. In another embodiment, the compounds are small, organic non-peptidic compounds. In a further embodiment, a small molecule is not biosynthetic.

As used herein, the term "oligonucleotide" includes two or more nucleotides covalently coupled to each other by linkages (e.g., phosphodiester linkages) or substitute linkages.

As used herein, the term "peptide" includes relatively short chains of amino acids linked by peptide bonds. The term "peptidomimetic" includes compounds containing non-peptidic structural elements that are capable of mimicking or antagonizing peptides.

As used herein, the term "reporter gene" includes genes that express a detectable gene product, which may be RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), *Nature* 282: 864-869) luciferase, and other enzyme detection systems, such as beta-galactosidase; firefly luciferase (deWet, et al. (1987), *Mol. Cell. Biol.* 7:725-737); bacterial luciferase (Engebrecht and Silverman (1984), *Proc. Natl. Acad. Sci., USA* 1: 4154-4158; Baldwin, et al. (1984), *Biochemistry* 23: 3663-3667); alkaline phosphatase (Toh, et al. (1989) *Eur. J. Biochem.* 182: 231-238, Hall, et al. (1983) *J. Mol. Appl. Gen.* 2: 101), human placental secreted alkaline phosphatase (Cullen and Malim (1992) *Methods in Enzymol.* 216:362-368) and green fluorescent protein (U.S. Pat. No. 5,491,084; WO 96/23898).

The term "treatment," as used herein, is defined as the application or administration of a therapeutic agent to a patient, or application or administration of a therapeutic agent to an isolated tissue or cell line from a patient, who has a disease, disorder, or infection, a symptom of a disease, disorder, or infection or a predisposition toward a disease, disorder, or infection, with the purpose of curing, healing, alleviating, relieving, altering, remedying, ameliorating, improving or affecting the disease, disorder, or infection, the symptoms of disease, disorder, or infection or the predisposition toward a disease, disorder, or infection. A therapeutic agent includes, but is not limited to, nucleic acid molecules, small molecules, peptides, peptidomimetics, antibodies, ribozymes, and sense and antisense oligonucleotides described herein.

The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic locus can be a single nucleotide, the identity of which differs in the other alleles. A polymorphic locus can also be more than one nucleotide long. The allelic form occurring most frequently in a selected population is often referred to as the reference and/or wild-type form. Other allelic forms are typically designated as alternative or variant alleles. Diploid organisms may be homozygous or heterozygous for allelic forms. A diallelic or biallelic polymorphism has two forms. A trialleleic polymorphism has three forms.

The term "single nucleotide polymorphism" (SNP) refers to a polymorphic site occupied by a single nucleotide, which is the site of variation between allelic sequences. A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site.

SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect.

As used herein, the term "misexpression" includes a non-wild-type pattern of gene expression. Expression as used herein includes transcriptional, post transcriptional, e.g., mRNA stability, translational, and post translational stages. Misexpression includes: expression at non-wild-type levels, i.e., over or under expression; a pattern of expression that differs from wild-type in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing of the mRNA, amino acid sequence, post-transitional modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "knockout" refers to an animal or cell therefrom, in which the insertion of a transgene disrupts an endogenous gene in the animal or cell therefrom. This disruption can essentially eliminate, for example, TRIM, e.g., cytoplasmic TRIM, e.g., TRIM5α, in the animal or cell.

In preferred embodiments, misexpression of the gene encoding the TRIM, e.g., cytoplasmic TRIM, e.g., TRIM5α, protein, is caused by disruption of the TRIM, e.g., cytoplasmic TRIM, e.g., TRIM5α, gene. For example, the TRIM5α gene can be disrupted through removal of DNA encoding all or part of the protein.

As used herein, "disruption of a gene" refers to a change in the gene sequence, e.g., a change in the coding region. Disruption includes: insertions, deletions, point mutations, and rearrangements, e.g., inversions. The disruption can occur in a region of the native TRIM DNA sequence (e.g., one or more exons) and/or the promoter region of the gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is a disruption. Preferred disruptions reduce TRIM levels to about 50% of wild-type, in heterozygotes or essentially eliminate TRIM in homozygotes.

As used herein, the term "transgenic cell" refers to a cell containing a transgene.

Various aspects of the invention are described in further detail in the following subsections:

I. Isolated Nucleic Acid Molecules

One aspect of the invention pertains to isolated nucleic acid molecules that encode TRIM polypeptides or biologically active portions thereof, as well as nucleic acid fragments sufficient for use as hybridization probes to identify TRIM-encoding nucleic acid molecules (e.g., TRIM mRNA) and fragments for use as PCR primers for the amplification or mutation of TRIM nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TRIM nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. Using all or a portion of the nucleic acid sequence of SEQ ID NO:1 as a hybridization probe, TRIM nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TRIM nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1. In another embodiment, the nucleic acid molecule consists of the nucleotide sequence set forth as SEQ ID NO:1.

In still another embodiment, an isolated nucleic acid molecule of the invention comprises a nucleic acid molecule which is a complement of the nucleotide sequence shown in SEQ ID NO:1, or a portion of thereof. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1, thereby forming a stable duplex.

In still another preferred embodiment, an isolated nucleic acid molecule of the present invention comprises a nucleotide sequence which is at least about 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the nucleotide sequence shown in SEQ ID NO:1 (e.g., to the entire length of the nucleotide sequence), or a portion thereof. In one embodiment, a nucleic acid molecule of the present invention comprises a nucleotide sequence which is at least (or no greater than) 50, 100, 200, 250, 300, 350, 400, 450, 500, 550, 600, 650, 700, 750, 800, 850, 900, 950, 1,000, 1,500, 2,000, 2,500 or more nucleotides in length and hybridizes under stringent hybridization conditions to a complement of a nucleic acid molecule of SEQ ID NO:1.

Moreover, the nucleic acid molecule of the invention can comprise only a portion of the nucleic acid sequence of SEQ ID NO:1, for example, a fragment which can be used as a probe or primer or a fragment encoding a portion of a TRIM polypeptide, e.g., a biologically active portion of a TRIM polypeptide. The nucleotide sequence determined from the cloning of the TRIM gene allows for the generation of probes and primers designed for use in identifying and/or cloning other TRIM family members, as well as TRIM homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:1, of an anti-sense sequence of SEQ ID NO:1, or of a naturally occurring allelic variant or mutant of SEQ ID NO:1.

Exemplary probes or primers are at least 12, 15, 20, 25, 30, 35, 40, 45, 50, 55, 60, 65, 70, 75 or more nucleotides in length and/or comprise consecutive nucleotides of an isolated nucleic acid molecule described herein. Probes based on the TRIM nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a TRIM sequence, e.g., a domain, region, e.g., RING or SPRY domain, site or other sequence described herein. The primers should be at least 5, 10, 20, 30, 40, 50, 60, 70, 80, 90, 100 or more nucleotides in length. Such probes can be used as a part of a diagnostic test kit for identifying cells or tissue which misexpress a TRIM polypeptide, such as by measuring a level of a TRIM-encoding nucleic acid in a sample of cells from a subject e.g., detecting TRIM mRNA levels or determining whether a genomic TRIM gene has been mutated or deleted.

A nucleic acid fragment encoding a "biologically active portion of a TRIM polypeptide" can be prepared by isolating a portion of the nucleotide sequence of SEQ ID NO:1, which encodes a polypeptide having a TRIM biological activity (the biological activities of the TRIM polypeptides are described herein), expressing the encoded portion of the TRIM polypeptide (e.g., by recombinant expression in vitro) and assessing the activity of the encoded portion of the TRIM polypeptide. In an exemplary embodiment, the nucleic acid molecule is at least 50, 100, 200, 250, 300, 350, 400, 450, 500, 550, 600, 650, 700, 750, 800, 850, 900, 950, 1,000, 1,500, 2,000, 2,500, or more nucleotides in length and encodes a polypeptide having a TRIM activity (as described herein).

The invention further encompasses nucleic acid molecules that differ from the nucleotide sequence shown in SEQ ID NO:1. Such differences can be due to due to degeneracy of the genetic code, thus resulting in a nucleic acid which encodes the same TRIM polypeptides as those encoded by the nucleotide sequence shown in SEQ ID NO:1. In another embodiment, an isolated nucleic acid molecule of the invention has a nucleotide sequence encoding a polypeptide having an amino acid sequence which differs by at least 1, 2, 3, but no greater than 5, 10, 20, 50 or 100 amino acid residues from the amino acid sequence shown in SEQ ID NO:2. In yet another embodiment, the nucleic acid molecule encodes the amino acid sequence of rhesus monkey TRIM. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, such as those described in Example 3), including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the TRIM polypeptides. Such genetic polymorphism in the TRIM genes may exist among individuals within a population due to natural allelic variation. As used herein, the terms "gene" and "recombinant gene" refer to nucleic acid molecules which include an open reading frame encoding a TRIM polypeptide, preferably a mammalian TRIM polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, wherein the nucleic acid molecule hybridizes to a complement of a nucleic acid molecule comprising SEQ ID NO:1, for example, under stringent hybridization conditions.

Allelic variants of TRIM include both functional and non-functional TRIM polypeptides. Functional allelic variants are naturally occurring amino acid sequence variants of the TRIM polypeptide that have a TRIM activity, e.g., maintain the ability to bind a TRIM binding partner and/or modulate HIV and/or SIV infection, ubiquitination or signaling of ubiquitination, degradation or signaling of degradation, or binding to HIV capsid protein. Functional allelic variants will typically contain only conservative substitution of one or more amino acids of SEQ ID NO:2, or substitution, deletion or insertion of non-critical residues in non-critical regions of the polypeptide.

Non-functional allelic variants are naturally occurring amino acid sequence variants of the TRIM polypeptide that do not have a TRIM activity, e.g., they do not have the ability to bind a TRIM binding partner and/or modulate HIV and/or SIV infection, ubiquitination or signaling of ubiquitination, degradation or signaling of degradation, or binding to HIV capsid protein. Non-functional allelic variants will typically contain a non-conservative substitution, a deletion, or insertion or premature truncation of the amino acid sequence of SEQ ID NO:2, or a substitution, insertion or deletion in critical residues or critical regions.

Nucleic acid molecules encoding other TRIM family members and, thus, which have a nucleotide sequence which differs from the TRIM sequence of SEQ ID NO:1 are intended to be within the scope of the invention. For example, another TRIM cDNA can be identified based on the nucleotide sequence of rhesus monkey TRIM. Moreover, nucleic acid molecules encoding TRIM polypeptides from different species, and which, thus, have a nucleotide sequence which differs from the TRIM sequences of SEQ ID NO:1 are intended to be within the scope of the invention. For example, a mouse TRIM cDNA can be identified based on the nucleotide sequence of a rhesus monkey TRIM.

Nucleic acid molecules corresponding to natural allelic variants and homologues of the TRIM cDNAs of the invention can be isolated based on their homology to the TRIM nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the TRIM cDNAs of the invention can further be isolated by mapping to the same chromosome or locus as the TRIM gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1. In other embodiment, the nucleic acid is at least 50, 100, 200, 250, 300, 350, 400, 450, 500 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of } A+T \text{ bases})+4(\# \text{ of } G+C \text{ bases})$. For hybrids between 18 and 49 base pairs in length, $T_m(° C.)=81.5+16.6(\log_{10}[Na^+])+0.41(\% \text{ G+C})-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) Proc. Natl. Acad. Sci. USA 81:1991-1995, (or alternatively 0.2×SSC, 1% SDS).

Preferably, an isolated nucleic acid molecule of the invention that hybridizes under stringent conditions to the sequence of SEQ ID NO:1 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the TRIM sequences that may exist in the population, the skilled artisan will further appreciate that changes can be introduced by mutation into the nucleotide sequences of SEQ ID NO:1, thereby leading to changes in the amino acid sequence of the encoded TRIM polypeptides, without altering the functional ability of the TRIM polypeptides. For example, nucleotide substitutions leading to amino acid substitutions at "non-essential" amino acid residues can be made in the sequence of SEQ ID NO:1. A "non-essential" amino acid residue is a residue that can be altered from the wild-type sequence of TRIM (e.g., the sequence of SEQ ID NO:1) without altering the biological activity, whereas an "essential" amino acid residue is required for biological activity. For example, amino acid residues that are conserved among the TRIM polypeptides of the present invention, e.g., those present in a RING domain, B-Box 2 domain, Coiled-coiled domain, or SPRY domain, are predicted to be particularly unamenable to alteration. Furthermore, additional amino acid residues that are conserved between the TRIM polypeptides of the present invention and other members of the TRIM family are not likely to be amenable to alteration.

Accordingly, another aspect of the invention pertains to nucleic acid molecules encoding TRIM polypeptides that contain changes in amino acid residues that are not essential for activity. Such TRIM polypeptides differ in amino acid sequence from SEQ ID NO:2, yet retain biological activity. In one embodiment, the isolated nucleic acid molecule comprises a nucleotide sequence encoding a polypeptide, wherein the polypeptide comprises an amino acid sequence at least about 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:2 (e.g., to the entire length of SEQ ID NO:2).

In one embodiment, the present invention provides an isolated nucleic acid molecule encoding a TRIM5α protein comprising amino acids 15-59, amino acid residues 321-346, and/or amino acids 297-497 of SEQ ID NO:2. The invention also includes an isolated nucleic acid molecule encoding a fusion protein comprising a TRIM5α fragment consisting essentially of amino acids 15-59, amino acid residues 321-346, and/or amino acids 297-497 of SEQ ID NO:2 and at least one non-TRIM5α polypeptide.

An isolated nucleic acid molecule encoding a TRIM polypeptide identical to the polypeptide of SEQ ID NO:2, can be created by introducing one or more nucleotide substitutions, additions or deletions into the nucleotide sequence of SEQ ID NO:1, such that one or more amino acid substitutions, additions or deletions are introduced into the encoded polypeptide. Mutations can be introduced into SEQ ID NO:1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a TRIM polypeptide is preferably replaced with another amino acid residue from the same side chain family. Alternatively, in another embodiment, mutations can be introduced randomly along all or part of a TRIM coding sequence, such as by saturation mutagenesis, and the resultant mutants can be screened for TRIM biological activity to identify mutants that retain activity. Following mutagenesis of SEQ ID NO:1, the encoded polypeptide can be expressed recombinantly and the activity of the polypeptide can be determined Mutations can also be introduced into a TRIM polypeptide to replace preferably a single, 2, 3, 4, or more amino acid residues present in a TRIM polypeptide from one species with the corresponding amino acid residues from another species.

In a preferred embodiment, a mutant TRIM polypeptide can be assayed for the ability to 1) modulate HIV infection and/or replication, 2) modulate ubiquitination or signaling of ubiquitination, 3) modulate protein degradation or signaling of protein degradation, 4) modulate binding to viral capsid proteins, e.g., HIV-1 capsid proteins, and 5) modulation of SIV infection and/or replication.

In addition to the nucleic acid molecules encoding TRIM polypeptides described above, another aspect of the invention pertains to isolated nucleic acid molecules which are antisense thereto. In an exemplary embodiment, the invention provides an isolated nucleic acid molecule which is antisense to a TRIM nucleic acid molecule (e.g., is antisense to the coding strand of a TRIM nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TRIM coding strand, or to only a portion thereof. In one embodiment, an antisense nucleic acid molecule is antisense to a "coding region" of the coding strand of a nucleotide sequence encoding TRIM. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding TRIM. The term "noncoding region" refers to 5' and 3' sequences which flank the coding region that are not translated into amino acids (i.e., also referred to as 5' and 3' untranslated regions).

Given the coding strand sequences encoding TRIM disclosed herein (e.g., nucleic acids 258-1739 of SEQ ID NO:1), antisense nucleic acids of the invention can be designed according to the rules of Watson and Crick base pairing. The antisense nucleic acid molecule can be complementary to the entire coding region of TRIM mRNA, but more preferably is an oligonucleotide which is antisense to only a portion of the coding or noncoding region of TRIM mRNA. For example, the antisense oligonucleotide can be complementary to the region surrounding the translation start site of TRIM mRNA (e.g., between the ±10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a TRIM polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intra-cellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier, et al. (1987) *Nucleic Acids. Res.* 15:6625-6641). The antisense nucleic acid molecule can also comprise a 2'-o-methylribonucleotide (Inoue, et al. (1987) *Nucleic Acids Res.* 15:6131-6148) or a chimeric RNA-DNA analogue (Inoue, et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave TRIM mRNA transcripts to thereby inhibit translation of TRIM mRNA. A ribozyme having specificity for a TRIM-encoding nucleic acid can be designed based upon the nucleotide sequence of a TRIM cDNA disclosed herein (i.e., SEQ ID NO:1). For example, a derivative of a *Tetrahymena* L-19 IVS RNA can be constructed in which the nucleotide sequence of the active site is complementary to the nucleotide sequence to be cleaved in a TRIM-encoding mRNA. See, e.g., Cech, et al. U.S. Pat. No. 4,987,071; and Cech, et al. U.S. Pat. No. 5,116,742. Alternatively, TRIM mRNA can be used to select a catalytic RNA having a specific ribonuclease activity from a pool of RNA molecules. See, e.g., Bartel, D. and Szostak, J. W. (1993) *Science* 261:1411-1418.

Alternatively, TRIM gene expression can be inhibited by targeting nucleotide sequences complementary to the regulatory region of the TRIM (e.g., the TRIM promoter and/or enhancers, e.g., interferon stimulating response elements, see FIG. 8) to form triple helical structures that prevent transcription of the TRIM gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In yet another embodiment, the TRIM nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, B. et al. (1996) supra; Perry-O'Keefe, et al. *Proc. Natl. Acad. Sci., USA* 93: 14670-675.

PNAs of TRIM nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of TRIM nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup. B. (1996) supra)); or as probes or primers for DNA sequencing or hybridization (Hyrup, B. et al. (1996) supra; Perry-O'Keefe supra).

In another embodiment, PNAs of TRIM can be modified, (e.g., to enhance their stability or cellular uptake), by attaching lipophilic or other helper groups to PNA, by the formation of PNA-DNA chimerae, or by the use of liposomes or other techniques of drug delivery known in the art. For example, PNA-DNA chimerae of TRIM nucleic acid molecules can be generated which may combine the advantageous properties of PNA and DNA. Such chimerae allow DNA recognition enzymes, (e.g., RNase H and DNA polymerases), to interact with the DNA portion while the PNA portion would provide high binding affinity and specificity. PNA-DNA chimerae can be linked using linkers of appropriate lengths selected in terms of base stacking, number of bonds between the nucleobases, and orientation (Hyrup B. (1996) supra). The synthesis of PNA-DNA chimerae can be performed as described in Hyrup, B. (1996) supra and Finn P. J., et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M., et al. (1989) *Nucleic Acids Res.* 17: 5973-88). PNA monomers are then coupled in a stepwise manner to produce a chimeric molecule with a 5' PNA segment and a 3' DNA segment (Finn, P. J., et al. (1996) supra). Alternatively, chimeric molecules can be synthesized with a 5' DNA segment and a 3' PNA segment (Peterser, K. H., et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger, et al. (1989) *Proc. Natl. Acad. Sci., USA* 86:6553-6556; Lemaitre, et al. (1987) *Proc. Natl. Acad. Sci., USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol, et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous TRIM gene within a cell line or microorganism may be modified by inserting a heterologous DNA regulatory element into the genome of a stable cell line or cloned microorganism such that the inserted regulatory element is operatively linked with the endogenous TRIM gene. For example, an endogenous TRIM gene which is normally "transcriptionally silent", i.e., a TRIM gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous TRIM gene may be activated by insertion of a promiscuous regulatory element that works across cell types.

A heterologous regulatory element may be inserted into a stable cell line or cloned microorganism, such that it is operatively linked with an endogenous TRIM gene, using techniques, such as targeted homologous recombination, which are well known to those of skill in the art, and described, e.g., in Chappel, U.S. Pat. No. 5,272,071; PCT Publication No. WO 91/06667, published May 16, 1991.

II. Isolated Trim Polypeptides and Anti-TRIM Antibodies

One aspect of the invention pertains to isolated TRIM or recombinant polypeptides and polypeptides, and biologically active portions thereof, as well as polypeptide fragments suitable for use as immunogens to raise anti-TRIM antibodies. In one embodiment, native TRIM polypeptides can be isolated from cells or tissue sources by an appropriate purification scheme using standard protein purification techniques. In another embodiment, TRIM polypeptides are produced by recombinant DNA techniques. Alternative to recombinant expression, a TRIM polypeptide or polypeptide can be synthesized chemically using standard peptide synthesis techniques.

An "isolated" or "purified" polypeptide or biologically active portion thereof is substantially free of cellular material or other contaminating proteins from the cell or tissue source from which the TRIM polypeptide is derived, or substantially free from chemical precursors or other chemicals when chemically synthesized. The language "substantially free of cellular material" includes preparations of TRIM polypeptide in which the polypeptide is separated from cellular components of the cells from which it is isolated or recombinantly produced. In one embodiment, the language "substantially free of cellular material" includes preparations of TRIM polypeptide having less than about 30% (by dry weight) of non-TRIM polypeptide (also referred to herein as a "contaminating protein"), more preferably less than about 20% of non-TRIM polypeptide, still more preferably less than about 10% of non-TRIM polypeptide, and most preferably less than about 5% non-TRIM polypeptide. When the TRIM polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of TRIM polypeptide in which the polypeptide is separated from chemical precursors or other chemicals which are involved in the synthesis of the polypeptide. In one embodiment, the language "substantially free of chemical precursors or other chemicals" includes preparations of TRIM polypeptide having less than about 30% (by dry weight) of chemical precursors or non-TRIM chemicals, more preferably less than about 20% chemical precursors or non-TRIM chemicals, still more preferably less than about 10% chemical precursors or non-TRIM chemicals, and most preferably less than about 5% chemical precursors or non-TRIM chemicals.

As used herein, a "biologically active portion" of a TRIM polypeptide includes a fragment of a TRIM polypeptide which participates in an interaction between a TRIM molecule and a non-TRIM molecule. Biologically active portions of a TRIM polypeptide include peptides comprising amino acid sequences sufficiently identical to or derived from the amino acid sequence of the TRIM polypeptide, e.g., the amino acid sequence shown in SEQ ID NO:2, which include less amino acids than the full length TRIM polypeptides, and exhibit at least one activity of a TRIM polypeptide. Typically, biologically active portions comprise a domain or motif with at least one activity of the TRIM polypeptide, e.g., inhibition of infection or replication by a virus, e.g., HIV. A biologically active portion of a TRIM polypeptide can be a polypeptide which is, for example, 25, 30, 35, 40, 45, 50, 75, 100, 125, 150, 175, 200, 225, 250, 275, 300, 325, 350, 375, 400, 425, 450, 475 or more amino acids in length. Biologically active portions of a TRIM polypeptide can be used as targets for developing agents which modulate a TRIM mediated activity.

In one embodiment, a biologically active portion of a TRIM polypeptide comprises at least one RING domain. In another embodiment, a biologically active portion of a TRIM polypeptide comprises at least one SPRY domain. In yet another embodiment, a biologically active portion of a TRIM polypeptide comprises at least one variable region of a SPRY domain, such as v1, v2, and/or v3, preferably v1, e.g., amino acid residues 321-346 of SEQ ID NO:2. It is to be understood that a preferred biologically active portion of a TRIM polypeptide of the present invention comprises at least one or more of the following domains: a RING domain, and/or a SPRY. Moreover, other biologically active portions, in which other regions of the polypeptide are deleted, can be prepared by recombinant techniques and evaluated for one or more of the functional activities of a native TRIM polypeptide.

Another aspect of the invention features fragments of the polypeptide having the amino acid sequence of SEQ ID NO:2, for example, for use as immunogens. In one embodiment, a fragment comprises at least 5 amino acids (e.g., contiguous or consecutive amino acids) of the amino acid sequence of SEQ ID NO:2. In another embodiment, a fragment comprises at least 10, 15, 20, 25, 30, 35, 40, 45, 50 or more amino acids (e.g., contiguous or consecutive amino acids) of the amino acid sequence of SEQ ID NO:2.

In a preferred embodiment, a TRIM polypeptide has an amino acid sequence shown in SEQ ID NO:2. In other embodiments, the TRIM polypeptide is substantially identical to SEQ ID NO:2, and retains the functional activity of the polypeptide of SEQ ID NO:2, yet differs in amino acid sequence due to natural allelic variation or mutagenesis, as described in detail in subsection I above. In another embodiment, the TRIM polypeptide is a polypeptide which comprises an amino acid sequence at least about 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to SEQ ID NO:2.

In another embodiment, the invention features a TRIM polypeptide which is encoded by a nucleic acid molecule consisting of a nucleotide sequence at least about 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to a nucleotide sequence of SEQ ID NO:1, or a complement thereof. This invention further features a TRIM polypeptide which is encoded by a nucleic acid molecule consisting of a nucleotide sequence which hybridizes under stringent hybridization conditions to a complement of a nucleic acid molecule comprising the nucleotide sequence of SEQ ID NO:1, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the TRIM amino acid sequence of SEQ ID NO:2). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.,* 4:11-17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to TRIM nucleic acid molecules of the invention. BLAST protein searches can be performed with the XBLAST program, score=100, wordlength=3, and a Blosum62 matrix to obtain amino acid sequences homologous to TRIM polypeptide molecules of the invention. To obtain gapped alignments for comparison purposes, Gapped BLAST can be utilized as described in Altschul, et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

In one embodiment, an isolated protein of the invention comprises or consists of the amino acid sequence set forth in SEQ ID NO:2. In another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to the amino acid sequence of SEQ ID NO:2, wherein percent identity is determined according to the LALIGN algorithm using a PAM120 weight residue table, a gap length penalty of 12 and a gap penalty of 4. In a further aspect, the invention provides an isolated protein comprising amino acids 15-59 and/or amino acids 297-497 of SEQ ID NO:2.

In another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 15-59 of SEQ ID NO:2, and having one or more of the following: glutamic acid (E) at amino acid residue 24, histidine (H) at amino acid residue 29, isoleucine (I) at amino acid residue 39, tyrosine (Y) at amino acid residue 49, and/or serine (R) at amino acid residue 54, and combinations thereof.

In one embodiment, the invention provides an isolated protein comprising an amino acid sequence which is at least 90% identical to amino acids 15-59 of SEQ ID NO:2. In another embodiment, the invention provides an isolated nucleic acid sequence comprising an amino acid sequence which is at least 90% identical to amino acids 297-497 of SEQ ID NO:2. In another embodiment, the invention provides an isolated nucleic acid sequence comprising an amino acid sequence which is at least 90% identical to amino acids 321-346 of SEQ ID NO:2. In yet another embodiment, the invention provides an isolated nucleic acid sequence comprising an amino acid sequence which is at least 90% identical to amino acids 15-59 and/or amino acid residues 297-487 of SEQ ID NO:2.

In yet another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 297-497 of SEQ ID NO:2, and having one or more of the following: leucine (L) at amino acid residue 305, threonine (T) at amino acid residue 307, histidine (H) at amino acid residue 312, alanine (A) at amino acid residue 316, arginine (R) at amino acid residue 325, asparagine (N) at amino acid residue 326, methionine (M) at amino acid residue 330, glutamine (Q) at amino acid residue 332, proline (P) at amino acid residue 334, leucine (L) at amino acid residue 337, phenylalanine (F) at amino acid residue 338, threonine (T) at amino acid residue 339, phenylalanine (F) at amino acid residue 340, leucine (L) at amino acid residue 343, threonine (T) at amino acid residue 344, valine (V) at amino acid residue 352, serine (S) at amino acid residue 373, serine (S) at amino acid residue 385, tyrosine (Y) at amino acid residue 389, glutamine (Q) at amino acid residue 393, glutamine (Q) at amino acid residue 409, tyrosine (Y) at amino acid residue 414, valine (V) at amino acid residue 416, glycine (G) at amino acid residue 420, serine (S) at amino acid residue 422, phenylalanine (F) at amino acid residue 426, alanine (A) at amino acid residue 427, valine (V) at amino acid residue 446, glutamine (Q) at amino acid residue 470, lysine (K) at amino acid residue 475, and/or threonine (T) at amino acid residue 487, and combinations thereof.

In one embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9 or more identical to amino acids 286-371 of SEQ ID NO:2, and having one or more of the following: a D at amino acid residue 288, an M at amino acid residue 289, an A at amino acid residue 296, an L at amino acid residue 305, a T at amino acid residue 307, an H at amino acid residue 312, an A at amino acid residue 316, an R at amino acid residue 325, an N at amino acid residue 326, an M at amino acid residue 330, an Q at amino acid residue 332, an P at amino acid residue 334, an L at amino acid residue 337, an F at amino acid residue 338, an T at amino acid residue 339, an F at amino acid residue 340, an L at amino acid residue 343, an T at amino acid residue 344, and/or a V at amino acid residue 352, and combinations thereof.

In another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 321-346 of SEQ ID NO:2, and having one or more of the following: an R at amino acid residue 325, an N at amino acid residue 326, an M at amino acid residue 330, an Q at amino acid residue 332, an P at amino acid residue 334, an L at amino acid residue 337, an F at amino acid residue 338, an T at amino acid residue 339, an F at amino acid residue 340, an L at amino acid residue 343, and/or an T at amino acid residue 344, and combinations thereof.

In another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 323-332 of SEQ ID NO:2, and having one or more of the following: an R at amino acid residue 325, an N at amino acid residue 326, an M at amino acid residue 330, and/or an Q at amino acid residue 332, and combinations thereof.

In yet another embodiment, the invention provides an isolated TRIM5α protein comprising an amino acid sequence at least 70%, 75%, 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to amino acids 323-328 of SEQ ID NO:2, and having one or more of the following: an R at amino acid residue 325, and/or an N at amino acid residue 326, and combinations thereof.

The invention also provides TRIM chimeric or fusion proteins. In one embodiment a TRIM "chimeric protein" or "fusion protein" comprises a TRIM polypeptide operatively linked to a non-TRIM polypeptide. In another embodiment, a TRIM "chimeric protein" comprises a rhesus monkey TRIM polypeptide linked to a non-rhesus monkey TRIM polypeptide, e.g., a human TRIM. A "TRIM polypeptide" refers to a polypeptide having an amino acid sequence corresponding to a TRIM protein, whereas a "non-TRIM polypeptide" refers to a polypeptide having an amino acid sequence corresponding to a polypeptide which is not substantially homologous to the TRIM polypeptide, e.g., a polypeptide which is different from the TRIM polypeptide, and which is derived from the same or a different organism. Within a TRIM fusion protein the TRIM polypeptide can correspond to all or a portion of a TRIM polypeptide. In a preferred embodiment, a TRIM fusion protein comprises at least one biologically active portion of a TRIM polypeptide, such as a RING domain and/or a SPRY domain, or a fragment of said domain, such as a variable region. In another preferred embodiment, a TRIM fusion protein comprises at least two biologically active portions of a TRIM polypeptide. Within the fusion protein, the term "operatively linked" is intended to indicate that the TRIM polypeptide and the non-TRIM or non-rhesus TRIM polypeptide are fused in-frame to each other. The non-TRIM or non-rhesus TRIM polypeptide can be fused to the N-terminus or C-terminus of the TRIM polypeptide.

For example, in one embodiment, the fusion protein is a GST-TRIM fusion protein in which the TRIM sequences are fused to the C-terminus of the GST sequences. Such fusion proteins can facilitate the purification of recombinant TRIM.

In another embodiment, the fusion protein is a TRIM polypeptide containing a heterologous signal sequence at its N-terminus. In certain host cells (e.g., mammalian host cells), expression and/or secretion of TRIM can be increased through the use of a heterologous signal sequence.

The TRIM fusion proteins of the invention can be incorporated into pharmaceutical compositions and administered to a subject in vivo. The TRIM fusion proteins can be used to affect the bioavailability of a TRIM substrate. Use of TRIM fusion proteins may be useful therapeutically for the treatment of disorders caused by, for example, (i) aberrant modification or mutation of a gene encoding a TRIM polypeptide; (ii) mis-regulation of the TRIM gene; and (iii) aberrant post-translational modification of a TRIM polypeptide.

Moreover, the TRIM-fusion proteins of the invention can be used as immunogens to produce anti-TRIM antibodies in a subject, to purify TRIM ligands and in screening assays to identify molecules which inhibit the interaction of TRIM with a TRIM substrate.

Preferably, a TRIM chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel, et al. John Wiley & Sons: 1992). Moreover, many expression vectors are commercially available that already encode a fusion moiety (e.g., a GST polypeptide). A TRIM-encoding nucleic acid can be cloned into such an expression vector such that the fusion moiety is linked in-frame to the TRIM polypeptide.

The present invention also pertains to variants of the TRIM polypeptides which function as either TRIM agonists (mimetics) or as TRIM antagonists. Variants of the TRIM polypeptides can be generated by mutagenesis, e.g., discrete point mutation or truncation of a TRIM polypeptide. An agonist of the TRIM polypeptides can retain substantially the same, or a subset, of the biological activities of the naturally occurring form of a TRIM polypeptide. An antagonist of a TRIM polypeptide can inhibit one or more of the activities of the naturally occurring form of the TRIM polypeptide by, for example, competitively modulating a TRIM-mediated activity of a TRIM polypeptide. Thus, specific biological effects can be elicited by treatment with a variant of limited function.

In one embodiment, variants of a TRIM polypeptide which function as either TRIM agonists (mimetics) or as TRIM antagonists can be identified by screening combinatorial libraries of mutants, e.g., truncation mutants or mutants containing point mutations, of a TRIM polypeptide for TRIM polypeptide agonist or antagonist activity. In one embodiment, a variegated library of TRIM variants is generated by combinatorial mutagenesis at the nucleic acid level and is encoded by a variegated gene library. A variegated library of TRIM variants can be produced by, for example, enzymatically ligating a mixture of synthetic oligonucleotides into gene sequences such that a degenerate set of potential TRIM sequences is expressible as individual polypeptides, or alternatively, as a set of larger fusion proteins (e.g., for phage display) containing the set of TRIM sequences therein. There are a variety of methods which can be used to produce libraries of potential TRIM variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TRIM sequences. Methods for synthesizing degenerate oligonucleotides are known in the art (see, e.g., Narang, S. A. (1983) *Tetrahedron* 39:3; Itakura, et al. (1984) *Annu. Rev. Biochem.* 53:323; Itakura, et al. (1984) *Science* 198:1056; Ike, et al. (1983) *Nucleic Acids Res.* 11:477.

In addition, libraries of fragments of a TRIM polypeptide coding sequence can be used to generate a variegated population of TRIM fragments for screening and subsequent selection of variants of a TRIM polypeptide. In one embodiment, a library of coding sequence fragments can be generated by treating a double stranded PCR fragment of a TRIM coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TRIM polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TRIM polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify TRIM variants (Arkin and Yourvan (1992) *Proc. Natl. Acad. Sci., USA* 89:7811-7815; Delgrave, et al. (1993) *Protein Engineering* 6(3):327-331).

In one embodiment, cell based assays can be exploited to analyze a variegated TRIM library. For example, a library of expression vectors can be transfected into a cell line, e.g., an endothelial cell line, which ordinarily responds to TRIM in a particular TRIM substrate-dependent manner. The transfected cells are then contacted with TRIM and the effect of expression of the mutant on signaling by the TRIM substrate can be detected, e.g., by monitoring ubiquitination. Alternatively, the transfected cells are then contacted with virus encoding an indicator gene, e.g., GFP, and cells are sorted based on their resistance to viral infection. Plasmid DNA can then be recovered from the cells which score for inhibition, or alternatively, potentiation of signaling by the TRIM substrate, and the individual clones further characterized. An isolated TRIM polypeptide, or a portion or fragment thereof, can be used as an immunogen to generate antibodies that bind TRIM using standard techniques for polyclonal and monoclonal antibody preparation. A full-length TRIM polypeptide can be used or, alternatively, the invention provides antigenic peptide fragments of TRIM for use as immunogens. The antigenic peptide of TRIM comprises at least 8 amino acid residues of the amino acid sequence shown in SEQ ID NO:2 and encompasses an epitope of TRIM such that an antibody raised against the peptide forms a specific immune complex with TRIM. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of TRIM that are located on the surface of the polypeptide, e.g., hydrophilic regions, as well as regions with high antigenicity.

A TRIM immunogen typically is used to prepare antibodies by immunizing a suitable subject, (e.g., rabbit, goat, mouse or other mammal) with the immunogen. An appropriate immunogenic preparation can contain, for example, recombinantly expressed TRIM polypeptide or a chemically synthesized TRIM polypeptide. The preparation can further include an adjuvant, such as Freund's complete or incomplete adjuvant, or similar immunostimulatory agent. Immunization of a suitable subject with an immunogenic TRIM preparation induces a polyclonal anti-TRIM antibody response.

Accordingly, another aspect of the invention pertains to anti-TRIM antibodies. The term "antibody" as used herein refers to immunoglobulin molecules and immunologically active portions of immunoglobulin molecules, i.e., molecules that contain an antigen binding site which specifically binds (immunoreacts with) an antigen, such as TRIM. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind TRIM. The term "monoclonal antibody" or "monoclonal antibody composition", as used herein, refers to a population of antibody molecules that contain only one species of an antigen binding site capable of immunoreacting with a particular epitope of TRIM. A monoclonal antibody composition thus typically displays a single binding affinity for a particular TRIM polypeptide with which it immunoreacts.

Polyclonal anti-TRIM antibodies can be prepared as described above by immunizing a suitable subject with a TRIM immunogen. The anti-TRIM antibody titer in the immunized subject can be monitored over time by standard techniques, such as with an enzyme linked immunosorbent assay (ELISA) using immobilized TRIM. If desired, the antibody molecules directed against TRIM can be isolated from the mammal (e.g., from the blood) and further purified by well known techniques, such as protein A chromatography to obtain the IgG fraction. At an appropriate time after immunization, e.g., when the anti-TRIM antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown, et al. (1981) *J. Immunol.* 127:539-46; Brown, et al. (1980) *J. Biol. Chem.* 255:4980-83; Yeh, et al. (1976) *Proc. Natl. Acad. Sci., USA* 76:2927-31; and Yeh, et al. (1982) *Int. J. Cancer* 29:269-75), the more recent human B cell hybridoma technique (Kozbor, et al. (1983) *Immunol Today* 4:72), the EBV-hybridoma technique (Cole, et al. (1985), *Monoclonal Antibodies and Cancer Therapy, Alan R. Liss, Inc., pp.* 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter, et al. (1977) *Somatic Cell Genet.* 3:231-36). Briefly, an immortal cell line (typically a myeloma) is fused to lymphocytes (typically splenocytes) from a mammal immunized with a TRIM immunogen as described above, and the culture supernatants of the resulting hybridoma cells are screened to identify a hybridoma producing a monoclonal antibody that binds TRIM.

Any of the many well known protocols used for fusing lymphocytes and immortalized cell lines can be applied for the purpose of generating an anti-TRIM monoclonal antibody (see, e.g., G. Galfre, et al. (1977) *Nature* 266:55052; Gefter, et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TRIM, e.g., using a standard ELISA assay.

Alternative to preparing monoclonal antibody-secreting hybridomas, a monoclonal anti-TRIM antibody can be identified and isolated by screening a recombinant combinatorial immunoglobulin library (e.g., an antibody phage display library) with TRIM to thereby isolate immunoglobulin library members that bind TRIM. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner, et al. U.S. Pat. No. 5,223,409; Kang, et al. PCT International Publication No. WO 92/18619; Dower, et al. PCT International Publication No. WO 91/17271; Winter, et al. PCT International Publication WO 92/20791; Markland, et al. PCT International Publication No. WO 92/15679; Breitling, et al. PCT International Publication WO 93/01288; McCafferty, et al. PCT International Publication No. WO 92/01047; Garrard, et al. PCT International Publication No. WO 92/09690; Ladner, et al. PCT International Publication No. WO 90/02809; Fuchs, et al. (1991) *Bio/Technology* 9:1370-1372; Hay, et al. (1992) *Hum. Antibod. Hybridomas* 3:81-85; Huse, et al. (1989) *Science* 246:1275-1281; Griffiths, et al. (1993) *EMBO J.* 12:725-734; Hawkins, et al. (1992) *J. Mol. Biol.* 226:889-896; Clarkson, et al. (1991) *Nature* 352:624-628; Gram, et al. (1992) *Proc. Natl. Acad. Sci., USA* 89:3576-3580; Garrad, et al. (1991) *Bio/Technology* 9:1373-1377; Hoogenboom, et al. (1991) *Nuc. Acids Res.* 19:4133-4137; Barbas, et al. (1991) *Proc. Natl. Acad. Sci., USA* 88:7978-7982; and McCafferty, et al. *Nature* (1990) 348:552-554.

Additionally, recombinant anti-TRIM antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson, et al. International Application No. PCT/US86/02269; Akira, et al. European Patent Application 184,187; Taniguchi, M., European Patent Application 171,496; Morrison et al. European Patent Application 173,494; Neuberger, et al. PCT International Publication No. WO 86/01533; Cabilly, et al. U.S. Pat. No. 4,816,567; Cabilly, et al. European Patent Application 125,023; Better, et al. (1988) *Science* 240:1041-1043; Liu, et al. (1987) *Proc. Natl. Acad. Sci., USA* 84:3439-3443; Liu, et al. (1987) *J. Immunol.* 139:3521-3526; Sun, et al. (1987) *Proc. Natl. Acad. Sci., USA* 84:214-218; Nishimura, et al. (1987) *Canc. Res.* 47:999-1005; Wood, et al. (1985) *Nature* 314:446-449; and Shaw, et al. (1988) *J. Natl. Cancer Inst.* 80:1553-1559); Morrison, S. L. (1985) *Science*

229:1202-1207; Oi, et al. (1986) *BioTechniques* 4:214; Winter, U.S. Pat. No. 5,225,539; Jones, et al. (1986) *Nature* 321: 552-525; Verhoeyan, et al. (1988) *Science* 239:1534; and Beidler, et al. (1988) *J. Immunol.* 141:4053-4060.

An anti-TRIM antibody (e.g., monoclonal antibody) can be used to isolate TRIM by standard techniques, such as affinity chromatography or immunoprecipitation. An anti-TRIM antibody can facilitate the purification of natural TRIM from cells and of recombinantly produced TRIM expressed in host cells. Moreover, an anti-TRIM antibody can be used to detect TRIM polypeptide (e.g., in a cellular lysate or cell supernatant) in order to evaluate the abundance and pattern of expression of the TRIM polypeptide. Anti-TRIM antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Expression Vectors and Host Cells

Another aspect of the invention pertains to vectors, for example expression vectors, containing a nucleic acid containing a TRIM nucleic acid molecule or vectors containing a nucleic acid molecule which encodes a TRIM polypeptide or a portion thereof, or a TRIM fusion protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or peptides, including fusion proteins or peptides, encoded by nucleic acids as described herein (e.g., TRIM polypeptides, mutant forms of TRIM polypeptides, TRIM variants, fusion proteins, and the like).

Accordingly, an exemplary embodiment provides a method for producing a polypeptide, preferably a TRIM polypeptide, by culturing in a suitable medium a host cell of the invention (e.g., a mammalian host cell such as a non-human mammalian cell) containing a recombinant expression vector, such that the polypeptide is produced.

The recombinant expression vectors of the invention can be designed for expression of TRIM polypeptides in prokaryotic or eukaryotic cells. For example, TRIM polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRITS (Pharmacia, Piscataway, N.J.) which fuse glutathione S-transferase (GST), maltose E binding protein, or protein A, respectively, to the target recombinant protein.

Purified fusion proteins can be utilized in TRIM activity assays, (e.g., direct assays or competitive assays described in detail below), or to generate antibodies specific for TRIM polypeptides, for example. In a preferred embodiment, a TRIM fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann, et al., (1988) *Gene* 69:301-315) and pET 11d (Studier, et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada, et al., (1992) *Nucleic Acids Res.* 20:2111-2118). Such alteration of nucleic acid sequences of the invention can be carried out by standard DNA synthesis techniques.

In another embodiment, the TRIM expression vector is a yeast expression vector. Examples of vectors for expression in yeast *S. cerevisiae* include pYepSec1 (Baldari, et al., (1987) *Embo J.* 6:229-234), pMFa (Kurjan and Herskowitz, (1982) *Cell* 30:933-943), pJRY88 (Schultz, et al., (1987) *Gene* 54:113-123), pYES2 (Invitrogen Corporation, San Diego, Calif.), and picZ (InVitrogen Corp, San Diego, Calif.).

Alternatively, TRIM polypeptides can be expressed in insect cells using baculovirus expression vectors. Baculovirus vectors available for expression of proteins in cultured insect cells (e.g., Sf 9 cells) include the pAc series (Smith, et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman, et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji, et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci., USA* 86:5473-5477), pancreas-specific promoters (Edlund, et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to TRIM mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics, Vol.* 1(1) 1986.

Another aspect of the invention pertains to host cells into which a TRIM nucleic acid molecule of the invention is introduced, e.g., a TRIM nucleic acid molecule within a vector (e.g., a recombinant expression vector) or a TRIM nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TRIM polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a TRIM polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a TRIM polypeptide. Accordingly, the invention further provides methods for producing a TRIM polypeptide using the host cells of the invention. In one embodiment, the method comprises culturing the host cell of the invention (into which a recombinant expression vector encoding a TRIM polypeptide has been introduced) in a suitable medium such that a TRIM polypeptide is produced. In another embodiment, the method further comprises isolating a TRIM polypeptide from the medium or the host cell.

The host cells of the invention can also be used to produce non-human transgenic animals. For example, in one embodiment, a host cell of the invention is a fertilized oocyte or an embryonic stem cell into which TRIM-coding sequences have been introduced. Such host cells can then be used to create non-human transgenic animals in which exogenous TRIM sequences have been introduced into their genome or homologous recombinant animals in which endogenous TRIM sequences have been altered. Such animals are useful for studying the function and/or activity of a TRIM and for identifying and/or evaluating modulators of TRIM activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous TRIM gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a TRIM-encoding nucleic acid into the male pronuclei of a fertilized oocyte, e.g., by microinjection, retroviral infection, and allowing the oocyte to develop in a pseudopregnant female foster animal. The TRIM cDNA sequence of SEQ ID NO:1 can be introduced as a transgene into the genome of a non-human animal. Alternatively, a TRIM gene homologue, such as another TRIM family member, can be isolated based on hybridization to the TRIM cDNA sequences of SEQ ID NO:1 (described further in subsection I above) and used as a transgene. Intronic sequences and polyadenylation signals can also be included in the transgene to increase the efficiency of expression of the transgene. A tissue-specific regulatory sequence(s) can be operably linked to a TRIM transgene to direct expression of a TRIM polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder, et al., U.S. Pat. No. 4,873,191 by Wagner, et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a TRIM transgene in its genome and/or expression of TRIM mRNA in tissues or cells of the animals. A transgenic founder animal can then be used to breed additional animals carrying the transgene. Moreover, transgenic animals carrying a transgene encoding a TRIM polypeptide can further be bred to other transgenic animals carrying other transgenes.

To create a homologous recombinant animal, a vector is prepared which contains at least a portion of a TRIM gene into which a deletion, addition or substitution has been introduced to thereby alter, e.g., functionally disrupt, the TRIM gene. The TRIM gene can be a rhesus monkey gene (e.g., SEQ ID NO:1), or a homologue thereof. In a preferred embodiment, the homologous recombination nucleic acid molecule is designed such that, upon homologous recombination, the endogenous TRIM gene is functionally disrupted (i.e., no longer encodes a functional protein; also referred to as a "knock-out" vector). Alternatively, the homologous recombination nucleic acid molecule can be designed such that, upon homologous recombination, the endogenous TRIM gene is mutated or otherwise altered but still encodes functional polypeptide (e.g., the upstream regulatory region can be altered to thereby alter the expression of the endogenous TRIM polypeptide). In the homologous recombination nucleic acid molecule, the altered portion of the TRIM gene is flanked at its 5' and 3' ends by additional nucleic acid sequence of the TRIM gene to allow for homologous recombination to occur between the exogenous TRIM gene carried by the homologous recombination nucleic acid molecule and an endogenous TRIM gene in a cell, e.g., an embryonic stem cell. The additional flanking TRIM nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced TRIM gene has homologously recombined with the endogenous TRIM gene are selected (see e.g., Li, E., et al. (1992) *Cell* 69:915). The selected cells can then injected into a blastocyst of an animal (e.g., a mouse) to form aggregation chimerae (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec, et al.; WO 91/01140 by Smithies, et al.; WO 92/0968 by Zijlstra, et al.; and WO 93/04169 by Berns, et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso, et al. (1992) *Proc. Natl. Acad. Sci., USA* 89:6232-6236. Another example of a recombinase system is the FLP recombinase system of *Saccharomyces cerevisiae* (O'Gorman, et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I., et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The TRIM nucleic acid molecules, fragments of TRIM polypeptides, and anti-TRIM antibodies (also referred to herein as "active compounds") of the invention can be incorporated into pharmaceutical compositions suitable for administration. Such compositions typically comprise the nucleic acid molecule, or polypeptide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, vaginal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., TRIM nucleic acid molecules, a fragment of a TRIM polypeptide or an anti-TRIM antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. Vaginal suppositories or foams for local mucosal delivery may also be prepared to block sexual transmission.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens and liposomes targeted to macrophages containing, for example, phosphatidylserine) can also be used as pharmaceutically acceptable carriers. These can be prepared according to methods known to those skilled in the art, for example, as described in U.S. Pat. Nos. 4,522,811 and 5,643,599, the entire contents of which are incorporated herein.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease, disorder, or infection, previous treatments, the general health and/or age of the subject, and other diseases present. Moreover, treatment of a subject with a therapeutically effective amount of a polypeptide or antibody can include a single treatment or, preferably, can include a series of treatments.

In a preferred example, a subject is treated with antibody or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon, et al., "Monoclonal Antibodies For Immunotargeting Of Drugs In Cancer Therapy", in Monoclonal Antibodies And Cancer Therapy, Reisfeld, et al. (eds.), pp. 243-56 (Alan R. Liss, Inc. 1985); Hellstrom, et al., "Antibodies For Drug Delivery", in Controlled Drug Delivery (2nd Ed.), Robinson, et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin, et al. (eds.), pp. 303-16 (Academic Press 1985), and Thorpe, et al., "The Preparation And Cytotoxic Properties Of Antibody-Toxin Conjugates", *Immunol. Rev.* 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen, et al. (1994) *Proc. Natl. Acad. Sci., USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions of the invention can also be delivered using a peptide, e.g., basic peptide, or fragment thereof, which is capable of crossing a biological membrane, either in vivo or in vitro, is included in the methods of the invention and may be used to transport TRIM modulators, e.g., polypeptides or nucleic acid molecules across cellular membranes for treatment or prevention of infection, e.g., HIV and/or SIV infection. These peptides can be synthesized by methods known to one of skill in the art. For example, several peptides have been identified which may be used as carrier peptides in the methods of the invention. These peptides include, for example, the homeodomain of antennapedia, a *Drosophila* transcription factor (Wang, et al., (1995) *Proc. Natl. Acad. Sci., USA* 92:3318-3322); a fragment representing the hydrophobic region of the signal sequence of Kaposi fibroblast growth factor with or without NLS domain (Antopolsky, et al. (1999) *Bioconj. Chem.*, 10, 598-606); a signal peptide sequence of *caiman crocodylus* Ig(5) light chain (Chaloin, et al. (1997) *Biochem. Biophys. Res. Comm.*, 243, 601-608); a fusion sequence of HIV envelope glycoprotein gp41, (Morris, et al. (1997) *Nucleic Acids Res.* 25:2730-2736); a transportan A-achimeric 27-mer consisting of N-terminal fragment of neuropeptide galanine and membrane interacting wasp venom peptide mastoporan (Lindgren, et al., (2000), *Bioconjugate Chem.* 11:619-626); a peptide derived from influenza virus hemagglutinin envelope glycoprotein (Bongartz, et al., (1994) *Nucleic Acids Res.* 22:468 1 4688); RGD peptide; and a peptide derived from the human immunodeficiency virus type-1 ("HIV-1"). Purified HIV-1 TAT protein is taken up from the surrounding medium by human cells growing in culture (A. D. Frankel and C. O. Pabo (1988) *Cell,* 55:1189-93). TAT protein trans-activates certain HIV genes and is essential for viral replication. The full-length HIV-1 TAT protein has 86 amino acid residues. The HIV tat gene has two exons. TAT amino acids 1-72 are encoded by exon 1, and amino acids 73-86 are encoded by exon 2. The full-length TAT protein is characterized by a basic region which contains two lysines and six arginines (amino acids 47-57) and a cysteine-rich region which contains seven cysteine residues (amino acids 22-37). The basic region (i.e., amino acids 47-57) is thought to be important for nuclear localization. Ruben, S., et al., *J. Virol.* 63: 1-8 (1989); Hauber, J., et al., *J. Virol.* 63 1181-1187 (1989); Rudolph, et al. (2003) 278(13):11411. The cysteine-rich region mediates the formation of metal-linked dimers in vitro (Frankel, A. D., et al., *Science* 240: 70-73 (1988); Frankel, A. D., et al., *Proc. Natl. Acad. Sci., USA* 85: 6297-6300 (1988)) and is essential for its activity as a transactivator (Garcia, J. A., et al., *EMBO J.* 7:3143 (1988); Sadaie, M. R., et al., *J. Virol.* 63: 1 (1989)). As in other regulatory proteins, the N-terminal region may be involved in protection against intracellular proteases (Bachmair, A., et al., *Cell* 56: 1019-1032 (1989)). The amino acid sequence of the full-length HIV-1 TAT peptide is set forth as SEQ ID NO:57 (GenBank Accession No.: gi:29119336).

In one embodiment of the invention, the basic peptide comprises amino acids 47-57 of the HIV-1 TAT peptide. In another embodiment, the basic peptide comprises amino acids 48-60 of the HIV-1 TAT peptide. In still another embodiment, the basic peptide comprises amino acids 49-57 of the HIV-1 TAT peptide. In yet another embodiment, the basic peptide comprises amino acids 49-57, 48-60, or 47-57 of the HIV-1 TAT peptide, does not comprise amino acids 22-36 of the HIV-1 TAT peptide, and does not comprise amino acids 73-86 of the HIV-1 TAT peptide. In still another embodiment, the specific peptides set forth in Table 1, below, may be used as carrier peptides in the methods and compositions of the invention. The invention is not limited to the use of these specific peptides.

TABLE 1

| Peptide | Sequence | SEQ ID NO: |
|---|---|---|
| HIV-1 TAT (49-57) | RKKRRQRRR | 3 |
| HIV-1 TAT (48-60) | GRKKRRQRRRTPQ | 4 |
| HIV-1 TAT (47-57) | YGRKKRRQRRR | 5 |
| Kaposi fibroblast growth factor | AAV ALL PAV LLA LLA P + VQR KRQ KLMP | 6 |
| of *caiman crocodylus* Ig(5) light chain | MGL GLH LLV LAA ALQ GA | 7 |
| HIV envelope glycoprotein gp41 | GAL FLG FLG AAG STM GA + PKS KRK 5 (NLS of the SV40) | 8 |
| *Drosophila* Antennapedia | RQI KIW FQN RRM KWK K amide | 9 |
| RGD peptide | X-RGD-X | 10 |
| influenza virus hemagglutinin envelope glycoprotein | GLFEAIAGFIENGWE GMIDGGGYC | 11 |
| transportan A | GWT LNS AGY LLG KIN LKA LAA LAK KIL | 12 |
| Pre-S-peptide | (S)DH QLN PAF | 13 |
| Somatostatin (tyr-3-octreotate) | (S)FC Y*W*K TCT | 14 |

(s) optional Serine for coupling; italic = optional D isomer for stability

Other arginine rich basic peptides may also be used. For example, a TAT analog comprising D-amino acid- and arginine-substituted TAT(47-60), RNA-binding peptides derived from virus proteins such as HIV-1 Rev, and flock house virus coat proteins, and the DNA binding sequences of leucine zipper proteins, such as cancer-related proteins c-Fos and c-Jun and the yeast transcription factor GCN4, all of which contain several arginine residues (see Futaki, et al. (2001) *J. Biol. Chem.* 276(8):5836-5840 and Futaki, S. (2002) *Int. J. Pharm.* 245(1-2):1-7, which are incorporated herein by reference). In one embodiment, the arginine rich peptide contains about 4 to about 11 arginine residues. In another embodiment, the arginine residues are contiguous residues.

The pharmaceutical compositions can be included in a container, pack, or dispenser together with instructions for administration.

V. Uses and Methods of the Invention

The nucleic acid molecules, proteins, small molecules and peptidomimetics described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a TRIM polypeptide of the invention has one or more of the following activities: 1) modulation of HIV infection and/or replication, 2) modulation of ubiquitination or signaling of ubiquitination, 3) modulation of protein degradation or signaling of protein degradation, 4) modulation of binding to viral capsid proteins, e.g., HIV capsid proteins, and 5) modulation of SIV infection and/or replication.

The isolated nucleic acid molecules of the invention can be used, for example, to express TRIM polypeptides (e.g., via a recombinant expression vector in a host cell in gene therapy applications), to detect TRIM mRNA (e.g., in a biological sample) or a genetic alteration in a TRIM gene, and to modulate TRIM activity, as described further below. The TRIM polypeptides can be used to treat or prevent viral e.g., HIV and/or SIV infections. In addition, the TRIM polypeptides can be used to screen for naturally occurring TRIM substrates, and to screen for drugs or compounds which modulate TRIM activity. Moreover, the anti-TRIM antibodies of the invention can be used to detect and isolate TRIM polypeptides, to regulate the bioavailability of TRIM polypeptides, and modulate TRIM activity.

A. Screening Assays

The invention provides methods (also referred to herein as "screening assays") for identifying modulators, i.e., candidate or test compounds or agents (e.g., peptidomimetics, small molecules or other drugs) which modulate, for example one or more TRIM activity, e.g., the ability to 1) modulate HIV infection or replication, 2) modulate ubiquitination or signaling of ubiquitination, 3) modulate protein degradation or signaling of protein degradation, 4) modulate binding to capsid proteins, and 5) modulation of SIV infection and/or replication, and/or for testing or optimizing the activity of such agents.

The assays can be used to identify agents that modulate the function of TRIM and/or a TRIM-binding molecule. For example, such agents may interact with TRIM or the TRIM-binding molecule (e.g., to inhibit or enhance their activity). The function of TRIM or the TRIM-binding molecule can be affected at any level, including transcription, protein expression, protein localization, and/or cellular activity. The subject assays can also be used to identify, e.g., agents that alter the interaction of TRIM or the TRIM-binding molecule with a binding partner, substrate, or cofactors, or modulate, e.g., increase, the stability of such interaction.

The subject screening assays can measure the activity of TRIM or a TRIM-binding protein directly (e.g., ubiquitination or capsid binding), or can measure a downstream event controlled by modulation of TRIM or a TRIM-binding protein (e.g., HIV and/or SIV infection or replication).

The subject screening assays employ indicator compositions. These indicator compositions comprise the components required for performing an assay that detects and/or measures a particular event. The indicator compositions of the invention provide a reference readout and changes in the readout can be monitored in the presence of one or more test compounds. A difference in the readout in the presence and the absence of the compound indicates that the test compound is a modulator of the molecule(s) present in the indicator composition.

The indicator composition used in the screening assay can be a cell that expresses a TRIM polypeptide or a TRIM-binding molecule. For example, a cell that naturally expresses or, more preferably, a cell that has been engineered to express the protein by introducing into the cell an expression vector encoding the protein may be used. Preferably, the cell is a mammalian cell, e.g., a human cell. In one embodiment, the cell is a T cell. In another embodiment, the cell is a non-T cell. Alternatively, the indicator composition can be a cell-free composition that includes the protein (e.g., a cell extract or a composition that includes e.g., either purified natural or recombinant protein).

In another embodiment, the indicator composition comprises more than one polypeptide. For example, in one embodiment the subject assays are performed in the presence of TRIM and at least one other TRIM and/or at least one TRIM-binding molecule.

Compounds that modulate the expression and/or activity of TRIM, identified using the assays described herein can be useful for treating a subject that would benefit from the modulation of TRIM production.

In one embodiment, secondary assays can be used to confirm that the modulating agent affects the TRIM molecule in a specific manner. For example, compounds identified in a primary screening assay can be used in a secondary screening assay to determine whether the compound affects a TRIM-related activity. Accordingly, in another aspect, the invention pertains to a combination of two or more of the assays described herein. For example, a modulating agent can be identified using a cell-based or a cell-free assay, and the ability of the agent to modulate the activity of TRIM can be confirmed in vivo, e.g., in an animal such as, for example, in an animal model of a disorder, e.g., HIV or AIDS or a TRIM transgenic animal, e.g., a TRIM transgenic animal.

Moreover, a modulator of TRIM expression and/or activity identified as described herein (e.g., a small molecule) may be used in an animal model to determine the efficacy, toxicity, or side effects of treatment with such a modulator. Alternatively, a modulator identified as described herein may be used in an animal model to determine the mechanism of action of such a modulator.

In one embodiment, the screening assays of the invention are high throughput or ultra high throughput (e.g., Fernandes, P. B., *Curr Opin Chem. Biol.* 1998 2:597; Sundberg, SA, *Curr Opin Biotechnol.* 2000, 11:47).

In one embodiment, secondary assays can be used to confirm that the modulating agent affects a TRIM in a TRIM related manner. For example, compounds identified in a primary screening assay can be used in a secondary screening assay to determine whether the compound affects a TRIM-related activity.

Exemplary cell based and cell free assays of the invention are described in more detail below.

i. Cell Based Assays

The indicator compositions of the invention may be cells that express a TRIM or a TRIM-interacting molecule. For example, a cell that naturally expresses endogenous polypeptide, or, more preferably, a cell that has been engineered to express one or more exogenous polypeptides, e.g., by introducing into the cell an expression vector encoding the protein may be used in a cell based assay.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell (e.g., a murine cell, rhesus monkey, or a human cell). In a preferred embodiment, the cell is a human cell.

Preferably a cell line is used which expresses low levels of endogenous TRIM and/or a TRIM-interacting polypeptide and is then engineered to express recombinant, mutant, or variant protein.

Recombinant expression vectors that may be used for expression of polypeptides are known in the art. For example, the cDNA is first introduced into a recombinant expression vector using standard molecular biology techniques. A cDNA can be obtained, for example, by amplification using the polymerase chain reaction (PCR) or by screening an appropriate cDNA library.

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329: 840) and pMT2PC (Kaufman, et al. (1987), *EMBO J.* 6:187-195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo, et al. (1982) *Cell* 29:99-108; Brinster, et al. (1982) *Nature* 296:39-42; Searle, et al. (1985) *Mol. Cell. Biol.* 5:1480-1489), heat shock (see e.g., Nouer, et al. (1991) in *Heat Shock Response*, e.d. Nouer, L., CRC, Boca Raton, Fla., pp 167-220), hormones (see e.g., Lee, et al. (1981) *Nature* 294:228-232; Hynes, et al. (1981) *Proc. Natl. Acad. Sci., USA* 78:2038-2042; Klock, et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci., USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert, et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji, et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci., USA* 86:5473-5477), pancreas-specific promoters (Edlund, et al. (1985) *Science* 230:912-916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Vector DNA may be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook, et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding TRIM or a TRIM-interacting polypeptide, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, may be used). Use of a recombinant expression vector that allows for constitutive expression of the genes in the indicator cell is preferred for identification of compounds that enhance or inhibit the activity of the molecule. In an alternative embodiment, within the expression vector the coding sequences are operatively linked to regulatory sequences of the endogenous gene (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

For example, an indicator cell can be transfected with an expression vector comprising a polypeptide TRIM, incubated in the presence and in the absence of a test compound, and the effect of the compound on the expression of the molecule or on a biological response regulated by TRIM, e.g., a TRIM-related activity, can be determined. The biological activities of TRIM include activities determined in vivo, or in vitro, according to standard techniques. Activity can be a direct activity, such as an association with or enzymatic activity on a target molecule (e.g., a capsid protein). Alternatively, activity may be an indirect activity, such as, for example, a cellular signaling activity occurring downstream of the interaction of the protein with a target molecule or a biological effect occurring as a result of the signaling cascade triggered by that interaction. For example, viral capsid assembly or disassembly.

Compounds that modulate TRIM production, expression and/or activity of may be identified using various "read-outs." For example, a variety of reporter genes are known in the art and are suitable for use in the screening assays of the invention. Examples of suitable reporter genes include those which encode chloramphenicol acetyltransferase, beta-galactosidase, alkaline phosphatase, GFP, or luciferase. Standard methods for measuring the activity of these gene products are known in the art.

For example, in one embodiment, gene expression of TRIM, or a TRIM-binding molecule can be measured. In another embodiment, expression of a gene controlled by TRIM can be measured.

To determine whether a test compound modulates expression, in vitro transcriptional assays can be performed. For example, mRNA or protein expression can be measured using methods well known in the art. For instance, one or more of Northern blotting, slot blotting, ribonuclease protection, quantitative RT-PCR, or microarray analysis (e.g., Current Protocols in Molecular Biology (1994) Ausubel, F M et al., eds., John Wiley & Sons, Inc.; Freeman W M, et al., *Biotechniques* 1999 26:112; Kallioniemi, et al. 2001 *Ann. Med.* 33:142; Blohm and Guiseppi-Eli 2001 *Curr Opin Biotechnol.* 12:41) may be used to confirm that expression is modulated in cells treated with a modulating agent.

In another example, agents that modulate the expression of a TRIM can be identified by operably linking the upstream regulatory sequences (e.g., the full length promoter and enhancer) of a TRIM to a reporter gene such as chloramphenicol acetyltransferase (CAT) or luciferase and introducing in into host cells. The ability of an agent to modulate the expression of the reporter gene product as compared to control cells (e.g., not exposed to the compound) can be measured.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

In one embodiment, the level of expression of the reporter gene in the indicator cell in the presence of the test compound is higher than the level of expression of the reporter gene in the indicator cell in the absence of the test compound and the test compound is identified as a compound that stimulates the expression of a TRIM gene. In another embodiment, the level of expression of the reporter gene in the indicator cell in the presence of the test compound is lower than the level of expression of the reporter gene in the indicator cell in the absence of the test compound and the test compound is identified as a compound that inhibits the expression of a TRIM gene.

In another embodiment, protein expression may be measured. For example, standard techniques such as Western blotting or in situ detection can be used.

In one embodiment a downstream effect of modulation of TRIM production, e.g., the effect of a compound on HIV and/or SIV infection of cells, e.g., T cells, may be used as an indicator of modulation of TRIM or a TRIM-interacting protein. HIV and/or SIV infection can be monitored directly (e.g. by microscopic examination of the cells), or indirectly, e.g., by monitoring one or more markers of HIV and/or SIV infection (e.g., an increase in mRNA for a gene product associated with HIV and/or SIV infection) or the expression of a cell surface marker. Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

The ability of the test compound to modulate TRIM or a TRIM-interacting polypeptide binding to a substrate or target molecule can also be determined. Determining the ability of the test compound to modulate, for example, TRIM, binding to a target molecule (e.g., a binding partner such as a substrate) can be accomplished, for example, by determining the ability of the molecules to be coimmunoprecipitated or by coupling the target molecule with a radioisotope or enzymatic label such that binding of the target molecule to TRIM or a TRIM-interacting polypeptide can be determined, e.g., by detecting the labeled TRIM target molecule in a complex. Alternatively, for example, TRIM, can be coupled with a radioisotope or enzymatic label to monitor the ability of a test compound to modulate, TRIM, binding to a target molecule in a complex.

Determining the ability of the test compound to bind to TRIM can be accomplished, for example, by coupling the compound with a radioisotope or enzymatic label such that binding of the compound can be determined by detecting the labeled compound in a complex. For example, targets can be labeled with $^{125}I$, $^{35}S$, $^{14}C$, or $^3H$, either directly or indirectly, and the radioisotope detected by direct counting of radioemmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

In another embodiment, fluorescence technologies can be used, e.g., fluorescence polarization, time-resolved fluorescence, and fluorescence resonance energy transfer (Selvin, P R, *Nat. Struct. Biol.* 2000 7:730; Hertzberg R P and Pope A J, *Curr Opin Chem. Biol.* 2000 4:445).

It is also within the scope of this invention to determine the ability of a compound to interact with TRIM, a TRIM-interacting molecule without the labeling of any of the interactants. For example, a microphysiometer may be used to detect the interaction of a compound with a TRIM, a TRIM-interacting molecule without the labeling of either the compound or the molecule (McConnell, H. M., et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate may be used as an indicator of the interaction between compounds.

In yet another aspect of the invention, the TRIM or a TRIM-interacting polypeptide protein or fragments thereof may be used as "bait protein" e.g., in a two-hybrid assay or three-hybrid assay (see, e.g., U.S. Pat. No. 5,283,317; Zervos, et al. (1993) *Cell* 72:223-232; Madura, et al. (1993) *J. Biol. Chem.* 268:12046-12054; Bartel, et al. (1993) *Biotechniques* 14:920-924; Iwabuchi, et al. (1993) *Oncogene* 8:1693-1696; and Brent WO 94/10300), to identify other proteins, which bind to or interact with TRIM or a TRIM-interacting polypeptide ("binding proteins" or "bp") and are involved in TRIM or a TRIM-interacting molecule activity. Such TRIM- or TRIM-interacting molecule-binding proteins are also likely to be involved in the propagation of signals by the TRIM or a TRIM-interacting molecule proteins. The two-hybrid system is based on the modular nature of most transcription factors, which consist of separable DNA-binding and activation domains. Briefly, the assay utilizes two different DNA constructs. In one construct, the gene that codes for a TRIM or a TRIM-interacting molecule protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a TRIM- or a TRIM-interacting molecule-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the TRIM or a TRIM-interacting molecule protein.

ii. Cell-free assays

Alternatively, the indicator composition can be a cell-free composition that includes a TRIM and/or a TRIM-interacting molecule, e.g., a cell extract from a cell expressing the protein or a composition that includes purified either natural or recombinant, variant, or mutant protein.

In one embodiment, the indicator composition is a cell free composition. Polypeptides expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies may be used to produce a purified or semi-purified protein that may be used in a cell free composition. Alternatively, a lysate or an extract of cells expressing the protein of interest can be prepared for use as cell-free composition. Cell extracts with the appropriate post-translation modifications of proteins can be prepared using commercially available resources found at, for example Promega, Inc., and include but are not limited to reticulocyte lysate, wheat germ extract and *E. coli* S30 extract.

In one embodiment, compounds that specifically modulate an activity of TRIM or a TRIM-binding molecule may be identified. For example, compounds that modulate an activity of TRIM (e.g., a TRIM related activity) are identified based on their ability to modulate the interaction of TRIM with a target molecule to which TRIM binds. In another embodiment, compounds that modulate an activity of TRIM are identified based on their ability to modulate interaction of TRIM with a TRIM-binding molecule. Suitable assays are known in the art that allow for the detection of protein-protein interactions (e.g., immunoprecipitations and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays may be used to identify compounds that modulate (e.g., inhibit or enhance) the interaction of TRIM or a TRIM-binding molecule with a target molecule.

In the methods of the invention for identifying test compounds that modulate an interaction between a TRIM-interacting protein and TRIM, the complete TRIM protein may be used in the method, or, alternatively, only portions of the protein may be used. For example, an isolated TRIM domain (e.g., a RING domain or a SPRY domain) may be used. An assay may be used to identify test compounds that either stimulate or inhibit the interaction between the TRIM protein and a target molecule. A test compound that stimulates the interaction between the protein and a target molecule is identified based upon its ability to increase the degree of interaction between (e.g., TRIM and a target molecule) as compared to the degree of interaction in the absence of the test compound and such a compound would be expected to increase the activity of TRIM in the cell. A test compound that inhibits the interaction between the protein and a target molecule is identified based upon its ability to decrease the degree of interaction between the protein and a target molecule as compared to the degree of interaction in the absence of the compound and such a compound would be expected to decrease TRIM activity.

In one embodiment, the amount of binding of TRIM to a TRIM-interacting molecule in the presence of the test compound is greater than the amount of binding in the absence of the test compound, in which case the test compound is identified as a compound that enhances binding of TRIM to a TRIM interacting molecule In another embodiment, the amount of binding of the TRIM to the binding molecule in the presence of the test compound is less than the amount of binding of TRIM to the binding molecule in the absence of the test compound, in which case the test compound is identified as a compound that inhibits binding of TRIM to the binding molecule.

For example, binding of the test compound to TRIM or a TRIM-interacting polypeptide can be determined either directly or indirectly as described above. Determining the ability of TRIM protein to bind to a test compound can also be accomplished using a technology such as real-time Biomolecular Interaction Analysis (BIA) (Sjolander, S, and Urbaniczky, C. (1991) *Anal. Chem.* 63:2338-2345; Szabo, et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) may be used as an indication of real-time reactions between biological molecules.

In another embodiment, the ability of a compound to modulate the ability of TRIM or a TRIM-interacting molecule to be acted on by an enzyme or to act on a substrate can be measured. In one embodiment, ubiquitination assays can be used to detect the ability of TRIMs to ubiqutinate a substrate. Such assays are well-known in the art (see, for example, Klotzbucher, A., et al. (2002) *Biol. Proceed. Online* 4:62, incorporated herein by reference).

In one embodiment of the above assay methods, it may be desirable to immobilize either TRIM or a TRIM-interacting polypeptide for example, to facilitate separation of complexed from uncomplexed forms of one or both of the proteins, or to accommodate automation of the assay. Binding to a surface can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or TRIM protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, proteins may be immobilized utilizing conjugation of biotin and streptavidin. Biotinylated protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or TRIM protein is trapped in the wells by antibody conjugation. Methods for detecting such complexes, in addition to those described above for the GST-immobilized complexes, include immunodetection of complexes using antibodies reactive with TRIM or a TRIM-interacting polypeptide or target molecule, as well as enzyme-linked assays which rely on detecting an enzymatic activity associated with the TRIM protein or binding molecule.

B. Test Compounds

A variety of test compounds can be evaluated using the screening assays described herein. The term "test compound" includes any reagent or test agent which is employed in the assays of the invention and assayed for its ability to influence the production, expression and/or activity of cytokines. More than one compound, e.g., a plurality of compounds, can be tested at the same time for their ability to modulate cytokine production, expression and/or activity in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening may be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin, et al. (1992). *J. Am. Chem. Soc.* 114:10987; DeWitt et al. (1993). *Proc. Natl. Acad. Sci., USA* 90:6909) peptoids (Zuckermann. (1994). *J. Med. Chem.* 37:2678) oligocarbamates (Cho, et al. (1993). *Science.* 261: 1303), and hydantoins (DeWitt, et al. supra). An approach for the synthesis of molecular libraries of small organic molecules with a diversity of 104-105 as been described (Carell, et al. (1994). *Angew. Chem. Int. Ed. Engl.* 33:2059; Carell, et al. (1994) *Angew. Chem. Int. Ed. Engl.* 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb, et al. (1994). *Proc. Natl. Acad. Sci., USA* 91:11422-; Horwell, et al. (1996) *Immunopharmacology* 33:68-; and in Gallop, et al. (1994); *J. Med. Chem.* 37:1233.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S., et al. (1991) *Nature* 354:82-84; Houghten, R., et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z., et al. (1993) *Cell* 72:767-778); 3) antibodies (e.g., antibodies (e.g., intracellular, polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of molecules (e.g., dominant negative mutant forms of TRIM or a TRIM-binding protein).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt, et al. (1993) *Proc. Natl. Acad. Sci., U.S.A.* 90:6909; Erb, et al. (1994) *Proc. Natl. Acad. Sci., USA* 91:11422; Zuckermann, et al. (1994) *J. Med. Chem.* 37:2678; Cho, et al. (1993) *Science* 261:1303; Carrell, et al. (1994) *Angew. Chem. Int. Ed. Engl.* 33:2059; Carell, et al. (1994) *Angew. Chem. Int. Ed. Engl.* 33:2061; and Gallop, et al., (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull, et al. (1992) *Proc. Natl. Acad. Sci., USA* 89:1865-1869) or phage (Scott and Smith (1990) *Science* 249:386-390; Devlin (1990) *Science* 249:404-406; Cwirla, et al. (1990) *Proc. Natl. Acad. Sci., USA* 87:6378-6382; Felici (1991) *J. Mol. Biol.* 222:301-310; Ladner supra.).

Compounds identified in the subject screening assays may be used, e.g., in methods of modulating HIV and SIV infection and/or replication, ubiquitination, protein degradation or capsid binding. It will be understood that it may be desirable to formulate such compound(s) as pharmaceutical compositions (described supra) prior to contacting them with cells.

Once a test compound is identified that directly or indirectly modulates, e.g., production, expression and/or activity of a gene regulated by TRIM and/or a TRIM-binding molecule, by one of the variety of methods described herein, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining TRIM polypeptide and/or nucleic acid expression as well as TRIM activity, in the context of a biological sample (e.g., blood, serum, cells, tissue) to thereby determine whether an individual is afflicted with an infection, disease or disorder, or is susceptible to or resistant to developing an infection, disease or disorder, e.g., viral infection, e.g., SIV infection, HIV infection and/or AIDS. The invention also provides for prognostic (or predictive) assays for determining whether an individual susceptible to or resistant to an infection, disease or disorder, e.g., viral infection, e.g., SIV infection, HIV infection and/or AIDS. For example, mutations in a TRIM gene can be assayed in a biological sample. Such assays can be used for prognostic or predictive purpose to thereby prophylactically treat an individual prior to the onset of a disorder characterized by or associated with TRIM polypeptide, nucleic acid expression or activity.

Another aspect of the invention pertains to monitoring the influence of agents (e.g., drugs, compounds) on the expression or activity of TRIM in clinical trials.

These and other agents are described in further detail in the following sections.

i. Diagnostic Assays

An exemplary method for detecting the presence or absence of TRIM polypeptide or nucleic acid in a biological sample involves obtaining a biological sample from a test subject and contacting the biological sample with a compound or an agent capable of detecting TRIM polypeptide or nucleic acid (e.g., mRNA, or genomic DNA) that encodes TRIM polypeptide such that the presence of TRIM polypeptide or nucleic acid is detected in the biological sample. In another aspect, the present invention provides a method for detecting the presence of TRIM activity in a biological sample by contacting the biological sample with an agent capable of detecting an indicator of TRIM activity such that the presence of TRIM activity is detected in the biological sample. A preferred agent for detecting TRIM mRNA or genomic DNA is a labeled nucleic acid probe capable of hybridizing to TRIM mRNA or genomic DNA. The nucleic acid probe can be, for example, the TRIM nucleic acid set forth in SEQ ID NO:1, or a portion thereof, such as an oligonucleotide of at least 15, 30, 50, 100, 250 or 500 nucleotides in length and sufficient to specifically hybridize under stringent conditions to TRIM mRNA or genomic DNA. Other suitable probes for use in the diagnostic assays of the invention are described herein.

A preferred agent for detecting TRIM polypeptide is an antibody capable of binding to TRIM polypeptide, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect TRIM mRNA, polypeptide, or genomic DNA in a biological sample in vitro as well as in vivo. For example, in vitro techniques for detection of TRIM mRNA include Northern hybridizations and in situ hybridizations. In vitro techniques for detection of TRIM polypeptide include enzyme linked immunosorbent assays (ELISAs), Western blots, immunoprecipitations and immunofluorescence. In vitro techniques for detection of TRIM genomic DNA include Southern hybridizations. Furthermore, in vivo techniques for detection of TRIM polypeptide include introducing into a subject a labeled anti-TRIM antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding a TRIM polypeptide; (ii) aberrant expression of a gene encoding a TRIM polypeptide; (iii) mis-regulation of the gene; and (iii) aberrant post-translational modification of a TRIM polypeptide, wherein a wild-type form of the gene encodes a polypeptide with a TRIM activity. "Misexpression or aberrant expression", as used herein, refers to a non-wild-type pattern of gene expression, at the RNA or protein level. It includes, but is not limited to, expression at non-wild-type levels (e.g., over or under expression); a pattern of expression that differs from wild-type in terms of the time or stage at which the gene is expressed (e.g., increased or decreased expression (as compared with wild-type) at a predetermined developmental period or stage); a pattern of expression that differs from wild-type in terms of decreased expression (as compared with wild-type) in a pre-determined cell type or tissue type; a pattern of expression that differs from wild-type in terms of the splicing size, amino acid sequence, post-transitional modification, or biological activity of the expressed polypeptide; a pattern of expression that differs from wild-type in terms of the effect of an environmental stimulus or extracellular stimulus on expression of the gene (e.g., a pattern of increased or decreased expression (as compared with wild-type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting TRIM polypeptide, mRNA, or genomic DNA, such that the presence of TRIM polypeptide, mRNA or genomic DNA is detected in the biological sample, and comparing the presence of TRIM polypeptide, mRNA or genomic DNA in the control sample with the presence of TRIM polypeptide, mRNA or genomic DNA in the test sample.

The invention also encompasses kits for detecting the presence of TRIM in a biological sample. For example, the kit can comprise a labeled compound or agent capable of detecting TRIM polypeptide or mRNA in a biological sample; means for determining the amount of TRIM in the sample; and means for comparing the amount of TRIM in the sample with a standard. The compound or agent can be packaged in a suitable container. The kit can further comprise instructions for using the kit to detect TRIM polypeptide or nucleic acid.

ii. Prognostic Assays

The diagnostic methods described herein can furthermore be utilized to identify subjects susceptible or resistant to viral infection, e.g., HIV and/or SIV infection. The assays described herein, such as the preceding diagnostic assays or the following assays, can be utilized to identify a subject who is susceptible or resistant to viral infection. Thus, the present invention provides a method for identifying subject susceptible or resistant to HIV in which a test sample is obtained from a subject and TRIM polypeptide or nucleic acid (e.g., mRNA or genomic DNA) is detected, wherein the presence of a particular nucleotide or amino acid residue at a particular polymorphic region is diagnostic for a subject susceptible or resistant to HIV. For example, certain individuals have been identified who are resistant to infection by HIV, referred to herein as long-term non-progressors (i.e., individuals who have been infected with HIV yet retain a CD4$^+$ cell count within the normal range). These individuals may be screened for the presence of polymorphisms which are associated with resistance to infection by HIV. These polymorphic regions may then be used to identify individuals who are also resistant to infection by HIV.

In another embodiment, the present invention provides a method for identifying subject susceptible or resistant to HIV in which a test sample is obtained from a subject and TRIM polypeptide is detected, wherein the ratio of TRIM proteins or TRIM isoforms in a sample is diagnostic for a subject susceptible or resistant to HIV. In one embodiment, a specific ratio of TRIM5α to other TRIM5 isoforms in a subject may confer resistance or susceptibility to viral infection, e.g., HIV and/or SIV infection.

As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat or prevent a viral infection, e.g., HIV and/or SIV infection.

The methods of the invention can be used to detect genetic alterations in a TRIM gene, thereby determining if a subject with the altered gene is susceptible or resistant to viral infection. In preferred embodiments, the methods include detecting, in a sample of cells from the subject, the presence or absence of a genetic alteration characterized by at least one of an alteration affecting the integrity of a gene encoding a TRIM-polypeptide, or the mis-expression of the TRIM gene. For example, such genetic alterations can be detected by ascertaining the existence of at least one of 1) a deletion of one or more nucleotides from a TRIM gene; 2) an addition of one or more nucleotides to a TRIM gene; 3) a substitution of one or more nucleotides of a TRIM gene, 4) a chromosomal rearrangement of a TRIM gene; 5) an alteration in the level of a messenger RNA transcript of a TRIM gene, 6) aberrant modification of a TRIM gene, such as of the methylation pattern of the genomic DNA, 7) the presence of a non-wild-type splicing pattern of a messenger RNA transcript of a TRIM gene, 8) a non-wild-type level of a TRIM-polypeptide, 9) allelic loss of a TRIM gene, and 10) inappropriate post-translational modification of a TRIM-polypeptide. As described herein, there are a large number of assays known in the art which can be used for detecting alterations in a TRIM gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran, et al. (1988) *Science* 241:1077-1080; and Nakazawa, et al. (1994) *Proc. Natl. Acad. Sci., USA* 91:360-364), the latter of which can be particularly useful for detecting point mutations in the TRIM-gene (see Abravaya, et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a TRIM gene under conditions such that hybridization and amplification of the TRIM-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C., et al., (1990) *Proc. Natl. Acad. Sci., USA* 87:1874-1878), transcriptional amplification system (Kwoh, D. Y., et al., (1989) *Proc. Natl. Acad. Sci., USA* 86:1173-1177), Q-Beta Replicase (Lizardi, P. M., et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a TRIM gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in TRIM can be identified by hybridizing a sample and control nucleic acids, e.g., DNA or RNA, to high density arrays containing hundreds or thousands of oligonucleotides probes (Cronin, M. T., et al. (1996) *Human Mutation* 7: 244-255; Kozal, M. J., et al. (1996) *Nature Medicine* 2: 753-759). For example, genetic mutations in TRIM can be identified in two dimensional arrays containing light-generated DNA probes as described in Cronin, M. T., et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the TRIM gene and detect mutations by comparing the sequence of the sample TRIM with the corresponding wild-type (control) sequence. Examples of sequencing reactions include those based on techniques developed by Maxam and Gilbert ((1977) *Proc. Natl. Acad. Sci., USA* 74:560) or Sanger ((1977) *Proc. Natl. Acad. Sci., USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen, et al. (1996) *Adv. Chromatogr.* 36:127-162; and Griffin, et al. (1993) *Appl. Biochem. Biotechnol.* 38:147-159).

Other methods for detecting mutations in the TRIM gene include methods in which protection from cleavage agents is used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labeled) RNA or DNA containing the wild-type TRIM sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton, et al. (1988) *Proc. Natl. Acad. Sci., USA* 85:4397; Saleeba, et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TRIM cDNAs obtained from samples of cells. For example, the mutY enzyme of *E. coli* cleaves A at G/A mismatches and the thymidine DNA glycosylase from HeLa cells cleaves T at G/T mismatches (Hsu, et al. (1994) *Carcinogenesis* 15:1657-1662). According to an exemplary embodiment, a probe based on a TRIM sequence, e.g., a wild-type TRIM sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TRIM genes. For example, single strand conformation polymorphism (SSCP) may be used to detect differences in electrophoretic mobility between mutant and wild-type nucleic acids (Orita, et al. (1989) *Proc. Natl. Acad. Sci., USA:* 86:2766, see also Cotton (1993) *Mutat. Res.* 285:125-144; and Hayashi (1992) *Genet. Anal. Tech. Appl.* 9:73-79). Single-stranded DNA fragments of sample and control TRIM nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen, et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers, et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations, e.g., SNPs, include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki, et al. (1986) *Nature* 324:163); Saiki, et al. (1989) *Proc. Natl. Acad. Sci., USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs, et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini, et al. (1992) *Mol. Cell. Probes* 6:1). It is anticipated that in certain embodiments amplification may also be performed using Taq ligase for amplification (Barany (1991) *Proc. Natl. Acad. Sci., USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a TRIM gene.

Furthermore, any cell type or tissue in which TRIM is expressed may be utilized in the prognostic assays described herein.

iii. Monitoring of Effects During Clinical Trials

Monitoring the influence of agents (e.g., drugs) on the expression or activity of a TRIM polypeptide (e.g., the modulation of HIV and/or SIV infection and/or replication, can be applied not only in basic drug screening, but also in clinical trials. For example, the effectiveness of an agent determined by a screening assay as described herein to increase TRIM gene expression, polypeptide levels, or upregulate TRIM activity, e.g., capsid binding, can be monitored in clinical trials of subjects having HIV infection or AIDS. In such clinical trials, the expression or activity of a TRIM gene, and preferably, other genes that have been implicated in, for example, susceptibility to HIV infection can be used as a "read out" or markers of the phenotype of a particular cell.

For example, and not by way of limitation, genes, including TRIM, that are modulated in cells by treatment with an agent (e.g., compound, drug or small molecule) which modulates TRIM activity (e.g., identified in a screening assay as described herein) can be identified. Thus, to study the effect of agents on viral infection, e.g., HIV infection, in a clinical trial, cells can be isolated and RNA prepared and analyzed for the levels of expression of TRIM and other genes. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of TRIM or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a TRIM polypeptide, mRNA, or genomic DNA in the preadministration sample; (iii) obtaining one or more post-administration samples from the subject; (iv) detecting the level of expression or activity of the TRIM polypeptide, mRNA, or genomic DNA in the post-administration samples; (v) comparing the level of expression or activity of the TRIM polypeptide, mRNA, or genomic DNA in the pre-administration sample with the TRIM polypeptide, mRNA, or genomic DNA in the post administration sample or samples; and (vi) altering the administration of the agent to the subject accordingly. According to such an embodiment, TRIM expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) an infectious disease or disorder, including, but not limited to, HIV. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with one or more agents according to that individual's drug response genotype. Pharmacogenomics allows a clinician or physician to target prophylactic or therapeutic treatments to patients who will most benefit from the treatment and to avoid treatment of patients who will experience toxic drug-related side effects.

i. Prophylactic Methods

In one aspect, the invention provides a method for preventing in a subject, an infectious disease or disorder, by administering to the subject one or more therapeutic agents as described herein. For example, the TRIM-related nucleic acids and proteins described herein may be used as microbicides to substantially reduce transmission of diseases transmitted by microbes, such as, for example, sexually transmitted infections (STIs), e.g., HIV or other viral infections. Subjects at risk for infection, can be identified by, for example, any known risk factors for infection by, for example, HIV.

Administration of a prophylactic agent can occur prior to the manifestation of symptoms characteristic of an infection, such that the infectious disease or disorder is prevented or, alternatively, delayed in its progression. Any mode of administration of the therapeutic agents of the invention, as described herein or as known in the art, including topical administration of the TRIM-related nucleic acids and proteins of the instant invention, may be utilized for the prophylactic treatment of an infectious disease or disorder.

Formulations of the active compounds as described herein may be administered to a subject at risk for a viral infection, such as, for example, HIV, or another sexually transmitted disease or infection, as a topically applied prophylactic. In another embodiment, specific cell populations may be targeted and transformed, e.g., using an expression vector, e.g., a viral vector, with a nucleic acid molecule which modulates TRIM expression or encodes a TRIM polypeptide as described herein. In another embodiment, the agent may be administered on mucosal membranes, e.g., orally, vaginally, or rectally, or topically to epithelia, to prevent transmission of a viral infection, such as, for example, HIV or another sexually transmitted disease or infection. In one embodiment, the compositions comprising the RNA interfering agent and the carrier polymer may be administered prior to exposure to the infectious agent.

For example, therapeutic agents described herein may be formulated as a spray, lotion, cream, foam, gel, and the like, or any other suitable delivery method known in the art or described herein, and may include, for example, standard lubricants and/or detergents or other additives. In one embodiment, these formulations are administered in combination with barrier methods for protection against sexually transmitted diseases, or may be applied to condoms or other barrier protection devices. The topically applied agents may also be used in combination with a spermicidal or other microbicidal agent as described in, for example, U.S. Pat. No. 6,302,108, the entire contents of which are expressly incorporated herein, or in combination with other prophylactic agents for the prevention of HIV or other STDs. The compounds can also be prepared in the form of suppositories (e.g., with conventional suppository bases such as cocoa butter and other glycerides) or retention enemas for rectal delivery.

ii. Therapeutic Methods

Another aspect of the invention pertains to methods of modulating TRIM expression or activity for therapeutic purposes. Accordingly, in an exemplary embodiment, the modulatory method of the invention involves contacting a cell capable of expressing TRIM with an agent that modulates one or more of the activities of TRIM polypeptide activity associated with the cell, such that TRIM activity in the cell is modulated. An agent that modulates TRIM polypeptide activity can be an agent as described herein, such as a nucleic acid or a polypeptide, a naturally-occurring target molecule of a TRIM polypeptide (e.g., a TRIM substrate), a naturally-occurring modulator of TRIM expression, e.g., interferons, a TRIM agonist or antagonist, a peptidomimetic of a TRIM agonist or antagonist, or other small molecule. In one embodiment, the agent stimulates one or more TRIM activities. Examples of such stimulatory agents include active TRIM polypeptide and a nucleic acid molecule encoding TRIM that has been introduced into the cell. In another embodiment, the agent inhibits one or more TRIM activities. Examples of such inhibitory agents include antisense TRIM nucleic acid molecules, anti-TRIM antibodies, and TRIM inhibitors. These modulatory methods can be performed in vitro (e.g., by culturing the cell with the agent) or, alternatively, in vivo (e.g., by administering the agent to a subject). As such, the present invention provides methods of treating an individual with a viral infection, e.g., an HIV infection or AIDS. In one embodiment, the method involves administering an agent (e.g., an agent identified by a screening assay described herein), or combination of agents that modulates (e.g., upregulates) TRIM expression or activity. Stimulation of TRIM activity is desirable in situations in which TRIM is abnormally down-regulated and/or in which increased TRIM activity is likely to have a beneficial effect.

The prophylactic or therapeutic pharmaceutical compositions of the invention can contain other pharmaceuticals, in conjunction with a vector according to the invention, when used to therapeutically treat or prevent an infectious disease or disorder and can also be administered in combination with other pharmaceuticals used to treat or prevent a viral infection, e.g., HIV. Examples of pharmaceuticals used to treat or prevent an infectious disease or disorder, e.g., HIV infection, AIDS, and AIDS-related diseases include, without limitation, antiretroviral therapies, e.g., protease inhibitors, immunomodulators, immunostimulants, antibiotics, antiprotozoal agents, antifungal agents, antiviral compounds, anticancer drugs, and other agents and treatments, and combinations thereof, that can be employed to treat or prevent an infectious disease or disorder, e.g., HIV infection, AIDS, and AIDS-related diseases or delay the progression thereof. Specific pharmaceuticals which may be used in combination with the modulators of the invention to treat or prevent HIV infection, AIDS, and AIDS-related diseases include, without limitation, Norvir, Kaletra, Nevirapine, Efavirenz, Delavirdine, Zidovudine, Didanosine, Zalcitabine, Stavudine, Lamivudine, Abacavir, Lamivudine+Zidovudine, Saquinavir, Ritonavir, Indinavir, Nelfinavir, Amprenavir, Lopinavir+Ritonavir, Azithromycin, Clarithromycin, Clindamycin; Ceftriaxone, Cefixime, Ciprofloxacin; Rifabutin, Trimethoprim/Sulphamethoxazole (IV); Pentamidine, Pyrimethamine, Sulfadiazine, Folinic acid, Acyclovir, Cidofovir, Ganciclovir, Forscarnet, Amphotericin B, Fluconazole, Itraconazole, Ketoconazole; Vinblastine, Etoposide, Bleomycin, and Vincristine.

EXAMPLES

This invention is further illustrated by the following examples which should not be construed as limiting. The contents of all references, figures, Sequence Listing, patents and published patent applications cited throughout this application are hereby incorporated by reference.

Example 1

A. Materials and Methods

Screen for HIV-1-resistant Cells.

A primary rhesus lung (PRL)[4] cDNA library ($3.2 \times 10^6$ independent clones) was inserted into the pLIB vector (Clontech) and used to transduce $3 \times 10^6$ HeLa cells. Three days later, a total of $6 \times 10^6$ transduced cells were reseeded in batches of $5 \times 10^5$ cells in 10-cm dishes and incubated with sufficient HIV-1.GFP to infect at least 99% of the cells. Approximately 0.5% of the cells were selected for the absence of fluorescence using a FACS Vantage SE cell sorter (Becton Dickinson). Collected cells were allowed to grow into 500-cell colonies and subjected to a second round of HIV-1.GFP infection at a high multiplicity of infection. GFP-negative colonies were identified by fluorescence microscopy, cloned and expanded. A total of 313 HeLa clones from seven sequential screens were selected and tested for susceptibility to HIV-1.GFP and SIV.GFP. Two clones with a selective block to HIV-1.GFP were identified. Eleven cDNA inserts from these two clones were recovered by PCR amplification of genomic DNA samples with oligonucleotide primers specific for the pLIB vector using the following conditions: 1 cycle at 95° C., 40 cycles of 95° C. for 1 minute, 68° C. for 1 minute and 72° C. for 5 minutes, and then 1 cycle at 72° C. for 10 minutes. Each cDNA was subcloned using the EcoRI and ClaI restriction sites of the pLPCX vector (Clontech) and sequenced. The cDNA encoding TRIM5α$_{rh}$ was the only monkey cDNA present in both HIV-1-resistant HeLa clones and was the only cDNA subsequently confirmed to inhibit HIV-1 infection.

Creation of Cells Stably Expressing TRIM5α Variants.

The pLPCX vectors with TRIM5 cDNAs or control empty pLPCX vectors were co-transfected into 293T cells with pVPack-GP (Stratagene) and pVPack-VSV-G (Stratagene) packaging plasmids. The resulting virus particles were used to transduce $5 \times 10^5$ HeLa cells in the presence of 5 μg/mL polybrene, followed by selection in 1 μg/mL puromycin (Sigma). Cells were transduced with either a vector (pLPCX-TRIM5α$_{rh}$(fl)) containing full-length TRIM5α$_{rh}$ cDNA, which includes the 5'- and 3'-untranslated regions, or a vector (pLPCX-TRIM5α$_{rh}$(cds)) that contains only the amino-acid-coding sequence of TRIM5α$_{rh}$.

Infection with Viruses Expressing GFP.

HIV-1.GFP, SIV.GFP, HIV(SCA).GFP and SIV(HCA-p2).GFP viruses were prepared as previously described (Hofmann, W., et al. (1999) *J. Virol.* 73, 10020-10028; Owens, C. M., et al. (2003) *J. Virol.* 77, 726-731; Dorfman, T. & Göttlinger, H. G. (1996) *J. Virol.* 70, 5751-5757). MLV.GFP was prepared by co-transfection of 293T cells with 15 μl g pFB-hrGFP (Stratagene), 15 μg pVPack-GP (Stratagene) and 4 μg pVPack-VSV-G (Stratagene). HIV and SIV viral stocks were quantified using reverse transcriptase (RT) activity, as previously described (Li, J., et al. (1992) *J. AIDS* 5, 639-646). MLV RT activity was determined by the same procedure except 20 mM $MnCl_2$ replaced $MgCl_2$. For infections, $3 \times 10^4$ HeLa cells or $2 \times 10^4$ PRL cells seeded in 24-well plates were incubated in the presence of virus for 24 hours. Cells were washed and returned to culture for 48 hours, and then subjected to FACS analysis (Becton Dickinson FACScan).

Infection with Replication-competent HIV-1 and SHIV.

Stocks of replication-competent HIV-1$_{HXBc2}$ and SHIV-HXBc2 (Li, J., et al. (1992) *J. AIDS* 5, 639-646) were prepared from supernatants of 293T cells transfected with the respective proviral clones. Spreading infections were initiated with stocks normalized according to RT activity and replication was monitored over time by analyzing culture supernatants for RT activity.

Quantitative Real-time PCR.

Virus stocks derived from transfection of 293T cells were treated with 50 U/mL Turbo DNAse (Ambion) for 60 minutes at 37° C. Cells ($2 \times 10^5$) were infected with $2 \times 10^4$ RT units of VSV G-pseudotyped HIV-1.GFP or control HIV-1.GFP lacking envelope glycoproteins, and genomic DNA was isolated at various time points (0-48 hours). Early HIV-1 reverse transcripts were quantified with primers ert2f and ert2r and the ERT2 probe, as described previously (Besnier, C., Takeuchi, Y. & Towers, G. (2002) *Proc. Natl. Acad. Sci., USA* 99, 11920-11925). Late HIV-1 reverse transcripts were quantified with primers MH531 and MH532 and the probe LRT-P, as previously described (Butler, S., et al. (2001) *Nat. Med.* 7, 631-634). Reaction mixtures contained Taqman universal master mix (PE Biosystems), 300 nM primers, 100 nM probe, and 500 ng genomic DNA. PCR was performed for 2 minutes at 50° C. and 10 minutes at 95° C., followed by 40 cycles of 15 seconds at 95° C. and 1 minute at 60° C., on an ABI Prism 7700 (Applied Biosystems).

Cloning of TRIM5 Isoforms and TRIM5α$_{rh}$ Mutagenesis.

The human TRIM5α open reading frame was amplified from a kidney cDNA library (Clontech), using primers derived from the NCBI RefSeq NM_033034 (gi:14719417; SEQ ID NO. 47; incorporated herein by reference) and inserted into pLPCX (Clontech) to create pTRIM5α$_{hu}$. The predicted sequence of this TRIM5α$_{hu}$ differs in three amino-acid residues from the NCBI reference sequence NM_033034 (SEQ ID NO. 47), derived from the TRIM5α of the retinoic acid-induced NT2 neuronal precursor line. Rhesus monkey TRIM5γ was amplified from the primary rhesus lung (PRL) cDNA library using primers derived from NCBI RefSeq NM_033092 (gi:15011943; SEQ ID NO.:51; incorporated herein by reference) and inserted into pLPCX to create pTRIM5γ$_{rh}$. In the pTRIM5α$_{rh}$-HA and pTRIM5α$_{hu}$-HA plasmids, an in-frame sequence encoding the influenza virus haemagglutinin (HA) epitope tag was included at the 3' end of TRIM5α$_{rh}$ and TRIM5α$_{hu}$, respectively. The pTRIM5γ$_{rh}$-HA plasmid contains a sequence encoding the initiator methionine and the HA epitope tag at the 5' end of TRIM5γ$_{rh}$. Cysteine-to-alanine changes (C15A and C15A/C18A) were introduced into the TRIM5α$_{rh}$ RING domain by using the Quick-change mutagenesis kit (Stratagene).

Immunoblotting.

HA-tagged proteins were expressed in HeLa cells by transfection using Lipofectamine 2000 (Invitrogen) or by transduction with pLPCX vectors as described above. The HA-tagged proteins were detected in whole cell lysates (100 mM $(NH_4)_2SO_4$, 20 mM Tris-HCl (pH 7.5), 10% glycerol, 1% NP40) by Western blotting, using the horseradish peroxidase-conjugated 3F10 antibody (Roche). β-actin was detected using the A5441 antibody (Sigma).

RNA Interference.

A total of 8 siRNA's directed against TRIM5α$_{rh}$ were selected and synthesized according to the recommendations of the manufacturer (Dharmacon RNA Technologies):

```
siRNA #1
(5'-GCUCAGGGAGGUCAAGUUGdTdT-3')    (SEQ ID NO.: 58)

siRNA #2
(5'-GAGAAAGCUUCCUGGAAGAdTdT-3')    (SEQ ID NO.: 59)

siRNA #3
(5'-GCCUUACGAAGUCUGAAACdTdT-3')    (SEQ ID NO.: 60)

siRNA #4
(5'-GGAGAGUGUUUCGAGCUCCdTdT-3')    (SEQ ID NO.: 61)

siRNA #5
(5'-CCUUCUUACACACUCAGCCdTdT-3')    (SEQ ID NO.: 62)

siRNA #6
(5'-CGUCCUGCACUCAUCAGUGdTdT-3')    (SEQ ID NO.: 63)

siRNA #7
(5'-CAGCCUUUCUAUAUCAUCGdTdT-3')    (SEQ ID NO.: 64)

siRNA #8
(5'-CUCCUGCUCUCCAUGUACdTdT-3')     (SEQ ID NO.: 65)
```

Four of the siRNAs (#1-4; SEQ ID Nos.:58, 59, 60, and 61) are directed against TRIM5 coding sequences that are common to the mRNAs of all of the TRIM5 isoforms. Four of the siRNAs (#5-8; SEQ ID Nos.:62, 63, 64, and 65) are directed against the 3' untranslated region specific to the mRNAs encoding TRIM5α and TRIM5ε. Two of the siRNAs (#2 and #8; SEQ ID Nos.:59 and 65) exhibited some toxicity to HeLa cells and were not studied further. The remaining six siRNA's all exhibited the ability to relieve the block to HIV-1.GFP infection following transfection of PRL cells (FIG. 4). A control siRNA (Nonspecific control duplex 1 (5'-AUGAACGUGAAUUGCUCAAUU-3') (SEQ ID NO.:66) (Dharmacon RNA Technologies)) was included in the experiments. HeLa cells (1×10$^5$) or PRL cells (5×10$^4$) were seeded in 6-well plates and transfected with 120 nM siRNA using 10 µl oligofectamine (Invitrogen). Forty-eight hours later, cells were reseeded for HIV-1.GFP infection. In some experiments, HeLa and PRL cells were transduced with a pLPCX vector encoding TRIM5α$_{rh}$-escape or an empty pLPCX vector as a control. Forty-eight hours later, the cells were transfected with siRNA. Two days later, the cells were replated and used for infection. In the vector encoding TRIM5α-escape, silent mutations at the siRNA #3 (SEQ ID No.:60) recognition site changed the wild-type sequence from

```
5'-GCCTTACGAAGTCTGAAAC-3'    (SEQ ID NO.: 75)
to
5'-GGTTAACGAAGAGCGAAAC-3'.   (SEQ ID NO.: 76)
```

B. Results

Rhesus Monkey TRIM5α$_{rh}$ Preferentially Blocks HIV-1 Infection.

Recombinant HIV-1 expressing green fluorescent protein (GFP) and pseudotyped with the vesicular stomatitis virus (VSV) G glycoprotein (HIV-1.GFP) can efficiently infect the cells of many mammalian species, including humans, but not those of Old World monkeys (Hofmann, W., et al. (1999) *J. Virol.* 73, 10020-10028; Owens, C. M., et al. (2003) *J. Virol.* 77, 726-731; Kootstra, N. A., et al. (2003) *Proc. Natl. Acad. Sci., USA* 100, 1298-1303; Cowan, S. et al. (2002) *Proc. Natl. Acad. Sci., USA* 99, 11914-11919; Besnier, C., Takeuchi, Y. & Towers, G. (2002) *Proc. Natl. Acad. Sci., USA* 99, 11920-11925; Munk, C., et al. (2002) *Proc. Natl. Acad., Sci. USA* 99, 13843-13848). A murine leukemia virus vector was used to transduce human HeLa cells, which are susceptible to HIV-1.GFP infection, with a cDNA library prepared from primary rhesus monkey lung fibroblasts (PRL cells). Two independent HeLa clones resistant to HIV-1.GFP infection, but susceptible to infection with recombinant simian immunodeficiency virus (SIV.GFP) or murine leukemia virus (MLV.GFP), were identified in a screen (See Methods). The only monkey cDNA insert common to both HIV-1.GFP-resistant clones was predicted to encode TRIM5α. TRIM5α is a member of the tripartite motif (TRIM) family of proteins, which contain RING domains, B-boxes and coiled coils (Reddy, B. A., et al. (1992) *Trends Biochem. Sci.* 17, 344-345; Borden, K. L. (1998) *Biochem. Cell Biol.* 76, 351-358; Reymond, A., et al. (2001) *EMBO J.* 20, 2140-2151). TRIM5α also contains a C-terminal B30.2 (SPRY) domain not found in the other TRIM5 isoforms (Reymond, A., et al. (2001) *EMBO J.* 20, 2140-2151) (FIG. 1A). The natural functions of TRIM5α, or of the cytoplasmic bodies in which the TRIM5 proteins localize (Reymond, A., et al. (2001) *EMBO J.* 20, 2140-2151; Xu, L., et al. (2003) *Exp. Cell Res.* 288, 84-93), are unknown. One TRIM5 isoform has been shown to have ubiquitin ligase activity typical of RING-containing proteins (Xu, L., et al. (2003) *Exp. Cell Res.* 288, 84-93). TRIM5 proteins are constitutively expressed in many tissues (Reymond, A., et al. (2001) *EMBO J.* 20, 2140-2151), consistent with the pattern of expression expected for the HIV-1-blocking factor in monkeys (Hofmann, W., et al. (1999) *J. Virol.* 73, 10020-10028).

Figure 1C:
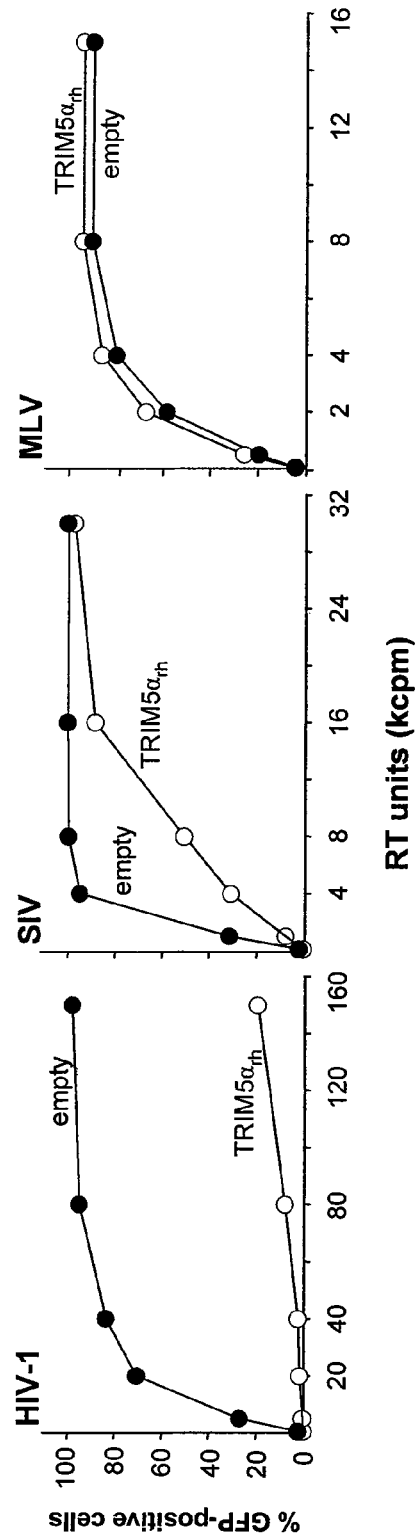
Figure 1D:
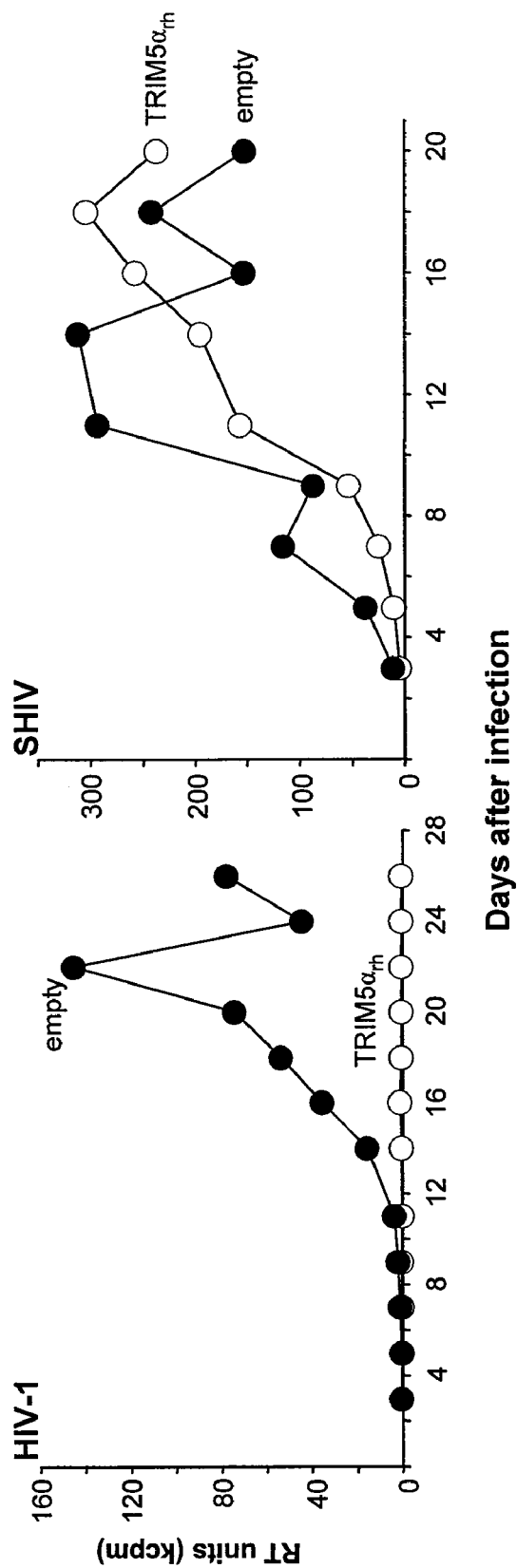
Figure 5:
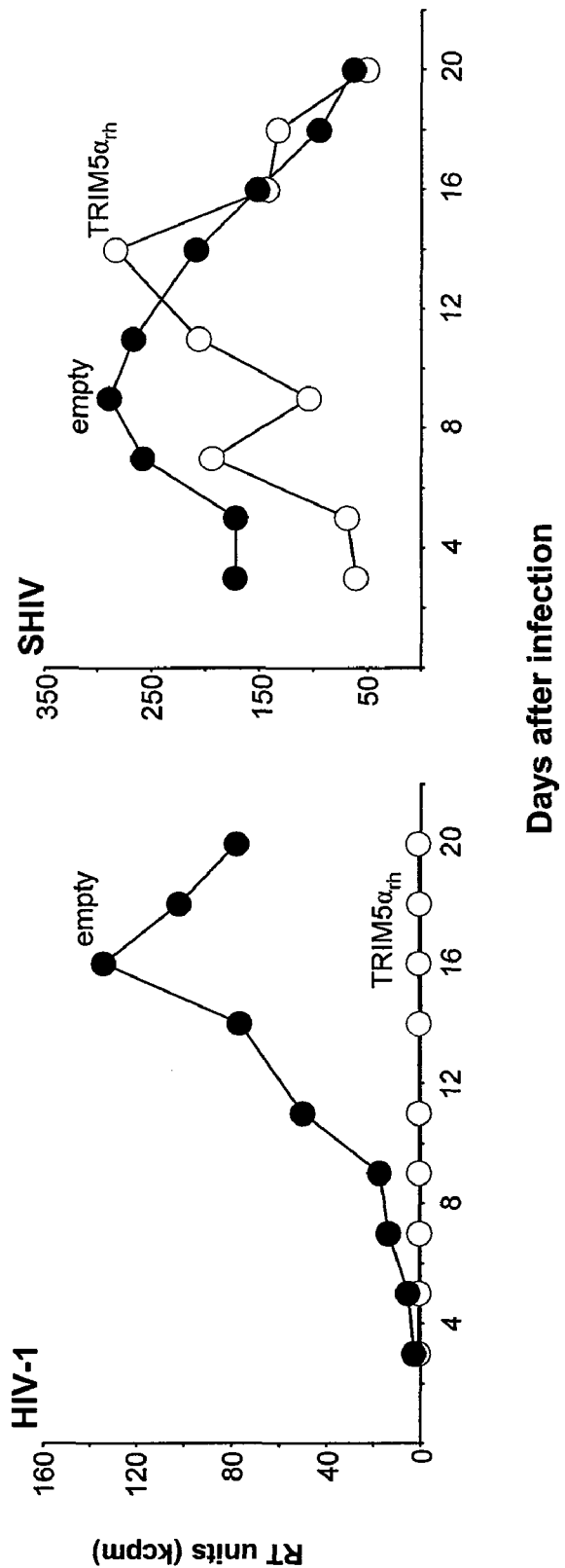
FIG. 5 depicts that TRIM5α$_{rh}$ restricts infectious HIV-1 replication at an increased multiplicity of infection. HeLa-CD4 cells (2×105) transduced with the pLPCX-TRIM5α$_{rh}$ (fl) vector expressing TRIM5α$_{rh}$ or an empty control vector were incubated with $8 \times 10^4$ RT units of infectious HIV-1 or SHIV virus. RT activity was analyzed at the indicated times.

HeLa cells stably expressing rhesus monkey TRIM5α (TRIM5α$_{rh}$) and control HeLa cells containing the empty vector were incubated with different amounts of recombinant HIV-1.GFP, SIV.GFP and MLV.GFP. TRIM5α$_{rh}$ expression resulted in a dramatic inhibition of infection by HIV-1.GFP, whereas MLV.GFP infected the control and TRIM5α$_{rh}$-expressing HeLa cells equivalently (FIGS. 1B and 1C). TRIM5α$_{rh}$ inhibited SIV.GFP expression less efficiently than that of HIV-1.GFP (FIG. 1C). Stable TRIM5α$_{rh}$ expression also inhibited the replication of infectious HIV-1 in HeLa-CD4 cells, which express the receptors for HIV-1 (Feng, Y., et al. (1996) *Science* 272, 872-877) (FIG. 1D). The replication of a simian-human immunodeficiency virus (SHIV) chimera, which contains core proteins (including the capsid protein) of SIV$_{mac}$ (Li, J., et al. (1992) *J. AIDS* 5, 639-646), was not inhibited in these TRIM5α$_{rh}$-expressing cells. When the infections were performed with 8-fold more HIV-1 and SHIV, similar results were obtained (FIG. 5). Therefore, expression of TRIM5α$_{rh}$ specifically and efficiently blocks infection by HIV-1, and exerts a slight inhibitory effect on SIV$_{mac}$ infection.

Figure 1E:
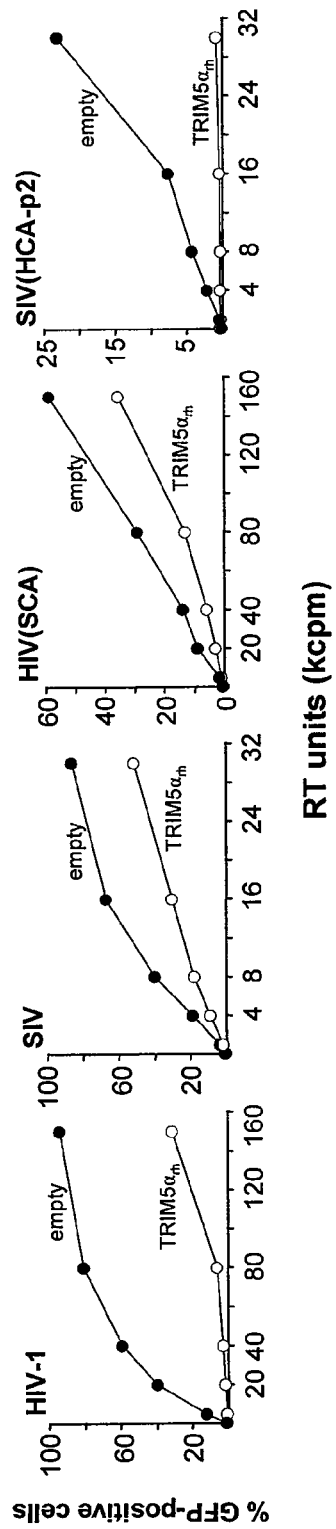

To investigate the viral target for the TRIM5α$_{rh}$-mediated restriction, HeLa cells expressing TRIM5α$_{rh}$ or control HeLa cells were incubated with recombinant HIV-1.GFP, SIV.GFP, SIV(HCA-p2).GFP and HIV(SCA).GFP. SIV(HCA-p2).GFP is identical to SIV.GFP except that the SIV capsid and adjacent p2 sequences have been replaced by those of HIV-1 (Dorfman, T. & Göttlinger, H. G. (1996) *J. Virol.* 70, 5751-5757); SIV(HCA-p2).GFP has previously been shown to be susceptible to the block in Old World monkey cells (Owens, C. M., et al. (2003) *J. Virol.* 77, 726-731; Cowan, S. et al. (2002) *Proc. Natl. Acad. Sci., USA* 99, 11914-11919). HIV(SCA).GFP is identical to HIV-1.GFP, except that most of the capsid protein has been replaced by that of SIV[5]; HIV(SCA).GFP has previously been shown to be less susceptible than HIV-1 to the block in Old World monkey cells (Owens, C. M., et al. (2003) *J. Virol.* 77, 726-731). HIV-1.GFP and SIV (HCA-p2).GFP were restricted to the same degree in TRIM5$\alpha_{rh}$-expressing HeLa cells; infections by SIV.GFP and HIV(SCA).GFP were less restricted in these cells (FIG. 1E). Thus, capsid sequences influence viral susceptibility to the TRIM5$\alpha_{rh}$-mediated restriction.

TRIM5$\alpha_{rh}$ Blocks HIV-1 Infection Prior to or During Early Reverse Transcription.

Figure 2:
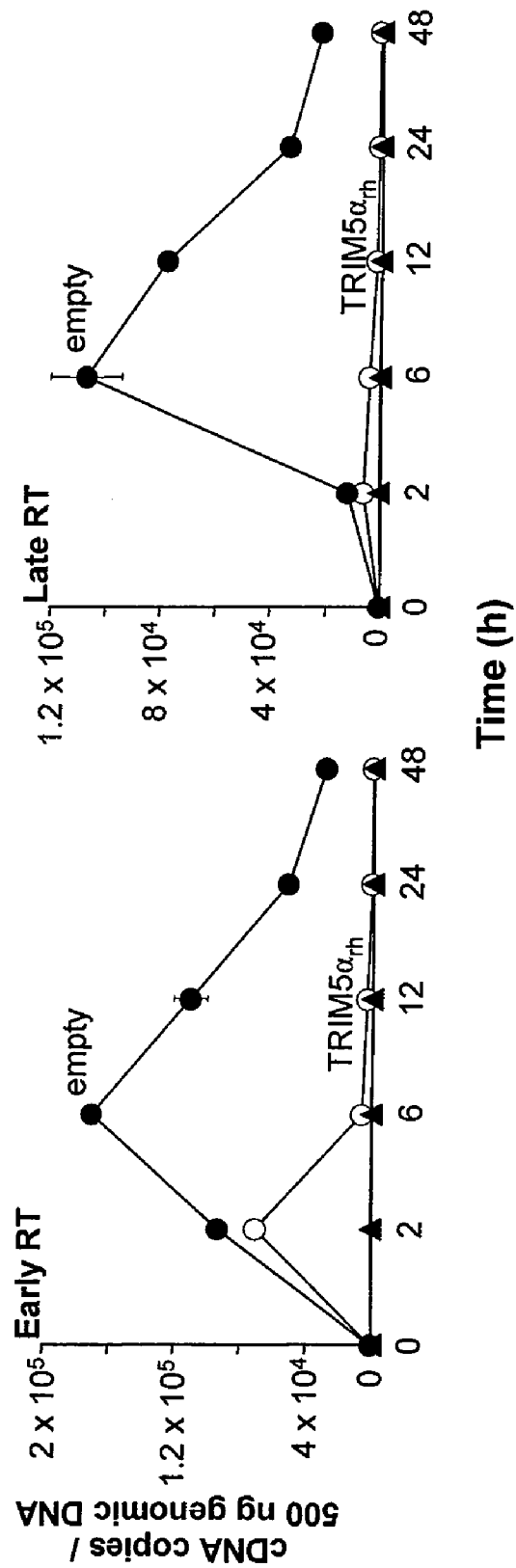
FIG. 2 depicts that TRIM5α$_{rh}$ blocks HIV-1 infection prior to or during early reverse transcription. HeLa cells stably transduced with the pLPCX-TRIM5α$_{rh}$(fl) vector expressing TRIM5α$_{rh}$ (open circle) or with an empty pLPCX vector (filled circle) were incubated with VSV G-pseudotyped, DNAse-treated HIV-1.GFP. HeLa cells transduced with the empty vector were also incubated with HIV-1.GFP viruses lacking envelope glycoproteins (filled triangle). The target cell DNA was isolated at the indicated times and used to detect early and late reverse transcripts. The means and standard deviations from duplicate experiments are shown.

To determine the level at which HIV-1 infection is blocked by TRIM5$\alpha_{rh}$, we used a real-time PCR assay to detect viral cDNA at various times after incubation of VSV G-pseudotyped HIV-1 with HeLa cells expressing TRIM5$\alpha_{rh}$ or control HeLa cells (FIG. 2). Two hours after virus-cell incubation, the levels of early reverse transcripts were comparable in the TRIM5$\alpha_{rh}$-expressing HeLa cells and the control HeLa cells. At later time points, both early and late reverse transcripts were barely detectable in the TRIM5$\alpha_{rh}$-expressing cells; by contrast, both early and late viral cDNAs were abundant in the control cells. As the VSV G glycoproteins support entry into these cells equivalently (see MLV.GFP infection in FIGS. 1B and 1C), these data indicate that early events following HIV-1 entry are impaired in the cells expressing TRIM5$\alpha_{rh}$.

TRIM5 Variants Block HIV-1 Infection Less Efficiently than TRIM5$\alpha_{rh}$.

Figure 3A:
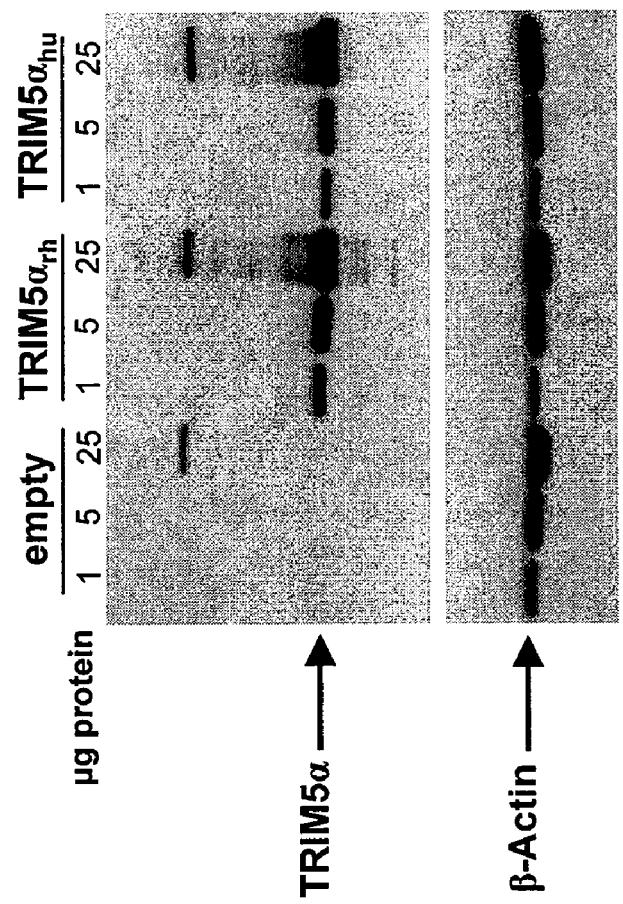
FIGS. 3A-3E depict that TRIM5 variants block HIV-1 infection less efficiently than TRIM5α$_{rh}$. A. The indicated amounts of total protein from lysates of HeLa cells transduced with the empty pLPCX vector or stably expressing human TRIM5α$_{hu}$-HA or rhesus monkey TRIM5α$_{rh}$-HA were Western blotted, probing with an anti-HA antibody. B. HeLa cells stably expressing TRIM5α$_{hu}$-HA (filled square) or TRIM5α$_{rh}$-HA (open circle), or transduced with an empty vector (filled circle), were incubated with the indicated amounts of GFP-expressing viruses. GFP-positive cells were enumerated by FACS. One set of SIV.GFP infections was carried out on cells expressing TRIM5α$_{hu}$ or TRIM5α$_{rh}$ proteins without HA epitope tags. C. Lysates, normalized for protein, from HeLa cells transfected with 4 μg of pLPCX-TRIM5α$_{rh}$(cds) variants expressing HA-tagged versions of TRIM5αrh, TRIM5αrh-C15A, TRIM5α$_{rh}$-C15A/C18A, or TRIM5γ were Western blotted, probing with an anti-HA antibody. D. HeLa cells stably expressing untagged versions of TRIM5α$_{rh}$ (open circle), TRIM5α$_{rh}$-C15A (filled square), TRIM5αrh-C15A/C18A (filled diamond), TRIM5γ (filled triangle), or an empty vector (filled circle) were incubated with the indicated GFP-expressing viruses. GFP-positive cells were counted by FACS. The results shown are typical of those obtained in at least three independent experiments. E. Primary rhesus lung (PRL) cells were transduced with an empty vector, or vectors expressing TRIM5α$_{rh}$-C15A, TRIM5α$_{rh}$-C15A/C18A, or TRIM5γ, and infected with $4 \times 10^4$ RT units of HIV-1.GFP. GFP-positive cells were counted by FACS. Similar results were obtained in three independent experiments.
Figure 3B:
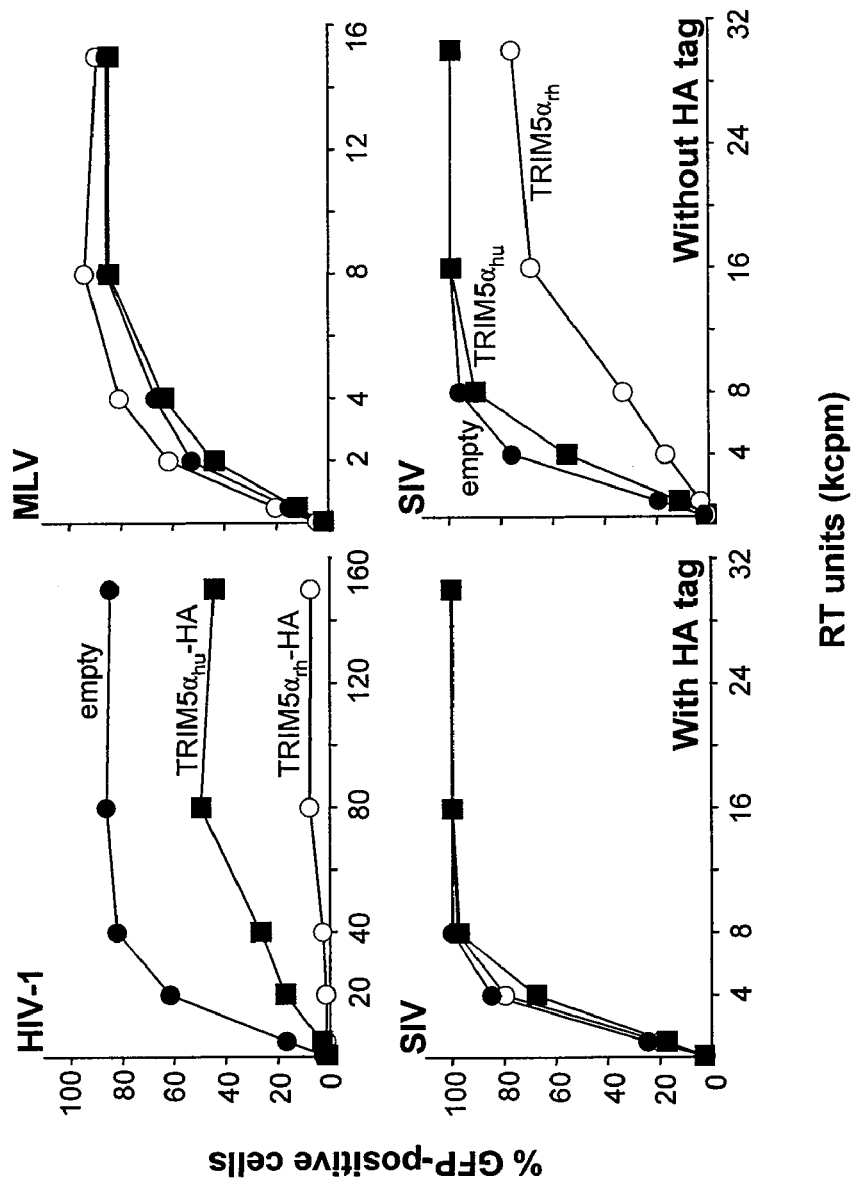
Figure 6:
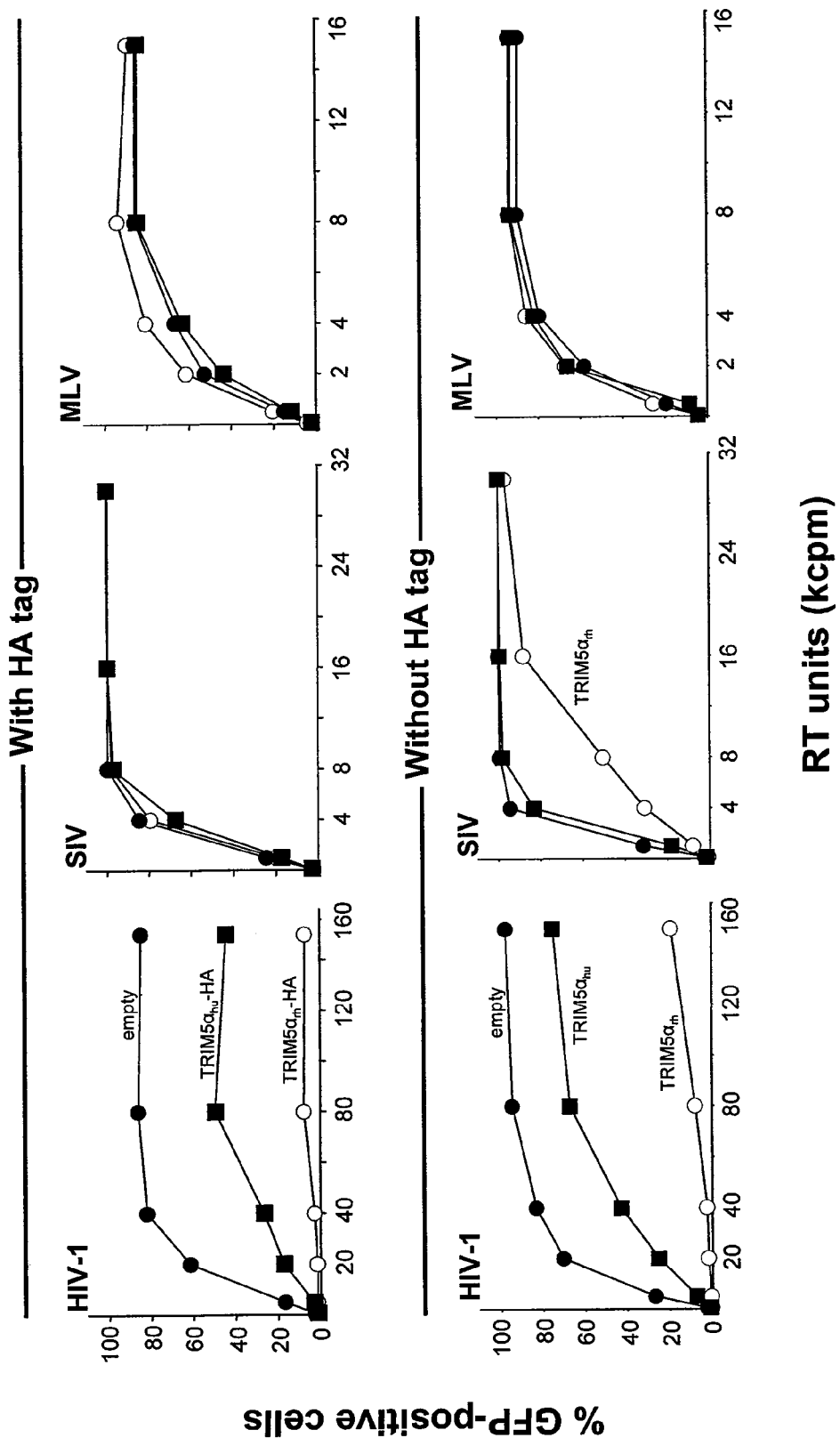
FIG. 6 depicts the effects of the HA tag on the ability of human and rhesus TRIM5α to restrict virus infection. HeLa cells stably expressing HA-tagged TRIM5α$_{hu}$-HA or TRIM5α$_{rh}$-HA, or untagged TRIM5αhu or TRIM5α$_{rh}$, were incubated with various amounts of the indicated viruses. Control HeLa cells transduced with an empty vector were included in the experiment. GFP-positive cells were counted by FACS.

The predicted sequences (FIG. 1A) of TRIM5$\alpha_{rh}$ and the human ortholog, TRIM5$\alpha_{hu}$, reveal some differences that might account for the species-specific nature of the early block to HIV-1 infection. To test this hypothesis, TRIM5$\alpha_{rh}$-HA and TRIM5$\alpha_{hu}$-HA proteins, which contain C-terminal epitope tags from influenza hemagglutinin, were expressed stably in HeLa cells. Similar levels of TRIM5$\alpha_{rh}$-HA and TRIM5$\alpha_{hu}$-HA were expressed in the HeLa cells (FIG. 3A). Neither TRIM5$\alpha_{rh}$-HA nor TRIM5$\alpha_{hu}$-HA affected the efficiency with which the HeLa cells were infected by MLV.GFP (FIG. 3B). TRIM5$\alpha_{hu}$-HA inhibited HIV-1.GFP infection less efficiently than TRIM5$\alpha_{rh}$-HA. Parallel experiments with TRIM5$\alpha$ proteins lacking the epitope tags demonstrated that the addition of the HA epitope tag to the C-terminus of TRIM5$\alpha_{rh}$ and TRIM5$\alpha_{hu}$ did not affect the efficiency with which these proteins suppressed HIV-1 infection (FIG. 6). By contrast, the modest inhibitory effect of TRIM5$\alpha_{rh}$ on SIV.GFP infection was not seen for the epitope-tagged TRIM5$\alpha_{rh}$-HA protein (FIG. 3b). Neither TRIM5$\alpha_{hu}$ nor TRIM5$\alpha_{hu}$-HA exerted significant effects on SIV.GFP infection. Thus, differences in the TRIM5$\alpha$ proteins of humans and monkeys likely contribute to the species-specific differences in susceptibility to HIV-1 infection.

Figure 3C:
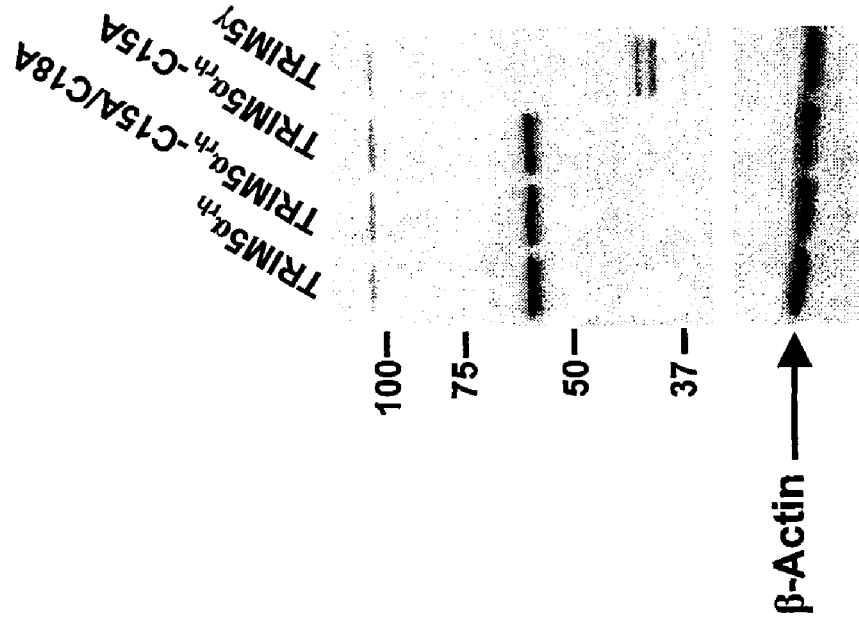
Figure 3D:
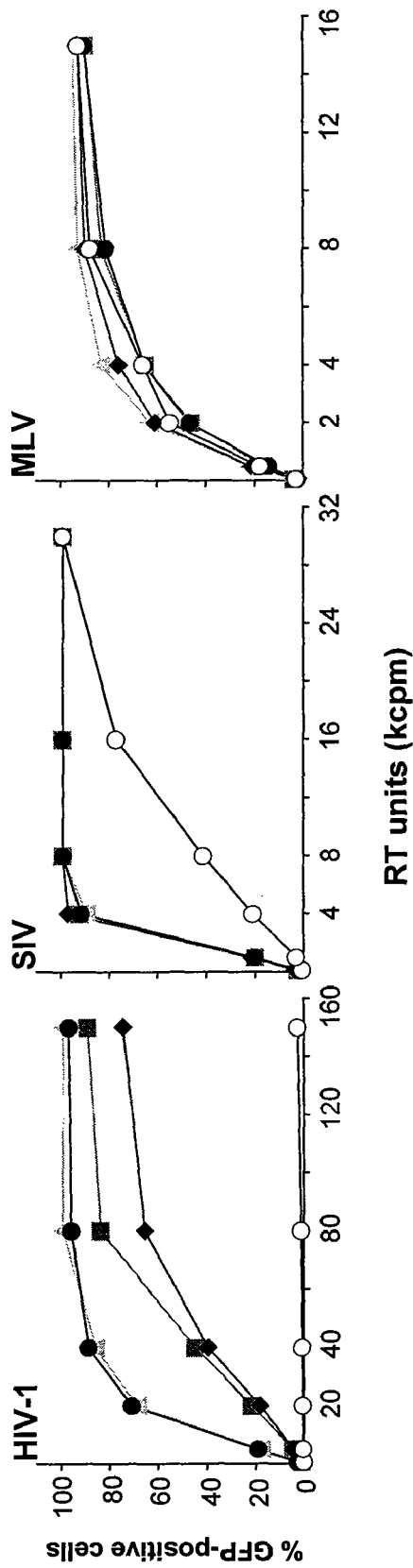

The ability of rhesus monkey TRIM5 variants to inhibit HIV-1 infection was examined. Differential splicing of TRIM5 transcripts results in the production of several isoforms that lack the TRIM5$\alpha$ a C-terminus (Reymond, A., et al. (2001) *EMBO J.* 20, 2140-2151). For example, the first 300 amino-acid residues of the TRIM5$\gamma_{rh}$ isoform are identical to those of TRIM5$\alpha_{rh}$, but the TRIM5$\gamma_{rh}$ sequence diverges and stops thereafter. To examine the contribution of the C-terminal B30.2 (SPRY) domain of TRIM5$\alpha_{rh}$ to the inhibition of HIV-1 infection, an epitope-tagged version of the TRIM5$\gamma_{rh}$ isoform was tested. Whether an intact RING domain is required for TRIM5$\alpha_{rh}$ inhibition of HIV-1 infection was also examined Studies of proteins containing RING domains, including TRIM5$\delta$, indicate that alteration of one or both of the two most N-terminal cysteines inactivates ubiquitin ligase activity (Xu, L., et al. (2003) *Exp. Cell Res.* 288, 84-93; Waterman, H., et al. (1999) *J. Biol. Chem.* 274, 22151-22154). Thus, we created and tested two HA-tagged TRIM5$\alpha_{rh}$ mutants, TRIM5$\alpha_{rh}$-C15A and TRIM5$\alpha_{rh}$-C15A/C18A. The levels of expression of TRIM5$\gamma_{rh}$ and the RING domain cysteine mutants were comparable to those of wild-type TRIM5$\alpha_{rh}$ (FIG. 3C). TRIM5$\gamma_{rh}$ did not inhibit HIV-1.GFP infection; compared with wild-type TRIM5$\alpha_{rh}$, TRIM5$\alpha_{rh}$-C15A and TRIM5$\alpha_{rh}$-C15A/C18A were significantly less effective in inhibiting HIV-1.GFP infection (FIG. 3D). Therefore, both the RING domain at the N-terminus and the B30.2 (SPRY) domain at the C-terminus of TRIM5$\alpha_{rh}$ contribute to the HIV-1-inhibitory activity of this protein.

Figure 3E:
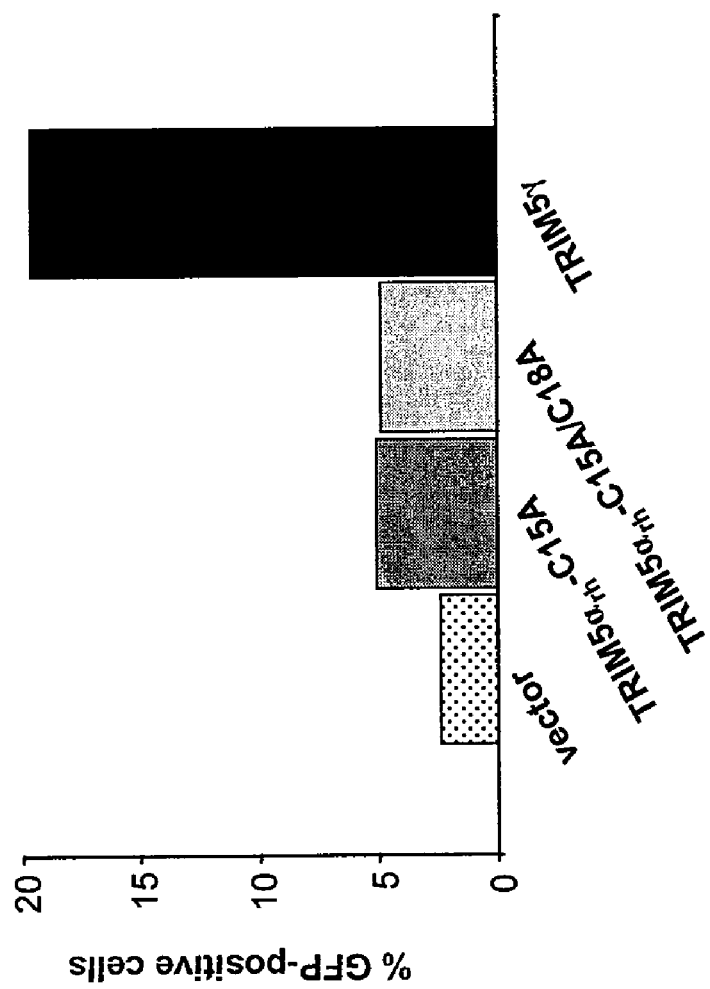

The TRIM5$\gamma_{rh}$, TRIM5$\alpha_{rh}$-C15A and TRIM5$\alpha_{rh}$-C15A/C18A variants were examined for dominant-negative activity in relieving the block to HIV-1.GFP infection in PRL cells. HIV-1.GFP infected PRL cells expressing TRIM5$\gamma_{rh}$ more efficiently than control PRL cells transduced with the empty vector or PRL cells expressing the RING domain cysteine mutants of TRIM5$\alpha_{rh}$ (FIG. 3E). Thus, TRIM5$\gamma_{rh}$ acts in a dominant-negative manner to suppress the restriction to HIV-1 in PRL cells.

TRIM5$\alpha_{rh}$ is Essential for the Block to HIV-1 Infection in Primary Rhesus Monkey Cells.

Figure 4A:
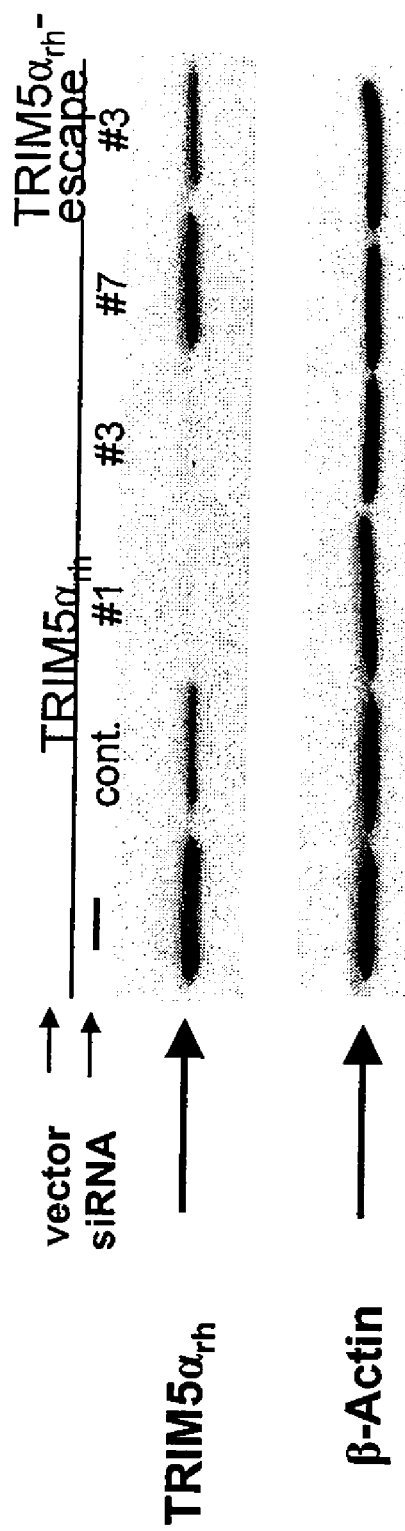
FIGS. 4A-4D depict that TRIM5α$_{rh}$ is essential for the blocking of HIV-1 infection in primary rhesus monkey cells. A. HeLa cells were cotransfected with 4 μg of pLPCX-TRIM5α$_{rh}$(cds) variants expressing HA-tagged TRIM5α$_{rh}$ or TRIM5α$_{rh}$-escape and 120 nM of the indicated siRNAs. Cell lysates were normalized for protein and Western blotted, probing for the HA epitope tag or β-actin. Note that the siRNA #7 target sequence, which resides in the 3'-untranslated region of the natural TRIM5α$_{rh}$ mRNA, is missing from the pLPCX-TRIM5α$_{rh}$(cds) plasmid used to express the HA-tagged TRIM5α$_{rh}$. Therefore, siRNA #7 serves as a negative control in this experiment. B. The indicated siRNAs were transfected into PRL cells, which were incubated with HIV-1.GFP. GFP-positive cells were counted by FACS. The means and standard deviations were derived from three independent experiments. Note that the natural TRIM5α$_{rh}$ mRNA in the PRL cells contains the target sequences for siRNAs #1, #3 and #7 and, therefore, all three siRNAs are expected to interfere with TRIM5α$_{rh}$ expression. C. Untreated PRL cells and PRL cells transduced with an empty control vector (pLPCX) or a vector expressing TRIM5α$_{rh}$-escape were transfected with 120 nM of either a control siRNA or siRNA #3. The cells were incubated with HIV-1.GFP or MLV.GFP and, after 48 hours, were visualized by fluorescence microscopy. All pictures were taken at the same magnification (4×). D. The indicated cells, either untreated (dark gray) or transduced (light gray) with an empty control vector or a vector expressing TRIM5αrh-escape, were transfected with 120 nM of either control siRNA (cont.) or siRNA #3. The cells were then incubated with the indicated GFP-expressing viruses. GFP-positive cells were counted by FACS. The values shown for the PRL cells represent the means and standard deviations derived from three independent experiments. The experiment in HeLa cells was performed twice with similar results.
Figure 4B:
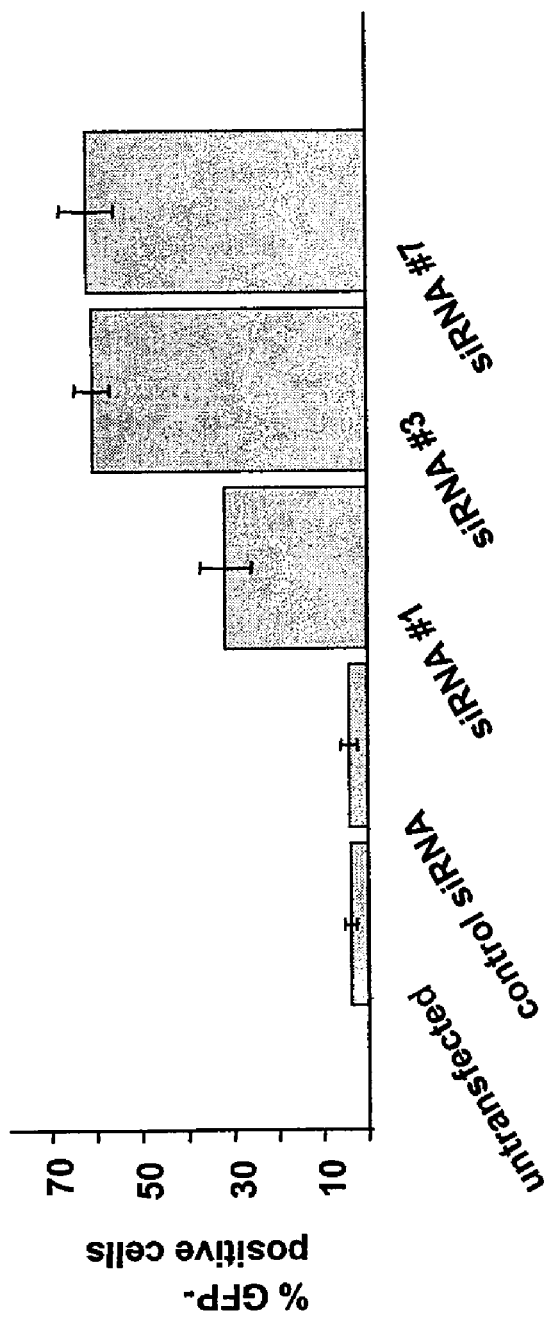
Figure 4C:
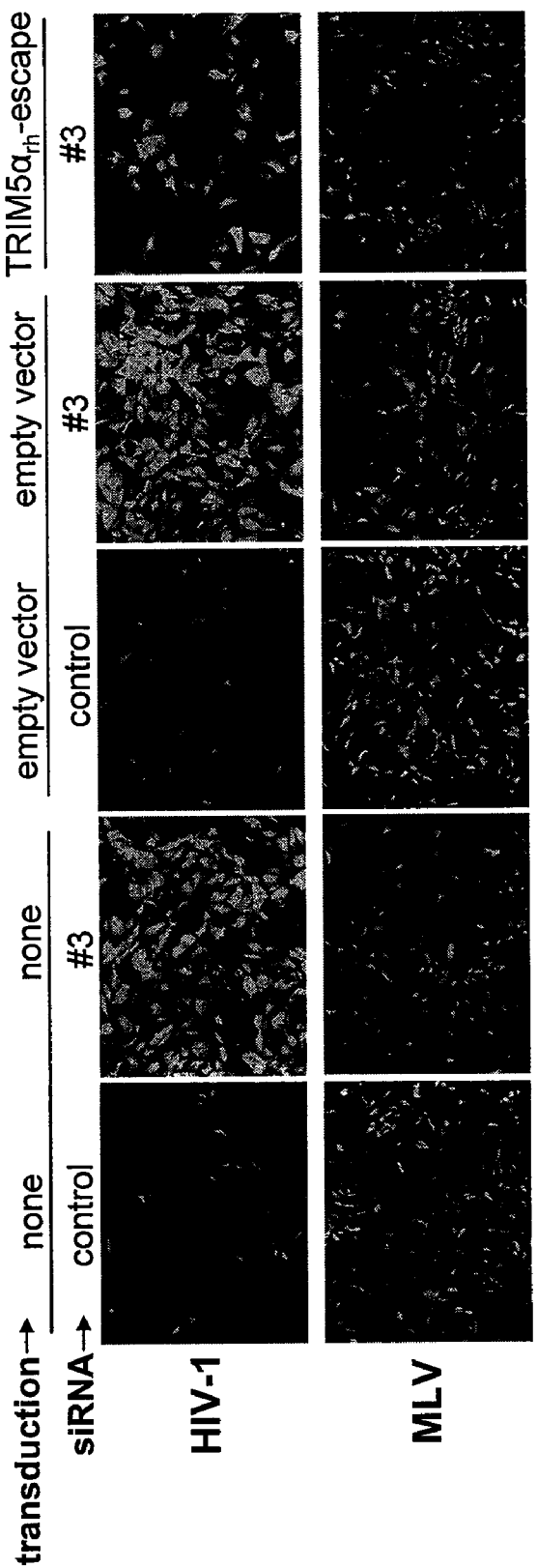
Figure 4D:
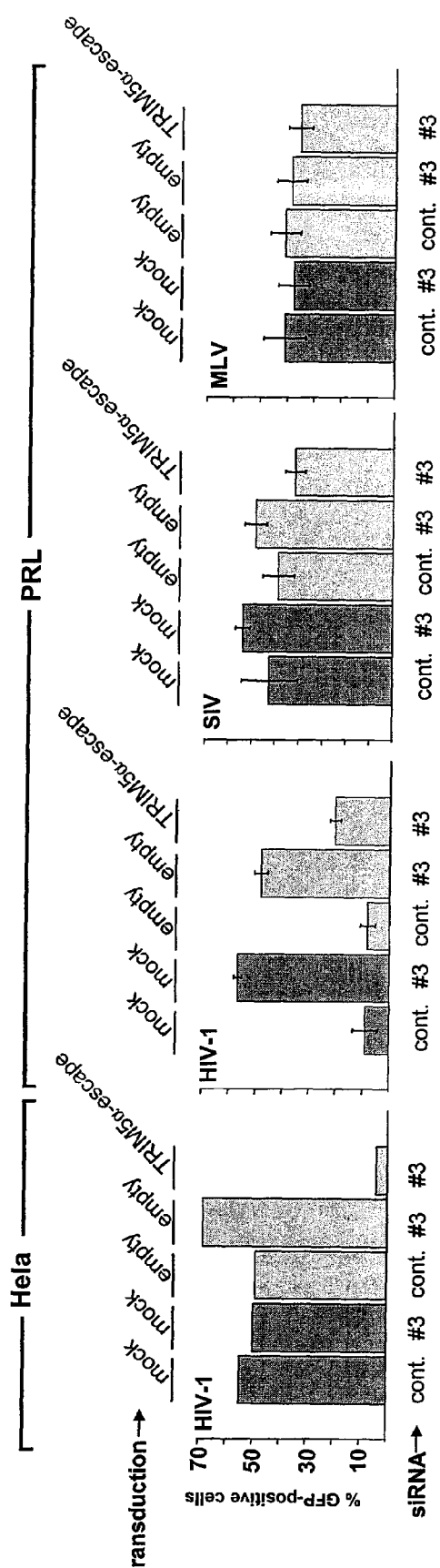
Figure 7:
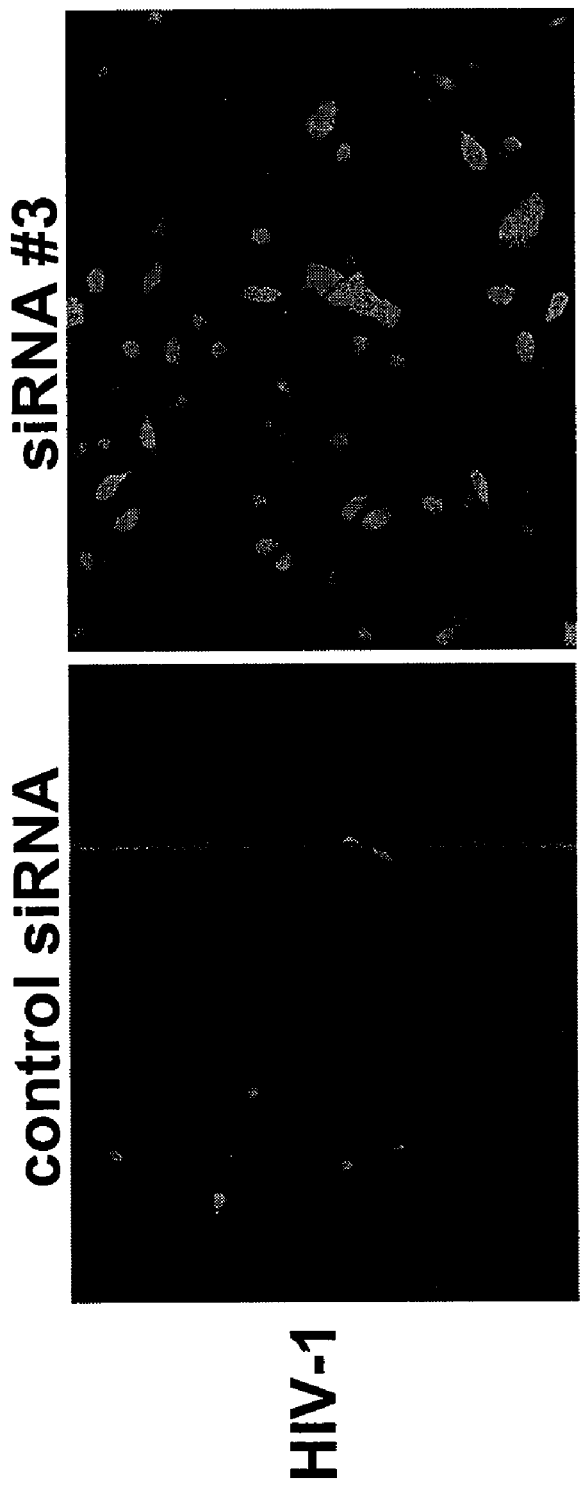
FIG. 7 depicts interference with TRIM5α$_{rh}$ expression in rhesus kidney cells relieves the post-entry restriction to HIV-1. The rhesus kidney cell line LLC-MK2 (ATCC) was transfected with the indicated siRNAs using oligofectamine and then incubated with HIV-1.GFP. GFP-positive cells were visualized by fluorescence microscopy.

To determine whether TRIM5$\alpha_{rh}$ is necessary for the restriction to HIV-1 infection in Old World monkey cells, small-interfering RNAs (siRNAs) directed against TRIM5$\alpha_{rh}$ were used to down-regulate its expression. Several different siRNAs directed against TRIM5$\alpha_{rh}$, including siRNA #1 and siRNA #3, were capable of reducing the level of TRIM5$\alpha_{rh}$-HA expression in HeLa cells (FIG. 4a). As expected, siRNA #3 did not inhibit the expression of TRIM5$\alpha_{rh}$-escape, a wild-type, HA-tagged protein encoded by an expression vector with six silent mutations in the siRNA #3 target sequence (FIG. 4A). Transfection of PRL cells with the TRIM5$\alpha_{rh}$-directed siRNAs, but not with a control siRNA, resulted in a dramatic increase in the efficiency of HIV-1.GFP infection (FIGS. 4B, 4c, and 4D). The siRNAs targeting TRIM5$\alpha_{rh}$ did not affect MLV.GFP infection (FIGS. 4c, and 4D). The increase observed after transfection of siRNA #3 was diminished when the PRL cells were transduced with a vector expressing TRIM5$\alpha_{rh}$-escape (FIGS. 4C and 4D). Although the restriction to HIV-1 infection is not as great in LLC-MK2 cells as in PRL cells, siRNA directed against TRIM5$\alpha_{rh}$ also increased the efficiency of HIV-1.GFP infection in the LLC-MK2 cells (FIG. 7). Therefore, TRIM5$\alpha_{rh}$ is an essential factor for the early block to HIV-1 in primary rhesus monkey cells.

Example 2

Identification of Polymorphisms in TRIM5$\alpha$

Starting with 0.05 μg of human DNA (i.e., from blood samples) from long term non-progressors (i.e., individuals who have been infected with HIV for 7-12 years and yet retain a CD4$^+$ cell count within the normal range) the eight exons of TRIM5$\alpha_{hu}$ (including the 5'- and 3'UTRs (SEQ ID NOs.:67, 68, 69, 70, 71, 72, 73, and 74) are amplified in separate reactions by PCR using primers with sequences for M13F or M13R Universal primers at 5' ends. The amplified fragments are purified and sequenced with the M13R and F primers to obtain the entire sequence of each exon. The amplified sequences are then compared to the normal cDNA sequence (SEQ ID NO.:47) to identify sequence variants.

Example 3

Species-specific Variation in the B30.2 (Spry) Domain of TRIM5α Determines the Potency of Human Immunodeficiency Virus (HIV) Restriction A. Materials and Methods TRIM5α Chimerae.

The TRIM5 cDNA from humans and rhesus monkeys were obtained from a kidney cDNA library (Clontech) and from a primary rhesus lung cDNA library, respectively (Stremlau, M., et al. (2004) Nature 427:848-8539). The nomenclature for the chimerae is TRIM5α A(Bx-y), in which the encoded TRIM5α amino acids from x to y from species B are inserted into the TRIM5α protein of species A (H=human; R=rhesus monkey). The numbering scheme is based on the human TRIM5α residue numbers; the same numbers are used for the rhesus monkey TRIM5α residues, after the TRIM5α$_{rh}$ sequence is aligned to that of TRIM5α$_{hu}$.

Some of the chimeric TRIM5 constructs were created by exchanging fragments generated by digestion with the restriction enzymes Bsml I (TRIM5α R(H286-493) and TRIM5α H(R286-493)) or Bsml I and BamH I (TRIM5α R(H286-371) and TRIM5α H(R286-371)). The following chimeric proteins were expressed by plasmids created by QuikChange mutagenesis (Stratagene): TRIM5α H(R305-314), R(H305-314), H(R323-332), R(H323-332), R(H335-340) and R(H337-338a). The predicted amino acid sequence of the TRIM5α R(H337-338a) protein in the region affected by the mutation is . . . GTLFQSLTNF . . . . The mutated plasmids were sequenced in the regions surrounding the introduced changes.

TRIM5α$_{hu}$ Mutants.

Plasmids expressing TRIM5α$_{hu}$ with single amino-acid changes were created by QuikChange mutagenesis (Stratagene). The nomenclature for these mutants is TRIM5α$_{hu}$ followed by the wild-type amino acid residue in single letter code, amino acid position, and the amino acid residue to which the change was made.

Creation of Cells Stably Expressing TRIM5α Variants.

Retroviral vectors encoding TRIM5α$_{hu}$, TRIM5α$_{rh}$ or chimeric TRIM5α proteins were created using the pLPCX vector (Stremlau, M., et al. (2004) Nature 427:848-853). The pLPCX vectors contain only the amino acid-coding sequence of the TRIM5α cDNA. In all constructs, the TRIM5α proteins possess C-terminal epitope tags derived from influenza hemagglutinin (HA). Recombinant viruses were produced in 293T cells by cotransfecting these pLPCX plasmids with the pVPack-GP and pVPack-VSV-G packaging plasmids (Stratagene). The pVPack-VSV-G plasmid encodes the vesicular stomatitis virus (VSV) G envelope glycoprotein, which allows efficient entry into a wide range of vertebrate cells. The resulting virus particles were used to transduce approximately 1×10$^6$ HeLa cells in the presence of 5 μg/ml polybrene. Cells were selected in 1 (μg/ml puromycin (Sigma).

Immunoblottinq.

HA-tagged proteins were expressed in HeLa cells by transduction with pLPCX vectors as described above. The HA-tagged TRIM5α proteins were detected in whole-cell lysates (100 mM (NH$_4$)$_2$SO$_4$, 20 mM Tris-HCl (pH 7.5), 10% glycerol, 1% Nonidet P40) by Western blotting with horseradish peroxidase (HRP)-conjugated 3F10 antibody (Roche), β-actin was detected with A5441 antibody (Sigma).

Infection with Viruses Expressing Green Fluorescent Protein (GFP).

Recombinant HIV-1 expressing GFP was prepared as described (Hofmann, W., et al. (1999) J. Virol. 73:10020-10028; Owens, C. M., et al. (2004) J. Virol. 78:5423-5437; Owens, C. M., et al. (2003) J. Virol. 77:726-731; Stremlau, M., et al. (2004) Nature 427:848-853), and MLV-GFP was prepared by co-transfecting 293T cells with 15 |ug of pFB-hrGFP, 15 μg of pVPack-GP and 4 μg of pVPack-VSV-G (all from Stratagene). HIV-1 viral stocks were quantified by measuring reverse transcriptase (RT) activity as described (Rho, H. M., et al. (1981) Virology 112:355-360). MLV RT activity was determined by the same procedure except that 20 mM MnCl$_2$ was used instead of MgCl$_2$. For infections, 3×10$^4$ HeLa cells seeded in 24-well plates were incubated in the presence of virus for 24 hours. Cells were washed and returned to culture for 48 hours, and then subjected to FACS analysis with a FACScan (Becton Dickinson).

B. Results

A Carboxy-terminal TRIM5α Determinant of Anti-HIV-1 Potency.

Figure 9:
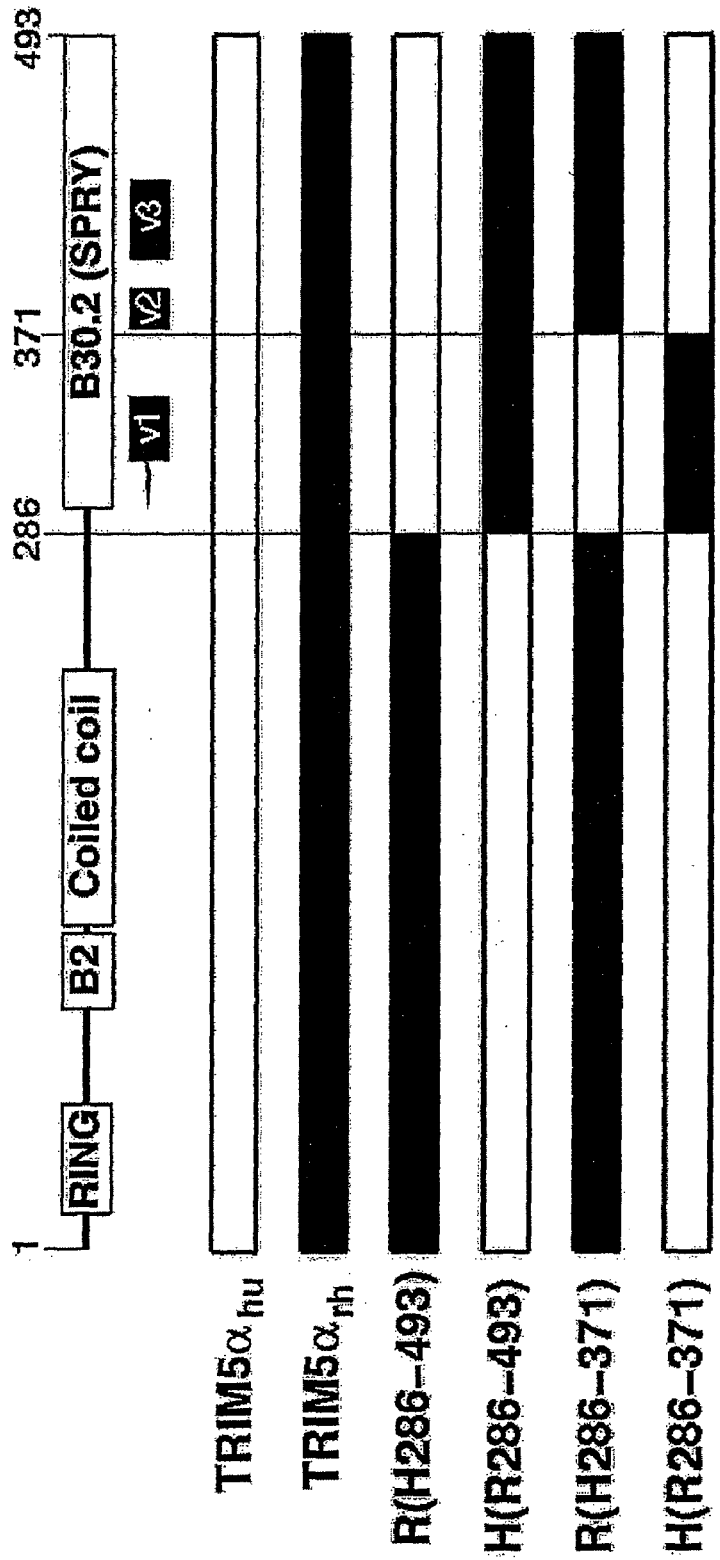
FIG. 9 depicts a schematic diagram of the chimeric TRIM5α$_{hu}$/TRIM5α$_{rh}$ proteins. A diagram of the TRIM5α protein is shown, with the known domains indicated (B2=B-box 2). The numbers of the residues at the N- and C-terminii of the protein and at the chimeric junctions are indicated. The species-specific variable regions (v1, v2 and v3) within the B30.2 domain are shown. The numbering scheme and nomenclature used for the chimeric proteins is based upon the TRIM5ahu sequence and is described in the Materials and Methods section.
Figure 10:
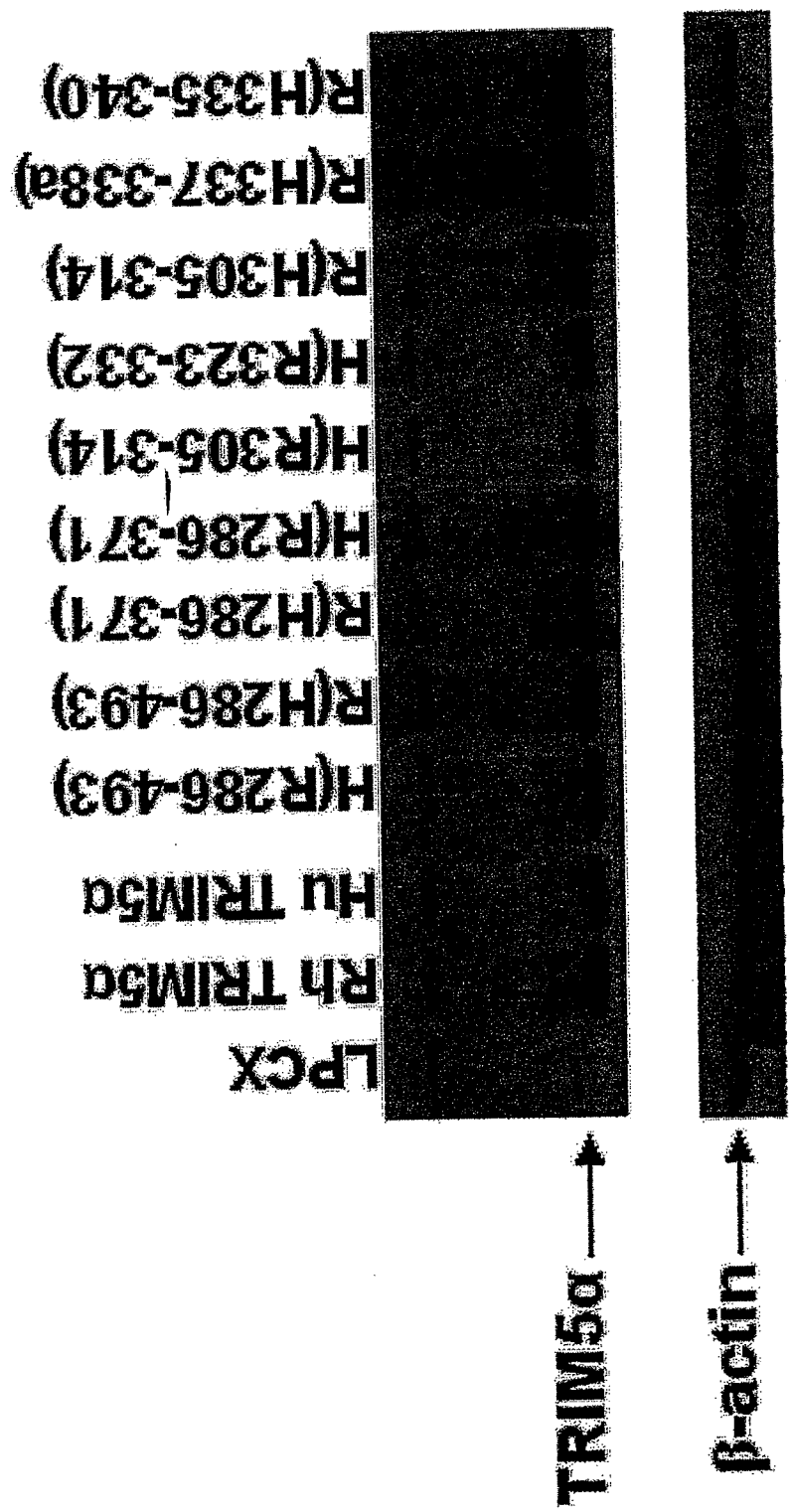
FIG. 10 depicts the expression of chimeric TRIM5α proteins. Lysates from HeLa cells expressing the parental and chimeric TRIM5α proteins, which contain C-terminal HA epitope tags, were subjected to Western blotting with an antibody against HA. Control lysates from HeLa cells transduced with the empty pLPCX vector were analyzed in parallel. The lysates were also Western blotted with an antibody directed against β-actin.
Figure 11:
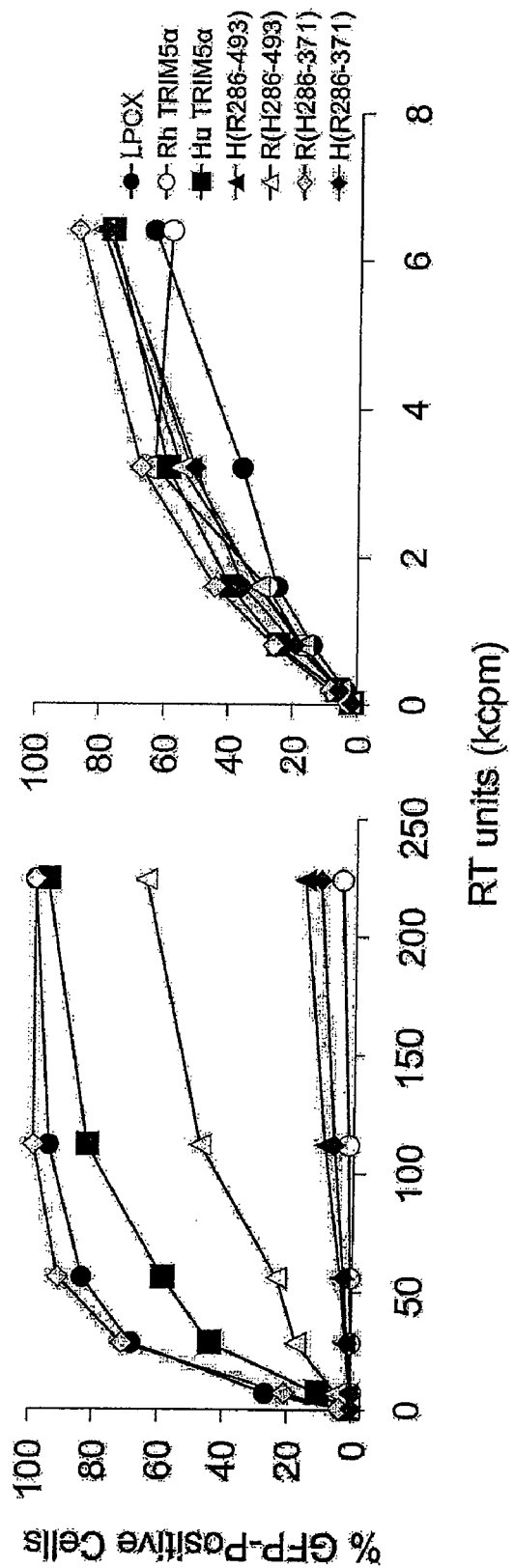
FIG. 11 depicts the effect of expression of the chimeric TRIM5α proteins on HIV-1 infection. HeLa cells expressing the parental and chimeric TRIM5α proteins, or control HeLa cells transduced with the empty pLPCX vector, were incubated with various amounts of HIV-1-GFP or Moloney MLV-GFP (MLV-GFP). Infected, GFP-positive cells were counted by FACS. The results of a typical experiment are shown. Similar results were obtained in three independent experiments.

TRIM5α$_{rh}$ exhibits significantly greater inhibitory activity against HIV-1 than TRIM5α$_{hu}$ (Stremlau, M., et al. (2004) Nature 427:848-853). To map the determinants of this potency, chimeric proteins between TRIM5α$_{rh}$ and T TRIM5α$_{hu}$ were created (FIG. 9). HeLa cells were transduced by pLPCX retroviral vectors expressing the wild-type and chimeric TRIM5α proteins, as described (Stremlau, M., et al. (2004) Nature 427:848-853). All of the TRIM5α proteins have a carboxy-terminal hemagglutinin (HA) tag, allowing documentation of expression levels in the transduced cells. TRIM5α chimerae containing the RING, B-box2 and coiled coil domains of one parent protein and the B30.2 domain of another were studied first. These chimerae, designated TRIM5α R(H286-493) and TRIM5α H(R286-493), were both expressed in HeLa cells at levels comparable to those of the parental TRIM5α proteins (FIG. 10). The HeLa cells were incubated with a recombinant HIV-1 vector (HIV-1-GFP) expressing green fluorescent protein (GFP) or, as a control, with a Moloney murine leukemia virus vector (MLV-GFP). FIG. 11 shows that, compared with HeLa cells transduced with the empty pLPCX vector, HeLa cells expressing TRIM5α$_{rh}$ were strongly resistant to HIV-1-GFP infection. A modest decrease in HIV-1-GFP infection was observed in cells expressing TRIM5α$_{hu}$. HeLa cells expressing the TRIM5α H(R286-493) protein were almost as resistant to infection by HIV-1-GFP as cells expressing TRIM5α$_{rh}$. An intermediate level of HIV-1-GFP inhibition was observed in the cells expressing TRIM5α R(H286-493). MLV-GFP infection of the cells expressing the various TRIM5α chimerae was similar to that of the control cells transduced with the empty pLPCX vector. Therefore, the B30.2 domain of TRIM5α$_{rh}$ is sufficient to confer potent anti-HIV-1 activity to TRIM5α$_{hu}$.

Functional Importance of Variation in the v1 Region of the TRIM5α B30.2 Domain.

Analysis of the sequence of rodent and primate TRIM5α proteins has revealed the existence of three regions within the B30.2 domain that exhibit dramatic species-specific length and amino-acid variation. These regions have been designated v1, v2 and v3 (FIG. 9). The v1 region of the TRIM5α B30.2 domain in Old World primates is longer than that of other primates. Thirteen of the 33 differences in amino acid sequence between the B30.2 domains of TRIM5α$_{hu}$ and TRIM5α$_{rh}$ occur within the v1 region. It was hypothesized that variation in the B30.2 v1 region contributes to the differences in HIV-1-restricting activity between the human and rhesus monkey TRIM5α proteins. To test this hypothesis, additional chimeric proteins that would allow an assessment of the contribution of the v1 region independently of the other B30.2 variable regions were created. These chimeric proteins, TRIM5α R(H286-371) and TRIM5α H(R286-371) (FIG. 9), were expressed stably in HeLa cells transduced with pLPCX vectors. The levels of expression of these chimeric proteins were equivalent to those of the wild-type TRIM5α$_{hu}$ and TRIM5α$_{rh}$ proteins (FIG. 10). The ability of the wild-type and chimeric proteins to inhibit HIV-1-GFP infection was examined (FIG. 11). The TRIM5α H(R286-371) chimera, which contains the B30.2 v1 region of TRIM5α$_{rh}$ in a TRIM5α$_{hu}$ background, suppressed HIV-1-GFP infection nearly as efficiently as TRIM5α$_{rh}$. Conversely, the reciprocal chimera, TRIM5α R(H286-371), exhibited no inhibitory activity against HIV-1-GFP infection. Expression of these chimeric TRIM5α proteins did not significantly affect the susceptibility of the HeLa cells to infection by MLV-GFP viruses. These results indicate that the major determinant of anti-HIV-1 potency in TRIM5α is located between residues 286 and 371, in a segment including the B30.2 v1 region.

Mapping of the Potency Determinant within the B30.2 v1 Region.

Figure 12:
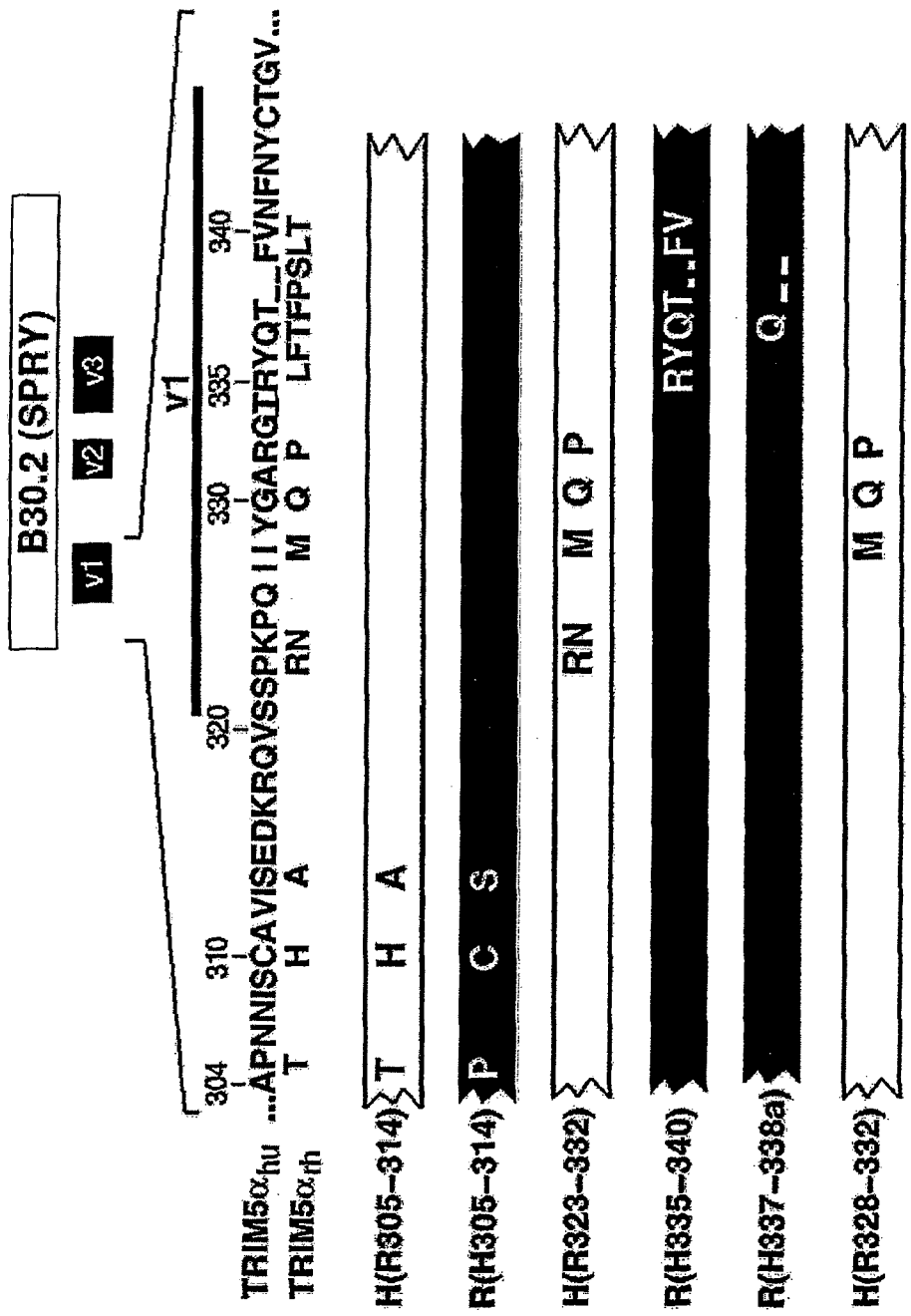
FIG. 12 depicts chimeric TRIM5α proteins containing heterologous elements of the B30.2 domain v1 region. A diagram of the TRIM5α B30.2 domain, with the variable regions (v1, v2 and v3) indicated, is provided at the top of the figure. The region of interest is expanded, with the primary amino acid sequence of TRIM5α$_{hu}$ shown. Amino acid residues in TRIM5α$_{rh}$ that differ from those in TRIM5α$_{hu}$ are shown. The numbers refer to the human TRIM5α residue. The relevant segments of the chimeric TRIM5α proteins are shown. The white segments indicate that the protein is identical to TRIM5α$_{hu}$ except for the amino acid residues shown. The black segments indicate that the protein is identical to TRIM5α$_{rh}$ except for the indicated residues.
Figure 13A:
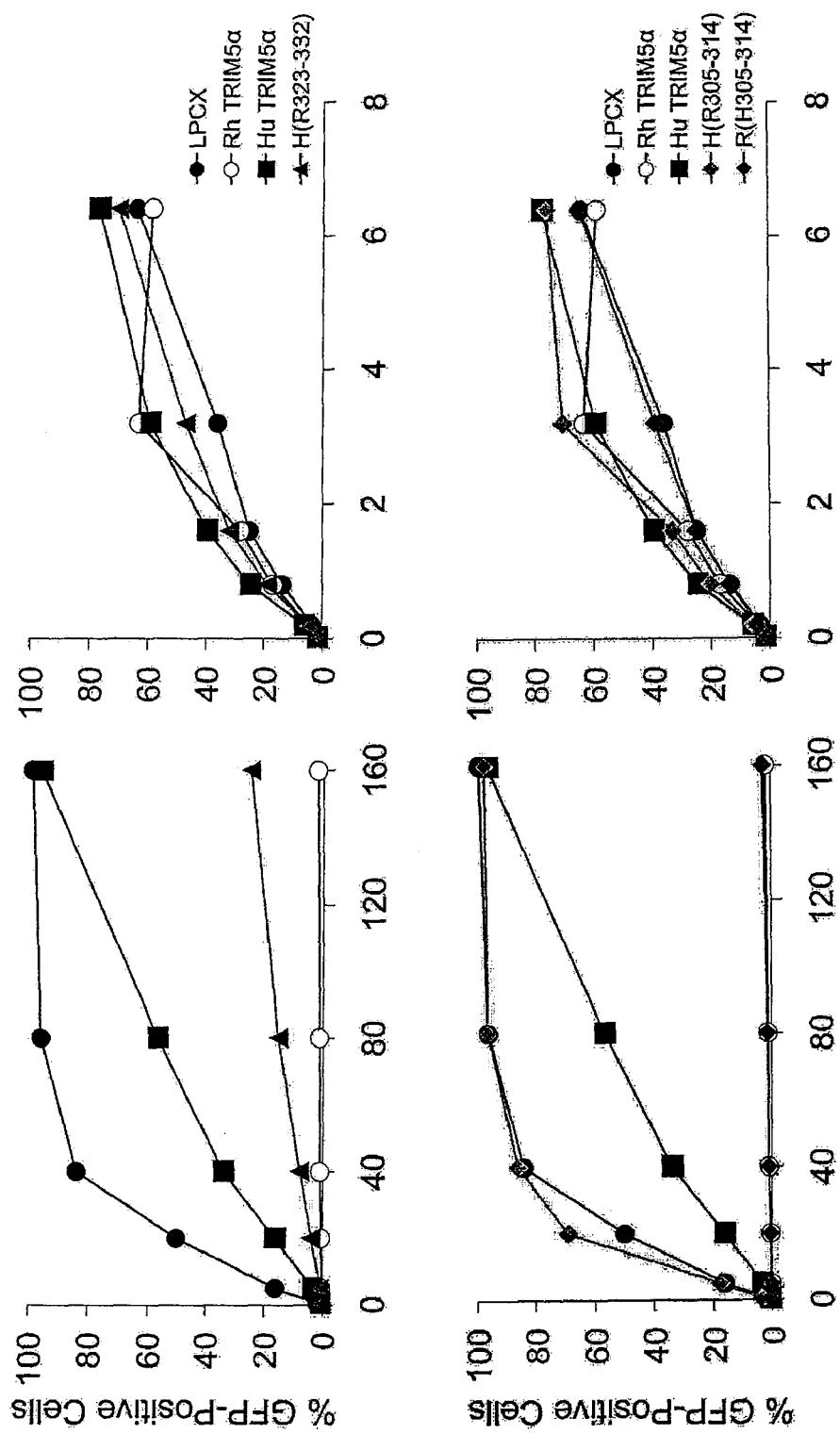
FIGS. 13A-13B depicts the N-terminal half of the B30.2 domain v1 region as a determinant of anti-HIV-1 potency. HeLa cells expressing the parental and chimeric TRIM5α proteins, or control HeLa cells transduced with the empty pLPCX vector, were incubated with various amounts of HIV-1-GFP or MLV-GFP. Infected, GFP-positive cells were counted by FACS. In the top panels of A, a human TRIM5α variant (TRIM5α H(R323-332)) containing the N-terminal half of the rhesus monkey TRIM5α B30.2 domain v1 region was tested. In the bottom panels of A and in B, TRIM5α chimerae containing heterologous segments other than the N-terminal portion of the B30.2 v1 region are tested. The results of typical experiments are shown. In A, the results of one experiment are separated into upper and lower panels for ease of viewing. Similar results were obtained in two independent experiments.

To investigate whether the determinant of anti-HIV-1 potency could be defined more precisely, specific changes within the B30.2 v1 region were made. The v1 region was arbitrarily divided into two segments and the appropriate chimerae constructed (FIG. 12). The importance to the TRIM5α phenotype of amino acid differences in a region N-terminal to the B30.2 v1 region (residues 305-314) was also tested (FIG. 12). After verifying that approximately equivalent levels of the chimeric proteins were made in transduced HeLa cells (FIG. 10), the ability of the cells to support HIV-1-GFP infection was tested. The TRIM5α H(R323-332) chimera, which contains the amino-terminal segment of the B30.2 v1 region, strongly inhibited HIV-1 infection (FIG. 13A). The inhibition observed for the TRIM5α H(R323-332) chimera was slightly less than that seen for the TRIM5α$_{rh}$ protein. The inhibition of HIV-1-GFP infection by the TRIM5α H(R323-332) and H(R286-371) chimerae was comparable. Therefore, the amino-terminal segment of the B30.2 v1 region is the major determinant of anti-HIV-1 potency.

Figure 13B:
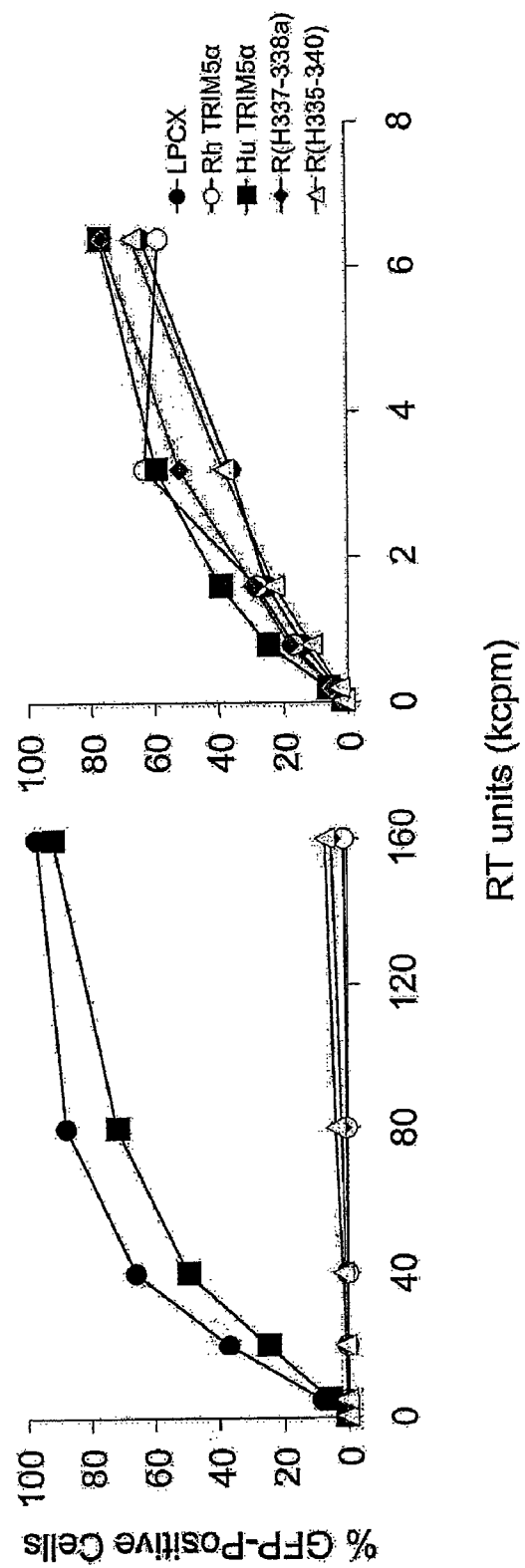

Insertion of carboxy-terminal segments of the B30.2 v1 region from the TRIM5α$_{hu}$ protein had no significant effect on the ability of the rhesus monkey TRIM5α molecule to restrict HIV-1 infection (see TRIM5α R(H335-340) and TRIM5α R(H337-338a) in FIGS. 12 and 13B). Similarly, substitution of the human TRIM5α sequences amino-terminal to the B30.2 v1 region into the TRIM5α$_{rh}$ protein did not affect the anti-HIV-1 potency of the latter molecule (see TRIM5α R(H305-314) in FIGS. 12 and 13C). The reciprocal chimera, TRIM5α H(R305-314), did not restrict HIV-1 infection (FIGS. 12 and 13C). These results indicate that, of the species-specific amino acid differences in the TRIM5α sequences extending from residue 304 to 340, those in the segment comprised of residues 323-332 appreciably impact the anti-HIV-1 potency of the molecule.

Contribution of Individual Amino Acids in the v1 Region to TRIM5α Antiviral Potency.

Figure 14A:
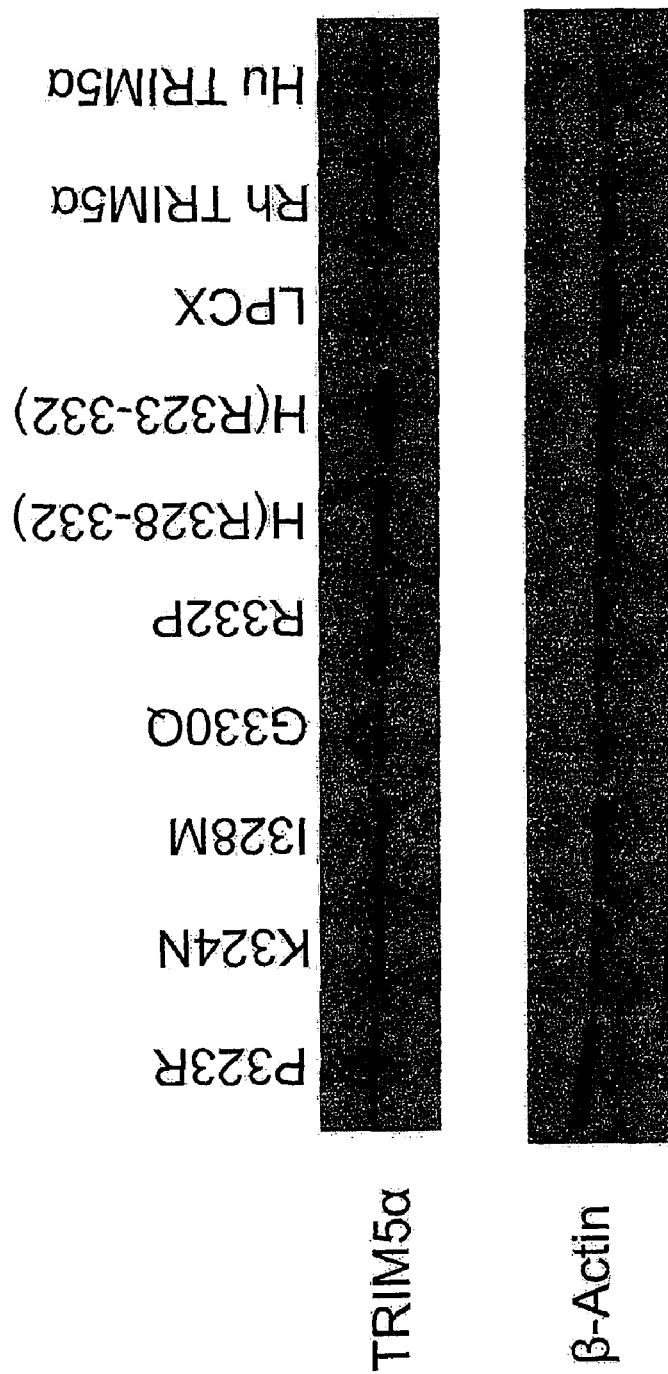
FIGS. 14A-14C depict the expression and antiviral activity of mutant TRIM5α proteins. A. Lysates from HeLa cells expressing the parental and mutant TRIM5α proteins, which contain C-terminal HA epitope tags, were subjected to Western blotting with an antibody against HA. Control lysates from HeLa cells transduced with the empty pLPCX vector were analyzed in parallel. The lysates were also Western blotted with an antibody directed against β-actin. B and C. HeLa cells expressing TRIM5α$_{rh}$, TRIM5α$_{hu}$ or TRIM5α$_{hu}$ mutants, or control HeLa cells transduced with the empty pLPCX vector, were incubated with various amounts of HIV-1-GFP (B) or SIV-GFP (C). Infected, GFP-positive cells were counted by FACS. The results of a typical experiment are shown. Similar results were obtained in two independent experiments.
Figure 14B:
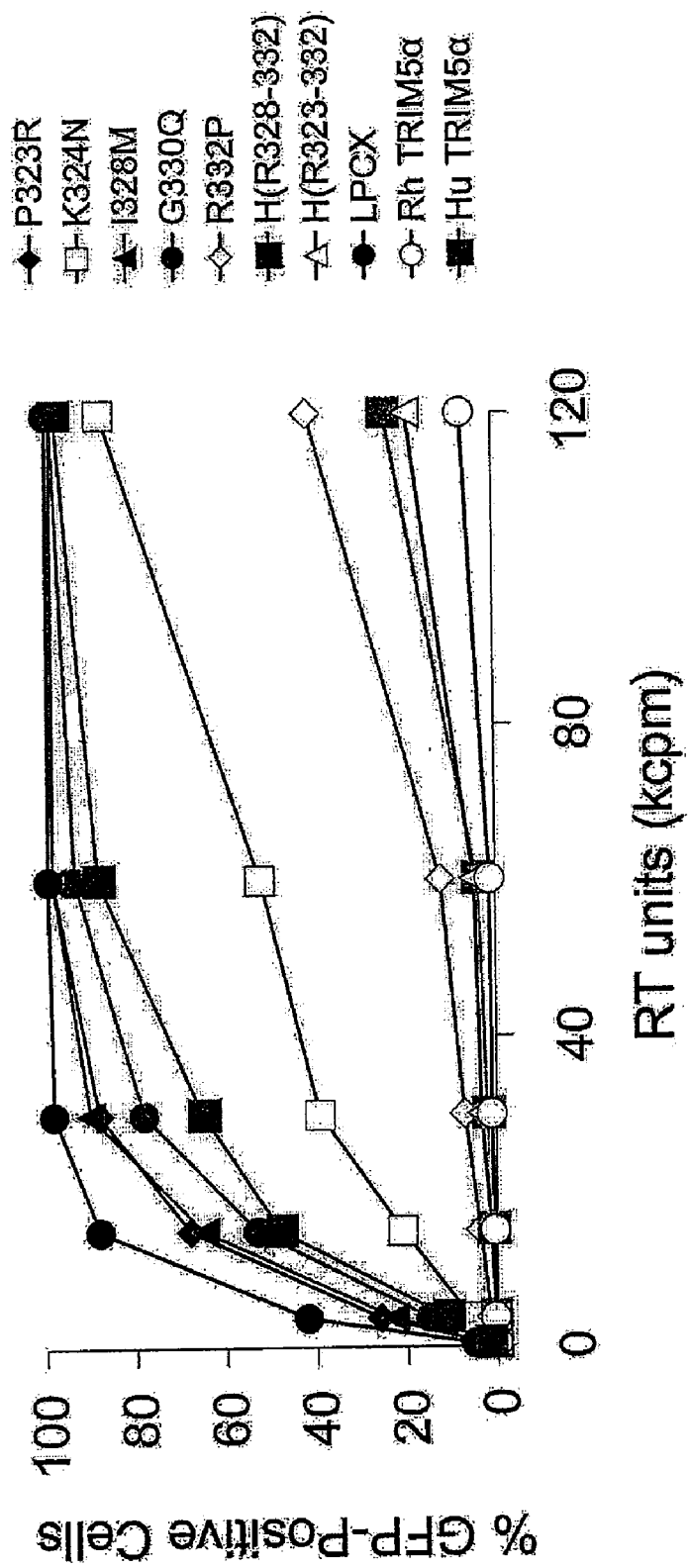

To dissect the species-specific determinants of TRIM5α antiviral potency further, additional TRIM5α$_{hu}$ mutants were created in which individual amino acid residues in the 323-332 segment were changed to those found in TRIM5α$_{rh}$. In addition, the TRIM5α$_{hu}$ sequence from residue 328-332 was changed to that found in TRIM5α$_{rh}$ (see TRIM5α H(R328-332) in FIG. 12). HeLa cells were transduced with vectors expressing these TRIM5α$_{hu}$ variants. All of the TRIM5α variants were expressed in these HeLa cells, although slight variation in the level of expression of the TRIM5α proteins was seen (FIG. 14A). The ability of these TRIM5α$_{hu}$ mutants to inhibit HIV-1-GFP infection was examined and compared with that of TRIM5α$_{rh}$, TRIM5α$_{hu}$ and TRIM5α H(R323-332) (FIG. 14B). The inhibition of HIV-1-GFP infection by the TRIM5α H(R328-332) and TRIM5α H(R323-332) proteins was comparable, and only slightly less potent than that seen in cells expressing the wild-type TRIM5α$_{rh}$ protein. Of the TRIM5α$_{hu}$ mutants with single amino acid changes, TRIM5α$_{rh}$ R332P was most potent at restricting HIV-1 infection. The TRIM5α$_{hu}$ K324N mutant was reproducibly more effective than the wild-type TRIM5α$_{hu}$ protein at inhibiting HIV-1. The other single amino acid changes did not potentiate the anti-HIV-1 activity of TRIM5α$_{hu}$. Therefore, one determinant of anti-HIV-1 potency of TRIM5α$_{rh}$ resides in the sequence 328-332, in which 3 amino acids differ between TRIM5α$_{rh}$ and TRIM5α$_{hu}$. Of the B30.2 domain v1 residues that differ between these two TRIM5α orthologs, differences in residue 332 and, to a lesser extent, 324 contribute to potency in restricting HIV-1 infection.

Figure 14C:
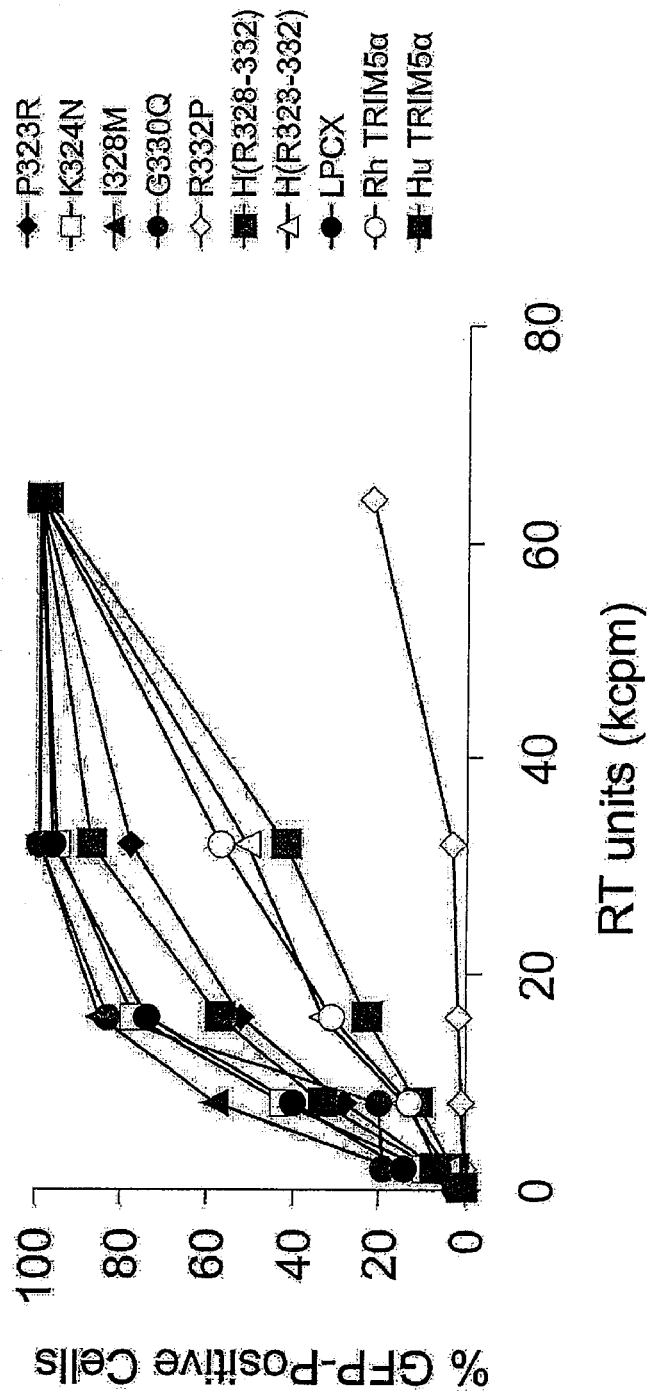

The mutant TRIM5α$_{hu}$ proteins were also studied for the ability to restrict SIVmac infection. As has been previously reported (Stremlau, M., et al. (2004) Nature 427:848-853), TRIM5α$_{hu}$ exerted little effect on the efficiency of SIV-GFP infection, whereas TRIM5α$_{rh}$ inhibited SIV-GFP infection partially (FIG. 14C). Most of the TRIM5α$_{hu}$ mutants were not appreciably better than the wild-type TRIM5α$_{hu}$ in restricting SIVmac infection. Two variants, TRIM5α H(R323-332) and TRIM5α H(R328-332), inhibited SIV-GFP infection to the same degree as TRIM5α$_{rh}$. The TRIM5α$_{hu}$ R332P mutant potently inhibited SIV-GFP infection. This inhibition was specific, as these cells were infectible by MLV-GFP to the same degree as cells transduced with the empty control vector. Therefore, a single amino acid change in the TRIM5α$_{hu}$ B30.2 v1 region results in a gain of SIVmac inhibitory activity beyond that exhibited by either TRIM5α$_{hu}$ or TRIM5α$_{rh}$.

It has been shown that the B30.2 domain is the major determinant of the differences in anti-HIV-1 potency between human and rhesus monkey TRIM5α. The B30.2 domain of TRIM5α$_{rh}$ has previously been shown to be essential for the ability to restrict HIV-1 infection (Stremlau, M., et al. (2004) Nature 427:848-853). The B30.2 domain is a component of a number of proteins, including some other TRIM proteins, butyrophilin-like proteins, and stonustoxin (Henry, J., et al. (1998) Mol. Biol. Evol. 15:1696-1705). Although B30.2 domain-containing proteins have proliferated in chordate lineages, the function of these domains is not well understood (Henry, J., et al. (1998) Mol. Biol. Evol. 15:1696-1705; Seto, M. H., et al. (1999) Proteins: Structure, Function, and Genetics 35:235-249). In a few instances, the B30.2 domain has been implicated in binding to intracellular ligands. For example, the B30.2 domain of butyrophilin has been reported to bind xanthine oxidase (Ishii, T., et al. (1995) Biochim. Biophys. Acta 1245:285-292.). The B30.2 domain of TRIM11 has been shown to be important for the interaction with humanin (Niikura, T., et al. (2003) Eur. J. Neurosci. 17:1150-1158). The results presented herein show that the B30.2 domain of TRIM5α plays a role in the interaction with the viral capsid. Of interest, in an HIV-1-restricting factor, TRIMCyp, found in owl monkeys, the TRIM5α B30.2 domain is replaced by cyclophilin A, which is known to bind the HIV-1 capsid (Nisole, S., et al. (2004) Proc. Natl. Acad. Sci. USA, in press; Sayah, D. M., et al. (2004) Nature, in press).

The amino acid sequence for TRIM5α proteins from a number of primate and rodent species has been determined. Although species-specific variation is observed in all of the TRIM5α domains, the type of variation in the B30.2 domain is noteworthy. Significant length polymorphism as well as individual amino acid variation is found in three regions within the B30.2 domains of TRIM5α proteins from different species. These variable regions (designated v1, v2 and v3) may represent surface-exposed loops, as such length variation would not be readily tolerated within the core fold of the protein. The v1 region is particularly long in Old World monkeys, apes and humans, whereas the v3 region exhibits additional length in New World monkeys. Thus, among the Old World primates, it appears that the B30.2 v1 region has evolved special features. These results demonstrate that the major determinant of the anti-HIV-1 potency of the TRIM5α$_{rh}$ protein resides within the amino-terminal half of the B30.2 v1 segment. The sequence of African green monkey TRIM5α, which also restricts HIV-1 infection (Hatziioannou, T., et al. (2004) *Proc. Natl. Acad. Sci. USA* 101:10774-10779; Keckesova, Z., et al. (2004). *Proc. Natl. Acad. Sci. USA* 101:10780-10785; Yap, M. W., et al. (2004) *Proc. Natl. Acad. Sci. USA* 101:10786-10791), is nearly identical to that of TRIM5α$_{rh}$ in this part of the v1 region. By contrast, within a stretch of ten residues in this region, five amino acid differences between TRIM5α$_{rh}$ and TRIM5α$_{hu}$ exist. These studies indicate that three differences, in residues 328, 330 and 332, largely explain the different anti-HIV-1 potencies of TRIM5α$_{rh}$ and TRIM5α$_{hu}$. Of particular importance is residue 332, a change which can increase the potency of HIV-1 restriction and result in a gain in anti-SIVmac activity beyond that of either parental TRIM5α protein. The amino acid composition of the TRIM5α 320-333 region is suggestive of that of a surface-exposed loop, consistent with a role in interaction with the HIV-1 capsid and/or TRIM5α cofactors.

Previous studies (Stremlau, M., et al. (2004) *Nature* 427: 848-853) and the experiments herein indicate that differences in the expression level of TRIM5α$_{hu}$ and TRIM5α$_{rh}$ cannot account for the observed differences in anti-HIV-1 potency. Nonetheless, for the panel of TRIM5α variants presented in FIG. 14, a correlation between anti-HIV-1 potency and steady-state level of expression is apparent. This correlation, however, was not evident with respect to anti-SIVmac activity. Nonetheless, the observed differences in steady-state levels reflect properties of the TRIM5α variants relevant to antiviral activity, such as subcellular compartmentalization or association with cofactors.

The TRIM5α H(R328-332) and H(R323-332) chimerae created in this study exhibit greater than 98% sequence identity to human TRIM5α, yet inhibit HIV-1 with potencies that approach that of the rhesus monkey TRIM5α protein. The TRIM5α H(R328-332) and H(R323-332) proteins, or similarly designed chimerae, are therefore useful in approaches designed to protect human cells from HIV-1 infection.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting HIV infection in one or more cells or conferring HIV infection resistance to one or more cells, comprising administering to one or more cells an agent selected from the group consisting of:
   (a) an isolated nucleic acid molecule comprising a nucleic acid sequence having at least 95% identity to the nucleotide sequence of SEQ ID NO:1, wherein the nucleic acid molecule encodes a Trim5α polypeptide and the Trim5α polypeptide is stably expressed in the cell; and
   (b) an isolated Trim5α polypeptide comprising an amino acid sequence having at least 95% identity to the amino acid sequence of SEQ ID NO:2.

2. The method of claim 1, wherein the isolated nucleic acid molecule comprises the nucleic acid sequence of SEQ ID NO:1.

3. The method of claim 1, wherein the isolated nucleic acid molecule consists of the nucleic acid sequence of SEQ ID NO:1.

4. The method of claim 1, wherein the isolated nucleic acid molecule encodes a polypeptide comprising the amino acid sequence of SEQ ID NO:2.

5. The method of claim 1, wherein the isolated nucleic acid molecule encodes a polypeptide consisting of the amino acid sequence of SEQ ID NO:2.

6. The method of claim 1, wherein the isolated Trim5α polypeptide comprises the amino acid sequence of SEQ ID NO:2.

7. The method of claim 1, wherein the isolated Trim5α polypeptide consists of the amino acid sequence of SEQ ID NO:2.

8. The method of any one of claims 1-7, wherein the agent is administered in a pharmaceutically acceptable formulation.

9. The method of any one of claims 1-7, further comprising administering at least one additional anti-viral agent.

10. The method of any one of claims 1-7, wherein the agent is encapsulated in a liposome.

11. The method of any one of claims 1-5, wherein the isolated nucleic acid molecule is administered using a vector.

12. The method of claim 11, wherein said vector is a viral vector.

13. The method of any one of claims 1-7, wherein the cells are in vitro, in vivo or ex vivo.

14. The method of any one of claims 1-7, wherein the cells are human cells.

15. The method of any one of claims 1-7, wherein the cells are in a subject at risk for HIV infection.

16. The method of claim 15, wherein the subject is a human.

17. The method of 15, wherein the cells are present in a mucosal membrane of the subject.

* * * * *